United States Patent
Geremia et al.

(10) Patent No.: US 11,584,805 B2
(45) Date of Patent: *Feb. 21, 2023

(54) OLIGOSACCHARIDE COMPOSITIONS AND METHODS FOR PRODUCING THEREOF

(71) Applicant: DSM Nutritional Products, LLC, Parsippany, NJ (US)

(72) Inventors: John M. Geremia, Watertown, MA (US); Anastasia V. Lioubomirov, N. Attleboro, MA (US); Scott Han, Lawrenceville, NJ (US); Benjamin A. Seigal, Newton, MA (US); Alicia Landry, N. Charleston, SC (US); Kyle Sherry, Rochester, NY (US); Stephen Panos, Lansing, MI (US); Devin Churchman, Arlington, MA (US); Andrew O'Connor, Lexington, MA (US)

(73) Assignee: DSM Nutritional Products, LLC, Parsippany, NJ (US)

( * ) Notice: Subject to any disclaimer, the term of this patent is extended or adjusted under 35 U.S.C. 154(b) by 406 days.

This patent is subject to a terminal disclaimer.

(21) Appl. No.: 16/912,368

(22) Filed: Jun. 25, 2020

(65) Prior Publication Data
US 2021/0002387 A1 Jan. 7, 2021

Related U.S. Application Data

(63) Continuation of application No. 14/795,720, filed on Jul. 9, 2015, now Pat. No. 10,752,705.
(Continued)

(51) Int. Cl.
*C08B 37/00* (2006.01)
*C07H 3/06* (2006.01)
(Continued)

(52) U.S. Cl.
CPC ............. *C08B 37/006* (2013.01); *C07H 1/00* (2013.01); *C07H 3/06* (2013.01); *A23K 20/163* (2016.05); *A23V 2002/00* (2013.01)

(58) Field of Classification Search
None
See application file for complete search history.

(56) References Cited

U.S. PATENT DOCUMENTS

| 2,027,904 A | 1/1936 | Farber |
| 2,436,967 A | 3/1948 | Leuck |

(Continued)

FOREIGN PATENT DOCUMENTS

| CA | 2420247 A1 | 2/2002 |
| CA | 2511190 A1 | 7/2004 |

(Continued)

OTHER PUBLICATIONS

First Office Action for Mexican Patent Application No. MX/a/2017/009730, dated Jul. 8, 2021 (6 pages).

(Continued)

*Primary Examiner* — Patricia A George
(74) *Attorney, Agent, or Firm* — Clark & Elbing LLP

(57) ABSTRACT

Described herein are methods for the production of oligosaccharides, including functionalized oligosaccharides, from one or more sugars, such as one or more monosaccharides, using polymeric and solid-supported catalysts containing acidic and ionic groups. Also provided are the oligosaccharide compositions, including functionalized oligosaccharide compositions, obtained using the methods.

24 Claims, 12 Drawing Sheets

Related U.S. Application Data

(60) Provisional application No. 62/108,035, filed on Jan. 26, 2015, provisional application No. 62/022,579, filed on Jul. 9, 2014.

(51) Int. Cl.
  *C07H 1/00* (2006.01)
  *A23K 20/163* (2016.01)

(56) References Cited

U.S. PATENT DOCUMENTS

| | | |
|---|---|---|
| 2,719,179 A | 9/1955 | Mora et al. |
| 3,766,165 A | 10/1973 | Rennhard et al. |
| 3,876,794 A | 4/1975 | Rennhard |
| 3,973,049 A | 8/1976 | Furda et al. |
| 4,671,967 A | 6/1987 | Patel et al. |
| 4,761,401 A | 8/1988 | Couchman et al. |
| 4,841,041 A | 6/1989 | van Boeckel et al. |
| 4,847,338 A | 7/1989 | Linhardt et al. |
| 4,927,811 A | 5/1990 | Quarles |
| 4,965,354 A | 10/1990 | Yanaki et al. |
| 5,051,500 A | 9/1991 | Elmore |
| 5,280,111 A | 1/1994 | Shoji et al. |
| 5,424,418 A | 6/1995 | Duflot |
| 5,558,899 A | 9/1996 | Kuzee et al. |
| 5,573,794 A | 11/1996 | Duflot |
| 5,580,762 A | 12/1996 | Karube et al. |
| 5,645,647 A | 7/1997 | Guzek et al. |
| 5,780,620 A | 7/1998 | Mandai et al. |
| 5,843,922 A | 12/1998 | Whistler et al. |
| 5,976,580 A | 11/1999 | Ivey et al. |
| 6,423,833 B1 | 7/2002 | Catani et al. |
| 6,475,552 B1 | 11/2002 | Shah et al. |
| 6,559,302 B1 | 5/2003 | Shah et al. |
| 6,630,586 B1 | 10/2003 | Fouache et al. |
| 6,638,916 B1 | 10/2003 | Cowden et al. |
| 6,677,142 B1 | 1/2004 | Weissmuller et al. |
| 7,608,291 B2 | 10/2009 | Baillon et al. |
| 7,608,436 B2 | 10/2009 | Harrison et al. |
| 7,615,365 B2 | 11/2009 | Caimi et al. |
| 8,057,840 B2 | 11/2011 | Harrison et al. |
| 8,143,235 B2 | 3/2012 | Gorselink et al. |
| 8,148,505 B2 | 4/2012 | Ando et al. |
| 8,227,448 B2 | 7/2012 | Van Laere et al. |
| 8,445,460 B2 | 5/2013 | Deremaux et al. |
| 8,466,242 B2 | 6/2013 | Geremia et al. |
| 8,476,388 B2 | 7/2013 | Geremia et al. |
| 8,591,919 B2 | 11/2013 | Stahl et al. |
| 8,741,376 B2 | 6/2014 | Broekaert et al. |
| 8,835,403 B2 | 9/2014 | Geng et al. |
| 8,993,039 A1 | 3/2015 | Harrison et al. |
| 9,079,171 B2 | 7/2015 | Geremia et al. |
| 9,205,418 B2 | 12/2015 | Geremia et al. |
| 9,238,845 B2 | 1/2016 | Baynes et al. |
| 9,410,216 B2 | 8/2016 | Eyal et al. |
| 9,481,739 B2 | 11/2016 | Essers et al. |
| 9,492,473 B2 | 11/2016 | von Maltzahn et al. |
| 9,512,239 B2 | 12/2016 | Naeye et al. |
| 9,725,776 B2 | 8/2017 | Dumesic et al. |
| 9,757,403 B2 | 9/2017 | von Maltzahn et al. |
| 9,783,619 B2 | 10/2017 | Bureau et al. |
| 10,131,721 B2 | 11/2018 | Geremia et al. |
| 10,752,705 B2 | 8/2020 | Geremia et al. |
| 10,849,337 B2 | 12/2020 | Geremia et al. |
| 2003/0162300 A1 | 8/2003 | Kunz et al. |
| 2004/0220389 A1 | 11/2004 | Buchwald et al. |
| 2004/0235789 A1 | 11/2004 | Day et al. |
| 2005/0004070 A1 | 1/2005 | Stahl et al. |
| 2005/0075311 A1 | 4/2005 | Lane |
| 2006/0008574 A1 | 1/2006 | Begli et al. |
| 2006/0014717 A1 | 1/2006 | Angstrom et al. |
| 2006/0051812 A1 | 3/2006 | Helin et al. |
| 2006/0127448 A1 | 6/2006 | Carlson et al. |
| 2007/0036840 A1 | 2/2007 | Tuduri et al. |
| 2007/0048432 A1 | 3/2007 | Holzgraefe et al. |
| 2007/0148728 A1 | 6/2007 | Johnson et al. |
| 2007/0249524 A1 | 10/2007 | Dieckgraefe |
| 2007/0254848 A1 | 11/2007 | Geng et al. |
| 2008/0051573 A1 | 2/2008 | Hirth et al. |
| 2009/0098240 A1 | 4/2009 | Mills et al. |
| 2009/0304852 A1 | 12/2009 | Hopkins et al. |
| 2010/0239584 A1 | 9/2010 | Mulard et al. |
| 2010/0284972 A1 | 11/2010 | Naeye et al. |
| 2011/0052538 A1 | 3/2011 | Brown et al. |
| 2011/0250235 A1 | 10/2011 | Saarinen et al. |
| 2011/0306757 A1 | 12/2011 | Lopez-Belmonte Encina et al. |
| 2012/0034366 A1 | 2/2012 | Hoffman et al. |
| 2012/0041189 A1 | 2/2012 | Clavel et al. |
| 2012/0220740 A1 | 8/2012 | Geremia et al. |
| 2013/0005684 A1 | 1/2013 | Fichert et al. |
| 2013/0028869 A1 | 1/2013 | Bruggeman et al. |
| 2013/0216693 A1 | 8/2013 | Harrison et al. |
| 2014/0060522 A1 | 3/2014 | Baynes et al. |
| 2014/0105864 A1 | 4/2014 | Di Leo |
| 2014/0187474 A1 | 7/2014 | Sonnenburg |
| 2014/0234912 A1 | 8/2014 | Dekany et al. |
| 2014/0335131 A1 | 11/2014 | Mazmanian et al. |
| 2015/0087616 A1 | 3/2015 | Ritter et al. |
| 2015/0202607 A1 | 7/2015 | Geremia et al. |
| 2015/0238948 A1 | 8/2015 | Geremia |
| 2015/0352133 A1 | 12/2015 | Jennewein |
| 2016/0007642 A1 | 1/2016 | Geremia et al. |
| 2016/0015065 A1 | 1/2016 | Sumner et al. |
| 2016/0032038 A1 | 2/2016 | Baynes et al. |
| 2016/0366909 A1 | 12/2016 | Geremia et al. |
| 2017/0151268 A1 | 6/2017 | von Maltzahn et al. |
| 2018/0000145 A1 | 1/2018 | Geremia et al. |
| 2018/0000146 A1 | 1/2018 | Geremia |
| 2018/0037599 A1 | 2/2018 | Duflot et al. |
| 2019/0209600 A1 | 7/2019 | Gubler |
| 2019/0307159 A1 | 10/2019 | Geremia et al. |
| 2020/0093845 A1 | 3/2020 | von Maltzahn et al. |
| 2021/0121486 A1 | 4/2021 | Geremia et al. |

FOREIGN PATENT DOCUMENTS

| | | |
|---|---|---|
| CA | 2805501 A1 | 1/2012 |
| CA | 2616065 C | 2/2012 |
| CA | 2818505 A1 | 5/2012 |
| CA | 2827294 A1 | 8/2012 |
| CA | 2833311 A1 | 11/2012 |
| CA | 2581487 C | 7/2013 |
| CN | 1600146 A | 3/2005 |
| CN | 1731938 A | 2/2006 |
| CN | 102892303 A | 1/2013 |
| CN | 103562401 A | 2/2014 |
| CN | 104171365 A | 12/2014 |
| EA | 11417 B1 | 2/2009 |
| EP | 0549478 A1 | 6/1993 |
| EP | 1634599 A | 3/2006 |
| EP | 1886696 A1 | 2/2008 |
| EP | 1887017 A1 | 2/2008 |
| EP | 2138048 A1 | 12/2009 |
| EP | 2248907 A1 | 11/2010 |
| EP | 2386563 A1 | 11/2011 |
| EP | 2401925 A1 | 1/2012 |
| EP | 2666788 A1 | 11/2013 |
| ES | 2304223 B2 | 5/2009 |
| JP | H06-121693 A | 5/1994 |
| JP | H10-316740 A | 12/1998 |
| JP | 2001-86999 A | 4/2001 |
| JP | 2003-516757 A | 5/2003 |
| JP | 2004-182628 A | 7/2004 |
| JP | 2008-81501 A | 4/2008 |
| JP | 4597630 B2 | 12/2010 |
| JP | 2011-501670 A | 1/2011 |
| JP | 2011-212386 A | 10/2011 |
| JP | 2012-158526 A | 8/2012 |
| JP | 2014-513985 A | 6/2014 |
| JP | 2014-205704 A | 10/2014 |
| RU | 2153503 C2 | 7/2000 |
| RU | 2509477 C1 | 3/2014 |
| WO | WO-87/05330 A1 | 9/1987 |
| WO | WO-2004/026341 A1 | 4/2004 |

(56) References Cited

FOREIGN PATENT DOCUMENTS

| WO | WO-2004/052121 A1 | 6/2004 |
|---|---|---|
| WO | WO-2005/003329 A1 | 1/2005 |
| WO | WO-2006/030100 A1 | 3/2006 |
| WO | WO-2006/041930 A2 | 4/2006 |
| WO | WO-2007/010084 A2 | 1/2007 |
| WO | WO-2007/050656 A2 | 5/2007 |
| WO | WO-2007/117175 A1 | 10/2007 |
| WO | WO-2008/037839 A1 | 4/2008 |
| WO | WO-2008/156354 A1 | 12/2008 |
| WO | WO-2009/051977 A1 | 4/2009 |
| WO | WO-2009/059283 A1 | 5/2009 |
| WO | WO-2009/082214 A1 | 7/2009 |
| WO | WO-2010/105207 A1 | 9/2010 |
| WO | WO-2010/136742 A1 | 12/2010 |
| WO | WO-2010/143961 A1 | 12/2010 |
| WO | WO-2011/008086 A1 | 1/2011 |
| WO | WO-2011/016866 A1 | 2/2011 |
| WO | WO-2012/076321 A1 | 6/2012 |
| WO | WO-2012/127410 A1 | 9/2012 |
| WO | WO-2012/156897 A1 | 11/2012 |
| WO | WO-2014/031956 A1 | 2/2014 |
| WO | WO-2014/043708 A1 | 3/2014 |
| WO | WO-2014/145276 A1 | 9/2014 |
| WO | WO-2014/18635 A2 | 11/2014 |
| WO | WO-2015/099755 A1 | 7/2015 |
| WO | WO-2015/153841 A1 | 10/2015 |
| WO | WO-2016/007778 A1 | 1/2016 |
| WO | WO-2016/122884 A1 | 8/2016 |
| WO | WO-2016/122885 A1 | 8/2016 |
| WO | WO-2016/122887 A1 | 8/2016 |
| WO | WO-2016/122889 A1 | 8/2016 |
| WO | WO-2016/172657 A2 | 10/2016 |
| WO | WO-2016/172658 A2 | 10/2016 |
| WO | WO-2017/083520 A1 | 5/2017 |
| WO | WO-2018/106845 A1 | 6/2018 |

OTHER PUBLICATIONS

Office Action for Chinese Patent Application No. 202010078515.9, dated Aug. 25, 2021 (27 pages).
U.S. Appl. No. 17/106,617, Geremia et al.
U.S. Appl. No. 16/921,562, Geremia et al.
"Generally Recognized as Safe (GRAS) Determination for the Addition of Polydextrose to Infant Formula as a Prebiotic Ingredient In Combination with Galactooligosaccharides," Aug. 2007 (115 pages).
Adamberg et al., "Degradation of fructans and production of propionic acid by *Bacteroides thetaiotaomicron* are enhanced by the shortage of amino acids," Front Nutr. 1(21):1-10 (2014).
ADM/Matsutani LLC, "Fibersol-LQ Data Information Sheet", retrieved from <www.Fibersol2.com> (1 page).
Aggrawal et al., "Technical Application Note 1151. Profiling galactosyloligosaccharide-containing samples by high-performance anion-exchange chromatography with pulsed amperometric detection (HPAE-PAD)," ThermoFisher Scientific, retrieved from <https://assets.thermofisher.com/TFS-Assets/CMD/Application-Notes/AN-1151-IC-Galactosyloligosaccharides-Prebiotics-AN71993-EN.pdf> on Aug. 27, 2019 (2018) (8 pages).
Ahmad et al., "Chapter 11: Beta-Glucan as a Food Ingredient", *Biopolymers for Food Design, Handbook of Food Bioengineering*, vol. 20. Alexandru M. Grumezescu and Alina M. Holban, 351-381 (2018).
Aida et al., "Mushroom as a potential source of prebiotics: a review," Trends in Food Science & Technology. 20(11-12):567-75 (2009).
Alam et al., "Efficacy of partially hydrolyzed guar gum-added oral rehydration solution in the treatment of severe cholera in adults," Digestion. 78(1):24-29 (2008).
Archer Daniels Midland Company, "ADM Ingredients Catalog," pp. I-32 (2016) (36 pages).

Ballongue et al., "Effects of Lactulose and Lactitol on Colonic Microflora and Enzymatic Activity," Scandinavian Journal. 222:41-44 (1997) (4 pages).
Beards et al., "Bacterial, SCFA and gas profiles of a range of food ingredients following in vitro fermentation by human colonic microbiota," Anaerobe. 16(4):420-5 (2010).
Belknap et al., "The effects of psyllium hydrophilic mucilloid on diarrhea in enterally fed patients," Heart Lung. 26(3):229-37 (1997).
Bergstrom et al., "Defective intestinal mucin-type O-glycosylation causes spontaneous colitis-associated cancer in mice," Gastroenterology. 151(1):152-64 (2016) (24 pages).
Boler et al., "Digestive physiological outcomes related to polydextrose and soluble maize fibre consumption by healthy adult men," Br J Nutr. 106(12):1864-71 (2011).
Caligur et al., "Glycobiology: glycosaminoglycans and polysaccharides," BioFiles. 3(10):1-26 (2008) (28 pages).
Casellas et al., "Oral oligofructose-enriched inulin supplementation in acute ulcerative colitis is well tolerated and associated with lowered faecal calprotectin," Aliment Pharmacol Ther. 25(9):1061-7 (2007).
Chen et al., "Comparative effects of cellulose and soluble fibers (pectin, konjac glucomannan, inulin) on fecal water toxicity toward Caco-2 cells, fecal bacteria enzymes, bile acid, and short-chain fatty acids," J Agric Food Chem. 58(18):10277-81 (2010).
Chiavaroli et al., "Dietary fiber effects in chronic kidney disease: a systematic review and meta-analysis of controlled feeding trials," Eur J Clin Nutr. 69(7):761-768 (2015).
Clemente et al., "The impact of the gut microbiota on human health: an integrative view," Cell. 148(6):1258-70 (2012).
Communication pursuant to Article 94(3) EPC for European Patent Application No. 15819734.3, dated May 19, 2020 (15 pages).
Coudray et al., "Effects of inulin-type fructans of different chain length and type of branching on intestinal absorption and balance of calcium and magnesium in rats," Eur J Nutr. 42(2):91-8 (2003).
Coulier et al., "In-depth characterization of prebiotic galacto-oligosaccharides by a combination of analytical techniques," J Agric Food Chem. 57(18):8488-95 (2009).
Courtin et al., "Dietary inclusion of wheat bran arabinoxylooligosaccharides induces beneficial nutritional effects in chickens," Cereal Chem. 85(5):607-13 (2008).
Courtin et al., "Effects of dietary inclusion of xylooligosaccharides, arabinoxylooligosaccharides and soluble arabinoxylan on the microbial composition of caecal contents of chickens," J Sci Food Agric. 88(14):2517-22 (2008).
Cummings et al., "Carbohydrate terminology and classification," Eur J Clin Nutr. 61 (Suppl 1):S5-18(2007).
Deng et al., "Effect of dietary fiber on intestinal barrier function of 5-Fu stressed rats," Res Exp Med (Berl). 199(2):111-9 (1999).
Dua et al., "Characterization of lacto-N-hexaose and two fucosylated derivatives from human milk by high-performance liquid chromatography and proton NMR spectroscopy," J Chromatogr. 328:259-69(1985).
Duggan et al., "Protective nutrients and functional foods for the gastrointestinal tract," Am J Clin Nutr. 75(5):789-808 (2002).
Duncan et al., "Lactate-utilizing bacteria, isolated from human feces, that produce butyrate as a major fermentation product," Appl Environ Microbiol. 70(10):5810-17 (2004).
Dutton et al., "The constitution of a synthetic xylan," Can J Chem. 40(8):1479-82 (1962).
Examination Report for Australian Patent Application No. 2015287703, dated Sep. 6, 2018 (5 pages).
Examination Report for Australian Patent Application No. 2019222849, dated Sep. 28, 2020 (6 pages).
Examination Report for Indian Patent Application No. 201717004105, mailed Dec. 20, 2019 (6 pages).
Examination Report for Indonesian Patent Application No. P00201700913, dated Feb. 5, 2020 (4 pages).
Examination Report for Malaysian Patent Application No. PI 2017000019, dated Nov. 10, 2020 (3 pages).
Examination Report No. 2 for Australian Patent Application No. 2015287703, dated Aug. 21, 2019 (6 pages).
Extended European Search Report for European Patent Application No. 15819734.3, dated Feb. 7, 2018 (12 pages).

(56) References Cited

OTHER PUBLICATIONS

Fasina et al., "Comparative efficacy of a yeast product and bacitracin methylene disalicylate in enhancing early growth and intestinal maturation in broiler chicks from breeder hens of different ages," Poult Sci. 90(5):1067-73 (2011).
Fetzer et al., "Effect of acid and heat on dextrose and dextrose polymers," Ind Eng Chem. 45(5):1075-83 (1953).
Fischer et al., "The gel-forming polysaccharide of psyllium husk (*Plantago ovata forsk*)," Carbohydr Res. 339(11):2009-17 (2004).
Fuhrer et al., "Milksialyllactose influences colitis in mice through selective intestinal bacterial colonization," J Exp Med. 207(13):2843-54 (2010).
Garber, "Drugging the gut microbiome," Nat Biotech. 33(3):228-31 (2015).
Gietl et al., "Factors involved in the in vitro fermentability of short carbohydrates in static faecal batch cultures," International Journal of Carbohydrate Chemistry. 2012:197809 (2012) (10 pages).
Goulas et al., "Development of a process for the production and purification of alpha- and beta-galactooligosaccharides from Bifidobacterium bifidum NCIMB 41171," Int Dairy J. 17(6):648-56 (2007).
Guerin-Deremaux et al., "Effects of a soluble dietary fibre NUTRIOSE® on colonic fermentation and excretion rates in rats," Nutr Res Pract. 4(6):470-6 (2010).
Gómez et al., "Purification, characterization, and prebiotic properties of pectic oligosaccharides from orange peel wastes," J Agric Food Chem. 62(40):9769-82 (2014).
Hamaker et al., "A perspective on the complexity of dietary fiber structures and their potential effect on the gut microbiota," J Mol Biol. 426(23):3838-50 (2014) (13 pages).
Hernot et al., "In vitro fermentation profiles, gas production rates, and microbiota modulation as affected by certain fructans, galactooligosaccharides, and polydextrose," J Agric Food Chem. 57(4):1354-61 (2009).
Holscher et al., "Agave inulin supplementation affects the fecal microbiota of healthy adults participating in a randomized, double-blind, placebo-controlled, crossover trial," J Nutr. 145(9):2025-32 (2015).
Hopkins et al., "Nondigestible oligosaccharides enhance bacterial colonization resistance against *Clostridium difficile* in vitro," Appl Environ Microbiol. 69(4):1920-27 (2003).
Houdijk et al., "Effects of dietary oligosaccharides on the growth performance and faecal characteristics of young growing pigs," Anim Feed Sci Tech. 71:35-48 (1998).
International Search Report and Written Opinion for International Application No. PCT/US2015/039795, dated Oct. 7, 2015 (9 pages).
Islek et al., "The role of Bifidobacterium lactis B94 plus inulin in the treatment of actue infectious diarrhea in children," Turk J Gastroenterol. 25(5):628-33 (2014).
Kau et al., "Human nutrition, the gut microbiome, and immune system: envisioning the future," Available in PMC Mar. 9, 2012. Published in final edited form as: Nature. 474(7351):327-336 (2011) (22 pages).
Kellow et al., "Metabolic benefits of dietary prebiotics in human subjects: a systematic review of randomised controlled trials," Br J Nutr. 111(7):1147-61 (2014).
Kobata, "Structures and application of oligosaccharides in human milk," Proc Jpn Acad Ser B Phys Biol Sci. 86(7):731-47 (2010) (17 pages).
Koropatkin et al., "Howglycan metabolism shapes the human gut microbiota," Nat Rev Microbiol. 10(5):323-35 (2012).
Kuechel et al., "Short communication: Development of a rapid laboratory method to polymerize lactose to nondigestible carbohydrates," J Dairy Sci. 101(4): 2862-2866 (2018) (5 pages).
Lewis et al., "Effect of the prebiotic oligofructose on relapse of Clostridium difficile-associated diarrhea: a randomized, controlled study," Clin Gastroenterol Hepatol. 3(5):442-8 (2005).
Lin et al., "Irinotecan (CPT-11) chemotherapy alters intestinal microbiota in tumour bearing rats," PLoS One. 7(7):e39764 (2012) (8 pages).
Louis et al., "Diversity of human colonic butyrate-producing bacteria revealed by analysis of the buyryl-CoA:acetate CoA-transferase gene," Environ Microbiol. 12(2):304-14 (2010).
Louis et al., "Diversity, metabolism and microbial ecology of butyrate-producing bacteria from the human large intestine," FEMS Microbiol Lett. 294(1):1-8 (2009).
Louis et al., "How to manipulate the microbiota: prebiotics," Adv Exp Med Biol. 902:119-42 (2016).
Louis et al., "Understanding the effects of diet on bacterial metabolism in the large intestine," J Appl Microbiol. 102(5):1197-208 (2007).
Man et al. "Study on Cultivation and Cryoprotectant of Bifidobacterium Bifidum," Data Knowledge Service Platform, 1-87 (2012) (5 pages).
Marlett et al., "A poorly fermented gel from psyllium seed husk increases excreta moisture and bile acid excretion in rats," J Nutr. 132(9):2638-43 (2002).
Mora et al., "Synthetic Polysaccharides. V. Polymerization of Various Aldoses," J Am Chem Soc. 82(13):3418-21 (1960).
Mountzouris et al., "Modeling of oligodextran production in an ultrafiltration stirred-cell membrane reactor," Enzyme Microb Technol. 24(1): 75-85 (1999).
Nakamura et al., "Suppressive effect of partially hydrolyzed guar gum on transitory diarrhea induced by ingestion of maltitol and lactitol in healthy humans," Eur J Clin Nutr. 61(9):1086-93 (2007).
Neyrinck et al., "Prebiotic effects of wheat arabinoxylan related to the increase in bifidobacteria, Roseburia and Bacteroides/Prevotella in diet-induced obese mice," PLoS One. 6(6):e20944 (2011) (12 pages).
Notice of Preliminary Rejection for Japanese Patent Application No. 2017-522455, dated Aug. 27, 2019 (12 pages).
Office Action for Brazilian Patent Application No. BR112017000345-7, dated Jan. 23, 2020 (Informal English language translation provided) (5 pages).
Office Action for Chinese Patent Application No. 201580048065.6, dated Oct. 31, 2018 (12 pages).
Office Action for Israeli Patent Application No. 249982, dated May 19, 2020 (4 pages).
Office Action for Japanese Patent Application No. 2017-522455, dated Jun. 16, 2020 (4 pages).
Olano-Martin et al., "In vitro fermentability of dextran, oligodextran and maltodextrin by human gut bacteria," Br J Nutr. 83(3):247-55 (2000).
Ouwerkerk et al., "Glycobiome: bacteria and mucus at the epithelial interface," Best Pract Res Clin Gastroenterol. 27(1):25-38 (2013).
Pfenninger et al., "Structural analysis of underivatized neutral human milk oligosaccharides in the negative ion mode by nano-electrospray MS(n) (part 2: application to isomeric mixtures)," J Am Soc Mass Spectrom. 13(11):1341-8 (2002) (8 pages).
Prisciandaro et al., "Probiotic factors partially improve parameters of 5-fluorouracil-induced intestinal mucositis in rats," Cancer Biol Ther. 11(7):671-7 (2011).
Pryde et al., "The microbiology of butyrate formation in the human colon," FEMS Microbiol Lett. 217(2):133-9 (2002).
Reichardt et al., "Phylogenetic distribution of three pathways for propionate production within the human gut microbiota," ISME J. 8(6):1323-35 (2014).
Roberfroid, "Prebiotics: the concept revisited," J Nutr. 137(3 Suppl 2):830S-7S (2007).
Rodriguez-Colinas et al., "Galacto-oligosaccharide synthesis from lactose solution or skim milk using the beta-galactosidase from Bacillus circulans," J Agric Food Chem. 60(25):6391-8 (2012).
Röytiöet al., "The fermentation of polydextrose in the large intestine and its beneficial effects," Benef Microbes. 5(3):305-13 (2014).
Saku et al., "Effects of polydextrose on serum lipids, lipoproteins, and apolipoproteins in healthy subjects," Clin Ther. 13(2):254-8 (1991) (Abstract only).
Salonen et al., "Impact of diet and individual variation on intestinal microbiota composition and fermentation products in obese men," ISME J. 8(11):2218-30 (2014).
Salvador et al., "Sugar composition of dietary fibre and short-chain fatty acid production during in vitro fermentation by human bacteria," Br J Nutr. 70(1):189-97 (1993).

(56) References Cited

OTHER PUBLICATIONS

Sanz et al., "Influence of glycosidic linkages and molecular weight on the fermentation of maltose-based oligosaccharides by human gut bacteria," J Agric Food Chem. 54(26):9779-84 (2006).
Sanz et al., "Selective fermentation of gentiobiose-derived oligosaccharides by human gut bacteria and influence of molecular weight," FEMS Microbiol Ecol. 56(3):383-8 (2006).
Schley et al., "The immune-enhancing effects of dietary fibres and prebiotics," Br J Nutr. 87 Suppl 2:S221-30 (2002).
Scott et al., "Prebiotic stiumlation of human colonic butyrate-producing bacteria and bifidobacteria, in vitro," FEMS Microbiol Ecol. 87(1):30-40 (2014).
Second Office Action for Chinese Patent Application No. 201580048065.6, dated Sep. 17, 2019 (31 pages).
Sharon, "Carbohydrates as future anti-adhesion drugs for infectious diseases," Biochim Biophys Acta. 1760(4):527-37 (2006).
Sheu et al., "Effects of xylooligosaccharides in type 2 diabetes mellitus," J Nutr Sci Vitaminol (Tokyo). 54(5):396-401 (2008).
Si et al., "Quantification of cell proliferation and alpha-toxin gene expression of Clostridium perfringens in the development of necrotic enteritis in broiler chickens," Appl Environ Microbiol. 73(21):7110-3 (2007).
Simpson et al., "Review article: dietary fibre-microbiota interactions," Aliment Pharmacol Ther. 42(2):158-79 (2015).
Smilowitz et al., "Breast milk oligosaccharides: structure-function relationships in the neonate," available in PMC Mar. 3, 2015, published in final edited form as: Annu Rev Nutr. 34:143-69 (2014) (32 pages).
Swennen et al., "Large-scale production and characterisation of wheat bran arabinoxylooligosaccharides," J Sci Food Agric 86(11):1722-31 (2006).
Synytsya et al., "Glucans from fruit bodies of cultivated mushrooms *Pleurotus ostreatus* and *Pleurotus eryngii*: Structure and potential prebiotic activity," Carbohydrate Polymers. 76(4):548-56 (2009).
Timbermont, et al., "Necrotic enteritis in broilers: an updated reviewon the pathogenesis," Avian Pathol. 40(4):341-7 (2011).
Tomlin et al., "A comparative study of the effects on colon function caused by feeding ispaghula husk and polydextrose," Aliment Pharmacol Ther. 2(6):513-9 (1988).
Tremaine et al., "Polymerization of lactose by twin-screw extrusion to produce indigestible oligosaccharides," International Dairy Journal. 36(1):74-81 (2014).
Tremaine, Andrea Jane, thesis: "Twin-Screw Extrusion of Commodity Grade Dairy Ingredients to Produce Value-Added Products," Master of Science, The Graduate School of the University of Minnesota, 2012 (152 pages).
Van den Abbeele et al., "Butyrate-producing Clostridium cluster XIVa species specifically colonize mucins in an in vitro gut model," ISME J. 7(5):949-61 (2013).
Velayudhan et al., "Characterization of Dietary Energy in Swine Feed and Feed Ingredients: A Review of Recent Research Results," Asian-Australas J Anim Sci. 28(1):1-13 (2015).
Wang et al., "Preparation and structural characterization of polymannose synthesized by phosphoric acid catalyzation under microwave irradiation," Carbohydr Polym. 121:355-61 (2015).
Wang et al., "Rapid microwave-assisted synthesis of polydextrose and identification of structure and function," Carbohydrate Polymers. 113:225-30 (2014).
Winfree et al., "Effects of Dietary Protein and Energy on Growth, Feed Conversion Efficiency and Body Composition of Tilapia aurea," J. Nutr. 111(6):1001-1012 (1981).
Wu et al., "Diminution of the gut resistome after a gut microbiota-targeted dietary intervention in obese children," Scientific Reports. 6:24030 (2016) (9 pages).
Zeuner et al., "Methods for improving enzymatic transglycosylation for synthesis of human milk oligosaccharide biomimetics," J Agric Food Chem. 62(40):9615-31 (2014).
Office Action for Canadian Patent Application No. 2,954,662, dated Feb. 11, 2022 (6 pages).
English Translation of Written Opinion for Brazilian Patent Application No. BR112017000345-7, received Dec. 1, 2021 (3 pages).
English Translation of Written Opinion for Brazilian Patent Application No. BR122022000256-0, received May 4, 2022 (4 pages).
Office Action and English Comments for Japanese Patent Application No. 2020-174799, dated Nov. 16, 2021 (8 pages).
"Basis of Sugar Chemistry." Kodansha. 11th edition: 92-117 (1995) (27 pages).
"Dictionary of Starch Science," Asakura Publishing Co., Ltd. 446-451 (2003).
Office Action for Canadian Patent Application No. 2,954,662, dated Sep. 8, 2022 (5 pages).

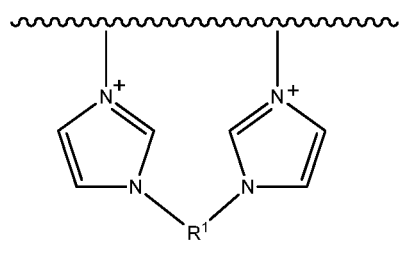
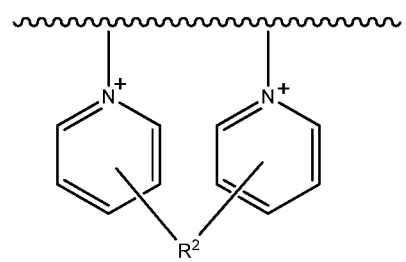
*FIG. 5A*  *FIG. 5B*
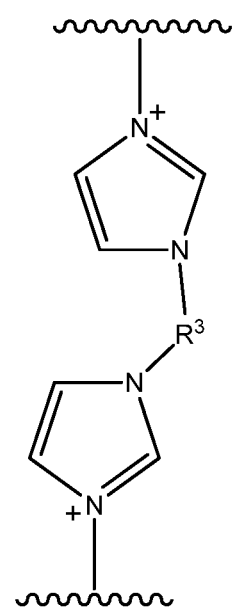
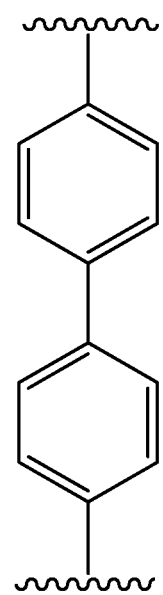
*FIG. 6A*  *FIG. 6B*

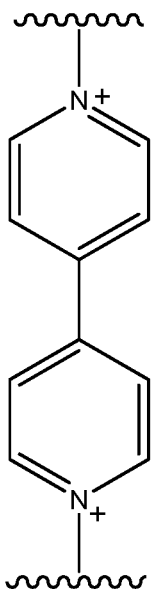
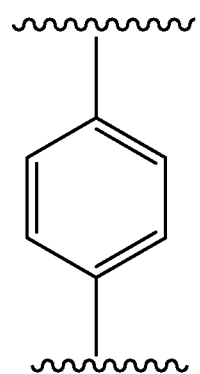
*FIG. 6C*  *FIG. 6D*
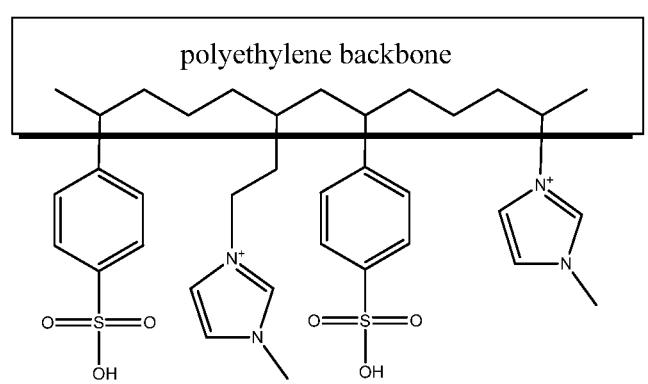
*FIG. 7*

OLIGOSACCHARIDE COMPOSITIONS AND METHODS FOR PRODUCING THEREOF

CROSS-REFERENCE TO RELATED APPLICATIONS

This application is a continuation of U.S. patent application Ser. No. 14/795,720 filed Jul. 9, 2015, now U.S. Pat. No. 10,752,705, which claims priority to U.S. Provisional Patent Application Nos. 62/022,579 filed Jul. 9, 2014, and 62/108,035 filed Jan. 26, 2015, the disclosures of which are hereby incorporated by reference in their entireties.

FIELD

The present disclosure relates generally to oligosaccharide compositions and methods of producing such oligosaccharide compositions, and more specifically to methods of using catalysts having acidic and ionic groups to polymerize sugars, such as glucose and galactose, to produce oligosaccharide compositions.

BACKGROUND

The condensation of sugars to soluble oligosaccharides is of great economic, nutritional, and therapeutic relevance. It is well known that the consumption of excess sugar by humans and animals has been linked to a variety of negative health indications, such as obesity and diabetes. It is further established that diets rich in fiber, such as indigestible oligosaccharides and polysaccharides, promote health and well being. Some dietary fibers interact favorably with the ecosystem of human and animal gut micro biota, stimulating the growth of advantageous gut bacteria, inhibiting the growth of undesirable gut bacteria, and inhibiting the ability of pathogenic bacteria to colonize the gut.

Oligosaccharides can be added to foods to empart favorable flavor, mouth feel, and consistency. Furthermore, oligosaccharides that are not digestible by humans contribute little or no caloric value to foods. There is significant commercial interest in replacing some portion of the raw sugar ingredients in foods with oligosaccharides to reduce the caloric content of those foods and improve their impact on the human microbiome. There is interest in incorporating oligosaccharide ingredients to reduce the sugar content and enhance the dietary fiber content of breakfast cereals, granola and other type of bars, yogurt, ice cream, breads, cake mixes, and nutritional shakes and supplements.

There is additional interest in incorporating oligosaccharide ingredients into animal feed to improve its nutritional quality. Oligosaccharides can be added to animal feed to improve gut health, increase weight gain, and promote feed efficiency. Furthermore, oligosaccharides that are not digestible by animals pass through the stomach and upper digestive system and can be fermented by gut micro-organisms. There is commercial interest in incorporating oligosaccharides into poultry, swine, aquaculture, and ruminant diets to improve the animal microbiome.

To achieve objectives pertaining to improved human and animal nutrition and health, oligosaccharides with a particular structure or range of structural properties are desired. At present, however, such oligosaccharides are limited to those obtained from sources such as corn meal, yeast bodies, dairy products, inulin, gums (such as guar gum or acacia gum), pectins, hemicellulose extracts, and other such agricultural and industrial food products. In other cases, oligosaccharides are produced by fermentation, roasting of starches and grains, and by polymerizing glucose in the presence of aqueous acids. The types of oligosaccharides obtained by biological production are limited in the variety of chemical structures that can be produced, the high cost of industrial fermentations, and the complex purification processes required to remove salts, buffers, and other fermentation byproducts to render the oligosaccharides suitable for human consumption.

Methods known in the art are limited in the variety of oligosaccharide structures that can be produced, and often have additional costly production steps. These can include neutralizing and/or removing aqueous acids or their salts, de-colorizing the product to a suitable level, and isolation and disposal of used catalyst that cannot be recycled.

As such, there is an ongoing need for improved methods of producing oligosaccharides on a commercially-viable scale.

BRIEF SUMMARY

The present disclosure addresses this need by providing methods of producing oligosaccharide compositions and functionalized oligosaccharide compositions using catalysts, including polymeric catalysts and solid-supported catalysts, that have acidic and ionic groups. Specifically, the catalysts described herein may be used to polymerize sugars, such as glucose, galactose, lactose, xylose, maltose, mannose, and others, to produce oligosaccharide compositions desirable for various applications, including nutrition and therapeutic applications in humans in animals. The catalyst described herein may also be used to produce functionalized oligosaccharide compositions, wherein one or more oligosaccharides of the composition are attached to one or more pendant functional groups and/or bridging functional groups. Due to the polymeric or solid-supported nature of the catalysts, the catalysts may be readily removed from the oligosaccharide composition produced.

In one aspect, provided is a method for producing an oligosaccharide composition, by: combining one or more sugars with a catalyst to produce an oligosaccharide composition.

In another aspect, provided is a method for producing an oligosaccharide composition, by: combining one or more sugars with a catalyst to produce a first product mixture, wherein the first product mixture comprises a first oligosaccharide composition and residual catalyst; isolating at least a portion of the residual catalyst from the first product mixture; and combining one or more additional sugars with the isolated residual catalyst to produce an additional product mixture, wherein the additional product mixture comprises an additional oligosaccharide composition.

In some variations, the catalytic activity of the isolated residual catalyst in the production of the additional oligosaccharide composition is at least 30% of the catalytic activity of the catalyst in the production of the first oligosaccharide composition. In other variations, the molar selectivity for the first oligosaccharide composition is at least 70%, at least 80%, at least 85%, at least 86%, at least 87%, at least 88%, at least 89%, at least 90%, at least 95%, or at least 99%. In yet other variations, the molar selectivity for the additional oligosaccharide composition is at least 70%, at least 80%, at least 85%, at least 86%, at least 87%, at least 88%, at least 89%, at least 90%, at least 95%, or at least 99%.

In another aspect, provided herein is a method for producing an oligosaccharide composition, by combining one or more sugars with a catalyst to produce the oligosaccharide composition, wherein the molar selectivity for the oligosaccharide composition is at least 70%, at least 80%, at least 85%, at least 86%, at least 87%, at least 88%, at least 89%, at least 90%, at least 95%, or at least 99%.

In some variations, the oligosaccharide composition is further combined with one or more functionalizing compounds to produce a functionalized oligosaccharide composition, wherein the one or more functionalizing compounds is independently selected from the group consisting of carboxylic acids, sugar alcohols, amino acids, amino sugars, alcohols, sulfates and phosphates.

In yet another aspect, provided herein is a method of producing a functionalized oligosaccharide composition, by:
  combining one or more sugars with a catalyst and one or more functionalizing compounds to produce the functionalized oligosaccharide composition;
    wherein the one or more functionalizing compounds is independently selected from the group consisting of carboxylic acids, sugar alcohols, amino acids, amino sugars, alcohols, sulfates and phosphates.

In yet another aspect, provided is a method of producing an oligosaccharide composition, by: combining feed sugar with a catalyst to form a reaction mixture, wherein the feed sugar comprises α-1,4 bonds, and converting at least a portion of the α-1,4 bonds in the feed sugar to one or more non-α-1,4 bonds to produce an oligosaccharide composition from at least a portion of the reaction mixture. In some embodiments, the non-α-1,4 bonds are selected from α-1,2 bonds, β-1,2 bonds, α-1,3 bonds, β-1,3 bonds, β-1,4 bonds, α-1,6 bonds, and β-1,6 bonds. In one embodiment, the non-α-1,4 bonds are selected from β-1,4 bonds, α-1,3 bonds, β-1,3 bonds, α-1,6 bonds, and β-1,6 bonds.

In yet another aspect, provided is a method of converting an α-1,4 polysaccharide to a polysaccharide having a mixture of linkages, by:
  contacting an α-1,4 polysaccharide with a catalyst,
    wherein the catalyst comprises acidic monomers and ionic monomers connected to form a polymeric backbone, or
    wherein the catalyst comprises a solid support, acidic moieties attached to the solid support, and ionic moieties attached to the solid support; and
  converting at least a portion of the α-1,4 bonds in the α-1,4 polysaccharide to one or more non-α-1,4 bonds selected from the group consisting of α-1,2 bonds, β-1,2 bonds, α-1,3 bonds, β-1,3 bonds, β-1,4 bonds, α-1,6 bonds, and β-1,6 bonds to produce a polysaccharide with a mixture of linkages from at least a portion of the α-1,4 polysaccharide. In some variations, the one or more non-α-1,4 bonds are selected from the group consisting of β-1,4 bonds, α-1,3 bonds, β-1,3 bonds, α-1,6 bonds, and β-1,6 bonds.

In some embodiments of the foregoing aspects, the catalyst is a polymeric catalyst that includes acidic monomers and ionic monomers connected to form a polymeric backbone; or the catalyst is a solid-supported catalyst that includes a solid support, acidic moieties attached to the solid support, and ionic moieties attached to the solid support.

In another aspect is an oligosaccharide, or oligosaccharide composition, obtained by the method of any one of the methods described herein. In some embodiments of the oligosaccharide composition, the monosaccharide monomers are connected by glycosidic bonds form oligomer backbones, and the oligomer backbones are optionally substituted with one or more pendant functional groups, one or more bridging functional groups, or a combination thereof.

In some of the foregoing aspects, the oligosaccharide composition includes monosaccharide monomers connected by glycosidic bonds; wherein the monosaccharide monomers are independently selected from the group consisting of C5 monosaccharides and C6 monosaccharides; each glycosidic bond is independently selected from the group consisting of α-1,4 bonds, α-1,2 bonds, β-1,2 bonds, α-1,3 bonds, β-1,3 bonds, β-1,4 bonds, α-1,6 bonds and α-1,6 bonds; at least 10% of the oligosaccharide composition has a degree of polymerization of at least three; and at least a portion of the oligosaccharide composition comprises at least two different glycosidic bonds.

In another aspect is the use of any one of the catalysts, including polymeric catalysts and the solid-supported catalysts, described herein comprising a plurality of acidic groups and a plurality of cationic groups for preparing an oligosaccharide composition from one or more sugars.

DESCRIPTION OF THE FIGURES

The following description sets forth exemplary compositions, methods, parameters and the like. It should be recognized, however, that such description is not intended as a limitation on the scope of the present disclosure but is instead provided as a description of exemplary embodiments.

FIG. 5A illustrates a portion of a polymeric catalyst with cross-linking within a given polymeric chain.

FIG. 5B illustrates a portion of a polymeric catalyst with cross-linking within a given polymeric chain.

FIG. 6A illustrates a portion of a polymeric catalyst with cross-linking between two polymeric chains.

FIG. 6B illustrates a portion of a polymeric catalyst with cross-linking between two polymeric chains.

FIG. 6C illustrates a portion of a polymeric catalyst with cross-linking between two polymeric chains.

FIG. 6D illustrates a portion of a polymeric catalyst with cross-linking between two polymeric chains.

FIG. 7 illustrates a portion of a polymeric catalyst with a polyethylene backbone.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Described herein are catalysts that can be used, in some embodiments, to produce oligosaccharide compositions, including functionalized oligosaccharide compositions, from one or more sugars, such as monosaccharides like glucose and galactose. Such catalysts may be polymeric catalysts or solid-supported catalysts.

Unlike methods using traditional catalysts known in the art to produce oligosaccharides and functionalized oligosaccharides (e.g., soluble acids, solid acid catalysts, such as zeolites, clays or ion-exchange resins, or soluble acid polymers), the methods of using catalysts described herein provide effective production of oligosaccharides, as well as ease of recycle and reuse of the catalyst. The ability to recycle and reuse the catalyst presents several advantages, including reducing the cost of oligosaccharide production. Unlike traditional catalysts, the catalysts used in the methods described herein contain both acidic and cationic monomers, which may serve to attract and/or stabilize the sugar reactants, resulting in higher yields and, in particular, improved selectivity providing oligosaccharide products to provide much lower levels of sugar degradation. The catalysts used in the methods described herein are less corrosive, more easily handled, and can be easily recovered because they naturally phase separate from aqueous products when compared to traditional catalyst. Thus, provided herein are stable, recyclable, catalysts that can efficiently produce oligosaccharide materials on a commercially-viable scale.

Figure 1:
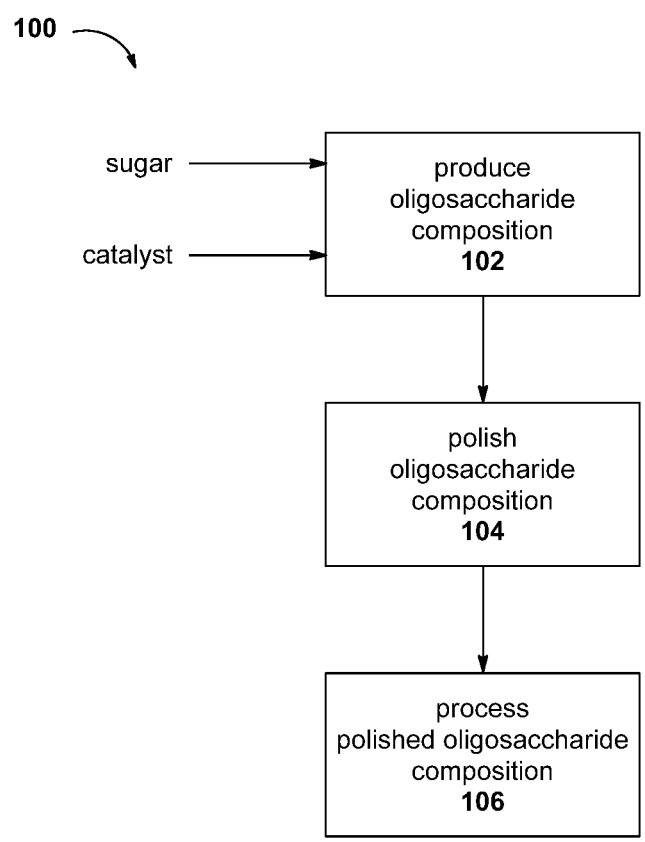
FIG. 1 depicts an exemplary process to produce an oligosaccharide composition from sugars in the presence of a catalyst.

With reference to FIG. 1, process 100 depicts an exemplary process to produce an oligosaccharide composition from sugars, and such oligosaccharide composition produced can subsequently be polished and further processed to form a food ingredient, such as an oligosaccharide syrup or powder. In step 102, one or more sugars are combined with a catalyst in a reactor. The sugars may include, for example, monosaccharides, disaccharides, and/or trisaccharides. The catalyst has both acidic and ionic groups. In some variations, the catalyst is a polymeric catalyst that includes acidic monomers and ionic monomers. In other variations, the catalyst is a solid-supported catalyst that includes acidic moieties and ionic moieties.

In step 104, the oligosaccharide composition in step 102 is polished to remove fine solids, reduce color, and reduce conductivity, and/or modify the molecular weight distribution. Any suitable methods known in the art to polish the oligosaccharide composition may be used, including, for example, the use of filtration units, carbon or other absorbents, chromatographic separators, or ion exchange columns. For example, in one variation, the oligosaccharide composition is treated with powdered activated carbon to reduce color, microfiltered to remove fine solids, and passed over a strong-acid cationic exchange resin and a weak-base anionic exchange resin to remove salts. In another variation, the oligosaccharide composition is microfiltered to remove fine solids and passed over a weak-base anionic exchange resin. In yet another variation, the oligosaccharide composition is passed through a simulated moving bed chromatographic separator to remove low molecular mass species.

In step 106, the polished oligosaccharide composition undergoes further processing to produce either an oligosaccharide syrup or powder. For example, in one variation, the polished oligosaccharide is concentrated to form a syrup. Any suitable methods known in the art to concentrate a solution may be used, such as the use of a vacuum evaporator. In another variation, the polished oligosaccharide composition is spray dried to form a powder. Any suitable methods known in the art to spray dry a solution to form a powder may be used.

In other variations, process 100 may be modified to have additional steps. For example, the oligosaccharide composition produced in step 102 may be diluted (e.g., in a dilution tank) and then undergo a carbon treatment to decolorize the oligosaccharide composition prior to polishing in step 104. In other variations, the oligosaccharide composition produced in step 102 may undergo further processing in a simulated moving bed (SMB) separation step to reduce digestible carbohydrate content.

In other variations, process 100 may be modified to have fewer steps. For example, in one variation, step 106 to produce the oligosaccharide syrup or powder may be omitted, and the polished oligosaccharide composition of step 104 may be used directly as an ingredient to produce a food product.

The catalysts described herein may also be used to produce functionalized oligosaccharide compositions, wherein at least a portion of the composition is attached to one or more pendant functional groups and/or bridging functional groups. Such functionalized oligosaccharide compositions may be produced in one step by combining sugars and functionalizing compounds in the presence of a catalyst; or may be produced in two steps by combining sugars and a catalyst to produce an oligosaccharide composition, then combining the oligosaccharide composition with functionalizing compounds in the presence of a catalyst. Thus, described herein are stable, recyclable, catalysts that can efficiently produce functionalized oligosaccharide materials on a commercially-viable scale.

Figure 14:
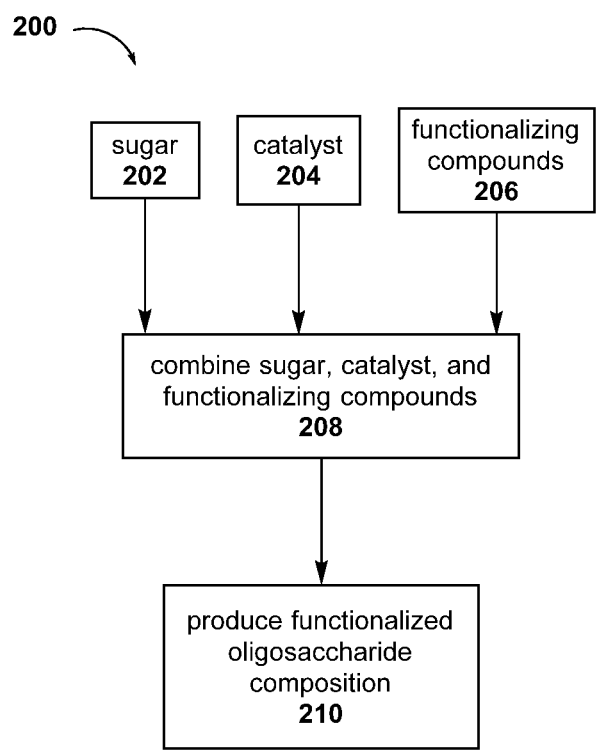
FIG. 14 depicts an exemplary process to produce a functionalized oligosaccharide composition by combining sugars and functionalizing compounds in the presence of a catalyst.

With reference to FIG. 14, process 200 depicts an exemplary process to produce a functionalized oligosaccharide composition from sugars and functionalizing compounds. In step 208, one or more sugars 202 are combined with a catalyst 204 and one or more functionalizing compounds 206 in a reactor. The sugars may include, for example, monosaccharides, disaccharides, and/or trisaccharides. The catalyst has both acidic and ionic groups. In some variations, the catalyst is a polymeric catalyst that includes acidic monomers and ionic monomers. In other variations, the catalyst is a solid-supported catalyst that includes acidic moieties and ionic moieties. The functionalizing compounds may include, for example, sugar alcohols, carboxylic acids, amino acids, amino sugars, alcohols and/or sulfates. The functionalized oligosaccharide composition is produced in step 210. It should be understood that process 200 may be modified to have additional steps. For example, in some variations, the functionalized oligosaccharide composition produced in step 210 is polished, concentrated, powdered, and/or decolorized.

Figure 15:
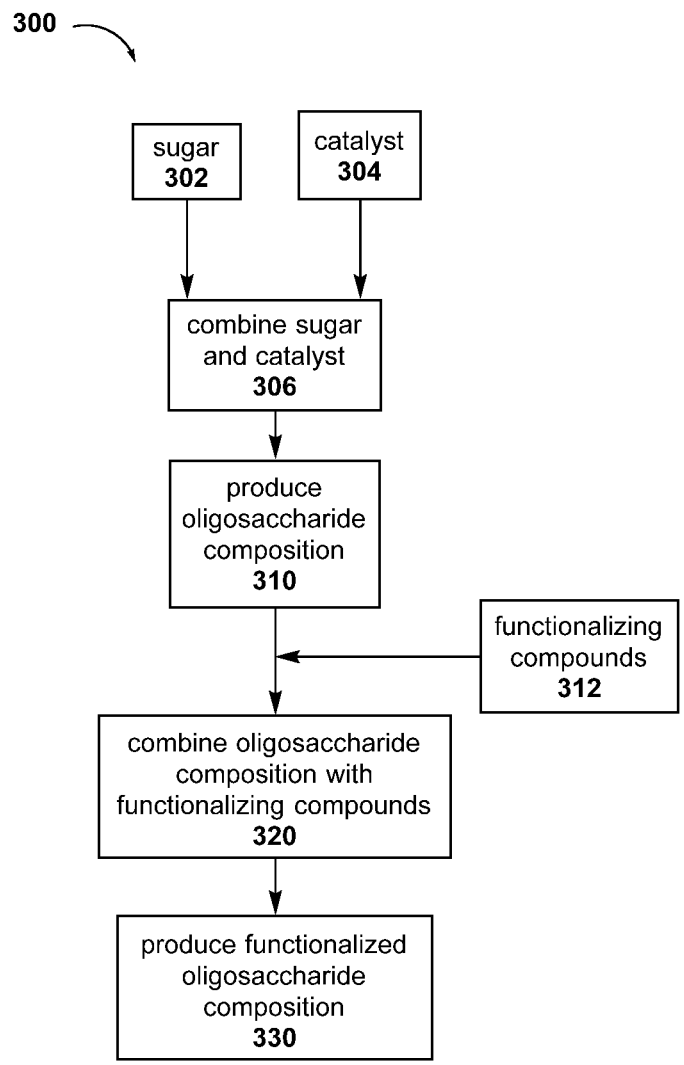
FIG. 15 depicts an exemplary process to produce a functionalized oligosaccharide composition by combining an oligosaccharide composition and functionalizing compounds in the presence of a catalyst.

With reference to FIG. 15, process 300 depicts an exemplary process to produce a functionalized oligosaccharide composition from an oligosaccharide composition and functionalizing compounds. In step 306, one or more sugars 302 are combined with a catalyst 304 in a reactor. The sugars may include, for example, monosaccharides, disaccharides, and/or trisaccharides. The catalyst has both acidic and ionic groups. In some variations, the catalyst is a polymeric catalyst that includes acidic monomers and ionic monomers. In other variations, the catalyst is a solid-supported catalyst that includes acidic moieties and ionic moieties. An oligosaccharide composition is produced in step 310. Functionalizing compounds 312 are combined with the oligosaccharide composition in step 320. The functionalizing compounds may include, for example, sugar alcohols, carboxylic acids, amino acids, amino sugars, alcohols and/or sulfates. The functionalized oligosaccharide composition is produced in step 330. It should be understood that process 300 may be modified to have additional steps. For example, in some variations, the functionalized oligosaccharide composition is polished, concentrated, powdered, and/or decolorized. For example, in some variations, the oligosaccharide composition produced in step 310 is polished, concentrated, powdered, and/or decolorized before being combined with the functionalizing compounds in step 320. In other variations, the functionalized composition produced in step 330 is polished, concentrated, powdered, and/or decolorized.

Each of the steps in exemplary processes 100, 200, and 300, the reactants and processing conditions in each step, as well as the compositions produced in each step are described in further detail below.

Definitions

As used herein, "alkyl" includes saturated straight-chain or branched-chain monovalent hydrocarbon radicals, and combinations of these, which contain only C and H when unsubstituted. Examples include methyl, ethyl, propyl, butyl and pentyl. When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl, and iso-propyl. The total number of carbon atoms in each such group is sometimes described herein. For example, when the group can contain up to ten carbon atoms it can be represented as 1-10C or as C1-C10 or C1-10. In some embodiments, alkyl may be substituted. Suitable alkyl substituents may include, for example, hydroxy, amino, and halo.

As used herein, "alkylene" refers to the same residues as alkyl, but having bivalency. Examples of alkylene include methylene ($-CH_2-$), ethylene ($-CH_2CH_2-$), propylene ($-CH_2CH_2CH_2-$), butylene ($-CH_2CH_2CH_2CH_2-$).

As used herein, "alkylene carbamate" refers to an alkylene moiety, in which one or more of the methylene units of the alkylene moiety has been replaced with a carbamate moiety ($-C(O)-O-NR-$ or $-O-C(O)-NR-$, where R can be, for example, alkyl or aryl). In some embodiments, alkylene carbamate may be substituted. Suitable alkylene carbamate substituents may include, for example, hydroxyl, amino, and halo.

As used herein, "alkylene ester" refers to an alkylene moiety, in which one or more of the methylene units of the alkylene moiety has been replaced with an ester moiety ($-C(O)-O-$ or $-O-C(O)-$). In some embodiments, alkylene ester may be substituted, further bearing one or more substituents. Suitable alkylene ester substituents may include, for example, hydroxyl, amino, and halo.

As used herein, "alkylene ether" refers to an alkylene moiety, in which one or more of the methylene units of the alkylene moiety has been replaced with an ether moiety ($-C(O)-$). In some embodiments, alkylene ether may be substituted, further bearing one or more substituents. Suitable alkylene ether substituents may include, for example, hydroxyl, amino, and halo.

As used herein, "alkenyl" refers to an unsaturated hydrocarbon group having at least one site of olefinic unsaturation (i.e., having at least one moiety of the formula C=C). Alkenyl contains only C and H when unsubstituted. When an alkenyl residue having a specific number of carbons is named, all geometric isomers having that number of carbons are intended to be encompassed and described; thus, for example, "butenyl" is meant to include n-butenyl, sec-butenyl, and iso-butenyl. Examples of alkenyl may include $-CH=CH_2$, $-CH_2-CH=CH_2$ and $-CH_2-CH=CH-CH=CH_2$. In some embodiments, alkenyl may be substituted. Suitable alkenyl substituents may include, for example, hydroxy, amino, and halo.

As used herein, "alkenylene" refers to the same residues as alkenyl, but having bivalency. Examples of alkenylene include ethylene ($-CH=CH-$), propylene ($-CH_2-CH=CH-$) and butylene ($-CH_2-CH=CH-CH_2-$).

As used herein, "alkynyl" refers to "an unsaturated hydrocarbon group having at least one site of acetylenic unsaturation (i.e., having at least one moiety of the formula C≡C. Alkynyl contains only C and H when unsubstituted. When an alkynyl residue having a specific number of carbons is named, all geometric isomers having that number of carbons are intended to be encompassed and described; thus, for example, "pentynyl" is meant to include n-pentynyl, sec-pentynyl, iso-pentynyl, and tert-pentynyl. Examples of alkynyl may include $-C≡CH$ or $-C≡C-CH_3$. In some embodiments, alkynyl may be substituted. Suitable alkynyl substituents may include, for example, hydroxy, amino, and halo.

As used herein, "aryl" refers to an unsaturated aromatic carbocyclic group having a single ring (e.g., phenyl) or multiple condensed rings (e.g., naphthyl or anthryl), which condensed rings may or may not be aromatic. Aryl contains only C and H when unsubstituted. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. Examples of aryl may include phenyl, phenol, and benzyl. In some embodiments, aryl may be substituted. Suitable aryl substituents may include, for example, alkyl, alkenyl, alkynyl, hydroxy, amino, and halo.

As used herein, "arylene" refers to the same residues as aryl, but having bivalency.

As used herein, "cycloalkyl" includes a carbocyclic, non-aromatic group that is connected via a ring carbon atom, which contains only C and H when unsubstituted. The cycloalkyl can consist of one ring, such as cyclohexyl, or multiple rings, such as adamantyl. A cycloalkyl with more than one ring may be fused, spiro or bridged, or combinations thereof. Examples of cycloalkyl groups include cyclopropyl, cyclobutyl, cyclopentyl, cyclohexyl, adamantyl, and decahydronaphthalenyl. In some embodiments, cycloalkyl may be substituted. Suitable cycloalkyl substituents may include, for example, alkyl, hydroxy, amino, and halo.

As used herein, "cycloalkylene" refers to the same residues as cycloalkyl, but having bivalency.

As used herein, "heteroaryl" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, pyridinyl, imidazolyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. Examples of heteroaryls may include pyridyl, pyridinyl, imidazolyl, and thiazolyl. In some embodiments, heteroaryl may be substituted. Suitable heteroaryl substituents may include, for example, alkyl, alkenyl, alkynyl, hydroxy, amino, and halo.

As used herein, "heteroarylene" refers to the same residues as heteroaryl, but having bivalency.

It should be understood that the alkyl, cycloalkyl, alkenyl, alkynyl, aryl, heteroaryl, ether, ester, and carbamate may be substituted, where the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described.

Methods of Producing Oligosaccharide Compositions

In one aspect are methods for the production of oligosaccharide compositions, including functionalized oligosaccharide compositions, from one or more sugars using the catalysts, including polymeric catalysts and solid-supported catalysts, described herein. The one or more sugars may be any suitable sugar, such as C5 or C6 monosaccharides, as described in detail infra. As used herein, "oligosaccharide" refers to a compound containing two or more monosaccharide units linked by glycosidic bonds.

In one aspect is provided a method for producing one or more oligosaccharides, comprising combining one or more sugars with a polymeric catalyst described herein having a plurality of acidic monomers and a plurality of cationic monomers, to form a reaction mixture that produces one or more oligosaccharides.

In another aspect is provided a method for producing one or more oligosaccharides, comprising combining one or more sugars with a solid-supported catalyst described herein having a solid support, a plurality of acidic moieties attached to the solid support, and a plurality of ionic moieties attached to the solid support, to form a reaction mixture that produces one or more oligosaccharides.

Sugar Reactants

The one or more sugars of the methods described herein may comprise any suitable sugar that is capable of producing the one or more corresponding oligosaccharides. In some embodiments, the one or more sugars are selected from monosaccharides, disaccharides, trisaccharides, and short-chain oligosaccharides, or any mixtures thereof. In certain embodiments, the one or more sugars is one or more monosaccharides, disaccharides, and/or trisaccharides. In some embodiments, the one or more sugars is one or more monosaccharides, such as one or more C5 or C6 monosaccharides. Exemplary monosaccharides include glucose, galactose, mannose, fructose, xylose, xylulose, arabinose, and the like. In some embodiments, the one or more sugars is one or more C5 monosaccharides. In other embodiments, the one or more sugars is or one or more C6 monosaccharides. In yet other embodiments, the one or more sugars is one or more C3 monosaccharides. In some embodiments, the one or more sugars are selected from glucose, galactose, ribose, allose, glyceraldehyde, and mannose. In other embodiments, the one or more sugars is selected from fructose, xylose, and arabinose. In some embodiments, the one or more sugars include one or more disaccharides. Exemplary disaccharides include lactose, maltose, sucrose, cellobiose, and the like. In some embodiments, the one or more sugars include one or more trisaccharides, such as raffinose. In certain embodiments, the one or more sugars include one or more deoxy sugars, such as fucose and rhamnose. In some embodiments, the one or more sugars comprise a mixture of short-chain oligosaccharides, such as malto-dextrins. In certain embodiments, the one or more sugars are corn syrup obtained from the partial hydrolysis of corn starch. In a particular embodiment, the one or more sugars is corn syrup with a dextrose equivalent (DE) below 50 (e.g., 10 DE corn syrup, 18 DE corn syrup, 25 DE corn syrup, or 30 DE corn syrup).

In some embodiments, the one or more sugars are selected from glucose, galactose, xylose, arabinose, fructose, mannose, fucose, lactose, maltose, ribose, allose, glyceraldehyde, and rhamnose.

In some embodiments, the method comprises combining two or more sugars with a polymeric catalyst to produce the one or more oligosaccharides. In some embodiments, the two or more sugars are selected from glucose, galactose, mannose and lactose (e.g., glucose and galactose).

In other embodiments, the method comprises combining a mixture of sugars (e.g., monosaccharides, disaccharides, trisaccharides, etc., and/or other short oligosaccharides) with a polymeric catalyst to product the one or more oligosaccharides. In a particular embodiment, the method comprises combining corn glucose syrup with a polymeric catalyst to produce the one or more oligosaccharides.

In other embodiments, the method comprises combing a polysaccharide with a polymeric catalyst to produce the one or more oligosaccharides. In some embodiments, the polysaccharide is selected from starch, guar gum, xanthan gum and acacia gum.

Functionalized Oligosaccharide Compositions

In some variations, the oligosaccharide compositions described herein are functionalized oligosaccharide compositions. Functionalized oligosaccharide compositions may be produced by combining one or more sugars with one or more functionalizing compounds in the presence of a catalyst; by combining an oligosaccharide composition with one or more functionalizing compounds in the presence of a catalyst; or by combining one or more sugars, an oligosaccharide composition, and one or more functionalizing compounds in the presence of a catalyst. Thus, in one aspect, provided herein are methods for the production of functionalized oligosaccharides from a mixture of one or more sugars, an oligosaccharide composition, or a combination thereof, and one or more functionalizing compounds using the catalysts, including polymeric catalysts and solid-supported catalysts, described herein. The one or more sugars may be any suitable sugar, such as C5, C6, or C3 monosaccharides, as described herein. As used herein, "functionalized oligosaccharide" refers to a compound containing two or more monosaccharide units linked by glycosidic bonds in which one or more hydroxyl groups in the monosaccharide units are independently replaced by a functionalizing compound, or comprise a linkage to a functionalizing compound. The functionalizing compound may be a compound that can attach to the oligosaccharide through an ether, ester, oxygen-sulfur, amine, or oxygen-phosphorous bond, and which does not contain a monosaccharide unit.

Functionalizing Compounds

In certain variations, the functionalizing compound comprises one or more functional groups independently selected from amine, hydroxyl, carboxylic acid, sulfur trioxide, sulfate, and phosphate. In some variations, one or more functionalizing compounds are independently selected from the group consisting of amines, alcohols, carboxylic acids, sulfates, phosphates, or sulfur oxides.

In some variations, the functionalizing compound has one or more hydroxyl groups. In some variations, the functionalizing compound with one or more hydroxyl groups is an alcohol. Such alcohols may include, for example, alkanols and sugar alcohols.

In certain variations, the functionalizing compound is an alkanol with one hydroxyl group. For example, in some variations, the functionalizing compound is selected from ethanol, propanol, butanol, pentanol, and hexanol. In other variations, the functionalizing compound has two or more hydroxyl groups. For example, in some variations, the functionalizing compound is selected from propanediol, butanediol, and pentanediol.

In other embodiments, the method comprises combining a mixture of sugars and sugar alcohols with a polymeric catalyst to produce the functionalized oligosaccharide composition. In particular embodiments, the method comprises combining one or more sugars and one or more alcohols selected from the group consisting of glucitol, sorbitol, xylitol, lacitol, and arabinatol, with a polymeric catalyst to produce the functionalized oligosaccharide composition. In certain variations, the functionalizing compound is a sugar alcohol. For example, in some variations the functionalizing compound is sorbitol, xylitol, arabitol, glycerol, erythritol, mannitol, galacitol, fucitol, iditol, inositol, volemitol, or lacitol, or any combinations thereof.

In certain variations, wherein the functionalizing compound comprises a hydroxyl group, the functionalizing compound may become attached to the monosaccharide unit through an ether bond. The oxygen of the ether bond may be derived from the monosaccharide unit, or from the functionalizing compound.

In other variations, the functionalizing compound comprises one or more carboxylic acid functional groups. For example, in some variations, the functionalizing compound is selected from lactic acid, acetic acid, citric acid, pyruvic acid, succinic acid, glutamic acid, itaconic acid, malic acid, maleic acid, propionic acid, butanoic acid, pentanoic acid, hexanoic acid, adipic acid, isobutyric acid, formic acid, levulinic acid, valeric acid, and isovaleric acid. In other variations, the functionalizing compound is a sugar acid. For example, in one embodiment, the functionalizing compound is gluconic acid. In certain variations, wherein the functionalizing compound comprises a carboxylic acid group, the functionalizing compound may become attached to the monosaccharide unit through an ester bond. The non-carbonyl oxygen of the ester bond may be derived from the monosaccharide unit, or from the functionalizing compound.

In still other variations, the functionalizing compound comprises one or more amine groups. For example, in some variations, the functionalizing compound is an amino acid, while in other variations the functionalizing compound is an amino sugar. In one variation, the functionalizing compound is selected from glutamic acid, aspartic acid, glucosamine and galactosamine. In certain variations, wherein the functionalizing compound comprises an amine group, the functionalizing compound may become attached to the monosaccharide unit through an amine bond.

In yet other variations, the functionalizing compound comprises a sulfur trioxide group or a sulfate group. For example, in one variation, the functionalizing compound is dimethylformamide sulfur trioxide complex. In another variation, the functionalizing compound is sulfate. In one embodiment, the sulfate is produced in situ, from, for example, sulfur trioxide. In certain variations wherein the functionalizing compound comprises a sulfur trioxide or sulfate group, the functionalizing compound may become attached to the monosaccharide unit through an oxygen-sulfur bond.

In still other variations, the functionalizing compound comprises a phosphate group. In certain variations wherein the functionalizing compound comprises a phosphate group, the functionalizing compound may become attached to the monosaccharide unit through an oxygen-phosphorous bond.

It should be understood that the functionalizing compounds described herein may contain a combination of functional groups. For example, the functionalizing compound may comprise one or more hydroxyl groups and one or more amine groups (for example, amino sugars). In other embodiments, the functionalizing compound may comprise one or more hydroxyl groups and one or more carboxylic acid groups (for example, sugar acids). In yet other embodiments, the functionalizing compound may comprise one or more amine groups and one or more carboxylic acid groups (for example, amino acids). In still other embodiments, the functionalizing compound comprises one or more additional functional groups, such as esters, amides, and/or ethers. For example, in certain embodiments, the functionalizing compound is a sialic acid (for example, N-acetylneuraminic acid, 2-keto-3-deoxynonic acid, and other N- or O-substituted derivatives of neuraminic acid).

It should further be understood that a functionalizing compound may belong to one or more of the groups described above. For example, a glutamic acid is both an amine and a carboxylic acid, and a gluconic acid is both a carboxylic acid and an alcohol.

In some variations, the functionalizing compound forms a pendant group on the oligosaccharide. In other variations, the functionalizing compound forms a bridging group between an oligomer backbone and a second oligomer backbone; wherein each oligomer backbone independently comprises two or more monosaccharide units linked by glycosidic bonds; and the functionalizing compound is attached to both backbones. In other variations, the functionalizing compound forms a bridging group between an oligomer backbone and a monosaccharide; wherein the oligomer backbone comprises two or more monosaccharide units linked by glycosidic bonds; and the functionalizing compound is attached to the backbone and the monosaccharide.

Pendant Functional Groups

In certain variations, combining one or more sugars and one or more functionalizing compounds in the presence of a catalyst, including polymeric catalysts and solid-supported catalysts described herein, produces a functionalized oligosaccharide composition. In certain embodiments, a functionalizing compound is attached to a monosaccharide subunit as a pendant functional group.

A pendant functional group may include a functionalization compound attached to one monosaccharide unit, and not attached to any other monosaccharide units. In some variations, the pendant functional group is a single functionalization compound attached to one monosaccharide unit. For example, in one variation, the functionalizing compound is acetic acid, and the pendant functional group is acetate bonded to a monosaccharide through an ester linkage. In another variation, the functionalizing compound in propionic acid, and the pendant functional group is propionate bonded to a monosaccharide through an ester linkage. In yet another variation, the functionalizing compound is butanoic acid, and the pendant functional group is butanoate bonded to a monosaccharide through an ester linkage. In other variations, a pendant functional group is formed from linking multiple functionalization compounds together. For example, in some embodiments, the functionalization compound is glutamic acid, and the pendant functional group is a peptide chain of two, three, four, five, six, seven, or eight glutamic acid residues, wherein the chain is attached to a monosaccharide through an ester linkage. In other embodiments, the peptide chain is attached to the monosaccharide through an amine linkage.

The pendant functional group may comprise a single linkage to the monosaccharide, or multiple linkages to the monosaccharide. For example, in one embodiment, the functionalization compound is ethanediol, and the pendant functional group is ethyl connected to a monosaccharide through two ether linkages.

Figure 16:
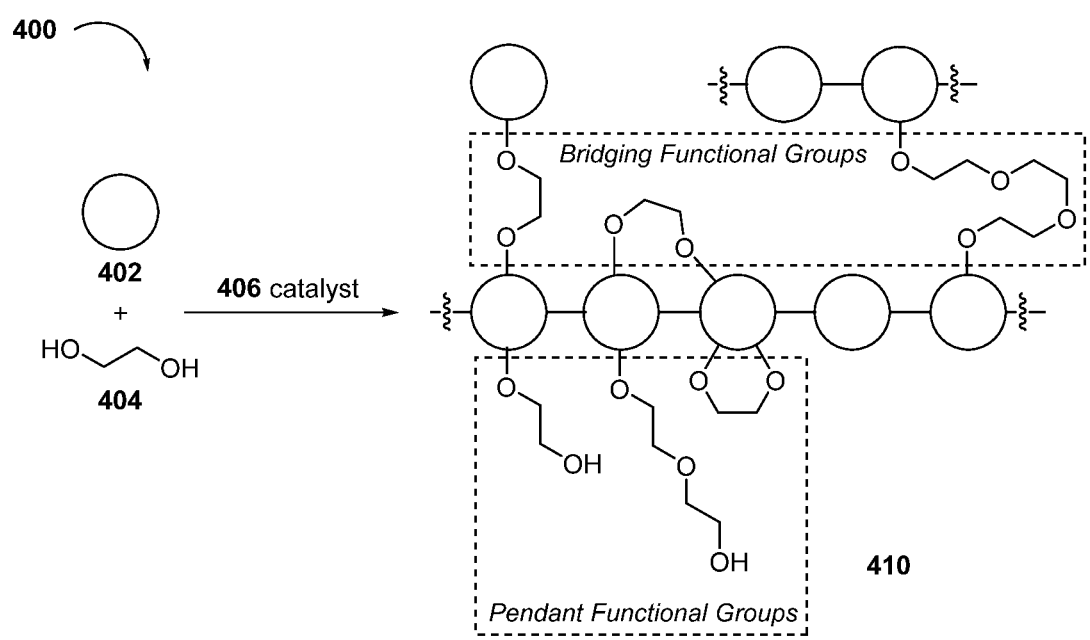
FIG. 16 depicts an exemplary process to produce a functionalized oligosaccharide composition, wherein a portion of an oligosaccharide comprising pendant functional groups and bridging functional groups is shown.

Referring to FIG. 16, process 400 depicts an exemplary scheme to produce an oligosaccharide containing different pendant functional groups. In process 400, monosaccharides 402 (represented symbolically) are combined with the functionalizing compound ethane diol 404 in the presence of catalyst 406 to produce an oligosaccharide. Portion 410 of the oligosaccharide is shown in FIG. 16, wherein the monosaccharides linked through glycosidic bonds are represented symbolically by circles and lines. The oligosaccharide comprises three different pendant functional groups, as indicated by the labeled section. These pendant functional groups include a single functionalization compound attached to a single monosaccharide unit through one linkage; two functionalization compounds linked together to form a pendant functional group, wherein the pendant functional group is linked to a single monosaccharide unit through one linkage; and a single functionalization compound attached to a single monosaccharide unit through two linkages. It should be understood that while the functionalization compound used in process 400 is ethanediol, any of the functionalization compounds or combinations thereof described herein may be used. It should be further understood that while a plurality of pendant functional groups is present in portion 410 of the oligosaccharide, the number and type of pendant functional groups may vary in other variations of process 400.

It should be understood that any functionalization compounds may form a pendant functional group. In some variations, the functionalized oligosaccharide composition contains one or more pendant groups selected from the group consisting of glucosamine, galactosamine, citric acid, succinic acid, glutamic acid, aspartic acid, glucuronic acid, butyric acid, itaconic acid, malic acid, maleic acid, propionic acid, butanoic acid, pentanoic acid, hexanoic acid, adipic acid, isobutyric acid, formic acid, levulinic acid, valeric acid, isovaleric acid, sorbitol, xylitol, arabitol, glycerol, erythritol, mannitol, galacitol, fucitol, iditol, inositol, volemitol, lacitol, ethanol, propanol, butanol, pentanol, hexanol, propanediol, butanediol, pentanediol, sulfate and phosphate.

Bridging Functional Groups

In certain variations, combining one or more sugars and one or more functionalizing compounds in the presence of a catalyst, including polymeric catalysts and solid-supported catalysts described herein, produces a functionalized oligosaccharide comprising a bridging functional group.

Bridging functional groups may include a functionalization compound attached to one monosaccharide unit and attached to at least one additional monosaccharide unit. The monosaccharide units may independently be monosaccharide units of the same oligosaccharide backbone, monosaccharide units of separate oligosaccharide backbones, or monosaccharide sugars that are not bonded to any additional monosaccharides. In some variations, the bridging functional compound is attached to one additional monosaccharide unit. In other variations, the bridging functional compound is attached to two or more additional monosaccharide units. For example, in some embodiments, the bridging functional compound is attached to two, three, four, five, six, seven, or eight additional monosaccharide units. In some variations, the bridging functional group is formed by linking a single functionalization compound to two monosaccharide units. For example, in one embodiment, the functionalization compound is glutamic acid, and the bridging functional group is a glutamate residue attached to one monosaccharide unit through an ester bond, and an additional monosaccharide unit through an amine bond. In other embodiments, the bridging functionalization group is formed by linking multiple functionalization compound molecules to each other. For example, in one embodiment, the functionalization compound is ethanediol, and the bridging functional group is a linear oligomer of four ethanediol molecules attached to each other through ether bonds, the first ethanediol molecule in the oligomer is attached to one monosaccharide unit through an ether bond, and the fourth ethanediol molecule in the oligomer is attached to an additional monosaccharide unit through an ether bond.

Referring again to FIG. 16, portion 410 of the oligosaccharide produced according to process 400 comprises three different bridging functional groups, as indicated by the labeled section. These bridging functional groups include a single functionalization compound attached to a monosaccharide unit of an oligosaccharide through one linkage, and attached to a monosaccharide sugar through an additional linkage; a single functionalization compound attached to two different monosaccharide units of the same oligosaccharide backbone; and two functionalization compounds linked together to form a bridging functional group, wherein the bridging functional group is linked to one monosaccharide unit through one linkage and to an additional monosaccharide unit through a second linkage. It should be understood that while the functionalization compound used in process 400 is ethanediol, any of the functionalization compounds or combinations thereof described herein may be used. It should be further understood that while a plurality of bridging functional groups is present in portion 410 of the oligosaccharide, the number and type of bridging functional groups may vary in other variations of process 400.

It should be understood that any functionalization compounds with two or more functional groups able to form bonds with a monosaccharide may form a bridging functional group. For example, bridging functional groups may be selected from polycarboxylic acids (such as succinic acid, itaconic acid, malic acid, maleic acid, and adipic acid), polyols (such as sorbitol, xylitol, arabitol, glycerol, erythritol, mannitol, galacitol, fucitol, iditol, inositol, volemitol, and lacitol), and amino acids (such as glutamic acid). In some variations, the functionalized oligosaccharide composition comprises one or more bridging groups selected from the group consisting of glucosamine, galactosamine, lactic acid, acetic acid, citric acid, pyruvic acid, succinic acid, glutamic acid, aspartic acid, glucuronic acid, itaconic acid, malic acid, maleic acid, adipic acid, sorbitol, xylitol, arabitol, glycerol, erythritol, mannitol, galacitol, fucitol, iditol, inositol, volemitol, lacitol, propanediol, butanediol, pentanediol, sulfate and phosphate.

Functionalized oligosaccharide compositions comprising a mixture of pendant functional groups and bridging functional groups may also be produced using the methods described herein. For example, in certain embodiments, one or more sugars are combined with a polyol in the presence of a catalyst, and a functionalized oligosaccharide composition is produced wherein at least a portion of the composition comprises pendant polyol functional groups attached to oligosaccharides through ether linkages, and at least a portion comprises bridging polyol functional groups wherein each group is attached to a first oligosaccharide through a first ether linkage and a second oligosaccharide through a second ether linkage.

It should further be understood that the one or more functionalization compounds combined with the sugars, oligosaccharide composition, or combination thereof may form bonds with other functionalization compounds, such that the functionalized oligosaccharide composition comprises monosaccharide units bonded to a first functionalization compound, wherein the first functionalization compound is bonded to a second functionalization compound.

Catalysts

The catalysts used in the methods described herein include polymeric catalysts and solid-supported catalysts.

Figure 2A:
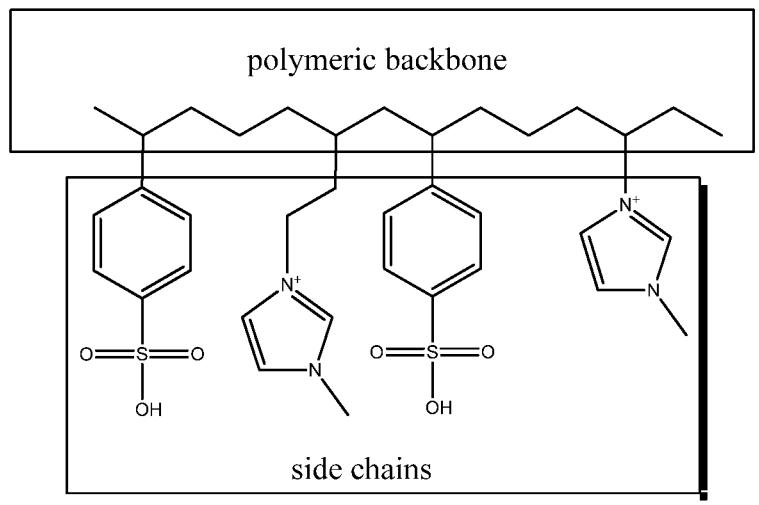
FIG. 2A illustrates a portion of a catalyst with a polymeric backbone and side chains.
Figure 2B:
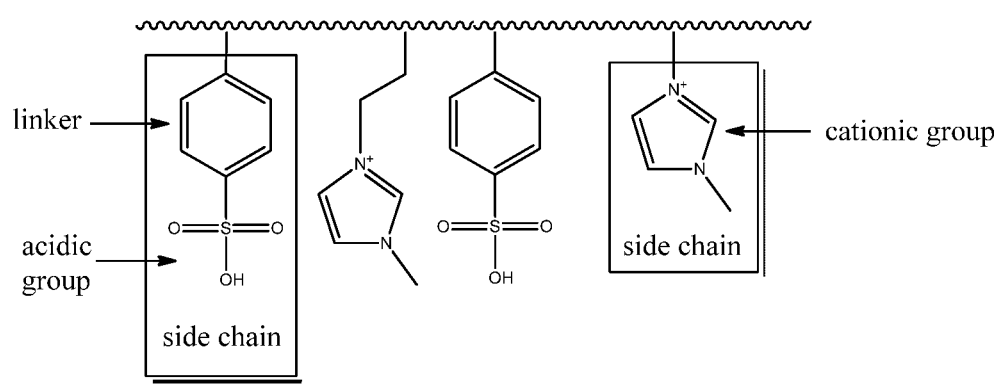
FIG. 2B illustrates a portion of an exemplary catalyst, in which a side chain with the acidic group is connected to the polymeric backbone by a linker and in which a side chain with the cationic group is connected directly to the polymeric backbone.

In some embodiments, the catalyst is a polymer made up of acidic monomers and ionic monomers (which are also referred to herein as "ionomers") connected to form a polymeric backbone. Each acidic monomer includes at least one Bronsted-Lowry acid, and each ionic monomer includes at least one nitrogen-containing cationic group, at least one phosphorous-containing cationic group, or any combination thereof. In certain embodiments of the polymeric catalyst, at least some of the acidic and ionic monomers may independently include a linker connecting the Bronsted-Lowry acid or the cationic group (as applicable) to a portion of the polymeric backbone. For the acidic monomers, the Bronsted-Lowry acid and the linker together form a side chain. Similarly, for the ionic monomers, the cationic group and the linker together form a side chain. With reference to the portion of the polymeric catalyst depicted in FIGS. 2A and 2B, the side chains are pendant from the polymeric backbone.

Figure 3:
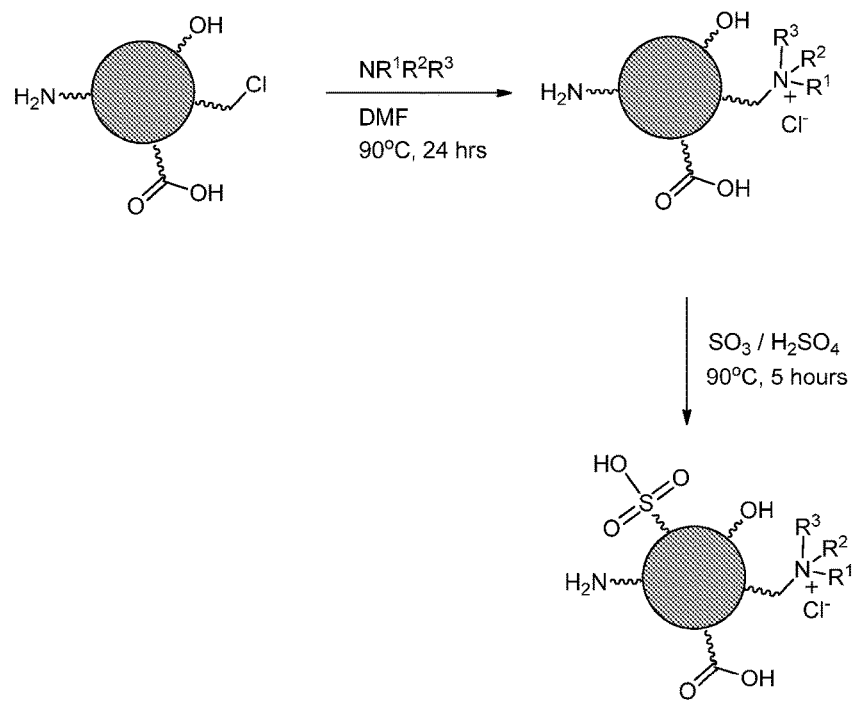
FIG. 3 depicts a reaction scheme to prepare a dual-functionalized catalyst from an activated carbon support, in which the catalyst has both acidic and ionic moieties.

In another aspect, the catalyst is solid-supported, having acidic moieties and ionic moieties each attached to a solid support. Each acidic moiety independently includes at least one Bronsted-Lowry acid, and each ionic moiety includes at least one nitrogen-containing cationic group, at least one phosphorous-containing cationic group, or any combination thereof. In certain embodiments of the solid-supported catalyst, at least some of the acidic and ionic moieties may independently include a linker connecting the Bronsted-Lowry acid or the cationic group (as applicable) to the solid support. With reference to FIG. 3, the produced catalyst is a solid-supported catalyst with acidic and ionic moieties.

Acidic Monomers and Moieties

The polymeric catalysts include a plurality of acidic monomers, whereas the solid-supported catalysts include a plurality of acidic moieties attached to a solid support.

In some embodiments, a plurality of acidic monomers (e.g., of a polymeric catalyst) or a plurality of acidic moieties (e.g., of a solid-supported catalyst) has at least one Bronsted-Lowry acid. In certain embodiments, a plurality of acidic monomers (e.g., of a polymeric catalyst) or a plurality of acidic moieties (e.g., of a solid-supported catalyst) has one Bronsted-Lowry acid or two Bronsted-Lowry acids. In certain embodiments, a plurality of the acidic monomers (e.g., of a polymeric catalyst) or a plurality of the acidic moieties (e.g., of a solid-supported catalyst) has one Bronsted-Lowry acid, while others have two Bronsted-Lowry acids.

In some embodiments, each Bronsted-Lowry acids is independently selected from sulfonic acid, phosphonic acid, acetic acid, isophthalic acid, and boronic acid. In certain embodiments, each Bronsted-Lowry acids is independently sulfonic acid or phosphonic acid. In one embodiment, each Bronsted-Lowry acid is sulfonic acid. It should be understood that the Bronsted-Lowry acids in an acidic monomer (e.g., of a polymeric catalyst) or an acidic moiety (e.g., of a solid-supported catalyst) may be the same at each occurrence or different at one or more occurrences.

In some embodiments, one or more of the acidic monomers of a polymeric catalyst are directly connected to the polymeric backbone, or one or more of the acidic moieties of a solid-supported catalyst are directly connected to the solid support. In other embodiments, one or more of the acidic monomers (e.g., of a polymeric catalyst) or one or more acidic moieties (e.g., of a solid-supported catalyst) each independently further includes a linker connecting the Bronsted-Lowry acid to the polymeric backbone or the solid support (as the case may be). In certain embodiments, some of the Bronsted-Lowry acids are directly connected to the polymeric backbone or the solid support (as the case may be), while other the Bronsted-Lowry acids are connected to the polymeric backbone or the solid support (as the case may be) by a linker.

In those embodiments where the Bronsted-Lowry acid is connected to the polymeric backbone or the solid support (as the case may be) by a linker, each linker is independently selected from unsubstituted or substituted alkyl linker, unsubstituted or substituted cycloalkyl linker, unsubstituted or substituted alkenyl linker, unsubstituted or substituted aryl linker, and unsubstituted or substituted heteroaryl linker. In certain embodiments, the linker is unsubstituted or substituted aryl linker, or unsubstituted or substituted heteroaryl linker. In certain embodiments, the linker is unsubstituted or substituted aryl linker. In one embodiment, the linker is a phenyl linker. In another embodiment, the linker is a hydroxyl-substituted phenyl linker.

In other embodiments, each linker in an acidic monomer (e.g., of a polymeric catalyst) or an acidic moiety (e.g., of a solid-supported catalyst) is independently selected from:
  unsubstituted alkyl linker;

alkyl linker substituted 1 to 5 substituents independently selected from oxo, hydroxy, halo, amino;

unsubstituted cycloalkyl linker;

cycloalkyl linker substituted 1 to 5 substituents independently selected from oxo, hydroxy, halo, amino;

unsubstituted alkenyl linker;

alkenyl linker substituted 1 to 5 substituents independently selected from oxo, hydroxy, halo, amino;

unsubstituted aryl linker;

aryl linker substituted 1 to 5 substituents independently selected from oxo, hydroxy, halo, amino;

unsubstituted heteroaryl linker; or heteroaryl linker substituted 1 to 5 substituents independently selected from oxo, hydroxy, halo, amino.

Further, it should be understood that some or all of the acidic monomers (e.g., of a polymeric catalyst) or one or more acidic moieties (e.g., of a solid-supported catalyst) connected to the polymeric backbone by a linker may have the same linker, or independently have different linkers.

In some embodiments, each acidic monomer (e.g., of a polymeric catalyst) and each acidic moiety (e.g., of a solid-supported catalyst) may independently have the structure of Formulas IA-VIA:

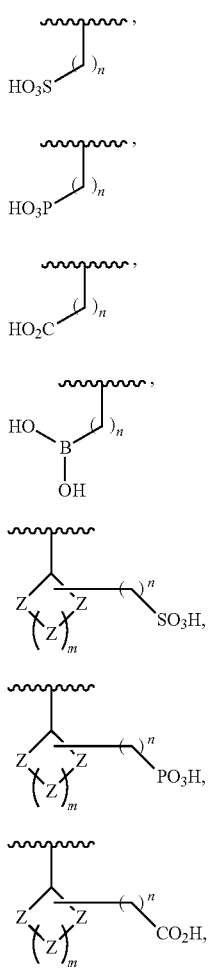

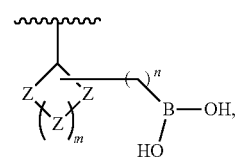

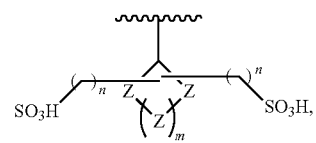

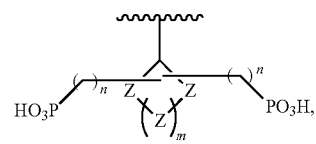

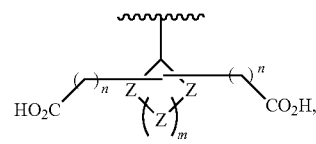

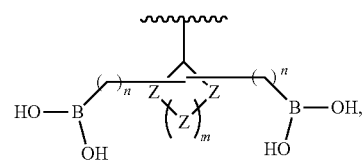

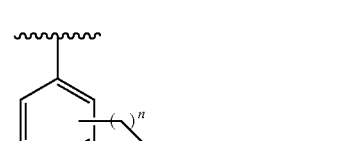

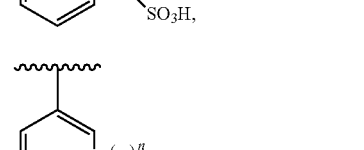

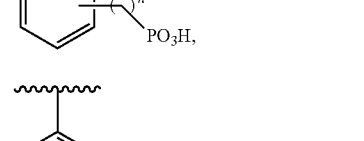

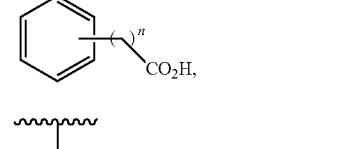

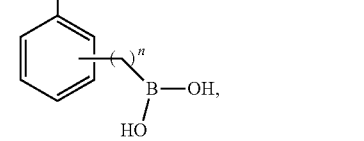

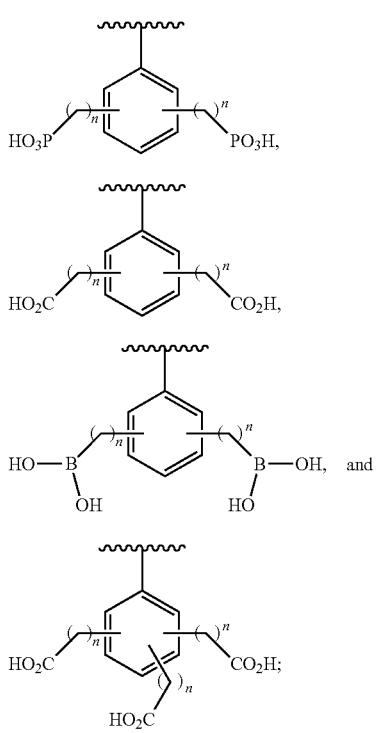

wherein:
each Z is independently C(R²)(R³), N(R⁴), S, S(R⁵)(R⁶), S(O)(R⁵)(R⁶), SO₂, or O, wherein any two adjacent Z can (to the extent chemically feasible) be joined by a double bond, or taken together to form cycloalkyl, heterocycloalkyl, aryl or heteroaryl;
each m is independently selected from 0, 1, 2, and 3;
each n is independently selected from 0, 1, 2, and 3;
each R², R³, and R⁴ is independently hydrogen, alkyl, heteroalkyl, cycloalkyl, heterocyclyl, aryl, or heteroaryl; and
each R⁵ and R⁶ is independently alkyl, heteroalkyl, cycloalkyl, heterocyclyl, aryl, or heteroaryl.

In some embodiments, each acidic monomer (e.g., of a polymeric catalyst) and each acidic moiety (e.g., of a solid-supported catalyst) may independently have the structure of Formulas IA, IB, IVA, or IVB. In other embodiments, each acidic monomer (e.g., of a polymeric catalyst) and each acidic moiety (e.g., of a solid-supported catalyst) may independently have the structure of Formulas IIA, IIB, ITC, IVA, IVB, or IVC. In other embodiments, each acidic monomer (e.g., of a polymeric catalyst) and each acidic moiety (e.g., of a solid-supported catalyst) may independently have the structure of Formulas IIIA, IIIB, or IIIC. In some embodiments, each acidic monomer (e.g., of a polymeric catalyst) and each acidic moiety (e.g., of a solid-supported catalyst) may independently have the structure of Formulas VA, VB, or VC. In some embodiments, each acidic monomer (e.g., of a polymeric catalyst) and each acidic moiety (e.g., of a solid-supported catalyst) may independently have the structure of Formula IA. In other embodiments, each acidic monomer (e.g., of a polymeric catalyst) and each acidic moiety (e.g., of a solid-supported catalyst) may independently have the structure of Formula IB.

In some embodiments, Z can be chosen from C(R₂)(R₃), N(R₄), SO₂, and O. In some embodiments, any two adjacent Z can be taken together to form a group selected from a heterocycloalkyl, aryl, and heteroaryl. In other embodiments, any two adjacent Z can be joined by a double bond. Any combination of these embodiments is also contemplated (as chemically feasible).

In some embodiments, m is 2 or 3. In other embodiments, n is 1, 2, or 3. In some embodiments, R¹ can be hydrogen, alkyl or heteroalkyl. In some embodiments, R¹ can be hydrogen, methyl, or ethyl. In some embodiments, each R², R³, and R⁴ can independently be hydrogen, alkyl, heterocyclyl, aryl, or heteroaryl. In other embodiments, each R², R³ and R⁴ can independently be heteroalkyl, cycloalkyl, heterocyclyl, or heteroaryl. In some embodiments, each R⁵ and R⁶ can independently be alkyl, heterocyclyl, aryl, or heteroaryl. In another embodiment, any two adjacent Z can be taken together to form cycloalkyl, heterocycloalkyl, aryl or heteroaryl.

In some embodiments, the polymeric catalysts and solid-supported catalysts described herein contain monomers or moieties, respectively, that have at least one Bronsted-Lowry acid and at least one cationic group. The Bronsted-Lowry acid and the cationic group can be on different monomers/moieties or on the same monomer/moiety.

In certain embodiments, the acidic monomers of the polymeric catalyst may have a side chain with a Bronsted-Lowry acid that is connected to the polymeric backbone by a linker. In certain embodiments, the acidic moieties of the solid-supported catalyst may have a Bronsted-Lowry acid that is attached to the solid support by a linker. Side chains (e.g., of a polymeric catalyst) or acidic moieties (e.g., of a solid-supported catalyst) with one or more Bronsted-Lowry acids connected by a linker can include, for example,

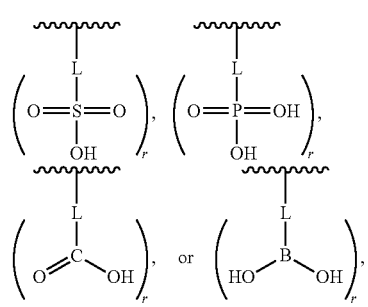

wherein:
L is an unsubstituted alkyl linker, alkyl linker substituted with oxo, unsubstituted cycloalkyl, unsubstituted aryl, unsubstituted heterocycloalkyl, and unsubstituted heteroaryl; and
r is an integer.

In certain embodiments, L is an alkyl linker. In other embodiments L is methyl, ethyl, propyl, butyl. In yet other embodiments, the linker is ethanoyl, propanoyl, benzoyl. In certain embodiments, r is 1, 2, 3, 4, or 5 (as applicable or chemically feasible).

In some embodiments, at least some of the acidic side chains (e.g., of a polymeric catalyst) and at least some of the acidic moieties (e.g., of a solid-supported catalyst) may be:

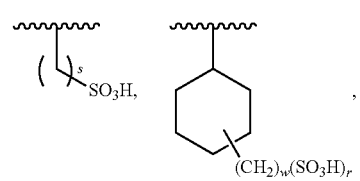

-continued

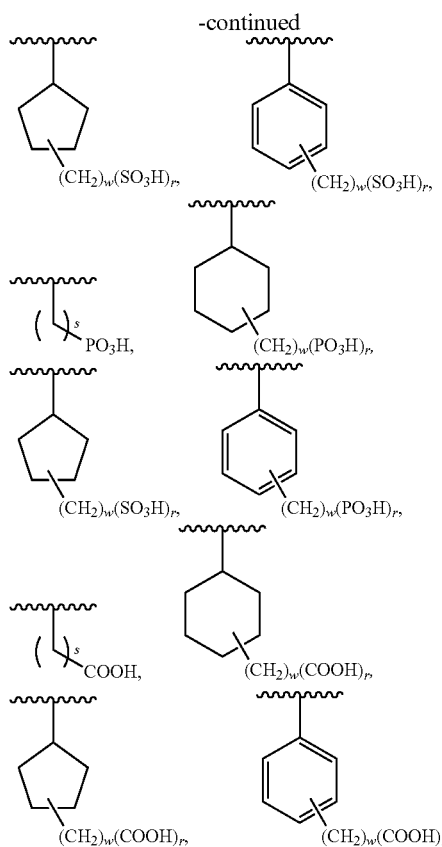
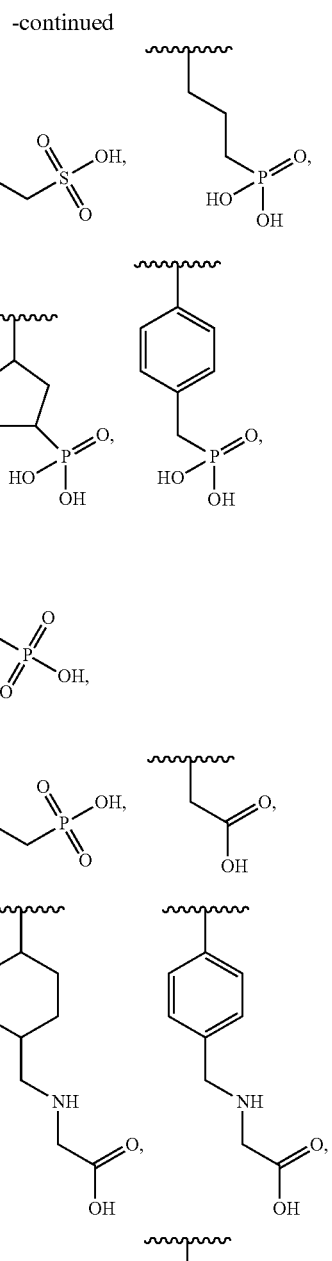

wherein:

s is 1 to 10;

each r is independently 1, 2, 3, 4, or 5 (as applicable or chemically feasible); and w is 0 to 10.

In certain embodiments, s is 1 to 9, or 1 to 8, or 1 to 7, or 1 to 6, or 1 to 5, or 1 to 4, or 1 to 3, or 2, or 1. In certain embodiments, w is 0 to 9, or 0 to 8, or 0 to 7, or 0 to 6, or 0 to 5, or 0 to 4, or 0 to 3, or 0 to 2, 1 or 0).

In certain embodiments, at least some of the acidic side chains (e.g., of a polymeric catalyst) and at least some of the acidic moieties (e.g., of a solid-supported catalyst) may be:

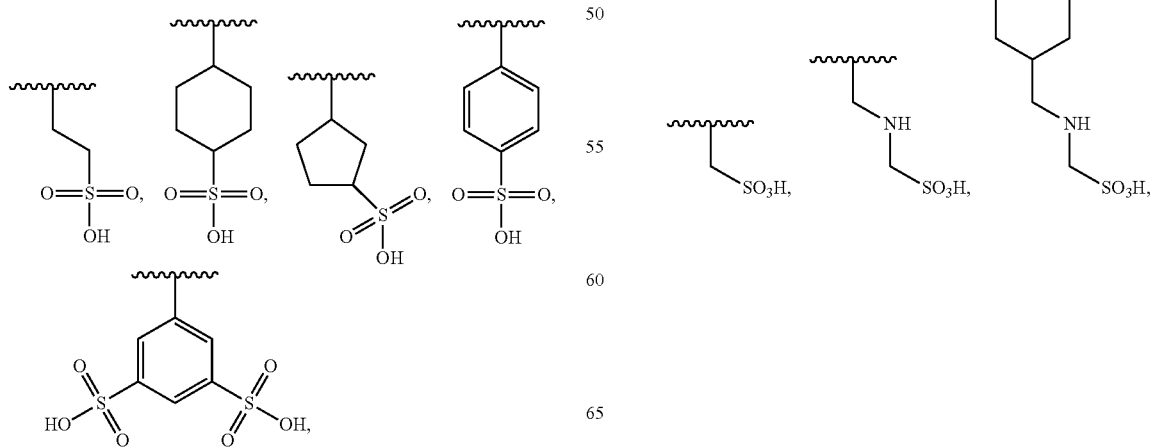

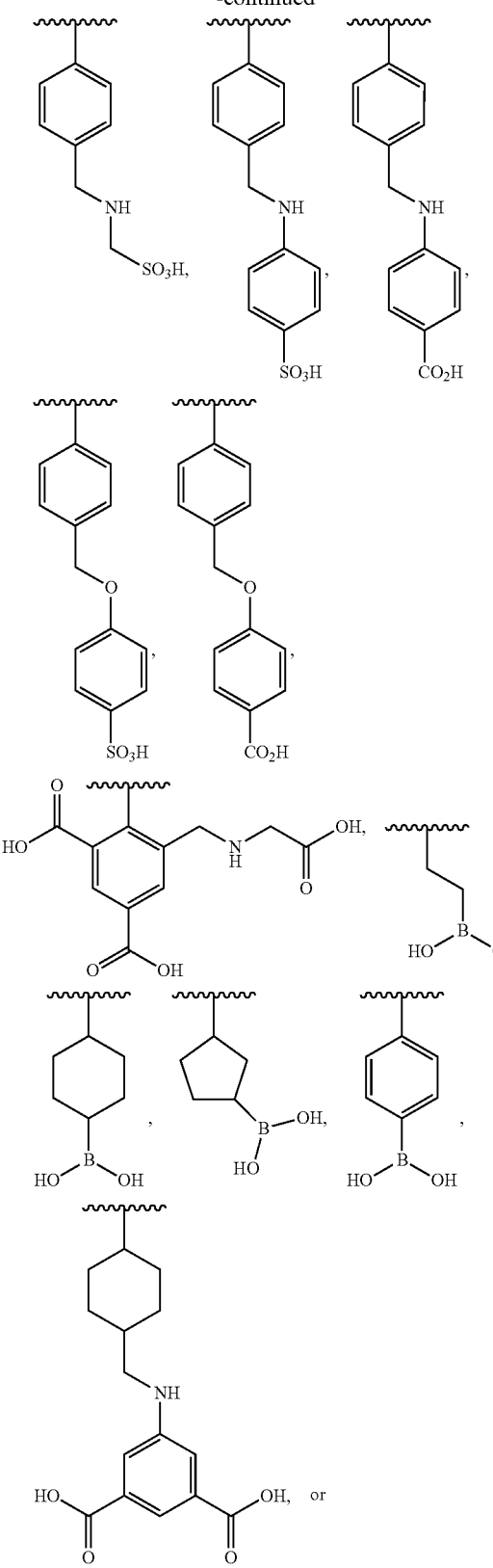

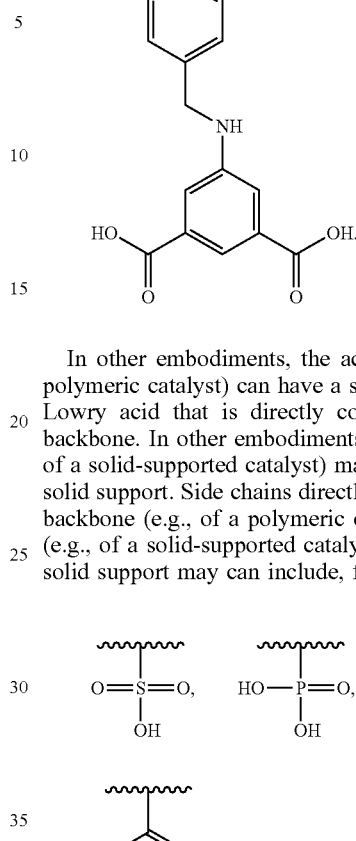

In other embodiments, the acidic monomers (e.g., of a polymeric catalyst) can have a side chain with a Bronsted-Lowry acid that is directly connected to the polymeric backbone. In other embodiments, the acidic moieties (e.g., of a solid-supported catalyst) may be directly attached to a solid support. Side chains directly connect to the polymeric backbone (e.g., of a polymeric catalyst) or acidic moieties (e.g., of a solid-supported catalyst) directly attached to the solid support may can include, for example,

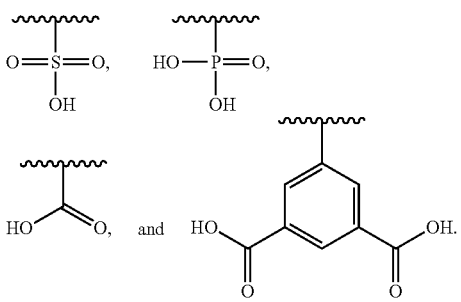

Ionic Monomers and Moieties

The polymeric catalysts include a plurality of ionic monomers, where as the solid-supported catalysts includes a plurality of ionic moieties attached to a solid support.

In some embodiments, a plurality of ionic monomers (e.g., of a polymeric catalyst) or a plurality of ionic moieties (e.g., of a solid-supported catalyst) has at least one nitrogen-containing cationic group, at least one phosphorous-containing cationic group, or any combination thereof. In certain embodiments, a plurality of ionic monomers (e.g., of a polymeric catalyst) or a plurality of ionic moieties (e.g., of a solid-supported catalyst) has one nitrogen-containing cationic group or one phosphorous-containing cationic group. In some embodiments, a plurality of ionic monomers (e.g., of a polymeric catalyst) or a plurality of ionic moieties (e.g., of a solid-supported catalyst) has two nitrogen-containing cationic groups, two phosphorous-containing cationic group, or one nitrogen-containing cationic group and one phosphorous-containing cationic group. In other embodiments, a plurality of ionic monomers (e.g., of a polymeric catalyst) or a plurality of ionic moieties (e.g., of a solid-supported catalyst) has one nitrogen-containing cationic group or phosphorous-containing cationic group, while others have two nitrogen-containing cationic groups or phosphorous-containing cationic groups.

In some embodiments, a plurality of ionic monomers (e.g., of a polymeric catalyst) or a plurality of ionic moieties (e.g., of a solid-supported catalyst) can have one cationic group, or two or more cationic groups, as is chemically feasible. When the ionic monomers (e.g., of a polymeric catalyst) or ionic moieties (e.g., of a solid-supported catalyst) have two or more cationic groups, the cationic groups can be the same or different.

In some embodiments, each ionic monomer (e.g., of a polymeric catalyst) or each ionic moiety (e.g., of a solid-supported catalyst) is a nitrogen-containing cationic group. In other embodiments, each ionic monomer (e.g., of a polymeric catalyst) or each ionic moiety (e.g., of a solid-supported catalyst) is a phosphorous-containing cationic group. In yet other embodiments, at least some of ionic monomers (e.g., of a polymeric catalyst) or at least some of the ionic moieties (e.g., of a solid-supported catalyst) are a nitrogen-containing cationic group, whereas the cationic groups in other ionic monomers (e.g., of a polymeric catalyst) or ionic moieties (e.g., of a solid-supported catalyst) are a phosphorous-containing cationic group. In an exemplary embodiment, each cationic group in the polymeric catalyst or solid-supported catalyst is imidazolium. In another exemplary embodiment, the cationic group in some monomers (e.g., of a polymeric catalyst) or moieties (e.g., of a solid-supported catalyst) is imidazolium, while the cationic group in other monomers (e.g., of a polymeric catalyst) or moieties (e.g., of a solid-supported catalyst) is pyridinium. In yet another exemplary embodiment, each cationic group in the polymeric catalyst or solid-supported catalyst is a substituted phosphonium. In yet another exemplary embodiment, the cationic group in some monomers (e.g., of a polymeric catalyst) or moieties (e.g., of a solid-supported catalyst) is triphenyl phosphonium, while the cationic group in other monomers (e.g., of a polymeric catalyst) or moieties (e.g., of a solid-supported catalyst) is imidazolium.

In some embodiments, the nitrogen-containing cationic group at each occurrence can be independently selected from pyrrolium, imidazolium, pyrazolium, oxazolium, thiazolium, pyridinium, pyrimidinium, pyrazinium, pyradizimium, thiazinium, morpholinium, piperidinium, piperizinium, and pyrollizinium. In other embodiments, the nitrogen-containing cationic group at each occurrence can be independently selected from imidazolium, pyridinium, pyrimidinium, morpholinium, piperidinium, and piperizinium. In some embodiments, the nitrogen-containing cationic group can be imidazolium.

In some embodiments, the phosphorous-containing cationic group at each occurrence can be independently selected from triphenyl phosphonium, trimethyl phosphonium, triethyl phosphonium, tripropyl phosphonium, tributyl phosphonium, trichloro phosphonium, and trifluoro phosphonium. In other embodiments, the phosphorous-containing cationic group at each occurrence can be independently selected from triphenyl phosphonium, trimethyl phosphonium, and triethyl phosphonium. In other embodiments, the phosphorous-containing cationic group can be triphenyl phosphonium.

In some embodiments, one or more of the ionic monomers of a polymeric catalyst are directly connected to the polymeric backbone, or one or more of the ionic moieties of a solid-supported catalyst are directly connected to the solid support. In other embodiments, one or more of the ionic monomers (e.g., of a polymeric catalyst) or one or more ionic moieties (e.g., of a solid-supported catalyst) each independently further includes a linker connecting the cationic group to the polymeric backbone or the solid support (as the case may be). In certain embodiments, some of the cationic groups are directly connected to the polymeric backbone or the solid support (as the case may be), while other the cationic groups are connected to the polymeric backbone or the solid support (as the case may be) by a linker.

In those embodiments where the cationic group is connected to the polymeric backbone or the solid support (as the case may be) by a linker, each linker is independently selected from unsubstituted or substituted alkyl linker, unsubstituted or substituted cycloalkyl linker, unsubstituted or substituted alkenyl linker, unsubstituted or substituted aryl linker, and unsubstituted or substituted heteroaryl linker. In certain embodiments, the linker is unsubstituted or substituted aryl linker, or unsubstituted or substituted heteroaryl linker. In certain embodiments, the linker is unsubstituted or substituted aryl linker. In one embodiment, the linker is a phenyl linker. In another embodiment, the linker is a hydroxyl-substituted phenyl linker.

In other embodiments, each linker in an ionic monomer (e.g., of a polymeric catalyst) or an ionic moiety (e.g., of a solid-supported catalyst) is independently selected from:
unsubstituted alkyl linker;
alkyl linker substituted 1 to 5 substituents independently selected from oxo, hydroxy, halo, amino;
unsubstituted cycloalkyl linker;
cycloalkyl linker substituted 1 to 5 substituents independently selected from oxo, hydroxy, halo, amino;
unsubstituted alkenyl linker;
alkenyl linker substituted 1 to 5 substituents independently selected from oxo, hydroxy, halo, amino;
unsubstituted aryl linker;
aryl linker substituted 1 to 5 substituents independently selected from oxo, hydroxy, halo, amino;
unsubstituted heteroaryl linker; or
heteroaryl linker substituted 1 to 5 substituents independently selected from oxo, hydroxy, halo, amino.

Further, it should be understood that some or all of the ionic monomers (e.g., of a polymeric catalyst) or one or more ionic moieties (e.g., of a solid-supported catalyst) connected to the polymeric backbone by a linker may have the same linker, or independently have different linkers.

In some embodiments, each ionic monomer (e.g., of a polymeric catalyst) or each ionic moiety (e.g., of a solid-supported catalyst) is independently has the structure of Formulas VIIA-XIB:

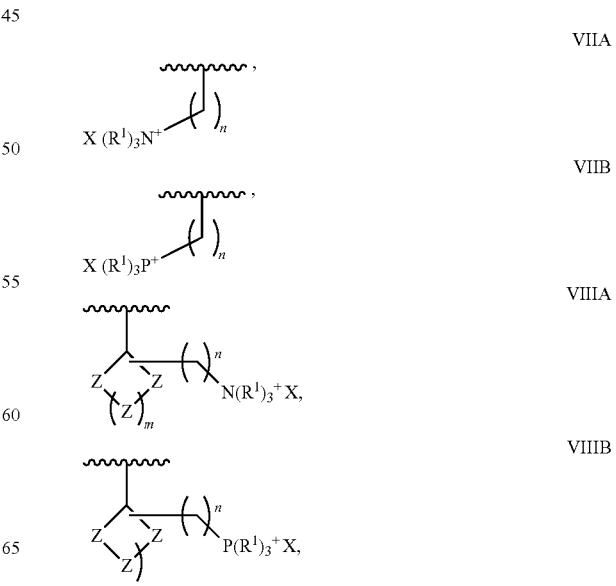

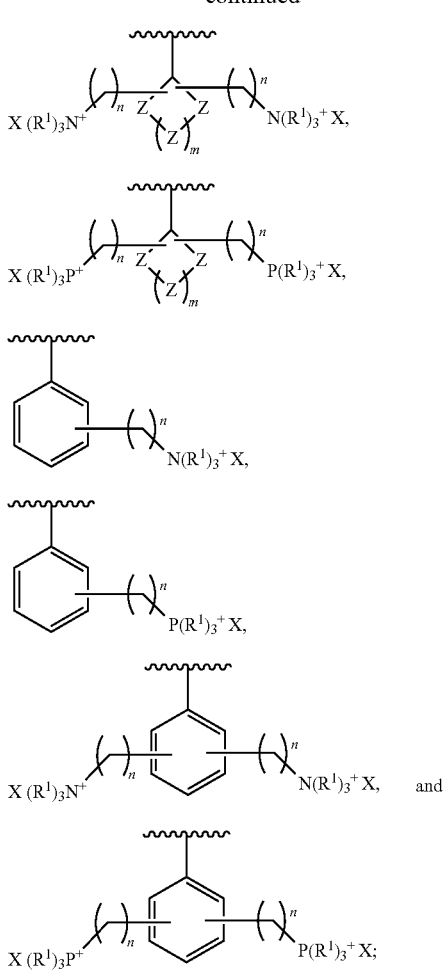

other embodiments, X is bisulfate. In other embodiments, X is chloride. In other embodiments, X is nitrate.

In some embodiments, m is 2 or 3. In other embodiments, n is 1, 2, or 3. In some embodiments, each $R^2$, $R^3$, and $R^4$ can be independently hydrogen, alkyl, heterocyclyl, aryl, or heteroaryl. In other embodiments, each $R^2$, $R^3$ and $R^4$ can be independently heteroalkyl, cycloalkyl, heterocyclyl, or heteroaryl. In some embodiments, each $R^5$ and $R^6$ can be independently alkyl, heterocyclyl, aryl, or heteroaryl. In another embodiment, any two adjacent Z can be taken together to form cycloalkyl, heterocycloalkyl, aryl or heteroaryl.

In certain embodiments, the ionic monomers of the polymeric catalyst may have a side chain with a cationic group that is connected to the polymeric backbone by a linker. In certain embodiments, the ionic moieties of the solid-supported catalyst may have a cationic group that is attached to the solid support by a linker. Side chains (e.g., of a polymeric catalyst) or ionic moieties (e.g., of a solid-supported catalyst) with one or more cationic groups connected by a linker can include, for example,

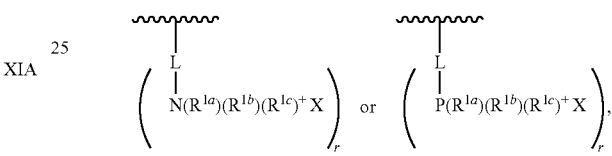

wherein:

L is an unsubstituted alkyl linker, alkyl linker substituted with oxo, unsubstituted cycloalkyl, unsubstituted aryl, unsubstituted heterocycloalkyl, and unsubstituted heteroaryl;

each $R^{1a}$, $R^{1b}$ and $R^{1c}$ are independently hydrogen or alkyl; or $R^{1a}$ and $R^{1b}$ are taken together with the nitrogen atom to which they are attached to form an unsubstituted heterocycloalkyl; or $R^{1a}$ and $R^{1b}$ are taken together with the nitrogen atom to which they are attached to form an unsubstituted heteroaryl or substituted heteroaryl, and $R^{1c}$ is absent;

r is an integer; and

X is as described above for Formulas VIIA-XIB.

In other embodiments L is methyl, ethyl, propyl, butyl. In yet other embodiments, the linker is ethanoyl, propanoyl, benzoyl. In certain embodiments, r is 1, 2, 3, 4, or 5 (as applicable or chemically feasible).

In other embodiments, each linker is independently selected from:

unsubstituted alkyl linker;

alkyl linker substituted 1 to 5 substituents independently selected from oxo, hydroxy, halo, amino;

unsubstituted cycloalkyl linker;

cycloalkyl linker substituted 1 to 5 substituents independently selected from oxo, hydroxy, halo, amino;

unsubstituted alkenyl linker;

alkenyl linker substituted 1 to 5 substituents independently selected from oxo, hydroxy, halo, amino;

unsubstituted aryl linker;

aryl linker substituted 1 to 5 substituents independently selected from oxo, hydroxy, halo, amino;

unsubstituted heterocyclyl linker; or heteroaryl linker substituted 1 to 5 substituents independently selected from oxo, hydroxy, halo, amino.

In certain embodiments, each linker is an unsubstituted alkyl linker or an alkyl linker with an oxo substituent. In one wherein:

each Z is independently $C(R^2)(R^3)$, $N(R^4)$, S, $S(R^5)(R^6)$, $S(O)(R^5)(R^6)$, $SO_2$, or O, wherein any two adjacent Z can (to the extent chemically feasible) be joined by a double bond, or taken together to form cycloalkyl, heterocycloalkyl, aryl or heteroaryl;

each X is independently $F^-$, $Cl^-$, $Br^-$, $I^-$, $NO_2^-$, $NO_3^-$, $SO_4^{2-}$, $R^7SO_4^-$, $R^7CO_2^-$, $PO_4^{2-}$, $R^7PO_3$, or $R^7PO_2^-$, where $SO_4^{2-}$ and $PO_4^{2-}$ are each independently associated with at least two cationic groups at any X position on any ionic monomer, and each m is independently 0, 1, 2, or 3;

each n is independently 0, 1, 2, or 3;

each $R^1$, $R^2$, $R^3$ and $R^4$ is independently hydrogen, alkyl, heteroalkyl, cycloalkyl, heterocyclyl, aryl, or heteroaryl;

each $R^5$ and $R^6$ is independently alkyl, heteroalkyl, cycloalkyl, heterocyclyl, aryl, or heteroaryl; and each $R^7$ is independently hydrogen, $C_{1-4}$ alkyl, or $C_{1-4}$ heteroalkyl.

In some embodiments, Z can be chosen from $C(R^2)(R^3)$, $N(R^4)$, $SO_2$, and O. In some embodiments, any two adjacent Z can be taken together to form a group selected from a heterocycloalkyl, aryl and heteroaryl. In other embodiments, any two adjacent Z can be joined by a double bond. In some embodiments, each X can be $Cl^-$, $NO_3^-$, $SO_4^{2-}$, $R^7SO_4^-$, or $R^7CO_2^-$, where $R^7$ can be hydrogen or $C_{1-4}$alkyl. In another embodiment, each X can be $Cl^-$, $Br^-$, $I^-$, $HSO_4^-$, $HCO_2^-$, $CH_3CO_2^-$, or $NO_3^-$. In other embodiments, X is acetate. In embodiment, each linker is —(CH$_2$)(CH$_2$)— or —(CH$_2$)(C=O). In certain embodiments, r is 1, 2, 3, 4, or 5 (as applicable or chemically feasible).

In some embodiments, at least some of the ionic side chains (e.g., of a polymeric catalyst) and at least some of the ionic moieties (e.g., of a solid-supported catalyst) may be:

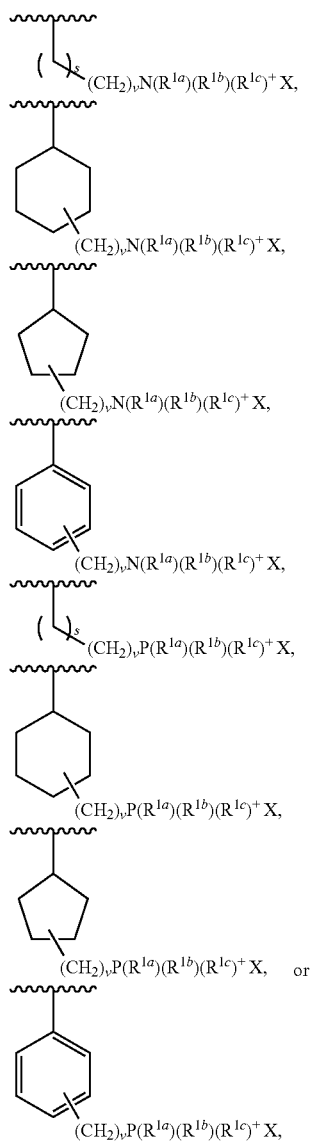

wherein:
  each R$^{1a}$, R$^{1b}$ and R$^{1c}$ are independently hydrogen or alkyl; or R$^{1a}$ and R$^{1b}$ are taken together with the nitrogen atom to which they are attached to form an unsubstituted heterocycloalkyl; or R$^{1a}$ and R$^{1b}$ are taken together with the nitrogen atom to which they are attached to form an unsubstituted heteroaryl or substituted heteroaryl, and R$^{1c}$ is absent;
  s is an integer;
  v is 0 to 10; and
  X is as described above for Formulas VIIA-XIB.

In certain embodiments, s is 1 to 9, or 1 to 8, or 1 to 7, or 1 to 6, or 1 to 5, or 1 to 4, or 1 to 3, or 2, or 1. In certain embodiments, v is 0 to 9, or 0 to 8, or 0 to 7, or 0 to 6, or 0 to 5, or 0 to 4, or 0 to 3, or 0 to 2, 1 or 0).

In certain embodiments, at least some of the ionic side chains (e.g., of a polymeric catalyst) and at least some of the ionic moieties (e.g., of a solid-supported catalyst) may be:

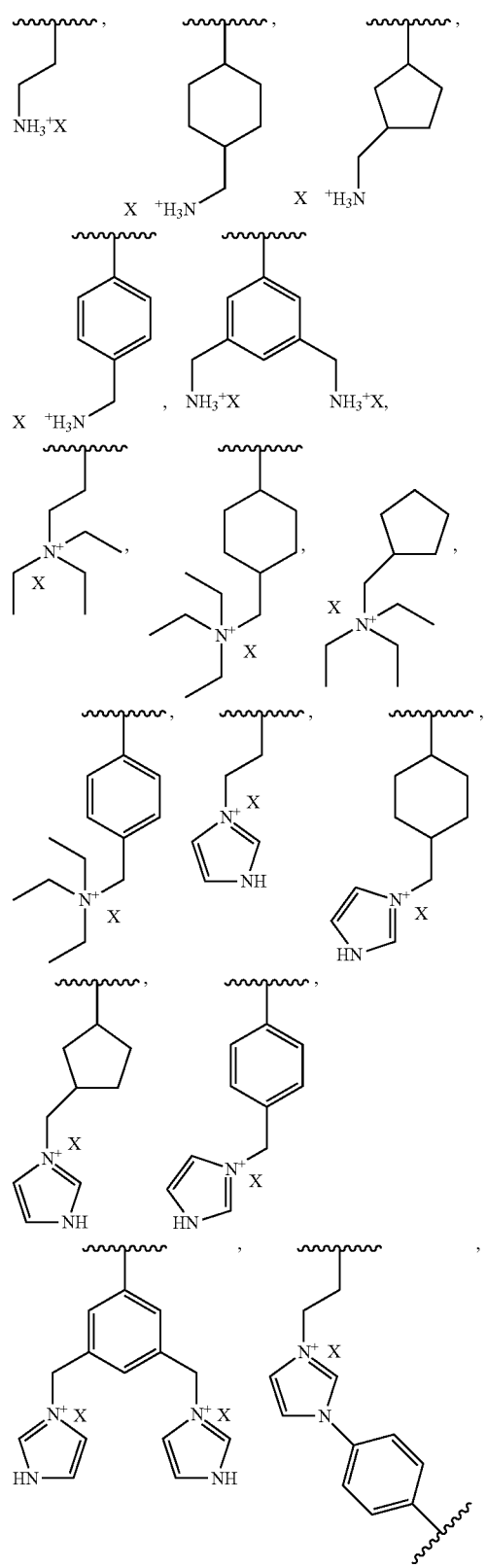

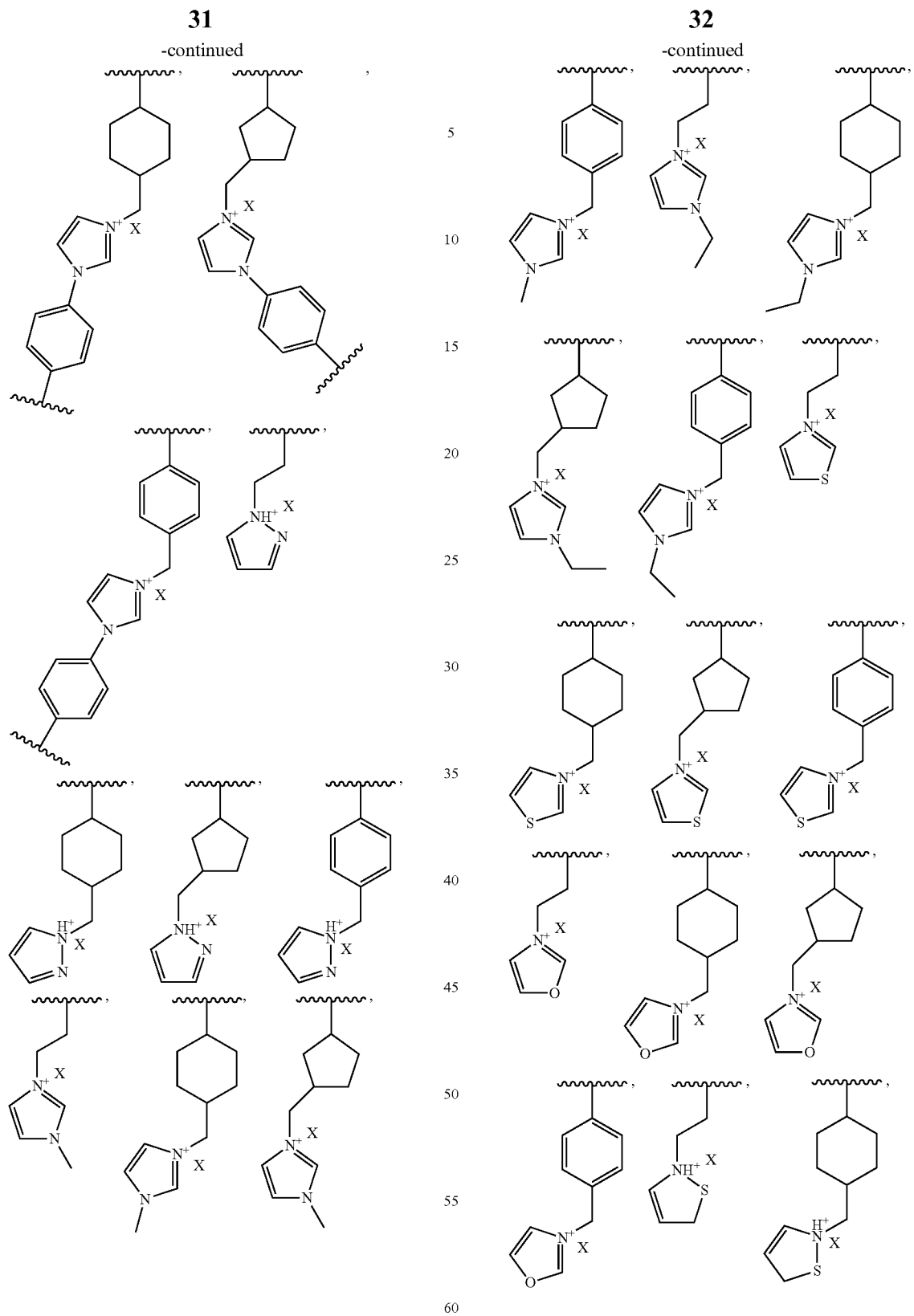

-continued
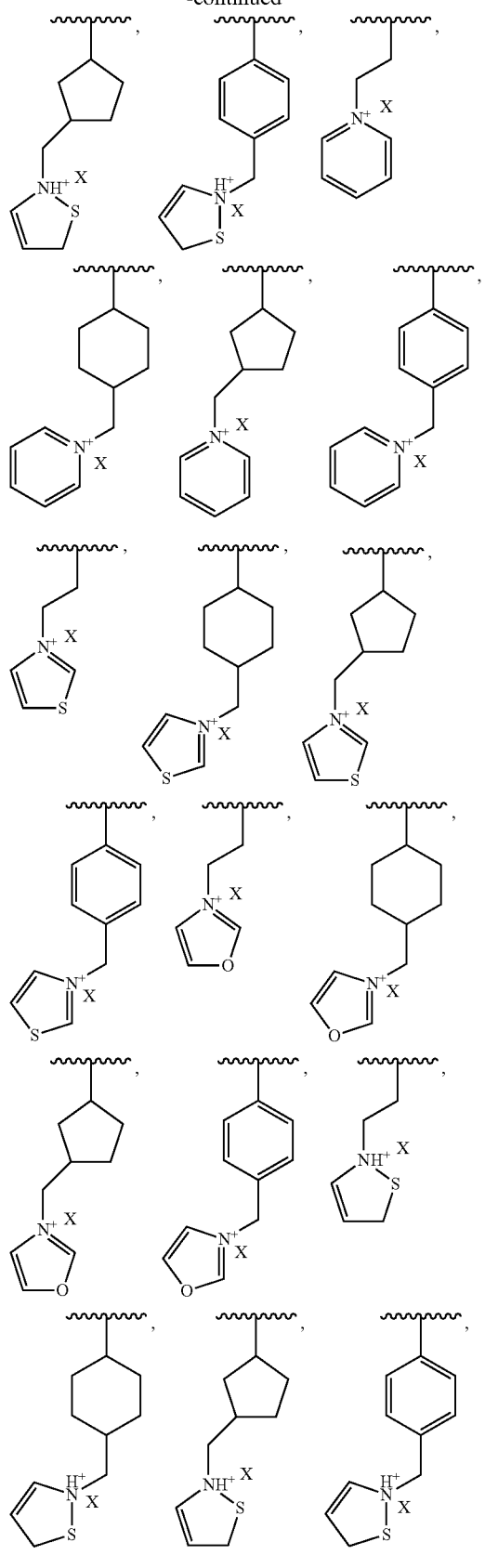
-continued
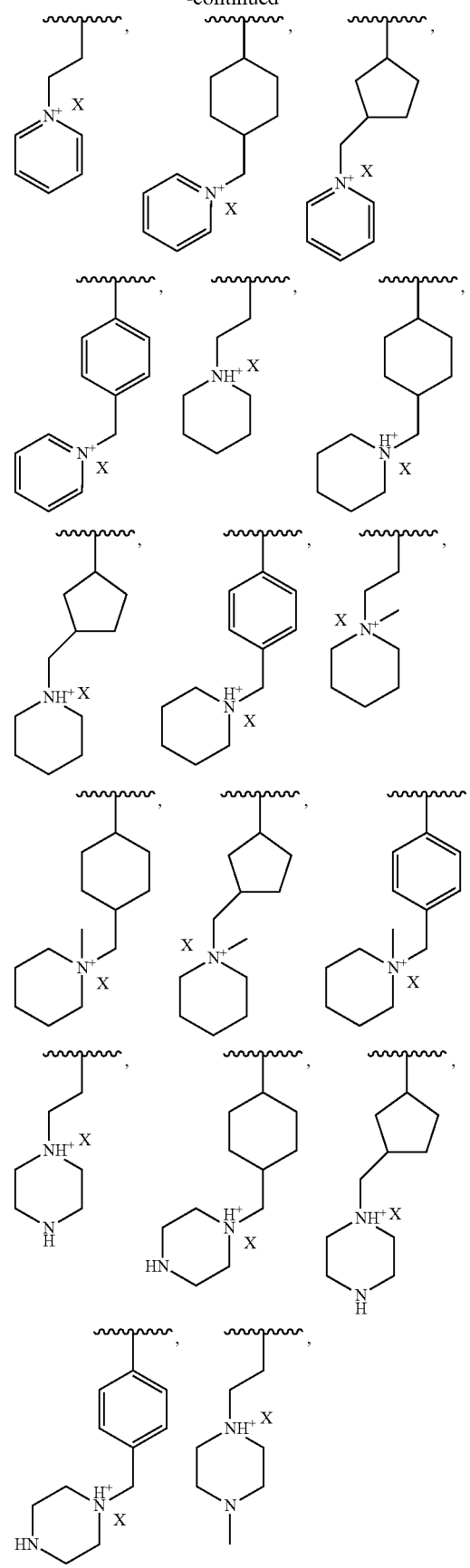

35
-continued
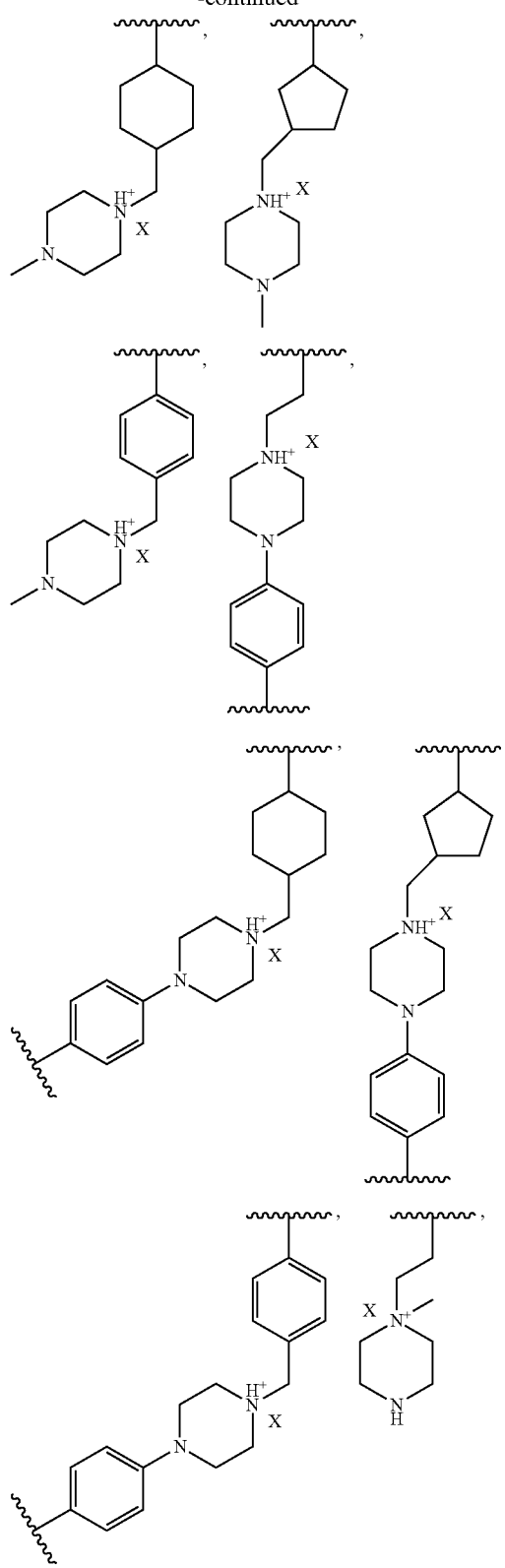
36
-continued
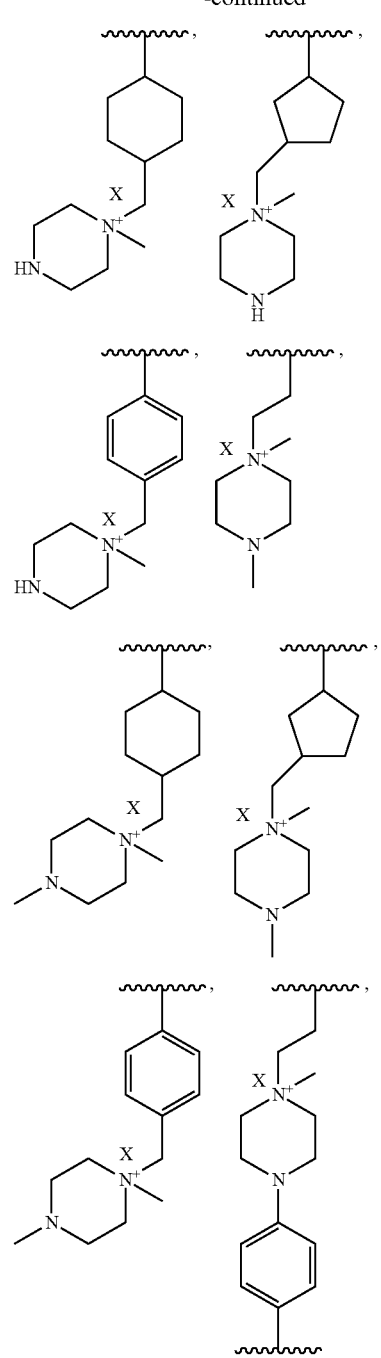

37
-continued
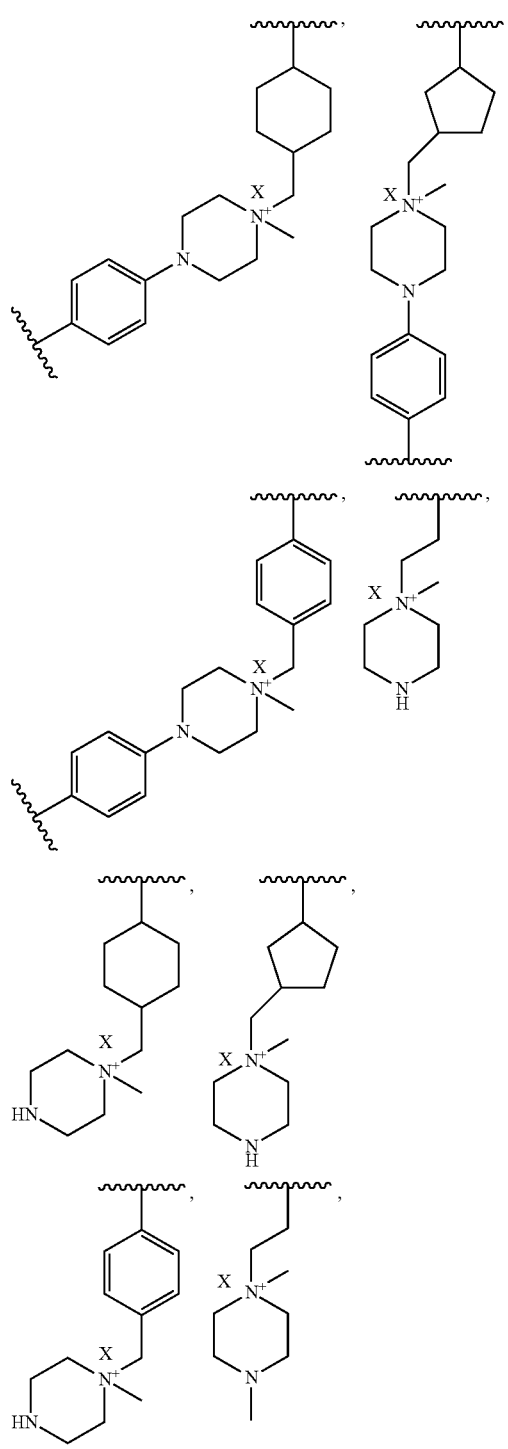
38
-continued
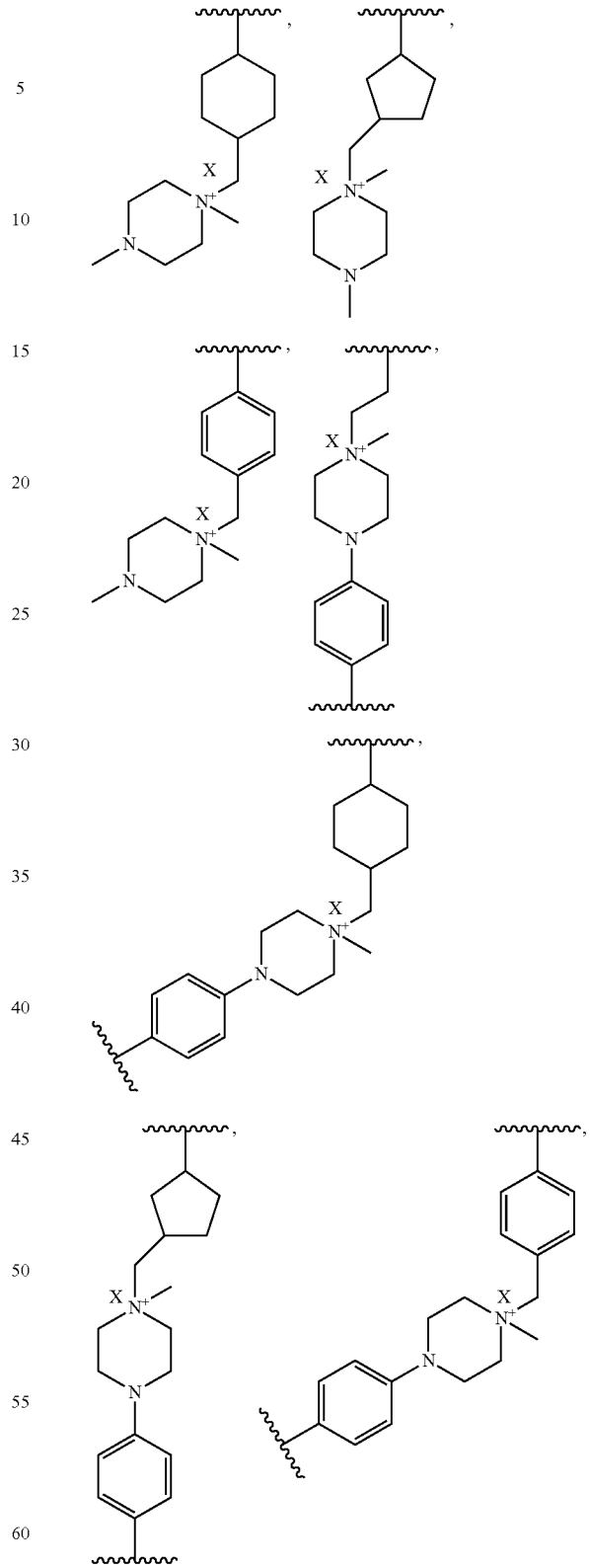

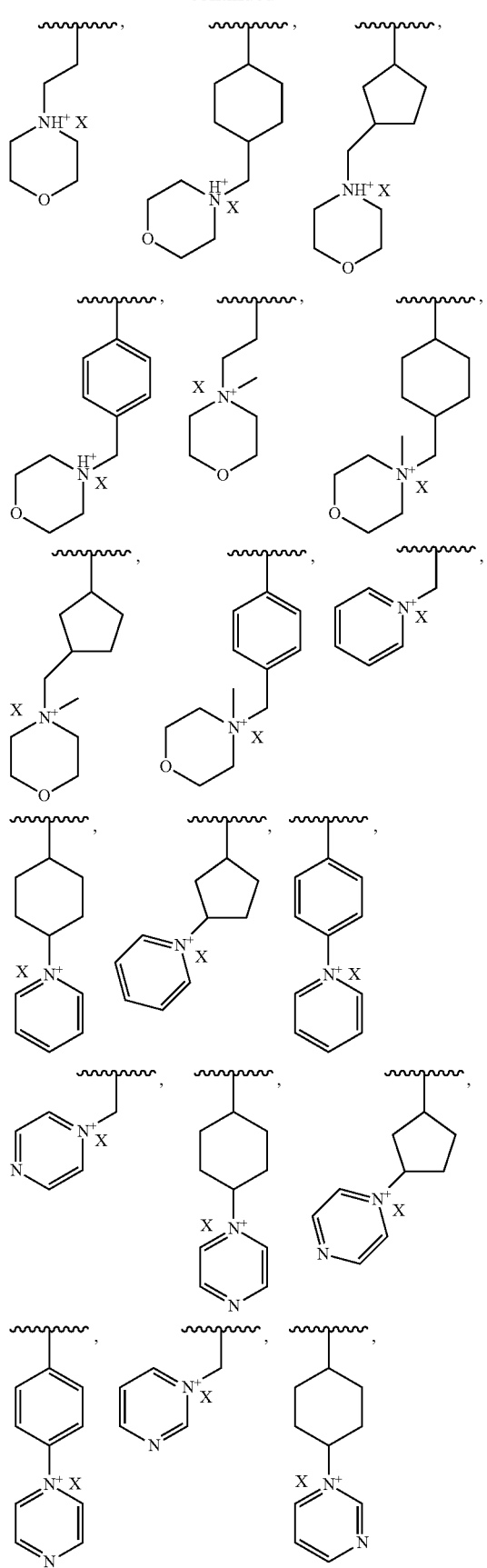
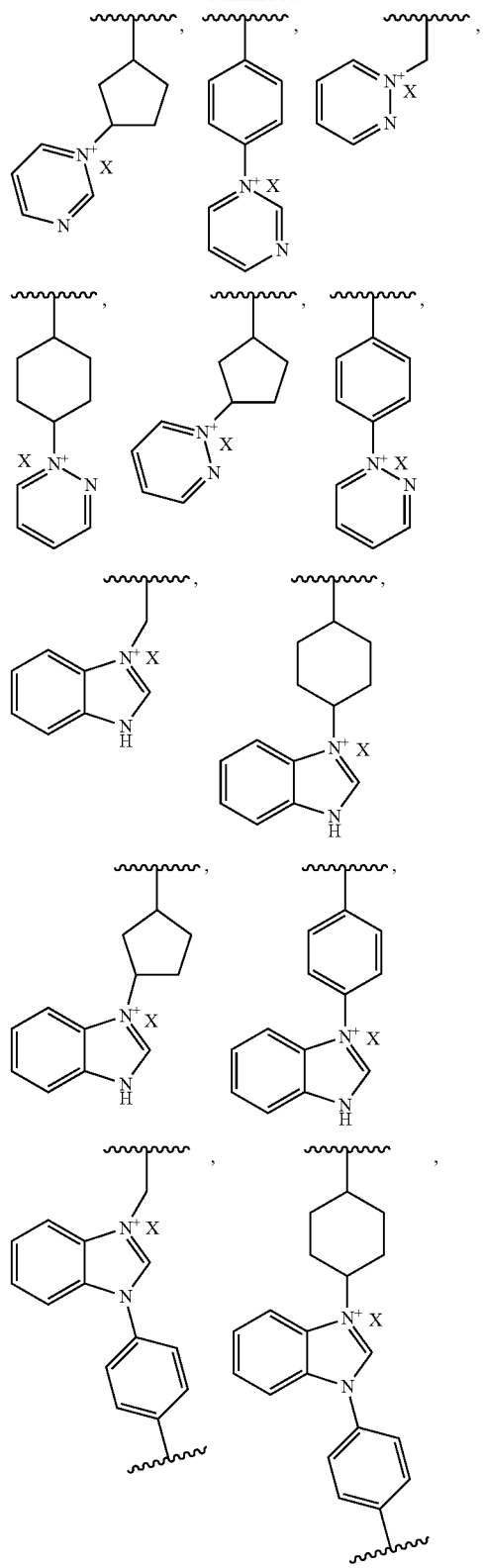

-continued

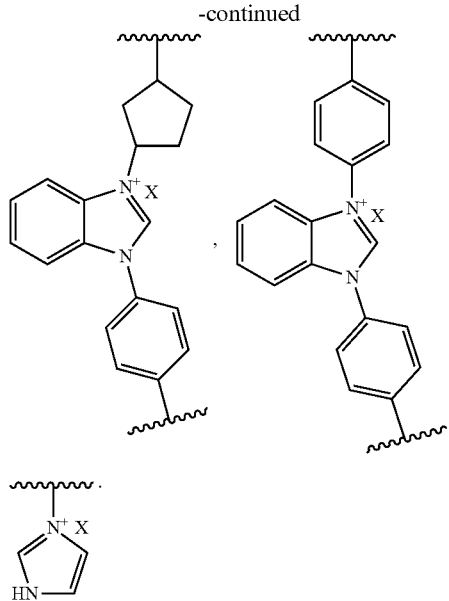,

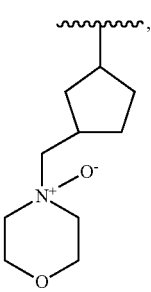, 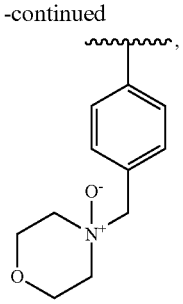 or

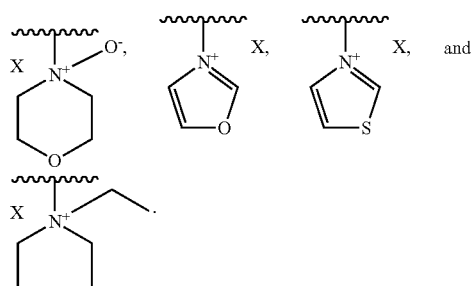

In other embodiments, the ionic monomers (e.g., of a polymeric catalyst) can have a side chain with a cationic group that is directly connected to the polymeric backbone. In other embodiments, the ionic moieties (e.g., of a solid-supported catalyst) can have a cationic group that is directly attached to the solid support. Side chains (e.g., of a polymeric catalyst) directly connect to the polymeric backbone or ionic moieties (e.g., of a solid-supported catalyst) directly attached to the solid support may can include, for example, In some embodiments, the nitrogen-containing cationic group can be an N-oxide, where the negatively charged oxide (O—) is not readily dissociable from the nitrogen cation. Non-limiting examples of such groups include, for example,

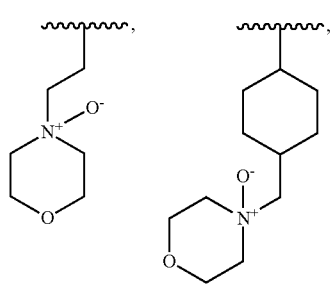

-continued

In some embodiments, the phosphorous-containing side chain (e.g., of a polymeric catalyst) or moiety (e.g., of a solid-supported catalyst) is independently:

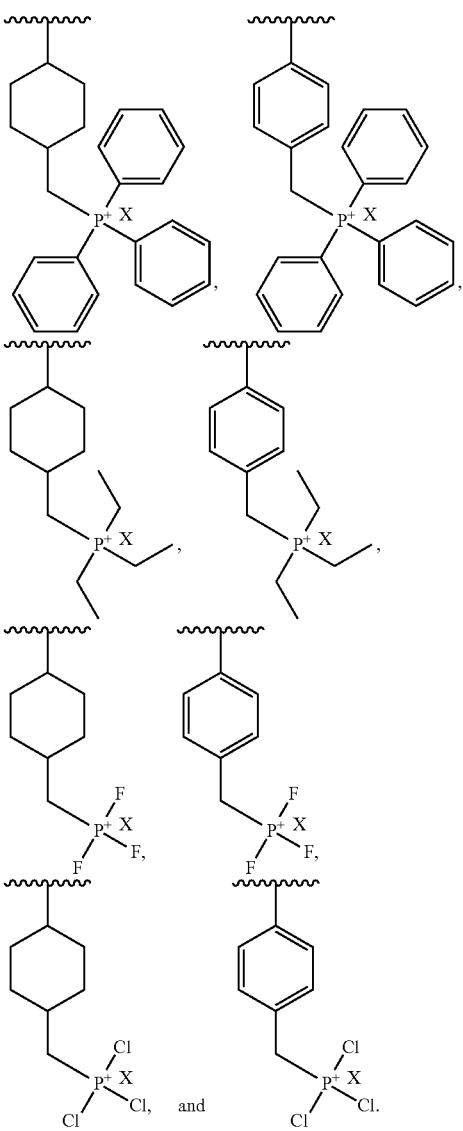

In other embodiments, the ionic monomers (e.g., of a polymeric catalyst) can have a side chain with a cationic group that is directly connected to the polymeric backbone. In other embodiments, the ionic moieties (e.g., of a solid-supported catalyst) can have a cationic group that is directly attached to the solid support. Side chains (e.g., of a polymeric catalyst) directly connect to the polymeric backbone or ionic moieties (e.g., of a solid-supported catalyst) directly attached to the solid support may can include, for example,

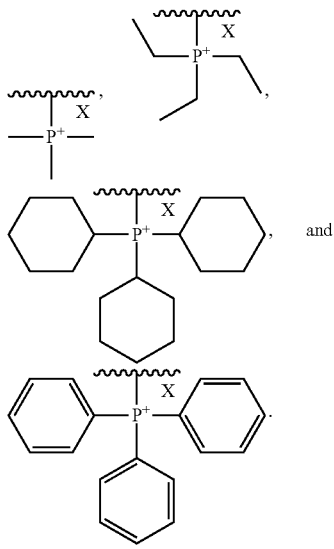

The ionic monomers (e.g., of a polymeric catalyst) or ionic moieties (e.g., of a solid-supported catalyst) can either all have the same cationic group, or can have different cationic groups. In some embodiments, each cationic group in the polymeric catalyst or solid-supported catalyst is a nitrogen-containing cationic group. In other embodiments, each cationic group in the polymeric catalyst or solid-supported catalyst is a phosphorous-containing cationic group. In yet other embodiments, the cationic group in some monomers or moieties of the polymeric catalyst or solid-supported catalyst, respectively, is a nitrogen-containing cationic group, whereas the cationic group in other monomers or moieties of the polymeric catalyst or solid-supported catalyst, respectively, is a phosphorous-containing cationic group. In an exemplary embodiment, each cationic group in the polymeric catalyst or solid-supported catalyst is imidazolium. In another exemplary embodiment, the cationic group in some monomers or moieties of the polymeric catalyst or solid-supported catalyst is imidazolium, while the cationic group in other monomers or moieties of the polymeric catalyst or solid-supported catalyst is pyridinium. In yet another exemplary embodiment, each cationic group in the polymeric catalyst or solid-supported catalyst is a substituted phosphonium. In yet another exemplary embodiment, the cationic group in some monomers or moieties of the polymeric catalyst or solid-supported catalyst is triphenyl phosphonium, while the cationic group in other monomers or moieties of the polymeric catalyst or solid-supported catalyst is imidazolium.

Acidic-Ionic Monomers and Moieties

Some of the monomers in the polymeric catalyst contain both the Bronsted-Lowry acid and the cationic group in the same monomer. Such monomers are referred to as "acidic-ionic monomers". Similarly, some of the moieties in the solid-supported catalyst contain both the Bronsted-Lowry acid and the cationic group in the same moieties. Such moieties are referred to as "acidic-ionic moieties". For example, in exemplary embodiments, the acidic-ionic monomer (e.g., of a polymeric catalyst) or an acidic-ionic moiety (e.g., of a solid-supported catalyst) can contain imidazolium and acetic acid, or pyridinium and boronic acid.

In some embodiments, the monomers (e.g., of a polymeric catalyst) or moieties (e.g., of a solid-supported catalyst) include both Bronsted-Lowry acid(s) and cationic group(s), where either the Bronsted-Lowry acid is connected to the polymeric backbone (e.g., of a polymeric catalyst) or solid support (e.g., of a solid-supported catalyst) by a linker, and/or the cationic group is connected to the polymeric backbone (e.g., of a polymeric catalyst) or is attached to the solid support (e.g., of a solid-supported catalyst) by a linker.

It should be understood that any of the Bronsted-Lowry acids, cationic groups and linkers (if present) suitable for the acidic monomers/moieties and/or ionic monomers/moieties may be used in the acidic-ionic monomers/moieties.

In certain embodiments, the Bronsted-Lowry acid at each occurrence in the acidic-ionic monomer (e.g., of a polymeric catalyst) or the acidic-ionic moiety (e.g., of a solid-supported catalyst) is independently selected from sulfonic acid, phosphonic acid, acetic acid, isophthalic acid, and boronic acid. In certain embodiments, the Bronsted-Lowry acid at each occurrence in the acidic-ionic monomer (e.g., of a polymeric catalyst) or the acidic-ionic moiety (e.g., of a solid-supported catalyst) is independently sulfonic acid or phosphonic acid. In one embodiment, the Bronsted-Lowry acid at each occurrence in the acidic-ionic monomer (e.g., of a polymeric catalyst) or the acidic-ionic moiety (e.g., of a solid-supported catalyst) is sulfonic acid.

In some embodiments, the nitrogen-containing cationic group at each occurrence in the acidic-ionic monomer (e.g., of a polymeric catalyst) or the acidic-ionic moiety (e.g., of a solid-supported catalyst) is independently selected from pyrrolium, imidazolium, pyrazolium, oxazolium, thiazolium, pyridinium, pyrimidinium, pyrazinium, pyradizimium, thiazinium, morpholinium, piperidinium, piperizinium, and pyrollizinium. In one embodiment, the nitrogen-containing cationic group is imidazolium.

In some embodiments, the phosphorous-containing cationic group at each occurrence in the acidic-ionic monomer (e.g., of a polymeric catalyst) or the acidic-ionic moiety (e.g., of a solid-supported catalyst) is independently selected from triphenyl phosphonium, trimethyl phosphonium, triethyl phosphonium, tripropyl phosphonium, tributyl phosphonium, trichloro phosphonium, and trifluoro phosphonium. In one embodiment, the phosphorous-containing cationic group is triphenyl phosphonium.

In some embodiments, the polymeric catalyst or solid-supported catalyst can include at least one acidic-ionic monomer or moiety, respectively, connected to the polymeric backbone or solid support, wherein at least one acidic-ionic monomer or moiety includes at least one Bronsted-Lowry acid and at least one cationic group, and wherein at least one of the acidic-ionic monomers or moieties includes a linker connecting the acidic-ionic monomer to the polymeric backbone or solid support. The cationic group can be a nitrogen-containing cationic group or a phosphorous-containing cationic group as described herein. The linker can also be as described herein for either the acidic or ionic moieties. For example, the linker can be selected from unsubstituted or substituted alkyl linker, unsubstituted or substituted cycloalkyl linker, unsubstituted or substituted alkenyl linker, unsubstituted or substituted aryl linker, and unsubstituted or substituted heteroaryl linker.

In other embodiments, the monomers (e.g., of a polymeric catalyst) or moieties (e.g., of a solid-supported catalyst) can have a side chain containing both a Bronsted-Lowry acid and a cationic group, where the Bronsted-Lowry acid is directly connected to the polymeric backbone or solid support, the cationic group is directly connected to the polymeric backbone or solid support, or both the Bronsted-Lowry acid and the cationic group are directly connected to the polymeric backbone or solid support.

In certain embodiments, the linker is unsubstituted or substituted aryl linker, or unsubstituted or substituted heteroaryl linker. In certain embodiments, the linker is unsubstituted or substituted aryl linker. In one embodiment, the linker is a phenyl linker. In another embodiment, the linker is a hydroxyl-substituted phenyl linker.

Monomers of a polymeric catalyst that have side chains containing both a Bronsted-Lowry acid and a cationic group can also be called "acidic ionomers". Acidic-ionic side chains (e.g., of a polymeric catalyst) or acidic-ionic moieties (e.g., of a solid-supported catalyst) that are connected by a linker can include, for example,

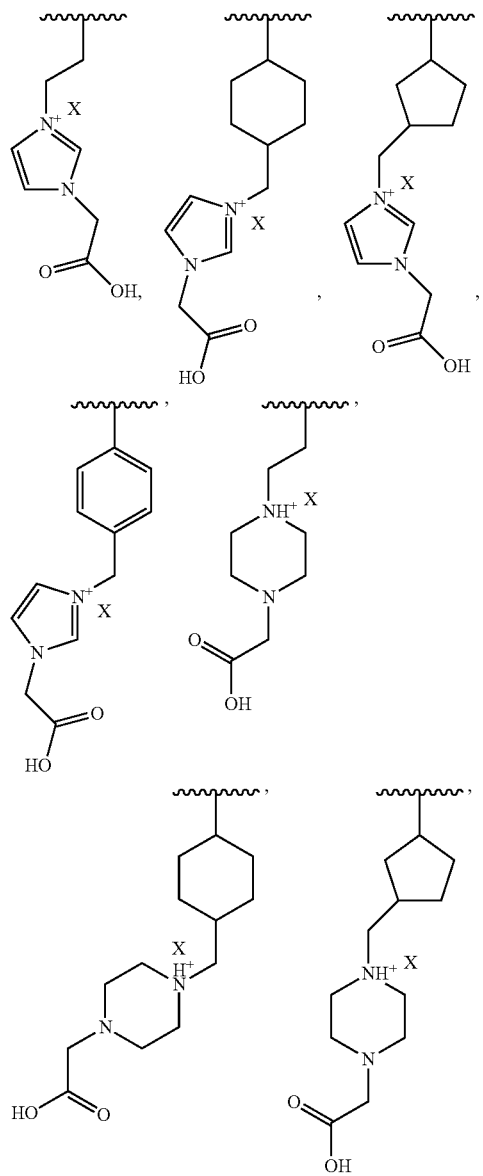

-continued

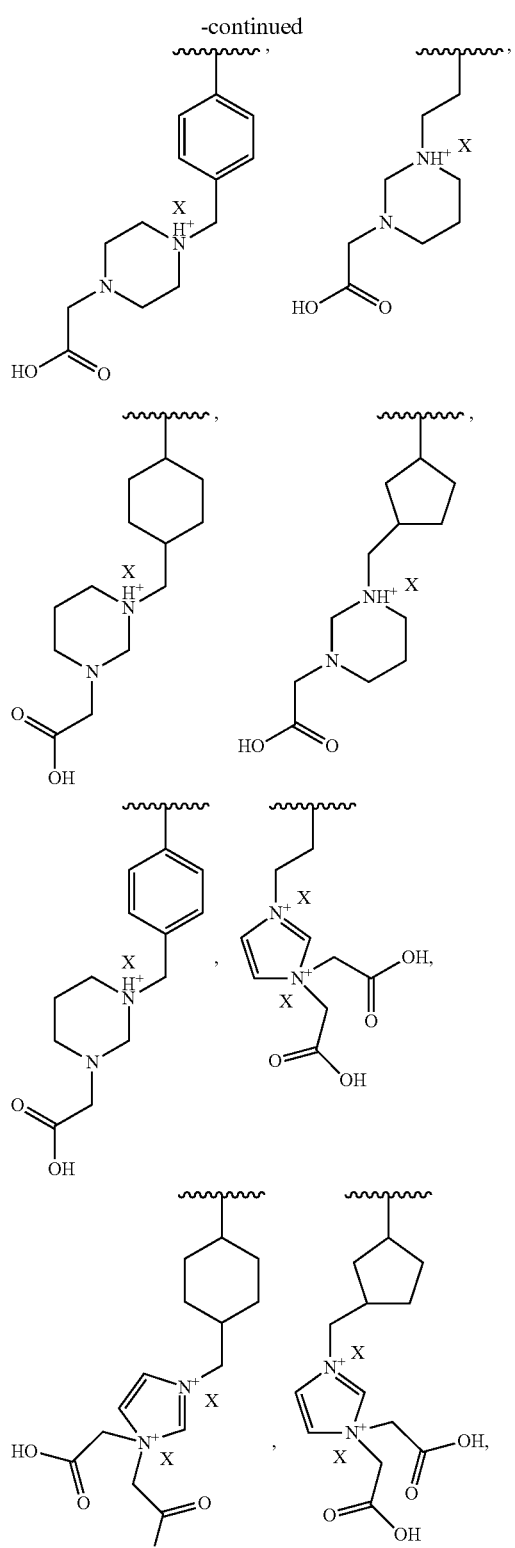

-continued

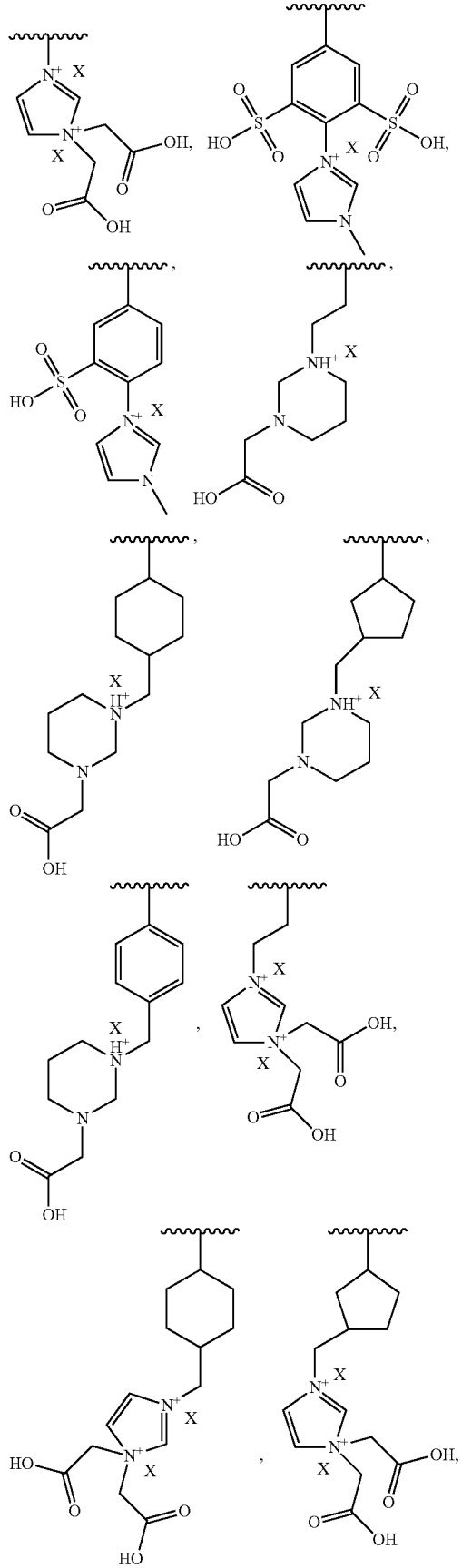
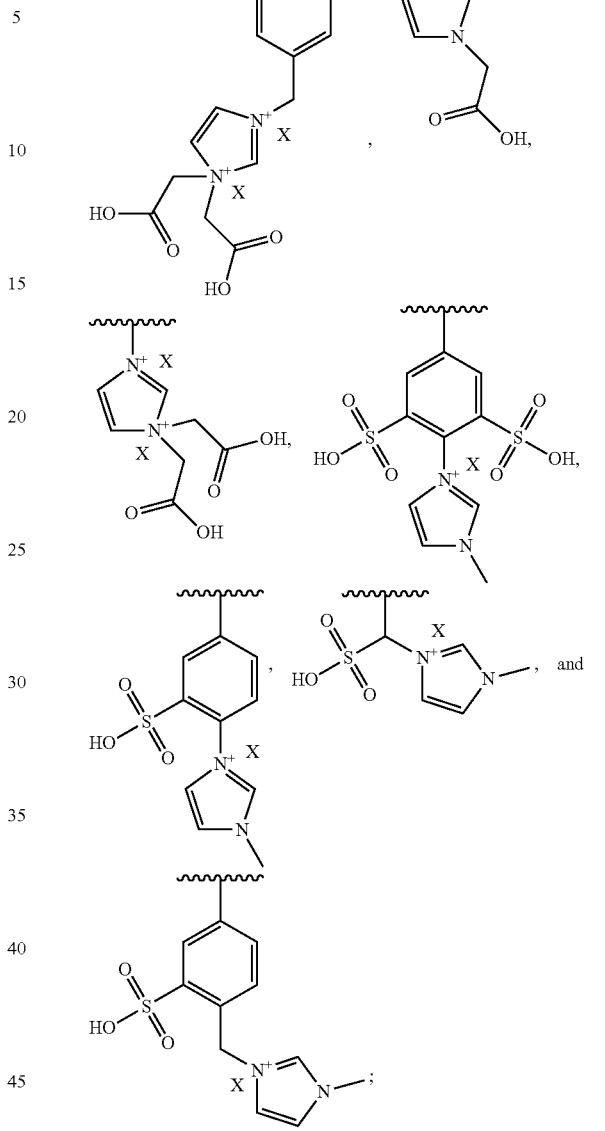

wherein:

each X is independently selected from $F^-$, $Cl^-$, $Br^-$, $I^-$, $NO_2^-$, $NO_3^-$, $SO_4^{2-}$, $R^7SO_4^-$, $R^7CO_2^-$, $PO_4^{2-}$, $R^7PO_3^-$, and $R^7PO_2^-$, where $SO_4^{2-}$ and $PO_4^{2-}$ are each independently associated with at least two Bronsted-Lowry acids at any X position on any side chain, and each $R^7$ is independently selected from hydrogen, $C_{1-4}$ alkyl, and $C_{1-4}$ heteroalkyl.

In some embodiments, $R^1$ can be selected from hydrogen, alkyl, and heteroalkyl. In some embodiments, $R^1$ can be selected from hydrogen, methyl, or ethyl. In some embodiments, each X can be selected from $Cl^-$, $NO_3^-$, $SO_4^{2-}$, $R^7SO_4^-$, and $R^7CO_2^-$, where $R^7$ can be selected from hydrogen and $C_{1-4}$ alkyl. In another embodiment, each X can be selected from $Cl^-$, $Br^-$, $I^-$, $HSO_4^-$, $HCO_2^-$, $CH_3CO_2^-$, and $NO_3^-$. In other embodiments, X is acetate. In other embodiments, X is bisulfate. In other embodiments, X is chloride. In other embodiments, X is nitrate.

In some embodiments, the acidic-ionic side chain (e.g., of a polymeric catalyst) or the acidic-ionic moiety (e.g., of a solid-supported catalyst) is independently:

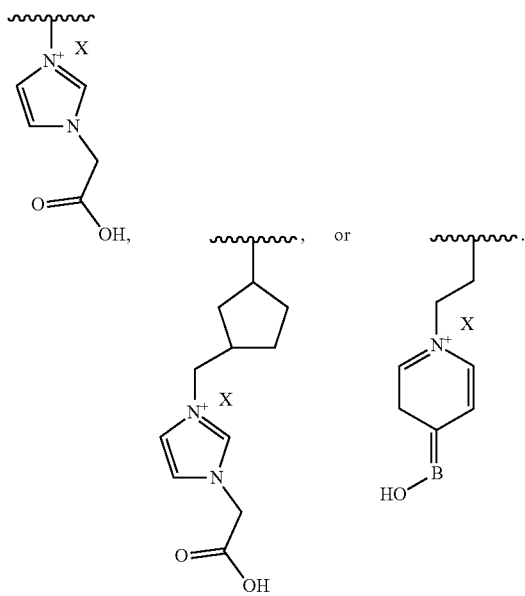

In some embodiments, the acidic-ionic side chain (e.g., of a polymeric catalyst) or the acidic-ionic moiety (e.g., of a solid-supported catalyst) is independently:

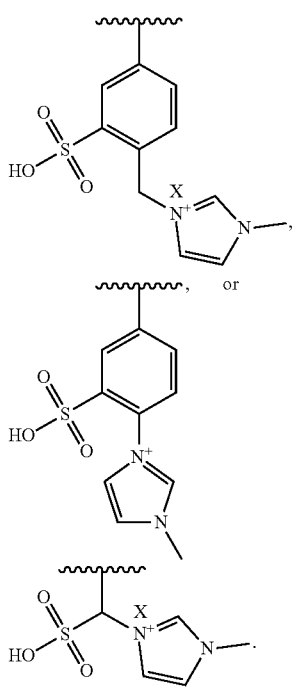

In other embodiments, the monomers (e.g., of a polymeric catalyst) or moieties (e.g., of a solid-supported catalyst) can have both a Bronsted-Lowry acid and a cationic group, where the Bronsted-Lowry acid is directly connected to the polymeric backbone or solid support, the cationic group is directly connected to the polymeric backbone or solid support, or both the Bronsted-Lowry acid and the cationic group are directly connected to the polymeric backbone or solid support. Such side chains in acidic-ionic monomers (e.g., of a polymeric catalyst) or moieties (e.g., of a solid-supported catalyst) can include, for example,

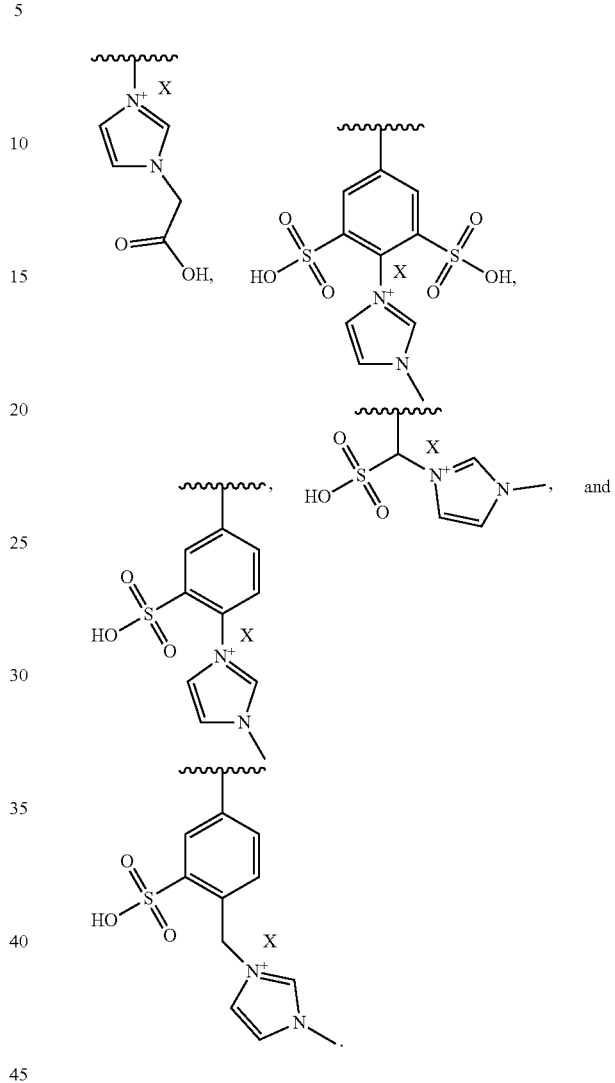

Hydrophobic Monomers and Moieties

In some embodiments, the polymeric catalyst further includes hydrophobic monomers connected to form the polymeric backbone. Similarly, in some embodiments, the solid-supported catalyst further includes hydrophobic moieties attached to the solid support. In either instances, each hydrophobic monomer or moiety has at least one hydrophobic group. In certain embodiments of the polymeric catalyst or solid-supported catalyst, each hydrophobic monomer or moiety, respectively, has one hydrophobic group. In certain embodiments of the polymeric catalyst or solid-supported catalyst, each hydrophobic monomer or moiety has two hydrophobic groups. In other embodiments of the polymeric catalyst or solid-supported catalyst, some of the hydrophobic monomers or moieties have one hydrophobic group, while others have two hydrophobic groups.

In some embodiments of the polymeric catalyst or solid-supported catalyst, each hydrophobic group is independently selected from an unsubstituted or substituted alkyl, an unsubstituted or substituted cycloalkyl, an unsubstituted or substituted aryl, and an unsubstituted or substituted heteroaryl. In certain embodiments of the polymeric catalyst or solid-supported catalyst, each hydrophobic group is an unsubstituted or substituted aryl, or an unsubstituted or substituted heteroaryl. In one embodiment, each hydrophobic group is phenyl. Further, it should be understood that the hydrophobic monomers may either all have the same hydrophobic group, or may have different hydrophobic groups.

In some embodiments of the polymeric catalyst, the hydrophobic group is directly connected to form the polymeric backbone. In some embodiments of the solid-supported catalyst, the hydrophobic group is directly attached to the solid support.

Other Characteristics of the Catalysts

In some embodiments, the acidic and ionic monomers make up a substantial portion of the polymeric catalyst. In some embodiments, the acidic and ionic moieties make up a substantial portion solid-supported catalyst. In certain embodiments, the acidic and ionic monomers or moieties make up at least about 30%, at least about 40%, at least about 50%, at least about 60%, at least about 70%, at least about 80%, at least about 90%, at least about 95%, or at least about 99% of the monomers or moieties of the catalyst, based on the ratio of the number of acidic and ionic monomers/moieties to the total number of monomers/moieties present in the catalyst.

In some embodiments, the polymeric catalyst or solid-supported catalyst has a total amount of Bronsted-Lowry acid of between about 0.1 and about 20 mmol, between about 0.1 and about 15 mmol, between about 0.01 and about 12 mmol, between about 0.05 and about 10 mmol, between about 1 and about 8 mmol, between about 2 and about 7 mmol, between about 3 and about 6 mmol, between about 1 and about 5, or between about 3 and about 5 mmol per gram of the polymeric catalyst or solid-supported catalyst.

In some embodiments of the polymeric catalyst or solid-supported catalyst, each ionic monomer further includes a counterion for each nitrogen-containing cationic group or phosphorous-containing cationic group. In certain embodiments of the polymeric catalyst or solid-supported catalyst, each counterion is independently selected from halide, nitrate, sulfate, formate, acetate, or organosulfonate. In some embodiments of the polymeric catalyst or solid-supported catalyst, the counterion is fluoride, chloride, bromide, or iodide. In one embodiment of the polymeric catalyst or solid-supported catalyst, the counterion is chloride. In another embodiment of the polymeric catalyst or solid-supported catalyst, the counterion is sulfate. In yet another embodiment of the polymeric catalyst or solid-supported catalyst, the counterion is acetate.

In some embodiments, the polymeric catalyst or solid-supported catalyst has a total amount of nitrogen-containing cationic groups and counterions or a total amount of phosphorous-containing cationic groups and counterions of between about 0.01 and about 10 mmol, between about 0.05 and about 10 mmol, between about 1 and about 8 mmol, between about 2 and about 6 mmol, or between about 3 and about 5 mmol per gram of the polymeric catalyst or solid-supported catalyst.

In some embodiments, the acidic and ionic monomers make up a substantial portion of the polymeric catalyst or solid-supported catalyst. In certain embodiments, the acidic and ionic monomers or moieties make up at least about 30%, at least about 40%, at least about 50%, at least about 60%, at least about 70%, at least about 80%, at least about 90%, at least about 95%, or at least about 99% of the monomers of the polymeric catalyst or solid-supported catalyst, based on the ratio of the number of acidic and ionic monomers or moieties to the total number of monomers or moieties present in the polymeric catalyst or solid-supported catalyst.

The ratio of the total number of acidic monomers or moieties to the total number of ionic monomers or moieties can be varied to tune the strength of the catalyst. In some embodiments, the total number of acidic monomers or moieties exceeds the total number of ionic monomers or moieties in the polymer or solid support. In other embodiments, the total number of acidic monomers or moieties is at least about 2, at least about 3, at least about 4, at least about 5, at least about 6, at least about 7, at least about 8, at least about 9 or at least about 10 times the total number of ionic monomers or moieties in the polymeric catalyst or solid-supported catalyst. In certain embodiments, the ratio of the total number of acidic monomers or moieties to the total number of ionic monomers or moieties is about 1:1, about 2:1, about 3:1, about 4:1, about 5:1, about 6:1, about 7:1, about 8:1, about 9:1 or about 10:1.

In some embodiments, the total number of ionic monomers or moieties exceeds the total number of acidic monomers or moieties in the catalyst. In other embodiments, the total number of ionic monomers or moieties is at least about 2, at least about 3, at least about 4, at least about 5, at least about 6, at least about 7, at least about 8, at least about 9 or at least about 10 times the total number of acidic monomers or moieties in the polymeric catalyst or solid-supported catalyst. In certain embodiments, the ratio of the total number of ionic monomers or moieties to the total number of acidic monomers or moieties is about 1:1, about 2:1, about 3:1, about 4:1, about 5:1, about 6:1, about 7:1, about 8:1, about 9:1 or about 10:1.

Arrangement of Monomers in Polymeric Catalysts

In some embodiments of the polymeric catalysts, the acidic monomers, the ionic monomers, the acidic-ionic monomers and the hydrophobic monomers, where present, can be arranged in alternating sequence or in a random order as blocks of monomers. In some embodiments, each block has not more than twenty, fifteen, ten, six, or three monomers.

Figure 9:
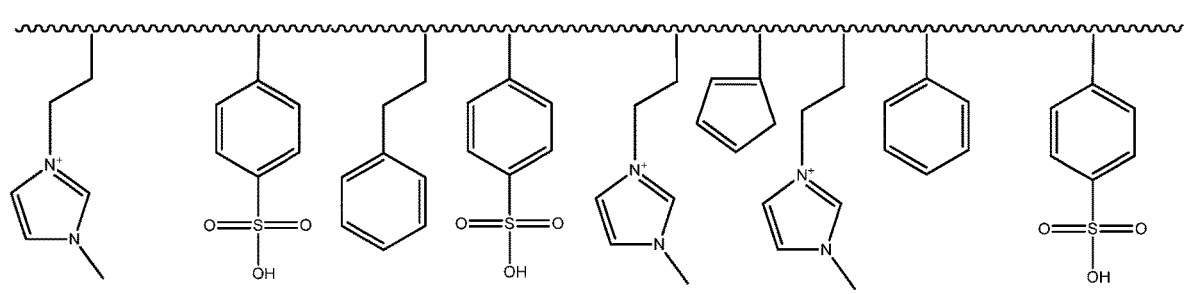
FIG. 9 illustrates a portion of a polymeric catalyst, in which the monomers are randomly arranged in an alternating sequence.

In some embodiments of the polymeric catalysts, the monomers of the polymeric catalyst are randomly arranged in an alternating sequence. With reference to the portion of the polymeric catalyst depicted in FIG. 9, the monomers are randomly arranged in an alternating sequence.

Figure 4:
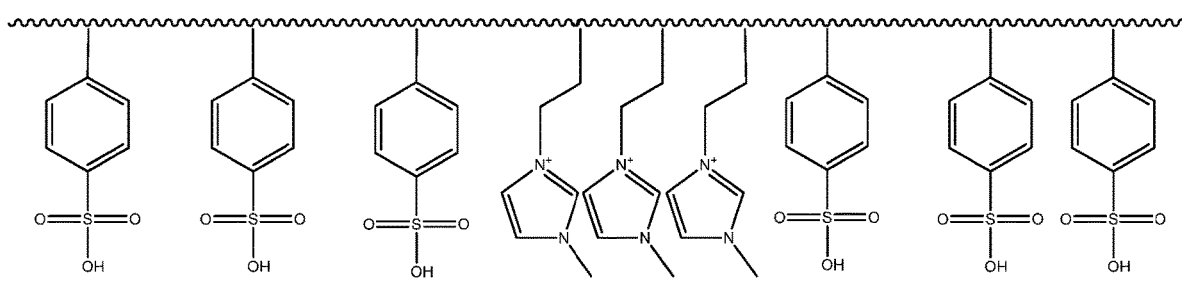
FIG. 4 illustrates a portion of a polymeric catalyst, in which the monomers are arranged in blocks of monomers, and the block of acidic monomers alternates with the block of ionic monomers.

In other embodiments of the polymeric catalysts, the monomers of the polymeric catalyst are randomly arranged as blocks of monomers. With reference to the portion of the polymeric catalyst depicted in FIG. 4, the monomers are arranged in blocks of monomers. In certain embodiments where the acidic monomers and the ionic monomers are arranged in blocks of monomers, each block has no more than 20, 19, 18, 17, 16, 15, 14, 13, 12, 11, 10, 9, 8, 7, 6, 5, 4, or 3 monomers.

The polymeric catalysts described herein can also be cross-linked. Such cross-linked polymeric catalysts can be prepared by introducing cross-linking groups. In some embodiments, cross-linking can occur within a given polymeric chain, with reference to the portion of the polymeric catalysts depicted in FIGS. 5A and 5B. In other embodiments, cross-linking can occur between two or more polymeric chains, with reference to the portion of the polymeric catalysts in FIGS. 6A, 6B, 6C and 6D.

With reference to FIGS. 5A, 5B and 6A, it should be understood that $R^1$, $R^2$ and $R^3$, respectively, are exemplary cross linking groups. Suitable cross-linking groups that can be used to form a cross-linked polymeric catalyst with the polymers described herein include, for example, substituted or unsubstituted divinyl alkanes, substituted or unsubstituted divinyl cycloalkanes, substituted or unsubstituted divinyl aryls, substituted or unsubstituted heteroaryls, dihaloalkanes, dihaloalkenes, and dihaloalkynes, where the substituents are those as defined herein. For example, cross-linking groups can include divinylbenzene, diallylbenzene, dichlorobenzene, divinylmethane, dichloromethane, divinylethane, dichloroethane, divinylpropane, dichloropropane, divinylbutane, dichlorobutane, ethylene glycol, and resorcinol. In one embodiment, the crosslinking group is divinyl benzene.

In some embodiments of the polymeric catalysts, the polymer is cross-linked. In certain embodiments, at least about 1%, at least about 2%, at least about 3%, at least about 4%, at least about 5%, at least about 6%, at least about 7%, at least about 8%, at least about 9%, at least about 10%, at least about 15%, at least about 20%, at least about 30%, at least about 40%, at least about 50%, at least about 60%, at least about 70%, at least about 80%, at least about 90% or at least about 99% of the polymer is cross-linked.

In some embodiments of the polymeric catalysts, the polymers described herein are not substantially cross-linked, such as less than about 0.9% cross-linked, less than about 0.5% cross-linked, less than about 0.1% cross-linked, less than about 0.01% cross-linked, or less than about 0.001% cross-linked.

Polymeric Backbones

In some embodiments, the polymeric backbone is formed from one or more substituted or unsubstituted monomers. Polymerization processes using a wide variety of monomers are well known in the art (see, e.g., International Union of Pure and Applied Chemistry, et al., IUPAC Gold Book, *Polymerization*. (2000)). One such process involves monomer(s) with unsaturated substitution, such as vinyl, propenyl, butenyl, or other such substituents(s). These types of monomers can undergo radical initiation and chain polymerization.

In some embodiments, the polymeric backbone is formed from one or more substituted or unsubstituted monomers selected from ethylene, propylene, hydroxyethylene, acetaldehyde, styrene, divinyl benzene, isocyanates, vinyl chloride, vinyl phenols, tetrafluoroethylene, butylene, terephthalic acid, caprolactam, acrylonitrile, butadiene, ammonias, diammonias, pyrrole, imidazole, pyrazole, oxazole, thiazole, pyridine, pyrimidine, pyrazine, pyradizimine, thiazine, morpholine, piperidine, piperizines, pyrollizine, triphenylphosphonate, trimethylphosphonate, triethylphosphonate, tripropylphosphonate, tributylphosphonate, trichlorophosphonate, trifluorophosphonate, and diazole.

The polymeric backbone of the polymeric catalysts described herein can include, for example, polyalkylenes, polyalkenyl alcohols, polycarbonates, polyarylenes, polyaryletherketones, and polyamide-imides. In certain embodiments, the polymeric backbone can be selected from polyethylene, polypropylene, polyvinyl alcohol, polystyrene, polyurethane, polyvinyl chloride, polyphenol-aldehyde, polytetrafluoroethylene, polybutylene terephthalate, polycaprolactam, and poly(acrylonitrile butadiene styrene). In certain embodiments of the polymeric catalyst, the polymeric backbone is polyethyelene or polypropylene. In one embodiment of the polymeric catalyst, the polymeric backbone is polyethylene. In another embodiment of the polymeric catalyst, the polymeric backbone is polyvinyl alcohol. In yet another embodiment of the polymeric catalyst, the polymeric backbone is polystyrene.

Figure 8:
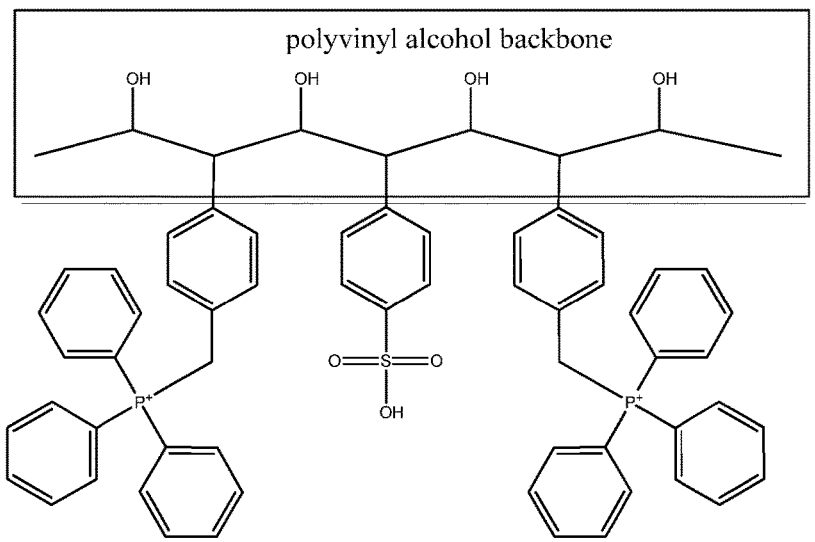
FIG. 8 illustrates a portion of a polymeric catalyst with a polyvinylalcohol backbone.

With reference to FIG. 7, in one embodiment, the polymeric backbone is polyethylene. With reference to FIG. 8, in another embodiment, the polymeric backbone is polyvinyl alcohol.

The polymeric backbone described herein can also include an ionic group integrated as part of the polymeric backbone. Such polymeric backbones can also be called "ionomeric backbones". In certain embodiments, the polymeric backbone can be selected from: polyalkyleneammonium, polyalkylenediammonium, polyalkylenepyrrolium, polyalkyleneimidazolium, polyalkylenepyrazolium, polyalkyleneoxazolium, polyalkylenethiazolium, polyalkylenepyridinium, polyalkylenepyrimidinium, polyalkylenepyrazinium, polyalkylenepyradizimium, polyalkylenethiazinium, polyalkylenemorpholinium, polyalkylenepiperidinium, polyalkylenepiperizinium, polyalkylenepyrollizinium, polyalkylenetriphenylphosphonium, polyalkylenetrimethylphosphonium, polyalkylenetriethylphosphonium, polyalkylenetripropylphosphonium, polyalkylenetributylphosphonium, polyalkylenetrichlorophosphonium, polyalkylenetrifluorophosphonium, and polyalkylenediazolium, polyarylalkyleneammonium, polyarylalkylenediammonium, polyarylalkylenepyrrolium, polyarylalkyleneimidazolium, polyarylalkylenepyrazolium, polyarylalkyleneoxazolium, polyarylalkylenethiazolium, polyarylalkylenepyridinium, polyarylalkylenepyrimidinium, polyarylalkylenepyrazinium, polyarylalkylenepyradizimium, polyarylalkylenethiazinium, polyarylalkylenemorpholinium, polyarylalkylenepiperidinium, polyarylalkylenepiperizinium, polyarylalkylenepyrollizinium, polyarylalkylenetriphenylphosphonium, polyarylalkylenetrimethylphosphonium, polyarylalkylenetriethylphosphonium, polyarylalkylenetripropylphosphonium, polyarylalkylenetributylphosphonium, polyarylalkylenetrichlorophosphonium, polyarylalkylenetrifluorophosphonium, and polyarylalkylenediazolium.

Cationic polymeric backbones can be associated with one or more anions, including for example $F^-$, $Cl^-$, $Br^-$, $I^-$, $NO_2^-$, $NO_3^-$, $SO_4^{2-}$, $R^7SO_4^-$, $R^7CO_2^-$, $PO_4^{2-}$, $R^7PO_3^-$, and $R^7PO_2^-$, where $R^7$ is selected from hydrogen, $C_{1-4}$ alkyl, and $C_{1-4}$ heteroalkyl. In one embodiment, each anion can be selected from $Cl^-$, $Br^-$, $I^-$, $HSO_4^-$, $HCO_2^-$, $CH_3CO_2^-$, and $NO_3^-$. In other embodiments, each anion is acetate. In other embodiments, each anion is bisulfate. In other embodiments, each anion is chloride. In other embodiments, X is nitrate.

In other embodiments of the polymeric catalysts, the polymeric backbone is alkyleneimidazolium, which refers to an alkylene moiety, in which one or more of the methylene units of the alkylene moiety has been replaced with imidazolium. In one embodiment, the polymeric backbone is selected from polyethyleneimidazolium, polyprolyeneimidazolium, and polybutyleneimidazolium. It should further be understood that, in other embodiments of the polymeric backbone, when a nitrogen-containing cationic group or a phosphorous-containing cationic group follows the term "alkylene", one or more of the methylene units of the alkylene moiety is substituted with that nitrogen-containing cationic group or phosphorous-containing cationic group.

In other embodiments, monomers having heteroatoms can be combined with one or more difunctionalized compounds, such as dihaloalkanes, di(alkylsulfonyloxy)alkanes, and di(arylsulfonyloxy)alkanes to form polymers. The monomers have at least two heteroatoms to link with the difunctionalized alkane to create the polymeric chain. These difunctionalized compounds can be further substituted as described herein. In some embodiments, the difunctionalized compound(s) can be selected from 1,2-dichloroethane, 1,2-dichloropropane, 1,3-dichloropropane, 1,2-dichlorobutane, 1,3-dichlorobutane, 1,4-dichlorobutane, 1,2-dichloropentane, 1,3-dichloropentane, 1,4-dichloropentane, 1,5-dichloropentane, 1,2-dibromoethane, 1,2-dibromopropane, 1,3-dibromopropane, 1,2-dibromobutane, 1,3-dibromobutane, 1,4-dibromobutane, 1,2-dibromopentane, 1,3-dibromopentane, 1,4-dibromopentane, 1,5-dibromopentane, 1,2-diiodoethane, 1,2-diiodopropane, 1,3-diiodopropane, 1,2-diiodobutane, 1,3-diiodobutane, 1,4-diiodobutane, 1,2-diiodopentane, 1,3-diiodopentane, 1,4-diiodopentane, 1,5-diiodopentane, 1,2-dimethanesulfoxyethane, 1,2-dimethanesulfoxypropane, 1,3-dimethanesulfoxypropane, 1,2-dimethanesulfoxybutane, 1,3-dimethanesulfoxybutane, 1,4-dimethanesulfoxybutane, 1,2-dimethanesulfoxypentane, 1,3-dimethanesulfoxypentane, 1,4-dimethanesulfoxypentane, 1,5-dimethanesulfoxypentane, 1,2-diethanesulfoxyethane, 1,2-diethanesulfoxypropane, 1,3-diethanesulfoxypropane, 1,2-diethanesulfoxybutane, 1,3-diethanesulfoxybutane, 1,4-diethanesulfoxybutane, 1,2-diethanesulfoxypentane, 1,3-diethanesulfoxypentane, 1,4-diethanesulfoxypentane, 1,5-diethanesulfoxypentane, 1,2-dibenzenesulfoxyethane, 1,2-dibenzenesulfoxypropane, 1,3-dibenzenesulfoxypropane, 1,2-dibenzenesulfoxybutane, 1,3-dibenzenesulfoxybutane, 1,4-dibenzenesulfoxybutane, 1,2-dibenzenesulfoxypentane, 1,3-dibenzenesulfoxypentane, 1,4-dibenzenesulfoxypentane, 1,5-dibenzenesulfoxypentane, 1,2-di-p-toluenesulfoxyethane, 1,2-di-p-toluenesulfoxypropane, 1,3-di-p-toluenesulfoxypropane, 1,2-di-p-toluenesulfoxybutane, 1,3-di-p-toluenesulfoxybutane, 1,4-di-p-toluenesulfoxybutane, 1,2-di-p-toluenesulfoxypentane, 1,3-di-p-toluene sulfoxypentane, 1,4-di-p-toluene sulfoxypentane, and 1,5-di-p-toluene sulfoxypentane.

Further, the number of atoms between side chains in the polymeric backbone can vary. In some embodiments, there are between zero and twenty atoms, zero and ten atoms, zero and six atoms, or zero and three atoms between side chains attached to the polymeric backbone.

In some embodiments, the polymer can be a homopolymer having at least two monomer units, and where all the units contained within the polymer are derived from the same monomer in the same manner. In other embodiments, the polymer can be a heteropolymer having at least two monomer units, and where at least one monomeric unit contained within the polymer that differs from the other monomeric units in the polymer. The different monomer units in the polymer can be in a random order, in an alternating sequence of any length of a given monomer, or in blocks of monomers.

Other exemplary polymers include, for example, polyalkylene backbones that are substituted with one or more groups selected from hydroxyl, carboxylic acid, unsubstituted and substituted phenyl, halides, unsubstituted and substituted amines, unsubstituted and substituted ammonias, unsubstituted and substituted pyrroles, unsubstituted and substituted imidazoles, unsubstituted and substituted pyrazoles, unsubstituted and substituted oxazoles, unsubstituted and substituted thiazoles, unsubstituted and substituted pyridines, unsubstituted and substituted pyrimidines, unsubstituted and substituted pyrazines, unsubstituted and substituted pyradizines, unsubstituted and substituted thiazines, unsubstituted and substituted morpholines, unsubstituted and substituted piperidines, unsubstituted and substituted piperizines, unsubstituted and substituted pyrollizines, unsubstituted and substituted triphenylphosphonates, unsubstituted and substituted trimethylphosphonates, unsubstituted and substituted triethylphosphonates, unsubstituted and substituted tripropylphosphonates, unsubstituted and substituted tributylphosphonates, unsubstituted and substituted trichlorophosphonates, unsubstituted and substituted trifluorophosphonates, and unsubstituted and substituted diazoles.

For the polymers as described herein, multiple naming conventions are well recognized in the art. For instance, a polyethylene backbone with a direct bond to an unsubstituted phenyl group (—$CH_2$—CH(phenyl)-$CH_2$—CH(phenyl)-) is also known as polystyrene. Should that phenyl group be substituted with an ethenyl group, the polymer can be named a polydivinylbenzene (—$CH_2$—CH(4-vinylphenyl)-$CH_2$—CH(4-vinylphenyl)-). Further examples of heteropolymers may include those that are functionalized after polymerization.

One suitable example would be polystyrene-co-divinylbenzene: (—$CH_2$—CH(phenyl)-$CH_2$—CH(4-ethylenephenyl)-$CH_2$—CH(phenyl)-$CH_2$—CH(4-ethylenephenyl)-). Here, the ethenyl functionality could be at the 2, 3, or 4 position on the phenyl ring.

Figure 12:
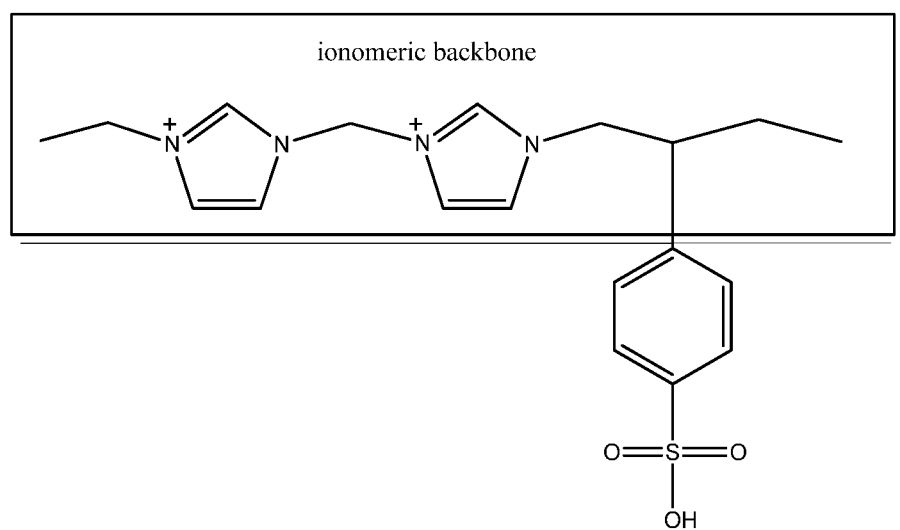
FIG. 12 illustrates a portion of a polymeric catalyst with an ionomeric backbone.

With reference to FIG. 12, in yet another embodiment, the polymeric backbone is a polyalkyleneimidazolium.

Figure 10:
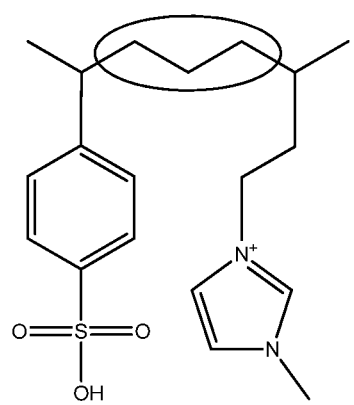
FIG. 10 illustrates two side chains in a polymeric catalyst, in which there are three carbon atoms between the side chain with the Bronsted-Lowry acid and the side chain with the cationic group.
Figure 11:
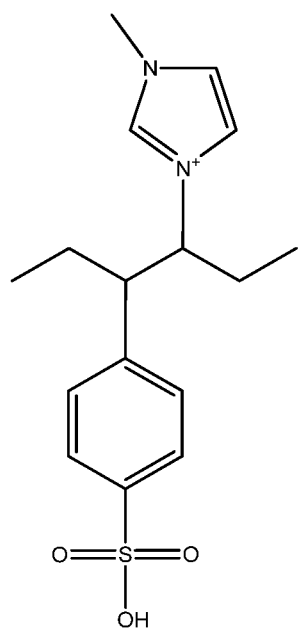
FIG. 11 illustrates two side chains in a polymeric catalyst, in which there are zero carbons between the side chain with the Bronsted-Lowry acid and the side chain with the cationic group.

Further, the number of atoms between side chains in the polymeric backbone can vary. In some embodiments, there are between zero and twenty atoms, zero and ten atoms, or zero and six atoms, or zero and three atoms between side chains attached to the polymeric backbone. With reference to FIG. 10, in one embodiment, there are three carbon atoms between the side chain with the Bronsted-Lowry acid and the side chain with the cationic group. In another example, with reference to FIG. 11, there are zero atoms between the side chain with the acidic moiety and the side chain with the ionic moiety.

Solid Particles for Polymeric Catalysts

The polymeric catalysts described herein can form solid particles. One of skill in the art would recognize the various known techniques and methods to make solid particles from the polymers described herein. For example, a solid particle can be formed through the procedures of emulsion or dispersion polymerization, which are known to one of skill in the art. In other embodiments, the solid particles can be formed by grinding or breaking the polymer into particles, which are also techniques and methods that are known to one of skill in the art. Methods known in the art to prepare solid particles include coating the polymers described herein on the surface of a solid core. Suitable materials for the solid core can include an inert material (e.g., aluminum oxide, corn cob, crushed glass, chipped plastic, pumice, silicon carbide, or walnut shell) or a magnetic material. Polymeric coated core particles can be made by dispersion polymerization to grow a cross-linked polymer shell around the core material, or by spray coating or melting.

Other methods known in the art to prepare solid particles include coating the polymers described herein on the surface of a solid core. The solid core can be a non-catalytic support. Suitable materials for the solid core can include an inert material (e.g., aluminum oxide, corn cob, crushed glass, chipped plastic, pumice, silicon carbide, or walnut shell) or a magnetic material. In one embodiment of the polymeric catalyst, the solid core is made up of iron. Polymeric coated core particles can be made by techniques and methods that are known to one of skill in the art, for example, by dispersion polymerization to grow a cross-linked polymer shell around the core material, or by spray coating or melting.

The solid supported polymer catalyst particle can have a solid core where the polymer is coated on the surface of the solid core. In some embodiments, at least about 5%, at least about 10%, at least about 20%, at least about 30%, at least about 40%, or at least about 50% of the catalytic activity of the solid particle can be present on or near the exterior surface of the solid particle. In some embodiments, the solid core can have an inert material or a magnetic material. In one embodiment, the solid core is made up of iron.

The solid particles coated with the polymer described herein have one or more catalytic properties. In some embodiments, at least about 50%, at least about 60%, at least about 70%, at least about 80% or at least about 90% of the catalytic activity of the solid particle is present on or near the exterior surface of the solid particle.

In some embodiments, the solid particle is substantially free of pores, for example, having no more than about 50%, no more than about 40%, no more than about 30%, no more than about 20%, no more than about 15%, no more than about 10%, no more than about 5%, or no more than about 1% of pores. Porosity can be measured by methods well known in the art, such as determining the Brunauer-Emmett-Teller (BET) surface area using the absorption of nitrogen gas on the internal and external surfaces of a material (Brunauer, S. et al., J. Am. Chem. Soc. 1938, 60:309). Other methods include measuring solvent retention by exposing the material to a suitable solvent (such as water), then removing it thermally to measure the volume of interior pores. Other solvents suitable for porosity measurement of the polymeric catalysts include, for example, polar solvents such as DMF, DMSO, acetone, and alcohols.

In other embodiments, the solid particles include a microporous gel resin. In yet other embodiments, the solid particles include a macroporous gel resin.

Support of the Solid-Supported Catalysts

In certain embodiments of the solid-supported catalyst, the support may be selected from biochar, carbon, amorphous carbon, activated carbon, silica, silica gel, alumina, magnesia, titania, zirconia, clays (e.g., kaolinite), magnesium silicate, silicon carbide, zeolites (e.g., mordenite), ceramics, and any combinations thereof. In one embodiment, the support is carbon. The support for carbon support can be biochar, amorphous carbon, or activated carbon. In one embodiment, the support is activated carbon.

The carbon support can have a surface area from 0.01 to 50 m$^2$/g of dry material. The carbon support can have a density from 0.5 to 2.5 kg/L. The support can be characterized using any suitable instrumental analysis methods or techniques known in the art, including for example scanning electron microscopy (SEM), powder X-ray diffraction (XRD), Raman spectroscopy, and Fourier Transform infrared spectroscopy (FTIR). The carbon support can be prepared from carbonaceous materials, including for example, shrimp shell, chitin, coconut shell, wood pulp, paper pulp, cotton, cellulose, hard wood, soft wood, wheat straw, sugarcane bagasse, cassava stem, corn stover, oil palm residue, bitumen, asphaltum, tar, coal, pitch, and any combinations thereof. One of skill in the art would recognize suitable methods to prepare the carbon supports used herein. See e.g., M. Inagaki, L. R. Radovic, *Carbon*, vol. 40, p. 2263 (2002), or A. G. Pandolfo and A. F. Hollenkamp, "Review: Carbon Properties and their role in supercapacitors," *Journal of Power Sources*, vol. 157, pp. 11-27 (2006).

In other embodiments, the support is silica, silica gel, alumina, or silica-alumina. One of skill in the art would recognize suitable methods to prepare these silica- or alumina-based solid supports used herein. See e.g., Catalyst supports and supported catalysts, by A. B. Stiles, Butterworth Publishers, Stoneham Mass., 1987.

In yet other embodiments, the support is a combination of a carbon support, with one or more other supports selected from silica, silica gel, alumina, magnesia, titania, zirconia, clays (e.g., kaolinite), magnesium silicate, silicon carbide, zeolites (e.g., mordenite), and ceramics.

Definitions

"Bronsted-Lowry acid" refers to a molecule, or substituent thereof, in neutral or ionic form that is capable of donating a proton (hydrogen cation, H$^+$).

"Homopolymer" refers to a polymer having at least two monomer units, and where all the units contained within the polymer are derived from the same monomer. One suitable example is polyethylene, where ethylene monomers are linked to form a uniform repeating chain (—CH$_2$—CH$_2$—CH$_2$—). Another suitable example is polyvinyl chloride, having a structure (—CH$_2$—CHCl—CH$_2$—CHCl—) where the —CH$_2$—CHCl— repeating unit is derived from the H$_2$C=CHCl monomer.

"Heteropolymer" refers to a polymer having at least two monomer units, and where at least one monomeric unit differs from the other monomeric units in the polymer. Heteropolymer also refers to polymers having difunctionalized or trifunctionalized monomer units that can be incorporated in the polymer in different ways. The different monomer units in the polymer can be in a random order, in an alternating sequence of any length of a given monomer, or in blocks of monomers. One suitable example is polyethyleneimidazolium, where if in an alternating sequence, would be the polymer depicted in FIG. 12. Another suitable example is polystyrene-co-divinylbenzene, where if in an alternating sequence, could be (—CH$_2$—CH(phenyl)-CH$_2$—CH(4-ethylenephenyl)-CH$_2$—CH(phenyl)-CH$_2$—CH(4-ethylenephenyl)-). Here, the ethenyl functionality could be at the 2, 3, or 4 position on the phenyl ring.

As used herein, ∿∿∿∿ denotes the attachment point of a moiety to the parent structure.

When a range of values is listed, it is intended to encompass each value and sub-range within the range. For example, "C$_{1-6}$ alkyl" (which may also be referred to as 1-6C alkyl, C1-C6 alkyl, or C1-6 alkyl) is intended to encompass, C$_1$, C$_2$, C$_3$, C$_4$, C$_5$, C$_6$, C$_{1-6}$, C$_{1-5}$, C$_{1-4}$, C$_{1-3}$, C$_{1-2}$, C$_{2-6}$, C$_{2-5}$, C$_{2-4}$, C$_{2-3}$, C$_{3-6}$, C$_{3-5}$, C$_{3-4}$, C$_{4-6}$, C$_{4-5}$, and C$_{5-6}$ alkyl.

"Alkyl" includes saturated straight-chained or branched monovalent hydrocarbon radicals, which contain only C and H when unsubstituted. In some embodiments, alkyl as used herein may have 1 to 10 carbon atoms (e.g., C$_{1-10}$ alkyl), 1 to 6 carbon atoms (e.g., C$_{1-6}$ alkyl), or 1 to 3 carbon atoms (e.g., C$_{1-3}$ alkyl). Representative straight-chained alkyls include, for example, methyl, ethyl, n-propyl, n-butyl, n-pentyl, and n-hexyl. Representative branched alkyls include, for example, isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, and 2,3-dimethylbutyl. When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl, and iso-propyl.

"Alkoxy" refers to the group —O-alkyl, which is attached to the parent structure through an oxygen atom. Examples of alkoxy may include methoxy, ethoxy, propoxy, and isopropoxy. In some embodiments, alkoxy as used herein has 1 to 6 carbon atoms (e.g., O—($C_{1-6}$ alkyl)), or 1 to 4 carbon atoms (e.g., O—($C_{1-4}$alkyl)).

"Alkenyl" refers to straight-chained or branched monovalent hydrocarbon radicals, which contain only C and H when unsubstituted and at least one double bond. In some embodiments, alkenyl has 2 to 10 carbon atoms (e.g., $C_{2-10}$ alkenyl), or 2 to 5 carbon atoms (e.g., C2-5 alkenyl). When an alkenyl residue having a specific number of carbons is named, all geometric isomers having that number of carbons are intended to be encompassed and described; thus, for example, "butenyl" is meant to include n-butenyl, sec-butenyl, and iso-butenyl. Examples of alkenyl may include —CH=$CH_2$, —$CH_2$—CH=$CH_2$ and —$CH_2$—CH=CH—CH=$CH_2$. The one or more carbon-carbon double bonds can be internal (such as in 2-butenyl) or terminal (such as in 1-butenyl). Examples of $C_{2-4}$ alkenyl groups include ethenyl (C2), 1-propenyl (C3), 2-propenyl (C3), 1-butenyl (C4), 2-butenyl (C4), and butadienyl (C4). Examples of C2-6 alkenyl groups include the aforementioned $C_{2-4}$ alkenyl groups as well as pentenyl (C5), pentadienyl (C5), and hexenyl (C6). Additional examples of alkenyl include heptenyl (C7), octenyl (C8), and octatrienyl (C8).

"Alkynyl" refers to straight-chained or branched monovalent hydrocarbon radicals, which contain only C and H when unsubstituted and at least one triple bond. In some embodiments, alkynyl has 2 to 10 carbon atoms (e.g., $C_{2-10}$ alkynyl), or 2 to 5 carbon atoms (e.g., $C_{2-5}$ alkynyl). When an alkynyl residue having a specific number of carbons is named, all geometric isomers having that number of carbons are intended to be encompassed and described; thus, for example, "pentynyl" is meant to include n-pentynyl, sec-pentynyl, iso-pentynyl, and tert-pentynyl. Examples of alkynyl may include —C≡CH or —C≡C—$CH_3$.

In some embodiments, alkyl, alkoxy, alkenyl, and alkynyl at each occurrence may independently be unsubstituted or substituted by one or more of substituents. In certain embodiments, substituted alkyl, substituted alkoxy, substituted alkenyl, and substituted alkynyl at each occurrence may independently have 1 to 5 substituents, 1 to 3 substituents, 1 to 2 substituents, or 1 substituent. Examples of alkyl, alkoxy, alkenyl, and alkynyl substituents may include alkoxy, cycloalkyl, aryl, aryloxy, amino, amido, carbamate, carbonyl, oxo (=O), heteroalkyl (e.g., ether), heteroaryl, heterocycloalkyl, cyano, halo, haloalkoxy, haloalkyl, and thio. In certain embodiments, the one or more substituents of substituted alkyl, alkoxy, alkenyl, and alkynyl is independently selected from cycloalkyl, aryl, heteroalkyl (e.g., ether), heteroaryl, heterocycloalkyl, cyano, halo, haloalkoxy, haloalkyl, oxo, —$OR_a$, —$N(R_a)_2$, —$C(O)N(R_a)_2$, —$N(R_a)C(O)R_a$, —$C(O)R_a$, —$N(R_a)S(O)_tR_a$ (where t is 1 or 2), —$SR_a$, and —$S(O)_tN(R_a)_2$ (where t is 1 or 2). In certain embodiments, each $R_a$ is independently hydrogen, alkyl, alkenyl, alkynyl, haloalkyl, heteroalkyl, cycloalkyl, aryl, heterocycloalkyl, heteroaryl (e.g., bonded through a ring carbon), —C(O)R' and —$S(O)_tR'$ (where t is 1 or 2), where each R' is independently hydrogen, alkyl, alkenyl, alkynyl, haloalkyl, heteroalkyl, cycloalkyl, aryl, heterocycloalkyl, or heteroaryl. In one embodiment, $R_a$ is independently hydrogen, alkyl, haloalkyl, cycloalkyl, aryl, aralkyl (e.g., alkyl substituted with aryl, bonded to parent structure through the alkyl group), heterocycloalkyl, or heteroaryl.

"Heteroalkyl", "heteroalkenyl" and "heteroalkynyl" includes alkyl, alkenyl and alkynyl groups, respectively, wherein one or more skeletal chain atoms are selected from an atom other than carbon, e.g., oxygen, nitrogen, sulfur, phosphorus, or any combinations thereof. For example, heteroalkyl may be an ether where at least one of the carbon atoms in the alkyl group is replaced with an oxygen atom. A numerical range can be given, e.g., $C_{1-4}$ heteroalkyl which refers to the chain length in total, which in this example is 4 atoms long. For example, a —$CH_2OCH_2CH_3$ group is referred to as a "$C_4$" heteroalkyl, which includes the heteroatom center in the atom chain length description. Connection to the rest of the parent structure can be through, in one embodiment, a heteroatom, or, in another embodiment, a carbon atom in the heteroalkyl chain. Heteroalkyl groups may include, for example, ethers such as methoxyethanyl (—$CH_2CH_2OCH_3$), ethoxymethanyl (—$CH_2OCH_2CH_3$), (methoxymethoxy)ethanyl (—$CH_2CH_2OCH_2OCH_3$), (methoxymethoxy)methanyl (—$CH_2OCH_2OCH_3$) and (methoxyethoxy)methanyl (—$CH_2OCH_2CH_2OCH_3$); amines such as —$CH_2CH_2NHCH_3$, —$CH_2CH_2N(CH_3)_2$, —$CH_2NHCH_2CH_3$, and —$CH_2N(CH_2CH_3)(CH_3)$. In some embodiments, heteroalkyl, heteroalkenyl, or heteroalkynyl may be unsubstituted or substituted by one or more of substituents. In certain embodiments, a substituted heteroalkyl, heteroalkenyl, or heteroalkynyl may have 1 to 5 substituents, 1 to 3 substituents, 1 to 2 substituents, or 1 substituent. Examples for heteroalkyl, heteroalkenyl, or heteroalkynyl substituents may include the substituents described above for alkyl.

"Carbocyclyl" may include cycloalkyl, cycloalkenyl or cycloalkynyl. "Cycloalkyl" refers to a monocyclic or polycyclic alkyl group. "Cycloalkenyl" refers to a monocyclic or polycyclic alkenyl group (e.g., containing at least one double bond). "Cycloalkynyl" refers to a monocyclic or polycyclic alkynyl group (e.g., containing at least one triple bond). The cycloalkyl, cycloalkenyl, or cycloalkynyl can consist of one ring, such as cyclohexyl, or multiple rings, such as adamantyl. A cycloalkyl, cycloalkenyl, or cycloalkynyl with more than one ring can be fused, spiro or bridged, or combinations thereof. In some embodiments, cycloalkyl, cycloalkenyl, and cycloalkynyl has 3 to 10 ring atoms (i.e., $C_3$-$C_{10}$ cycloalkyl, $C_3$-$C_{10}$ cycloalkenyl, and $C_3$-$C_{10}$ cycloalkynyl), 3 to 8 ring atoms (e.g., $C_3$-$C_8$ cycloalkyl, $C_3$-$C_8$ cycloalkenyl, and $C_3$-$C_8$ cycloalkynyl), or 3 to 5 ring atoms (i.e., $C_3$-$C_5$ cycloalkyl, $C_3$-$C_5$ cycloalkenyl, and $C_3$-$C_5$ cycloalkynyl). In certain embodiments, cycloalkyl, cycloalkenyl, or cycloalkynyl includes bridged and spiro-fused cyclic structures containing no heteroatoms. In other embodiments, cycloalkyl, cycloalkenyl, or cycloalkynyl includes monocyclic or fused-ring polycyclic (i.e., rings which share adjacent pairs of ring atoms) groups. $C_{3-6}$ carbocyclyl groups may include, for example, cyclopropyl ($C_3$), cyclobutyl ($C_4$), cyclopentyl ($C_5$), cyclopentenyl ($C_5$), cyclohexyl ($C_6$), cyclohexenyl ($C_6$), and cyclohexadienyl ($C_6$). $C_{3-8}$ carbocyclyl groups may include, for example, the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, and bicyclo[2.2.2]octanyl. $C_{3-10}$ carbocyclyl groups may include, for example, the aforementioned $C_{3-8}$ carbocyclyl groups as well as octahydro-1H-indenyl, decahydronaphthalenyl, and spiro[4.5]decanyl.

"Heterocyclyl" refers to carbocyclyl as described above, with one or more ring heteroatoms independently selected from nitrogen, oxygen, phosphorous, and sulfur. Heterocyclyl may include, for example, heterocycloalkyl, heterocycloalkenyl, and heterocycloalknyl. In some embodiments, heterocyclyl is a 3- to 18-membered non-aromatic monocyclic or polycyclic moiety that has at least one heteroatom selected from nitrogen, oxygen, phosphorous and sulfur. In certain embodiments, the heterocyclyl can be a monocyclic or polycyclic (e.g., bicyclic, tricyclic or tetracyclic), wherein polycyclic ring systems can be a fused, bridged or spiro ring system. Heterocyclyl polycyclic ring systems can include one or more heteroatoms in one or both rings.

An N-containing heterocyclyl moiety refers to an non-aromatic group in which at least one of the skeletal atoms of the ring is a nitrogen atom. The heteroatom(s) in the heterocyclyl group is optionally oxidized. One or more nitrogen atoms, if present, are optionally quaternized. In certain embodiments, heterocyclyl may also include ring systems substituted with one or more oxide (—O—) substituents, such as piperidinyl N-oxides. The heterocyclyl is attached to the parent molecular structure through any atom of the ring(s).

In some embodiments, heterocyclyl also includes ring systems with one or more fused carbocyclyl, aryl or heteroaryl groups, wherein the point of attachment is either on the carbocyclyl or heterocyclyl ring. In some embodiments, heterocyclyl is a 5-10 membered non-aromatic ring system having ring carbon atoms and 1-4 ring heteroatoms, wherein each heteroatom is independently selected from nitrogen, oxygen and sulfur (e.g., 5-10 membered heterocyclyl). In some embodiments, a heterocyclyl group is a 5-8 membered non-aromatic ring system having ring carbon atoms and 1-4 ring heteroatoms, wherein each heteroatom is independently selected from nitrogen, oxygen and sulfur (e.g., 5-8 membered heterocyclyl). In some embodiments, a heterocyclyl group is a 5-6 membered non-aromatic ring system having ring carbon atoms and 1-4 ring heteroatoms, wherein each heteroatom is independently selected from nitrogen, oxygen and sulfur (e.g., 5-6 membered heterocyclyl). In some embodiments, the 5-6 membered heterocyclyl has 1-3 ring heteroatoms selected from nitrogen, oxygen and sulfur. In some embodiments, the 5-6 membered heterocyclyl has 1-2 ring heteroatoms selected from nitrogen, oxygen and sulfur. In some embodiments, the 5-6 membered heterocyclyl has 1 ring heteroatom selected from nitrogen, oxygen and sulfur.

"Aryl" refers to an aromatic group having a single ring (e.g., phenyl), multiple rings (e.g., biphenyl), or multiple fused rings (e.g., naphthyl, fluorenyl, and anthryl). In some embodiments, aryl as used herein has 6 to 10 ring atoms (e.g., $C_6$-$C_{10}$ aromatic or $C_6$-$C_{10}$ aryl) which has at least one ring having a conjugated pi electron system. For example, bivalent radicals formed from substituted benzene derivatives and having the free valences at ring atoms are named as substituted phenylene radicals. In certain embodiments, aryl may have more than one ring where at least one ring is non-aromatic can be connected to the parent structure at either an aromatic ring position or at a non-aromatic ring position. In certain embodiments, aryl includes monocyclic or fused-ring polycyclic (i.e., rings which share adjacent pairs of ring atoms) groups.

"Heteroaryl" refers to an aromatic group having a single ring, multiple rings, or multiple fused rings, with one or more ring heteroatoms independently selected from nitrogen, oxygen, phosphorous, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl is a 5- to 18-membered monocyclic or polycyclic (e.g., bicyclic or tricyclic) aromatic ring system (e.g., having 6, 10 or 14 pi electrons shared in a cyclic array) having ring carbon atoms and 1 to 6 ring heteroatoms provided in the aromatic ring system, wherein each heteroatom is independently selected from nitrogen, oxygen, phosphorous and sulfur (e.g., 5-18 membered heteroaryl). In certain embodiments, heteroaryl may have a single ring (e.g., pyridyl, pyridinyl, imidazolyl) or multiple condensed rings (e.g., indolizinyl, benzothienyl) which condensed rings may or may not be aromatic. In other embodiments, heteroaryl may have more than one ring where at least one ring is non-aromatic can be connected to the parent structure at either an aromatic ring position or at a non-aromatic ring position. In one embodiment, heteroaryl may have more than one ring where at least one ring is non-aromatic is connected to the parent structure at an aromatic ring position. Heteroaryl polycyclic ring systems can include one or more heteroatoms in one or both rings.

For example, in one embodiment, an N-containing "heteroaryl" refers to an aromatic group in which at least one of the skeletal atoms of the ring is a nitrogen atom. One or more heteroatom(s) in the heteroaryl group can be optionally oxidized. One or more nitrogen atoms, if present, are optionally quaternized. In other embodiments, heteroaryl may include ring systems substituted with one or more oxide (—O—) substituents, such as pyridinyl N-oxides. The heteroaryl may be attached to the parent molecular structure through any atom of the ring(s).

In other embodiments, heteroaryl may include ring systems with one or more fused aryl groups, wherein the point of attachment is either on the aryl or on the heteroaryl ring. In yet other embodiments, heteroaryl may include ring systems with one or more carbocyclyl or heterocycyl groups wherein the point of attachment is on the heteroaryl ring. For polycyclic heteroaryl groups wherein one ring does not contain a heteroatom (e.g., indolyl, quinolinyl, and carbazolyl) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur (e.g., 5-10 membered heteroaryl). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur (e.g., 5-8 membered heteroaryl). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur (e.g., 5-6 membered heteroaryl). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

In some embodiments, carbocyclyl (including, for example, cycloalkyl, cycloalkenyl or cycloalkynyl), aryl, heteroaryl, and heterocyclyl at each occurrence may independently be unsubstituted or substituted by one or more of substituents. In certain embodiments, a substituted carbocyclyl (including, for example, substituted cycloalkyl, substituted cycloalkenyl or substituted cycloalkynyl), substituted aryl, substituted heteroaryl, substituted heterocyclyl at each occurrence may be independently may independently have 1 to 5 substituents, 1 to 3 substituents, 1 to 2 substituents, or 1 substituent. Examples of carbocyclyl (including, for example, cycloalkyl, cycloalkenyl or cycloalkynyl), aryl, heteroaryl, heterocyclyl substituents may include alkyl alkenyl, alkoxy, cycloalkyl, aryl, heteroalkyl (e.g., ether), heteroaryl, heterocycloalkyl, cyano, halo, haloalkoxy, haloalkyl, oxo (=O), —OR$_a$, —N(R$_a$)$_2$, —C(O)N(R$_a$)$_2$, —N(R$_a$)C(O)R$_a$, —C(O)R$_a$, —N(R$_a$)S(O)$_t$R$_a$ (where t is 1 or 2), —SR$_a$, and —S(O)$_t$N(R$_a$)$_2$ (where t is 1 or 2), wherein R$_a$ is as described herein.

It should be understood that, as used herein, any moiety referred to as a "linker" refers to the moiety has having bivalency. Thus, for example, "alkyl linker" refers to the same residues as alkyl, but having bivalency. Examples of alkyl linkers include —CH$_2$—, —CH$_2$CH$_2$—, —CH$_2$CH$_2$CH$_2$—, and —CH$_2$CH$_2$CH$_2$CH$_2$—. "Alkenyl linker" refers to the same residues as alkenyl, but having bivalency. Examples of alkenyl linkers include —CH=CH—, —CH$_2$—CH=CH— and —CH$_2$—CH=CH—CH$_2$—. "Alkynyl linker" refers to the same residues as alkynyl, but having bivalency. Examples alkynyl linkers include —C≡C— or —C≡C—CH$_2$—. Similarly, "carbocyclyl linker", "aryl linker", "heteroaryl linker", and "heterocyclyl linker" refer to the same residues as carbocyclyl, aryl, heteroaryl, and heterocyclyl, respectively, but having bivalency.

"Amino" or "amine" refers to —N(R$_a$)(R$_b$), where each R$_a$ and R$_b$ is independently selected from hydrogen, alkyl, alkenyl, alkynyl, haloalkyl, heteroalkyl (e.g., bonded through a chain carbon), cycloalkyl, aryl, heterocycloalkyl (e.g., bonded through a ring carbon), heteroaryl (e.g., bonded through a ring carbon), —C(O)R' and —S(O)$_t$R' (where t is 1 or 2), where each R' is independently hydrogen, alkyl, alkenyl, alkynyl, haloalkyl, heteroalkyl, cycloalkyl, aryl, heterocycloalkyl, or heteroaryl. It should be understood that, in one embodiment, amino includes amido (e.g., —NR$_a$C(O)R$_b$). It should be further understood that in certain embodiments, the alkyl, alkenyl, alkynyl, haloalkyl, heteroalkyl, cycloalkyl, aryl, heterocycloalkyl, or heteroaryl moiety of R$_a$ and R$_b$ may be further substituted as described herein. R$_a$ and R$_b$ may be the same or different. For example, in one embodiment, amino is —NH$_2$ (where R$_a$ and R$_b$ are each hydrogen). In other embodiments where R$_a$ and R$_b$ are other than hydrogen, R$_a$ and R$_b$ can be combined with the nitrogen atom to which they are attached to form a 3-, 4-, 5-, 6-, or 7-membered ring. Such examples may include 1-pyrrolidinyl and 4-morpholinyl.

"Ammonium" refers to —N(R$_a$)(R$_b$)(R$_c$)$^+$, where each R$_a$, R$_b$ and R$_c$ is independently selected from hydrogen, alkyl, alkenyl, alkynyl, haloalkyl, heteroalkyl (e.g., bonded through a chain carbon), cycloalkyl, aryl, heterocycloalkyl (e.g., bonded through a ring carbon), heteroaryl (e.g., bonded through a ring carbon), —C(O)R' and —S(O)$_t$R' (where t is 1 or 2), where each R' is independently hydrogen, alkyl, alkenyl, alkynyl, haloalkyl, heteroalkyl, cycloalkyl, aryl, heterocycloalkyl, or heteroaryl; or any two of R$_a$, R$_b$ and R$_c$ may be taken together with the atom to which they are attached to form a cycloalkyl, heterocycloalkyl; or any three of R$_a$, R$_b$ and R$_c$ may be taken together with the atom to which they are attached to form aryl or heteroaryl. It should be further understood that in certain embodiments, the alkyl, alkenyl, alkynyl, haloalkyl, heteroalkyl, cycloalkyl, aryl, heterocycloalkyl, or heteroaryl moiety of any one or more of R$_a$, R$_b$ and R$_c$ may be further substituted as described herein. R$_a$, R$_b$ and R$_c$ may be the same or different.

In certain embodiments, "amino" also refers to N-oxides of the groups —N$^+$(H)(R$_a$)O$^-$, and —N$^+$(R$_a$)(R$_b$)O—, where R$_a$ and R$_b$ are as described herein, where the N-oxide is bonded to the parent structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O) N(R$_a$)(R$_b$) or —NR$^a$C(O)R$_b$, where R$_a$ and R$_b$ at each occurrence are as described herein. In some embodiments, amido is a C$_{1-4}$ amido, which includes the amide carbonyl in the total number of carbons in the group. When a —C(O) N(R$_a$)(R$_b$) has R$_a$ and R$_b$ other than hydrogen, they can be combined with the nitrogen atom to form a 3-, 4-, 5-, 6-, or 7-membered ring.

"Carbonyl" refers to —C(O)R$_a$, where R$_a$ is hydrogen, alkyl, alkenyl, alkynyl, haloalkyl, heteroalkyl, cycloalkyl, aryl, heterocycloalkyl, heteroaryl, —N(R')$_2$, —S(O)$_t$R', where each R' is independently hydrogen, alkyl, alkenyl, alkynyl, haloalkyl, heteroalkyl, cycloalkyl, aryl, heterocycloalkyl, or heteroaryl, and t is 1 or 2. In certain embodiments where each R' are other than hydrogen, the two R' moieties can be combined with the nitrogen atom to which they are attached to form a 3-, 4-, 5-, 6-, or 7-membered ring. It should be understood that, in one embodiment, carbonyl includes amido (e.g., —C(O) N(R$_a$)(R$_b$)).

"Carbamate" refers to any of the following groups: —O—C(=O)—N(R$_a$)(R$_b$) and —N(R$_a$)—C(=O)—OR$_b$, wherein R$_a$ and R$_b$ at each occurrence are as described herein.

"Cyano" refers to a —CN group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy moieties as described above, wherein one or more hydrogen atoms are replaced by halo. For example, where a residue is substituted with more than one halo groups, it may be referred to by using a prefix corresponding to the number of halo groups attached. For example, dihaloaryl, dihaloalkyl, and trihaloaryl refer to aryl and alkyl substituted with two ("di") or three ("tri") halo groups, which may be, but are not necessarily, the same halogen; thus, for example, 3,5-difluorophenyl, 3-chloro-5-fluorophenyl, 4-chloro-3-fluorophenyl, and 3,5-difluoro-4-chlorophenyl is within the scope of dihaloaryl. Other examples of a haloalkyl group include difluoromethyl (—CHF$_2$), trifluoromethyl (—CF$_3$), 2,2,2-trifluoroethyl, and 1-fluoromethyl-2-fluoroethyl. Each of the alkyl, alkenyl, alkynyl and alkoxy groups of haloalkyl, haloalkenyl, haloalkynyl and haloalkoxy, respectively, can be optionally substituted as defined herein. "Perhaloalkyl" refers to an alkyl or alkylene group in which all of the hydrogen atoms have been replaced with a halogen (e.g., fluoro, chloro, bromo, or iodo). In some embodiments, all of the hydrogen atoms are each replaced with fluoro. In some embodiments, all of the hydrogen atoms are each replaced with chloro. Examples of perhaloalkyl groups include —CF$_3$, —CF$_2$CF$_3$, —CF$_2$CF$_2$CF$_3$, —CCl$_3$, —CFCl$_2$, and —CF$_2$Cl.

"Thio" refers to —SR$_a$, wherein R$_a$ is as described herein.
"Thiol" refers to the group —R$_a$SH, wherein R$_a$ is as described herein.

"Sulfinyl" refers to —S(O)R$_a$. In some embodiments, sulfinyl is —S(O)N(R$_a$)(R$_b$). "Sulfonyl" refers to the —S(O$_2$)R$_a$. In some embodiments, sulfonyl is —S(O$_2$) N(R$_a$)(R$_b$) or —S(O$_2$)OH. For each of these moieties, it should be understood that R$_a$ and R$_b$ are as described herein.

"Moiety" refers to a specific segment or functional group of a molecule. Chemical moieties are often recognized chemical entities embedded in or appended to a molecule.

As used herein, the term "unsubstituted" means that for carbon atoms, only hydrogen atoms are present besides those valencies linking the atom to the parent molecular group. One example is propyl (—$CH_2$—$CH_2$—$CH_3$). For nitrogen atoms, valencies not linking the atom to the parent molecular group are either hydrogen or an electron pair. For sulfur atoms, valencies not linking the atom to the parent molecular group are either hydrogen, oxygen or electron pair(s).

As used herein, the term "substituted" or "substitution" means that at least one hydrogen present on a group (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from alkyl alkenyl, alkoxy, cycloalkyl, aryl, heteroalkyl (e.g., ether), heteroaryl, heterocycloalkyl, cyano, halo, haloalkoxy, haloalkyl, oxo (=O), —$OR_a$, —$N(R_a)_2$, —$C(O)N(R_a)_2$, —$N(R_a)C(O)R_a$, —$C(O)R_a$, —$N(R_a)S(O)_tR_a$ (where t is 1 or 2), —$SR_a$, and —$S(O)_tN(R_a)_2$ (where t is 1 or 2), wherein $R_a$ is as described herein.

Where substituent groups are specified by their conventional chemical formulae, written from left to right, they equally encompass the chemically identical substituents that would result from writing the structure from right to left, e.g., —$CH_2O$— is equivalent to —$OCH_2$—.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

Reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of between ±0.1% and ±15% of the stated number. For example, in one variation, "about 1" refers to a range between 0.85 and 1.15.

Reference to "between" two values or parameters herein includes (and describes) embodiments that include those two values or parameters per se. For example, description referring to "between x and y" includes description of "x" and "y" per se.

Representative Examples of Catalysts

It should be understood that the polymeric catalysts and the solid-supported catalysts can include any of the Bronsted-Lowry acids, cationic groups, counterions, linkers, hydrophobic groups, cross-linking groups, and polymeric backbones or solid supports (as the case may be) described herein, as if each and every combination were listed separately. For example, in one embodiment, the catalyst can include benzenesulfonic acid (i.e., a sulfonic acid with a phenyl linker) connected to a polystyrene backbone or attached to the solid support, and an imidazolium chloride connected directly to the polystyrene backbone or attached directly to the solid support. In another embodiment, the polymeric catalyst can include boronyl-benzyl-pyridinium chloride (i.e., a boronic acid and pyridinium chloride in the same monomer unit with a phenyl linker) connected to a polystyrene backbone or attached to the solid support. In yet another embodiment, the catalyst can include benzenesulfonic acid and imidazolium sulfate each individually connected to a polyvinyl alcohol backbone or individually attached to the solid support.

In some embodiments, the polymeric catalyst is selected from:

poly [styrene-co-4-vinylbenzenesulfonic acid-co-3-methyl-1-(4-vinylbenzyl)-3H-imidazol-1-ium chloride-co-divinylbenzene];

poly [styrene-co-4-vinylbenzenesulfonic acid-co-3-methyl-1-(4-vinylbenzyl)-3H-imidazol-1-ium bisulfate-co-divinylbenzene];

poly [styrene-co-4-vinylbenzenesulfonic acid-co-3-methyl-1-(4-vinylbenzyl)-3H-imidazol-1-ium acetate-co-divinylbenzene];

poly [styrene-co-4-vinylbenzenesulfonic acid-co-3-methyl-1-(4-vinylbenzyl)-3H-imidazol-1-ium nitrate-co-divinylbenzene];

poly [styrene-co-4-vinylbenzenesulfonic acid-co-3-ethyl-1-(4-vinylbenzyl)-3H-imidazol-1-ium chloride-co-divinylbenzene];

poly [styrene-co-4-vinylbenzenesulfonic acid-co-3-ethyl-1-(4-vinylbenzyl)-3H-imidazol-1-ium bisulfate-co-divinylbenzene];

poly [styrene-co-4-vinylbenzenesulfonic acid-co-3-ethyl-1-(4-vinylbenzyl)-3H-imidazol-1-ium acetate-co-divinylbenzene];

poly [styrene-co-4-vinylbenzenesulfonic acid-co-3-ethyl-1-(4-vinylbenzyl)-3H-imidazol-1-ium nitrate-co-divinylbenzene];

poly [styrene-co-4-vinylbenzenesulfonic acid-co-1-(4-vinylbenzyl)-3H-imidazol-1-ium chloride-co-divinylbenzene];

poly [styrene-co-4-vinylbenzenesulfonic acid-co-1-(4-vinylbenzyl)-3H-imidazol-1-ium iodide-co-divinylbenzene];

poly [styrene-co-4-vinylbenzenesulfonic acid-co-1-(4-vinylbenzyl)-3H-imidazol-1-ium bromide-co-divinylbenzene];

poly [styrene-co-4-vinylbenzenesulfonic acid-co-1-(4-vinylbenzyl)-3H-imidazol-1-ium bisulfate-co-divinylbenzene];

poly [styrene-co-4-vinylbenzenesulfonic acid-co-1-(4-vinylbenzyl)-3H-imidazol-1-ium acetate-co-divinylbenzene];

poly [styrene-co-4-vinylbenzenesulfonic acid-co-3-methyl-1-(4-vinylbenzyl)-3H-benzoimidazol-1-ium chloride-co-divinylbenzene];

poly [styrene-co-4-vinylbenzenesulfonic acid-co-3-methyl-1-(4-vinylbenzyl)-3H-benzoimidazol-1-ium bisulfate-co-divinylbenzene];

poly [styrene-co-4-vinylbenzenesulfonic acid-co-3-methyl-1-(4-vinylbenzyl)-3H-benzoimidazol-1-ium acetate-co-divinylbenzene];

poly [styrene-co-4-vinylbenzenesulfonic acid-co-3-methyl-1-(4-vinylbenzyl)-3H-benzoimidazol-1-ium formate-co-divinylbenzene];

poly [styrene-co-4-vinylbenzenesulfonic acid-co-1-(4-vinylbenzyl)-pyridinium-chloride-co-divinylbenzene];

poly [styrene-co-4-vinylbenzenesulfonic acid-co-1-(4-vinylbenzyl)-pyridinium-bisulfate-co-divinylbenzene];

poly [styrene-co-4-vinylbenzenesulfonic acid-co-1-(4-vinylbenzyl)-pyridinium-acetate-co-divinylbenzene];

poly [styrene-co-4-vinylbenzenesulfonic acid-co-1-(4-vinylbenzyl)-pyridinium-nitrate-co-divinylbenzene];
poly[styrene-co-4-vinylbenzenesulfonic acid-co-1-(4-vinylbenzyl)-pyridinium-chloride-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-bromide-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-iodide-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-bisulfate-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-acetate-co-3-methyl-1-(4-vinylbenzyl)-3H-imidazol-1-ium bisulfate-co-divinylbenzene];
poly[styrene-co-4-vinylbenzenesulfonic acid-co-4-methyl-4-(4-vinylbenzyl)-morpholin-4-ium chloride-co-divinylbenzene];
poly[styrene-co-4-vinylbenzenesulfonic acid-co-4-methyl-4-(4-vinylbenzyl)-morpholin-4-ium bisulfate-co-divinylbenzene];
poly[styrene-co-4-vinylbenzenesulfonic acid-co-4-methyl-4-(4-vinylbenzyl)-morpholin-4-ium acetate-co-divinylbenzene];
poly[styrene-co-4-vinylbenzenesulfonic acid-co-4-methyl-4-(4-vinylbenzyl)-morpholin-4-ium formate-co-divinylbenzene];
poly[styrene-co-4-vinylbenzenesulfonic acid-co-triphenyl-(4-vinylbenzyl)-phosphonium chloride-co-divinylbenzene];
poly[styrene-co-4-vinylbenzenesulfonic acid-co-triphenyl-(4-vinylbenzyl)-phosphonium bisulfate-co-divinylbenzene];
poly[styrene-co-4-vinylbenzenesulfonic acid-co-triphenyl-(4-vinylbenzyl)-phosphonium acetate-co-divinylbenzene];
poly[styrene-co-4-vinylbenzenesulfonic acid-co-1-methyl-1-(4-vinylbenzyl)-piperidin-1-ium chloride-co-divinylbenzene];
poly[styrene-co-4-vinylbenzenesulfonic acid-co-1-methyl-1-(4-vinylbenzyl)-piperidin-1-ium bisulfate-co-divinylbenzene];
poly[styrene-co-4-vinylbenzenesulfonic acid-co-1-methyl-1-(4-vinylbenzyl)-piperidin-1-ium acetate-co-divinylbenzene];
poly[styrene-co-4-vinylbenzenesulfonic acid-co-4-(4-vinylbenzyl)-morpholine-4-oxide-co-divinyl benzene];
poly[styrene-co-4-vinylbenzenesulfonic acid-co-triethyl-(4-vinylbenzyl)-ammonium chloride-co-divinylbenzene];
poly[styrene-co-4-vinylbenzenesulfonic acid-co-triethyl-(4-vinylbenzyl)-ammonium bisulfate-co-divinylbenzene];
poly[styrene-co-4-vinylbenzenesulfonic acid-co-triethyl-(4-vinylbenzyl)-ammonium acetate-co-divinylbenzene];
poly[styrene-co-3-methyl-1-(4-vinylbenzyl)-3H-imidazol-1-ium chloride-co-4-boronyl-1-(4-vinylbenzyl)-pyridinium chloride-co-divinylbenzene];
poly[styrene-co-3-methyl-1-(4-vinylbenzyl)-3H-imidazol-1-ium chloride-co-1-(4-vinylphenyl)methylphosphonic acid-co-divinylbenzene];
poly[styrene-co-3-methyl-1-(4-vinylbenzyl)-3H-imidazol-1-ium bisulfate-co-1-(4-vinylphenyl)methylphosphonic acid-co-divinylbenzene];
poly[styrene-co-3-methyl-1-(4-vinylbenzyl)-3H-imidazol-1-ium acetate-co-1-(4-vinylphenyl)methylphosphonic acid-co-divinylbenzene];
poly[styrene-co-3-methyl-1-(4-vinylbenzyl)-3H-imidazol-1-ium nitrate-co-1-(4-vinylphenyl)methylphosphonic acid-co-divinylbenzene];
poly[styrene-co-4-vinylbenzenesulfonic acid-co-vinylbenzylchloride-co-1-methyl-2-vinyl-pyridinium chloride-co-divinylbenzene];
poly[styrene-co-4-vinylbenzenesulfonic acid-co-vinylbenzylchloride-co-1-methyl-2-vinyl-pyridinium bisulfate-co-divinylbenzene];
poly[styrene-co-4-vinylbenzenesulfonic acid-co-vinylbenzylchloride-co-1-methyl-2-vinyl-pyridinium acetate-co-divinylbenzene];
poly[styrene-co-4-vinylbenzenesulfonic acid-co-4-(4-vinylbenzyl)-morpholine-4-oxide-co-divinyl benzene];
poly [styrene-co-4-vinylphenylphosphonic acid-co-3-methyl-1-(4-vinylbenzyl)-3H-imidazol-1-ium chloride-co-divinylbenzene];
poly [styrene-co-4-vinylphenylphosphonic acid-co-3-methyl-1-(4-vinylbenzyl)-3H-imidazol-1-ium bisulfate-co-divinylbenzene];
poly [styrene-co-4-vinylphenylphosphonic acid-co-3-methyl-1-(4-vinylbenzyl)-3H-imidazol-1-ium acetate-co-divinylbenzene];
poly[styrene-co-3-carboxymethyl-1-(4-vinylbenzyl)-3H-imidazol-1-ium chloride-co-divinylbenzene];
poly[styrene-co-3-carboxymethyl-1-(4-vinylbenzyl)-3H-imidazol-1-ium bisulfate-co-divinylbenzene];
poly[styrene-co-3-carboxymethyl-1-(4-vinylbenzyl)-3H-imidazol-1-ium acetate-co-divinylbenzene];
poly[styrene-co-5-(4-vinylbenzylamino)-isophthalic acid-co-3-methyl-1-(4-vinylbenzyl)-3H-imidazol-1-ium chloride-co-divinylbenzene];
poly[styrene-co-5-(4-vinylbenzylamino)-isophthalic acid-co-3-methyl-1-(4-vinylbenzyl)-3H-imidazol-1-ium bisulfate-co-divinylbenzene];
poly[styrene-co-5-(4-vinylbenzylamino)-isophthalic acid-co-3-methyl-1-(4-vinylbenzyl)-3H-imidazol-1-ium acetate-co-divinylbenzene];
poly[styrene-co-(4-vinylbenzylamino)-acetic acid-co-3-methyl-1-(4-vinylbenzyl)-3H-imidazol-1-ium chloride-co-divinylbenzene];
poly[styrene-co-(4-vinylbenzylamino)-acetic acid-co-3-methyl-1-(4-vinylbenzyl)-3H-imidazol-1-ium bisulfate-co-divinylbenzene];
poly[styrene-co-(4-vinylbenzylamino)-acetic acid-co-3-methyl-1-(4-vinylbenzyl)-3H-imidazol-1-ium acetate-co-divinylbenzene];
poly(styrene-co-4-vinylbenzenesulfonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzenephosphonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzenesulfonic acid-co-vinylbenzylmethylimidazolium bisulfate-co-vinylbenzylmethylmorpholinium bisulfate-co-vinylbenzyltriphenyl phosphonium bisulfate-co-divinylbenzene);
poly(styrene-co-4-vinylbenzenephosphonic acid-co-vinylbenzylmethylimidazolium bisulfate-co-vinylbenzylmethylmorpholinium bisulfate-co-vinylbenzyltriphenyl phosphonium bisulfate-co-divinylbenzene);
poly(styrene-co-4-vinylbenzenesulfonic acid-co-vinylbenzylmethylimidazolium acetate-co-vinylbenzylmethylmorpholinium acetate-co-vinylbenzyltriphenyl phosphonium acetate-co-divinylbenzene);

poly(styrene-co-4-vinylbenzenephosphonic acid-co-vinylbenzylmethylimidazolium acetate-co-vinylbenzylmethylmorpholinium acetate-co-vinylbenzyltriphenyl phosphonium acetate-co-divinylbenzene);
poly(styrene-co-4-vinylbenzenesulfonic acid-co-vinylbenzylmethylmorpholinium chloride-co-vinylbenzyltriphenylphosphonium chloride-co-divinylbenzene);
poly(styrene-co-4-vinylbenzenephosphonic acid-co-vinylbenzylmethylmorpholinium chloride-co-vinylbenzyltriphenylphosphonium chloride-co-divinylbenzene);
poly(styrene-co-4-vinylbenzenesulfonic acid-co-vinylbenzylmethylmorpholinium bisulfate-co-vinylbenzyltriphenylphosphonium bisulfate-co-divinylbenzene);
poly(styrene-co-4-vinylbenzenephosphonic acid-co-vinylbenzylmethylmorpholinium bisulfate-co-vinylbenzyltriphenylphosphonium bisulfate-co-divinylbenzene);
poly(styrene-co-4-vinylbenzenesulfonic acid-co-vinylbenzylmethylmorpholinium acetate-co-vinylbenzyltriphenylphosphonium bisulfate-co-divinylbenzene);
poly(styrene-co-4-vinylbenzenephosphonic acid-co-vinylbenzylmethylmorpholinium acetate-co-vinylbenzyltriphenylphosphonium bisulfate-co-divinylbenzene)
poly(styrene-co-4-vinylbenzenesulfonic acid-co-vinylmethylimidazolium chloride-co-divinylbenzene);
poly(styrene-co-4-vinylbenzenesulfonic acid-co-vinylmethylimidazolium bisulfate-co-divinylbenzene);
poly(styrene-co-4-vinylbenzenesulfonic acid-co-vinylmethylimidazolium acetate-co-divinylbenzene);
poly(styrene-co-4-vinylbenzenesulfonic acid-co-vinylmethylimidazolium nitrate-co-divinylbenzene);
poly(styrene-co-4-vinylbenzenephosphonic acid-co-vinylmethylimidazolium chloride-co-divinylbenzene);
poly(styrene-co-4-vinylbenzenephosphonic acid-co-vinylmethylimidazolium bisulfate-co-divinylbenzene);
poly(styrene-co-4-vinylbenzenephosphonic acid-co-vinylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium bisulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium bisulfate-co-divinylbenzene);
poly(styrene-co-4-vinylbenzenephosphonic acid-co-vinylbenzyltriphenylphosphonium acetate-co-divinylbenzene);
poly(styrene-co-4-vinylbenzenesulfonic acid-co-vinylbenzylmethylimidazolium chloride-co-divinylbenzene);
poly(styrene-co-4-vinylbenzenesulfonic acid-co-vinylbenzylmethylimidazolium bisulfate-co-divinylbenzene);
poly(styrene-co-4-vinylbenzenesulfonic acid-co-vinylbenzylmethylimidazolium acetate-co-divinylbenzene);
poly(styrene-co-4-vinylbenzenephosphonic acid-co-vinylbenzylmethylimidazolium chloride-co-divinylbenzene);
poly(styrene-co-4-vinylbenzenephosphonic acid-co-vinylbenzylmethylimidazolium bisulfate-co-divinylbenzene);
poly(styrene-co-4-vinylbenzenephosphonic acid-co-vinylbenzylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium bisulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium bisulfate-co-divinylbenzene);
poly(styrene-co-4-vinylbenzenephosphonic acid-co-vinylbenzyltriphenylphosphonium acetate-co-divinylbenzene);
poly(butyl-vinylimidazolium chloride-co-butylimidazolium bisulfate-co-4-vinylbenzenesulfonic acid);
poly(butyl-vinylimidazolium bisulfate-co-butylimidazolium bisulfate-co-4-vinylbenzenesulfonic acid);
poly(benzyl alcohol-co-4-vinylbenzylalcohol sulfonic acid-co-vinylbenzyltriphenylphosphonium chloride-co-divinylbenzyl alcohol); and
poly(benzyl alcohol-co-4-vinylbenzylalcohol sulfonic acid-co-vinylbenzyltriphenylphosphonium bisulfate-co-divinylbenzyl alcohol).

In some embodiments, the solid-supported catalyst is selected from:
amorphous carbon-supported pyrrolium chloride sulfonic acid;
amorphous carbon-supported imidazolium chloride sulfonic acid;
amorphous carbon-supported pyrazolium chloride sulfonic acid;
amorphous carbon-supported oxazolium chloride sulfonic acid;
amorphous carbon-supported thiazolium chloride sulfonic acid;
amorphous carbon-supported pyridinium chloride sulfonic acid;
amorphous carbon-supported pyrimidinium chloride sulfonic acid;
amorphous carbon-supported pyrazinium chloride sulfonic acid;
amorphous carbon-supported pyradizimium chloride sulfonic acid;
amorphous carbon-supported thiazinium chloride sulfonic acid;
amorphous carbon-supported morpholinium chloride sulfonic acid;
amorphous carbon-supported piperidinium chloride sulfonic acid;
amorphous carbon-supported piperizinium chloride sulfonic acid;
amorphous carbon-supported pyrollizinium chloride sulfonic acid;
amorphous carbon-supported triphenyl phosphonium chloride sulfonic acid;
amorphous carbon-supported trimethyl phosphonium chloride sulfonic acid;
amorphous carbon-supported triethyl phosphonium chloride sulfonic acid;
amorphous carbon-supported tripropyl phosphonium chloride sulfonic acid;
amorphous carbon-supported tributyl phosphonium chloride sulfonic acid;
amorphous carbon-supported trifluoro phosphonium chloride sulfonic acid;
amorphous carbon-supported pyrrolium bromide sulfonic acid;
amorphous carbon-supported imidazolium bromide sulfonic acid;

amorphous carbon-supported pyrazolium bromide sulfonic acid;
amorphous carbon-supported oxazolium bromide sulfonic acid;
amorphous carbon-supported thiazolium bromide sulfonic acid;
amorphous carbon-supported pyridinium bromide sulfonic acid;
amorphous carbon-supported pyrimidinium bromide sulfonic acid;
amorphous carbon-supported pyrazinium bromide sulfonic acid;
amorphous carbon-supported pyradizimium bromide sulfonic acid;
amorphous carbon-supported thiazinium bromide sulfonic acid;
amorphous carbon-supported morpholinium bromide sulfonic acid;
amorphous carbon-supported piperidinium bromide sulfonic acid;
amorphous carbon-supported piperizinium bromide sulfonic acid;
amorphous carbon-supported pyrollizinium bromide sulfonic acid;
amorphous carbon-supported triphenyl phosphonium bromide sulfonic acid;
amorphous carbon-supported trimethyl phosphonium bromide sulfonic acid;
amorphous carbon-supported triethyl phosphonium bromide sulfonic acid;
amorphous carbon-supported tripropyl phosphonium bromide sulfonic acid;
amorphous carbon-supported tributyl phosphonium bromide sulfonic acid;
amorphous carbon-supported trifluoro phosphonium bromide sulfonic acid;
amorphous carbon-supported pyrrolium bisulfate sulfonic acid;
amorphous carbon-supported imidazolium bisulfate sulfonic acid;
amorphous carbon-supported pyrazolium bisulfate sulfonic acid;
amorphous carbon-supported oxazolium bisulfate sulfonic acid;
amorphous carbon-supported thiazolium bisulfate sulfonic acid;
amorphous carbon-supported pyridinium bisulfate sulfonic acid;
amorphous carbon-supported pyrimidinium bisulfate sulfonic acid;
amorphous carbon-supported pyrazinium bisulfate sulfonic acid;
amorphous carbon-supported pyradizimium bisulfate sulfonic acid;
amorphous carbon-supported thiazinium bisulfate sulfonic acid;
amorphous carbon-supported morpholinium bisulfate sulfonic acid;
amorphous carbon-supported piperidinium bisulfate sulfonic acid;
amorphous carbon-supported piperizinium bisulfate sulfonic acid;
amorphous carbon-supported pyrollizinium bisulfate sulfonic acid;
amorphous carbon-supported triphenyl phosphonium bisulfate sulfonic acid;
amorphous carbon-supported trimethyl phosphonium bisulfate sulfonic acid;
amorphous carbon-supported triethyl phosphonium bisulfate sulfonic acid;
amorphous carbon-supported tripropyl phosphonium bisulfate sulfonic acid;
amorphous carbon-supported tributyl phosphonium bisulfate sulfonic acid;
amorphous carbon-supported trifluoro phosphonium bisulfate sulfonic acid;
amorphous carbon-supported pyrrolium formate sulfonic acid;
amorphous carbon-supported imidazolium formate sulfonic acid;
amorphous carbon-supported pyrazolium formate sulfonic acid;
amorphous carbon-supported oxazolium formate sulfonic acid;
amorphous carbon-supported thiazolium formate sulfonic acid;
amorphous carbon-supported pyridinium formate sulfonic acid;
amorphous carbon-supported pyrimidinium formate sulfonic acid;
amorphous carbon-supported pyrazinium formate sulfonic acid;
amorphous carbon-supported pyradizimium formate sulfonic acid;
amorphous carbon-supported thiazinium formate sulfonic acid;
amorphous carbon supported morpholinium formate sulfonic acid;
amorphous carbon-supported piperidinium formate sulfonic acid;
amorphous carbon-supported piperizinium formate sulfonic acid;
amorphous carbon-supported pyrollizinium formate sulfonic acid;
amorphous carbon-supported triphenyl phosphonium formate sulfonic acid;
amorphous carbon-supported trimethyl phosphonium formate sulfonic acid;
amorphous carbon-supported triethyl phosphonium formate sulfonic acid;
amorphous carbon-supported tripropyl phosphonium formate sulfonic acid;
amorphous carbon-supported tributyl phosphonium formate sulfonic acid;
amorphous carbon-supported trifluoro phosphonium formate sulfonic acid;
amorphous carbon-supported pyrrolium acetate sulfonic acid;
amorphous carbon-supported imidazolium acetate sulfonic acid;
amorphous carbon-supported pyrazolium acetate sulfonic acid;
amorphous carbon-supported oxazolium acetate sulfonic acid;
amorphous carbon-supported thiazolium acetate sulfonic acid;
amorphous carbon-supported pyridinium acetate sulfonic acid;
amorphous carbon-supported pyrimidinium acetate sulfonic acid;
amorphous carbon-supported pyrazinium acetate sulfonic acid;

amorphous carbon-supported pyradizimium acetate sulfonic acid;
amorphous carbon-supported thiazinium acetate sulfonic acid;
amorphous carbon-supported morpholinium acetate sulfonic acid;
amorphous carbon-supported piperidinium acetate sulfonic acid;
amorphous carbon-supported piperizinium acetate sulfonic acid;
amorphous carbon-supported pyrollizinium acetate sulfonic acid;
amorphous carbon-supported triphenyl phosphonium acetate sulfonic acid;
amorphous carbon-supported trimethyl phosphonium acetate sulfonic acid;
amorphous carbon-supported triethyl phosphonium acetate sulfonic acid;
amorphous carbon-supported tripropyl phosphonium acetate sulfonic acid;
amorphous carbon-supported tributyl phosphonium acetate sulfonic acid;
amorphous carbon-supported trifluoro phosphonium acetate sulfonic acid;
amorphous carbon-supported pyrrolium chloride phosphonic acid;
amorphous carbon-supported imidazolium chloride phosphonic acid;
amorphous carbon-supported pyrazolium chloride phosphonic acid;
amorphous carbon-supported oxazolium chloride phosphonic acid;
amorphous carbon-supported thiazolium chloride phosphonic acid;
amorphous carbon-supported pyridinium chloride phosphonic acid;
amorphous carbon-supported pyrimidinium chloride phosphonic acid;
amorphous carbon-supported pyrazinium chloride phosphonic acid;
amorphous carbon-supported pyradizimium chloride phosphonic acid;
amorphous carbon-supported thiazinium chloride phosphonic acid;
amorphous carbon-supported morpholinium chloride phosphonic acid;
amorphous carbon-supported piperidinium chloride phosphonic acid;
amorphous carbon-supported piperizinium chloride phosphonic acid;
amorphous carbon-supported pyrollizinium chloride phosphonic acid;
amorphous carbon-supported triphenyl phosphonium chloride phosphonic acid;
amorphous carbon-supported trimethyl phosphonium chloride phosphonic acid;
amorphous carbon-supported triethyl phosphonium chloride phosphonic acid;
amorphous carbon-supported tripropyl phosphonium chloride phosphonic acid;
amorphous carbon-supported tributyl phosphonium chloride phosphonic acid;
amorphous carbon-supported trifluoro phosphonium chloride phosphonic acid;
amorphous carbon-supported pyrrolium bromide phosphonic acid;
amorphous carbon-supported imidazolium bromide phosphonic acid;
amorphous carbon-supported pyrazolium bromide phosphonic acid;
amorphous carbon-supported oxazolium bromide phosphonic acid;
amorphous carbon-supported thiazolium bromide phosphonic acid;
amorphous carbon-supported pyridinium bromide phosphonic acid;
amorphous carbon-supported pyrimidinium bromide phosphonic acid;
amorphous carbon-supported pyrazinium bromide phosphonic acid;
amorphous carbon-supported pyradizimium bromide phosphonic acid;
amorphous carbon-supported thiazinium bromide phosphonic acid;
amorphous carbon-supported morpholinium bromide phosphonic acid;
amorphous carbon-supported piperidinium bromide phosphonic acid;
amorphous carbon-supported piperizinium bromide phosphonic acid;
amorphous carbon-supported pyrollizinium bromide phosphonic acid;
amorphous carbon-supported triphenyl phosphonium bromide phosphonic acid;
amorphous carbon-supported trimethyl phosphonium bromide phosphonic acid;
amorphous carbon-supported triethyl phosphonium bromide phosphonic acid;
amorphous carbon-supported tripropyl phosphonium bromide phosphonic acid;
amorphous carbon-supported tributyl phosphonium bromide phosphonic acid;
amorphous carbon-supported trifluoro phosphonium bromide phosphonic acid;
amorphous carbon-supported pyrrolium bisulfate phosphonic acid;
amorphous carbon-supported imidazolium bisulfate phosphonic acid;
amorphous carbon-supported pyrazolium bisulfate phosphonic acid;
amorphous carbon-supported oxazolium bisulfate phosphonic acid;
amorphous carbon-supported thiazolium bisulfate phosphonic acid;
amorphous carbon-supported pyridinium bisulfate phosphonic acid;
amorphous carbon-supported pyrimidinium bisulfate phosphonic acid;
amorphous carbon-supported pyrazinium bisulfate phosphonic acid;
amorphous carbon-supported pyradizimium bisulfate phosphonic acid;
amorphous carbon-supported thiazinium bisulfate phosphonic acid;
amorphous carbon-supported morpholinium bisulfate phosphonic acid;
amorphous carbon-supported piperidinium bisulfate phosphonic acid;
amorphous carbon-supported piperizinium bisulfate phosphonic acid;
amorphous carbon-supported pyrollizinium bisulfate phosphonic acid;

amorphous carbon-supported triphenyl phosphonium bisulfate phosphonic acid;
amorphous carbon-supported trimethyl phosphonium bisulfate phosphonic acid;
amorphous carbon-supported triethyl phosphonium bisulfate phosphonic acid;
amorphous carbon-supported tripropyl phosphonium bisulfate phosphonic acid;
amorphous carbon-supported tributyl phosphonium bisulfate phosphonic acid;
amorphous carbon-supported trifluoro phosphonium bisulfate phosphonic acid;
amorphous carbon-supported pyrrolium formate phosphonic acid;
amorphous carbon-supported imidazolium formate phosphonic acid;
amorphous carbon-supported pyrazolium formate phosphonic acid;
amorphous carbon-supported oxazolium formate phosphonic acid;
amorphous carbon-supported thiazolium formate phosphonic acid;
amorphous carbon-supported pyridinium formate phosphonic acid;
amorphous carbon-supported pyrimidinium formate phosphonic acid;
amorphous carbon-supported pyrazinium formate phosphonic acid;
amorphous carbon-supported pyradizimium formate phosphonic acid;
amorphous carbon-supported thiazinium formate phosphonic acid;
amorphous carbon-supported morpholinium formate phosphonic acid;
amorphous carbon-supported piperidinium formate phosphonic acid;
amorphous carbon-supported piperizinium formate phosphonic acid;
amorphous carbon-supported pyrollizinium formate phosphonic acid;
amorphous carbon-supported triphenyl phosphonium formate phosphonic acid;
amorphous carbon-supported trimethyl phosphonium formate phosphonic acid;
amorphous carbon-supported triethyl phosphonium formate phosphonic acid;
amorphous carbon-supported tripropyl phosphonium formate phosphonic acid;
amorphous carbon-supported tributyl phosphonium formate phosphonic acid;
amorphous carbon-supported trifluoro phosphonium formate phosphonic acid;
amorphous carbon-supported pyrrolium acetate phosphonic acid;
amorphous carbon-supported imidazolium acetate phosphonic acid;
amorphous carbon-supported pyrazolium acetate phosphonic acid;
amorphous carbon-supported oxazolium acetate phosphonic acid;
amorphous carbon-supported thiazolium acetate phosphonic acid;
amorphous carbon-supported pyridinium acetate phosphonic acid;
amorphous carbon-supported pyrimidinium acetate phosphonic acid;
amorphous carbon-supported pyrazinium acetate phosphonic acid;
amorphous carbon-supported pyradizimium acetate phosphonic acid;
amorphous carbon-supported thiazinium acetate phosphonic acid;
amorphous carbon-supported morpholinium acetate phosphonic acid;
amorphous carbon-supported piperidinium acetate phosphonic acid;
amorphous carbon-supported piperizinium acetate phosphonic acid;
amorphous carbon-supported pyrollizinium acetate phosphonic acid;
amorphous carbon-supported triphenyl phosphonium acetate phosphonic acid;
amorphous carbon-supported trimethyl phosphonium acetate phosphonic acid;
amorphous carbon-supported triethyl phosphonium acetate phosphonic acid;
amorphous carbon-supported tripropyl phosphonium acetate phosphonic acid;
amorphous carbon-supported tributyl phosphonium acetate phosphonic acid;
amorphous carbon-supported trifluoro phosphonium acetate phosphonic acid;
amorphous carbon-supported ethanoyl-triphosphonium sulfonic acid;
amorphous carbon-supported ethanoyl-methylmorpholinium sulfonic acid; and
amorphous carbon-supported ethanoyl-imidazolium sulfonic acid.
In other embodiments, the solid-supported catalyst is selected from:
activated carbon-supported pyrrolium chloride sulfonic acid;
activated carbon-supported imidazolium chloride sulfonic acid;
activated carbon-supported pyrazolium chloride sulfonic acid;
activated carbon-supported oxazolium chloride sulfonic acid;
activated carbon-supported thiazolium chloride sulfonic acid;
activated carbon-supported pyridinium chloride sulfonic acid;
activated carbon-supported pyrimidinium chloride sulfonic acid;
activated carbon-supported pyrazinium chloride sulfonic acid;
activated carbon-supported pyradizimium chloride sulfonic acid;
activated carbon-supported thiazinium chloride sulfonic acid;
activated carbon-supported morpholinium chloride sulfonic acid;
activated carbon-supported piperidinium chloride sulfonic acid;
activated carbon-supported piperizinium chloride sulfonic acid;
activated carbon-supported pyrollizinium chloride sulfonic acid;
activated carbon-supported triphenyl phosphonium chloride sulfonic acid;
activated carbon-supported trimethyl phosphonium chloride sulfonic acid;

activated carbon-supported triethyl phosphonium chloride sulfonic acid;
activated carbon-supported tripropyl phosphonium chloride sulfonic acid;
activated carbon-supported tributyl phosphonium chloride sulfonic acid;
activated carbon-supported trifluoro phosphonium chloride sulfonic acid;
activated carbon-supported pyrrolium bromide sulfonic acid;
activated carbon-supported imidazolium bromide sulfonic acid;
activated carbon-supported pyrazolium bromide sulfonic acid;
activated carbon-supported oxazolium bromide sulfonic acid;
activated carbon-supported thiazolium bromide sulfonic acid;
activated carbon-supported pyridinium bromide sulfonic acid;
activated carbon-supported pyrimidinium bromide sulfonic acid;
activated carbon-supported pyrazinium bromide sulfonic acid;
activated carbon-supported pyradizimium bromide sulfonic acid;
activated carbon-supported thiazinium bromide sulfonic acid;
activated carbon-supported morpholinium bromide sulfonic acid;
activated carbon-supported piperidinium bromide sulfonic acid;
activated carbon-supported piperizinium bromide sulfonic acid;
activated carbon-supported pyrollizinium bromide sulfonic acid;
activated carbon-supported triphenyl phosphonium bromide sulfonic acid;
activated carbon-supported trimethyl phosphonium bromide sulfonic acid;
activated carbon-supported triethyl phosphonium bromide sulfonic acid;
activated carbon-supported tripropyl phosphonium bromide sulfonic acid;
activated carbon-supported tributyl phosphonium bromide sulfonic acid;
activated carbon-supported trifluoro phosphonium bromide sulfonic acid;
activated carbon-supported pyrrolium bisulfate sulfonic acid;
activated carbon-supported imidazolium bisulfate sulfonic acid;
activated carbon-supported pyrazolium bisulfate sulfonic acid;
activated carbon-supported oxazolium bisulfate sulfonic acid;
activated carbon-supported thiazolium bisulfate sulfonic acid;
activated carbon-supported pyridinium bisulfate sulfonic acid;
activated carbon-supported pyrimidinium bisulfate sulfonic acid;
activated carbon-supported pyrazinium bisulfate sulfonic acid;
activated carbon-supported pyradizimium bisulfate sulfonic acid;
activated carbon-supported thiazinium bisulfate sulfonic acid;
activated carbon-supported morpholinium bisulfate sulfonic acid;
activated carbon-supported piperidinium bisulfate sulfonic acid;
activated carbon-supported piperizinium bisulfate sulfonic acid;
activated carbon-supported pyrollizinium bisulfate sulfonic acid;
activated carbon-supported triphenyl phosphonium bisulfate sulfonic acid;
activated carbon-supported trimethyl phosphonium bisulfate sulfonic acid;
activated carbon-supported triethyl phosphonium bisulfate sulfonic acid;
activated carbon-supported tripropyl phosphonium bisulfate sulfonic acid;
activated carbon-supported tributyl phosphonium bisulfate sulfonic acid;
activated carbon-supported trifluoro phosphonium bisulfate sulfonic acid;
activated carbon-supported pyrrolium formate sulfonic acid;
activated carbon-supported imidazolium formate sulfonic acid;
activated carbon-supported pyrazolium formate sulfonic acid;
activated carbon-supported oxazolium formate sulfonic acid;
activated carbon-supported thiazolium formate sulfonic acid;
activated carbon-supported pyridinium formate sulfonic acid;
activated carbon-supported pyrimidinium formate sulfonic acid;
activated carbon-supported pyrazinium formate sulfonic acid;
activated carbon-supported pyradizimium formate sulfonic acid;
activated carbon-supported thiazinium formate sulfonic acid;
activated carbon supported morpholinium formate sulfonic acid;
activated carbon-supported piperidinium formate sulfonic acid;
activated carbon-supported piperizinium formate sulfonic acid;
activated carbon-supported pyrollizinium formate sulfonic acid;
activated carbon-supported triphenyl phosphonium formate sulfonic acid;
activated carbon-supported trimethyl phosphonium formate sulfonic acid;
activated carbon-supported triethyl phosphonium formate sulfonic acid;
activated carbon-supported tripropyl phosphonium formate sulfonic acid;
activated carbon-supported tributyl phosphonium formate sulfonic acid;
activated carbon-supported trifluoro phosphonium formate sulfonic acid;
activated carbon-supported pyrrolium acetate sulfonic acid;
activated carbon-supported imidazolium acetate sulfonic acid;

activated carbon-supported pyrazolium acetate sulfonic acid;
activated carbon-supported oxazolium acetate sulfonic acid;
activated carbon-supported thiazolium acetate sulfonic acid;
activated carbon-supported pyridinium acetate sulfonic acid;
activated carbon-supported pyrimidinium acetate sulfonic acid;
activated carbon-supported pyrazinium acetate sulfonic acid;
activated carbon-supported pyradizimium acetate sulfonic acid;
activated carbon-supported thiazinium acetate sulfonic acid;
activated carbon-supported morpholinium acetate sulfonic acid;
activated carbon-supported piperidinium acetate sulfonic acid;
activated carbon-supported piperizinium acetate sulfonic acid;
activated carbon-supported pyrollizinium acetate sulfonic acid;
activated carbon-supported triphenyl phosphonium acetate sulfonic acid;
activated carbon-supported trimethyl phosphonium acetate sulfonic acid;
activated carbon-supported triethyl phosphonium acetate sulfonic acid;
activated carbon-supported tripropyl phosphonium acetate sulfonic acid;
activated carbon-supported tributyl phosphonium acetate sulfonic acid;
activated carbon-supported trifluoro phosphonium acetate sulfonic acid;
activated carbon-supported pyrrolium chloride phosphonic acid;
activated carbon-supported imidazolium chloride phosphonic acid;
activated carbon-supported pyrazolium chloride phosphonic acid;
activated carbon-supported oxazolium chloride phosphonic acid;
activated carbon-supported thiazolium chloride phosphonic acid;
activated carbon-supported pyridinium chloride phosphonic acid;
activated carbon-supported pyrimidinium chloride phosphonic acid;
activated carbon-supported pyrazinium chloride phosphonic acid;
activated carbon-supported pyradizimium chloride phosphonic acid;
activated carbon-supported thiazinium chloride phosphonic acid;
activated carbon-supported morpholinium chloride phosphonic acid;
activated carbon-supported piperidinium chloride phosphonic acid;
activated carbon-supported piperizinium chloride phosphonic acid;
activated carbon-supported pyrollizinium chloride phosphonic acid;
activated carbon-supported triphenyl phosphonium chloride phosphonic acid;
activated carbon-supported trimethyl phosphonium chloride phosphonic acid;
activated carbon-supported triethyl phosphonium chloride phosphonic acid;
activated carbon-supported tripropyl phosphonium chloride phosphonic acid;
activated carbon-supported tributyl phosphonium chloride phosphonic acid;
activated carbon-supported trifluoro phosphonium chloride phosphonic acid;
activated carbon-supported pyrrolium bromide phosphonic acid;
activated carbon-supported imidazolium bromide phosphonic acid;
activated carbon-supported pyrazolium bromide phosphonic acid;
activated carbon-supported oxazolium bromide phosphonic acid;
activated carbon-supported thiazolium bromide phosphonic acid;
activated carbon-supported pyridinium bromide phosphonic acid;
activated carbon-supported pyrimidinium bromide phosphonic acid;
activated carbon-supported pyrazinium bromide phosphonic acid;
activated carbon-supported pyradizimium bromide phosphonic acid;
activated carbon-supported thiazinium bromide phosphonic acid;
activated carbon-supported morpholinium bromide phosphonic acid;
activated carbon-supported piperidinium bromide phosphonic acid;
activated carbon-supported piperizinium bromide phosphonic acid;
activated carbon-supported pyrollizinium bromide phosphonic acid;
activated carbon-supported triphenyl phosphonium bromide phosphonic acid;
activated carbon-supported trimethyl phosphonium bromide phosphonic acid;
activated carbon-supported triethyl phosphonium bromide phosphonic acid;
activated carbon-supported tripropyl phosphonium bromide phosphonic acid;
activated carbon-supported tributyl phosphonium bromide phosphonic acid;
activated carbon-supported trifluoro phosphonium bromide phosphonic acid;
activated carbon-supported pyrrolium bisulfate phosphonic acid;
activated carbon-supported imidazolium bisulfate phosphonic acid;
activated carbon-supported pyrazolium bisulfate phosphonic acid;
activated carbon-supported oxazolium bisulfate phosphonic acid;
activated carbon-supported thiazolium bisulfate phosphonic acid;
activated carbon-supported pyridinium bisulfate phosphonic acid;
activated carbon-supported pyrimidinium bisulfate phosphonic acid;
activated carbon-supported pyrazinium bisulfate phosphonic acid;

activated carbon-supported pyradizimium bisulfate phosphonic acid;

activated carbon-supported thiazinium bisulfate phosphonic acid;

activated carbon-supported morpholinium bisulfate phosphonic acid;

activated carbon-supported piperidinium bisulfate phosphonic acid;

activated carbon-supported piperizinium bisulfate phosphonic acid;

activated carbon-supported pyrollizinium bisulfate phosphonic acid;

activated carbon-supported triphenyl phosphonium bisulfate phosphonic acid;

activated carbon-supported trimethyl phosphonium bisulfate phosphonic acid;

activated carbon-supported triethyl phosphonium bisulfate phosphonic acid;

activated carbon-supported tripropyl phosphonium bisulfate phosphonic acid;

activated carbon-supported tributyl phosphonium bisulfate phosphonic acid;

activated carbon-supported trifluoro phosphonium bisulfate phosphonic acid;

activated carbon-supported pyrrolium formate phosphonic acid;

activated carbon-supported imidazolium formate phosphonic acid;

activated carbon-supported pyrazolium formate phosphonic acid;

activated carbon-supported oxazolium formate phosphonic acid;

activated carbon-supported thiazolium formate phosphonic acid;

activated carbon-supported pyridinium formate phosphonic acid;

activated carbon-supported pyrimidinium formate phosphonic acid;

activated carbon-supported pyrazinium formate phosphonic acid;

activated carbon-supported pyradizimium formate phosphonic acid;

activated carbon-supported thiazinium formate phosphonic acid;

activated carbon-supported morpholinium formate phosphonic acid;

activated carbon-supported piperidinium formate phosphonic acid;

activated carbon-supported piperizinium formate phosphonic acid;

activated carbon-supported pyrollizinium formate phosphonic acid;

activated carbon-supported triphenyl phosphonium formate phosphonic acid;

activated carbon-supported trimethyl phosphonium formate phosphonic acid;

activated carbon-supported triethyl phosphonium formate phosphonic acid;

activated carbon-supported tripropyl phosphonium formate phosphonic acid;

activated carbon-supported tributyl phosphonium formate phosphonic acid;

activated carbon-supported trifluoro phosphonium formate phosphonic acid;

activated carbon-supported pyrrolium acetate phosphonic acid;

activated carbon-supported imidazolium acetate phosphonic acid;

activated carbon-supported pyrazolium acetate phosphonic acid;

activated carbon-supported oxazolium acetate phosphonic acid;

activated carbon-supported thiazolium acetate phosphonic acid;

activated carbon-supported pyridinium acetate phosphonic acid;

activated carbon-supported pyrimidinium acetate phosphonic acid;

activated carbon-supported pyrazinium acetate phosphonic acid;

activated carbon-supported pyradizimium acetate phosphonic acid;

activated carbon-supported thiazinium acetate phosphonic acid;

activated carbon-supported morpholinium acetate phosphonic acid;

activated carbon-supported piperidinium acetate phosphonic acid;

activated carbon-supported piperizinium acetate phosphonic acid;

activated carbon-supported pyrollizinium acetate phosphonic acid;

activated carbon-supported triphenyl phosphonium acetate phosphonic acid;

activated carbon-supported trimethyl phosphonium acetate phosphonic acid;

activated carbon-supported triethyl phosphonium acetate phosphonic acid;

activated carbon-supported tripropyl phosphonium acetate phosphonic acid;

activated carbon-supported tributyl phosphonium acetate phosphonic acid;

activated carbon-supported trifluoro phosphonium acetate phosphonic acid;

activated carbon-supported ethanoyl-triphosphonium sulfonic acid;

activated carbon-supported ethanoyl-methylmorpholinium sulfonic acid; and activated carbon-supported ethanoyl-imidazolium sulfonic acid.

Methods to prepare the polymeric and solid-supported catalysts described herein can be found in WO 2014/031956, which is hereby incorporated herein specifically with respect to paragraphs [0345]-[0380] and [0382]-[0472].

Reaction Conditions for Catalytic Oligosaccharide Formation

In some embodiments, the feed sugar and catalyst (e.g., polymeric catalyst or solid-supported catalyst) are allowed to react for at least 5 minutes, at least 10 minutes, at least 15 minutes, at least 30 minutes, at least 45 minutes, at least 1 hour, at least 2 hours, at least 3 hours, at least 4 hours, at least 6 hours, at least 8 hours, at least 16 hours, at least 24 hours, at least 36 hours, or at least 48 hours; or between 15-60 minutes, 30-60 minutes, 45-60 minutes, 1-24 hours, between 2-12 hours, between 3-6 hours, between 1-96 hours, between 12-72 hours, or between 12-48 hours.

In some embodiments, the degree of polymerization of the one or more oligosaccharides produced according to the methods described herein can be regulated by the reaction time. For example, in some embodiments, the degree of polymerization of the one or more oligosaccharides is increased by increasing the reaction time, while in other embodiments, the degree of polymerization of the one or more oligosaccharides is decreased by decreasing the reaction time.

Reaction Pressure

The reaction pressure in the methods described herein may affect the rate of reaction. In some embodiments, the reaction pressure is maintained in the range of about 0.05 bar to about 5.0 bar. In certain embodiments, the pressure is from about 0.3 bar to about 1.0 bar, about 0.3 to about 0.9 bar, about 0.4 to about 0.7 bar, or about 0.4 to about 0.6 bar.

Reaction Temperature

The reaction temperature in the methods described herein may affect the rate of reaction and yield. In some embodiments, the reaction temperature is maintained in the range of about 25° C. to about 180° C. In certain embodiments, the temperature is from about 60° C. to about 160° C., about 90° C. to about 150° C., about 100° C. to about 150° C., about 110° C. to about 1500° C., about 95° C. to about 105° C., or about 140° C. to 150° C.

Amount of Feed Sugar

The amount of the feed sugar used in the methods described herein relative to the amount solvent used may affect the rate of reaction and yield. The amount of the feed sugar used may be characterized by the dry solids content. In certain embodiments, dry solids content refers to the total solids of a slurry as a percentage on a dry weight basis. In some embodiments, the dry solids content of the feed sugar is between about 5 wt % to about 95 wt %, between about 10 wt % to about 80 wt %, between about 15 to about 75 wt %, or between about 15 to about 50 wt %.

Amount of Catalyst

The amount of the catalyst used in the methods described herein may depend on several factors including, for example, the selection of the type of feed sugar, the concentration of the feed sugar, and the reaction conditions (e.g., temperature, time, and pressure). In some embodiments, the weight ratio of the catalyst to the feed sugar is about 0.01 g/g to about 50 g/g, about 0.01 g/g to about 5 g/g, about 0.05 g/g to about 1.0 g/g, about 0.05 g/g to about 0.5 g/g, about 0.05 g/g to about 0.2 g/g, or about 0.1 g/g to about 0.2 g/g.

Solvent

In certain embodiments, the methods of using the catalyst are carried out in an aqueous environment. One suitable aqueous solvent is water, which may be obtained from various sources. Generally, water sources with lower concentrations of ionic species (e.g., salts of sodium, phosphorous, ammonium, or magnesium) are preferable, as such ionic species may reduce effectiveness of the catalyst. In some embodiments where the aqueous solvent is water, the water has a resistivity of at least 0.1 megaohm-centimeters, of at least 1 megaohm-centimeters, of at least 2 megaohm-centimeters, of at least 5 megaohm-centimeters, or of at least 10 megaohm-centimeters.

Water Content

Moreover, as the dehydration reaction of the methods progresses, water is produced with each coupling of the one or more sugars. In certain embodiments, the methods described herein may further include monitoring the amount of water present in the reaction mixture and/or the ratio of water to sugar or catalyst over a period of time. In some embodiments, the method further includes removing at least a portion of water produced in the reaction mixture (e.g., by removing at least about any of 10%, 20%, 30%, 40%, 50%, 60%, 70%, 80%, 90%, 95%, 97%, 99%, or 100%, such as by vacuum distillation). It should be understood, however, that the amount of water to sugar may be adjusted based on the reaction conditions and specific catalyst used.

Any method known in the art may be used to remove water in the reaction mixture, including, for example, by membrane filtration, vacuum distillation, heating, and/or evaporation. In some embodiments, the method comprises including water in the reaction mixture.

In some aspects, provided herein are methods of producing an oligosaccharide composition, by: combining a feed sugar and a catalyst having acidic and ionic moieties to form a reaction mixture, wherein water is produced in the reaction mixture; and removing at least a portion of the water produced in the reaction mixture. In certain variations, at least a portion of water is removed to maintain a water content in the reaction mixture of less than 99%, less than 90%, less than 80%, less than 70%, less than 60%, less than 50%, less than 40%, less than 30%, less than 20%, less than 10%, less than 5%, or less than 1% by weight.

In some embodiments, the degree of polymerization of the oligosaccharide composition or the functionalized oligosaccharide composition produced according to the methods described herein can be regulated by adjusting or controlling the concentration of water present in the reaction mixture. For example, in some embodiments, the degree of polymerization of the oligosaccharide composition is increased by decreasing the water concentration, while in other embodiments, the degree of polymerization of the oligosaccharide composition is decreased by increasing the water concentration. In some embodiments, the water content of the reaction is adjusted during the reaction to regulate the degree of polymerization of the oligosaccharide composition produced.

Batch Versus Continuous Processing

Generally, the catalyst and the feed sugar are introduced into an interior chamber of a reactor, either concurrently or sequentially. The reaction can be performed in a batch process or a continuous process. For example, in one embodiment, method is performed in a batch process, where the contents of the reactor are continuously mixed or blended, and all or a substantial amount of the products of the reaction are removed. In one variation, the method is performed in a batch process, where the contents of the reactor are initially intermingled or mixed but no further physical mixing is performed. In another variation, the method is performed in a batch process, wherein once further mixing of the contents, or periodic mixing of the contents of the reactor, is performed (e.g., at one or more times per hour), all or a substantial amount of the products of the reaction are removed after a certain period of time.

In some embodiments, the method is repeated in a sequential batch process, wherein at least a portion of the catalyst is separated from at least a portion of the oligosaccharide composition produced (e.g., as described in more detail infra) and is recycled by further contacting additional feed sugar.

For example, in one aspect, provided is a method for producing an oligosaccharide composition, by:

a) combining feed sugar with a catalyst to form a reaction mixture;

wherein the catalyst comprises acidic monomers and ionic monomers connected to form a polymeric backbone, or wherein the catalyst comprises a solid support, acidic moieties attached to the solid support, and ionic moieties attached to the solid support; and b) producing an oligosaccharide composition from at least a portion of the reaction mixture;

c) separating the oligosaccharide composition from the catalyst;

d) combining additional feed sugar with the separated catalyst to form additional reaction mixture; and e) producing additional oligosaccharide composition from at least a portion of the additional reaction mixture.

In some of embodiments wherein the method is performed in a batch process, the catalyst is recycled (e.g., steps (c)-(e) above are repeated) at least 1, at least 2, at least 3, at least 4, at least 5, at least 6, at least 7, at least 8, at least 9 or at least 10 times. In some of these embodiments, the catalyst retains at least 80% activity (e.g., at least 90%, 95%, 96%, 97%, 98%, or 99% activity) after being recycled 1, 2, 3, 4, 5, 6, 7, 8, 9 or 10 times, when compared to the catalytic activity under identical conditions prior to being recycled.

In other embodiments, the method is performed in a continuous process, where the contents flow through the reactor with an average continuous flow rate. After introduction of the catalyst and the feed sugar into the reactor, the contents of the reactor are continuously or periodically mixed or blended, and after a period of time, less than all of the products of the reaction are removed. In one variation, the method is performed in a horizontal thin film reactor. In another variation, the method is performed in a horizontal or vertical reactor containing a static mixer. In yet another variation, the method is performed in a continuous process, where the mixture containing the catalyst and one or more sugars is not actively mixed. Additionally, mixing of catalyst and feed sugar may occur as a result of the redistribution of catalysts settling by gravity, or the non-active mixing that occurs as the material flows through a continuous reactor. In some embodiments of the methods, the steps of combining the feed sugar with a catalyst and isolating the oligosaccharide composition produced are performed concurrently.

Reactors

The reactors used for the methods described herein may be open or closed reactors suitable for use in containing the chemical reactions described herein. Suitable reactors may include, for example, a fed-batch stirred reactor, a batch stirred reactor, a continuous flow stirred reactor with ultra-filtration, a horizontal thin-film reactor, a vertical thin-film reactor, a continuous plug-flow column reactor, an attrition reactor, or a reactor with intensive stirring induced by an electromagnetic field. See e.g., Fernanda de Castilhos Corazza, Flavio Faria de Moraes, Gisella Maria Zanin and Ivo Neitzel, Optimal control in fed-batch reactor for the cellobiose hydrolysis, *Acta Scientiarum. Technology*, 25: 33-38 (2003); Gusakov, A. V., and Sinitsyn, A. P., Kinetics of the enzymatic hydrolysis of cellulose: 1. A mathematical model for a batch reactor process, *Enz. Microb. Technol.*, 7: 346-352 (1985); Ryu, S. K., and Lee, J. M., Bioconversion of waste cellulose by using an attrition bioreactor, Biotechnol. Bioeng. 25: 53-65(1983); Gusakov, A. V., Sinitsyn, A. P., Davydkin, I. Y., Davydkin, V. Y., Protas, O. V., Enhancement of enzymatic cellulose hydrolysis using a novel type of bioreactor with intensive stirring induced by electromagnetic field, *Appl. Biochem. Biotechnol.*, 56: 141-153(1996). Other suitable reactor types may include, for example, fluidized bed, upflow blanket, immobilized, and extruder type reactors for hydrolysis and/or fermentation.

In certain embodiments where the method is performed as a continuous process, the reactor may include a continuous mixer, such as a screw mixer. The reactors may be generally fabricated from materials that are capable of withstanding the physical and chemical forces exerted during the processes described herein. In some embodiments, such materials used for the reactor are capable of tolerating high concentrations of strong liquid acids; however, in other embodiments, such materials may not be resistant to strong acids.

It should also be understood that additional feed sugar and/or catalyst may be added to the reactor, either at the same time or one after the other.

Separation and Purification

In some embodiments, the methods described herein further include isolating the one or more produced oligosaccharides. In some embodiments, the methods described herein further include isolating the one or more produced functionalized oligosaccharides. In some of these embodiments, isolating the one or more oligosaccharides and/or functionalized oligosaccharides comprises separating at least a portion of the one or more oligosaccharides from at least a portion of the polymeric catalyst (e.g., by vacuum filtration, pressure filtration, centrifugation, sedimentation, or cyclonic separation). In some of these embodiments, isolating the one or more oligosaccharides further comprises separating at least a portion of the one or more oligosaccharides from at least a portion of any unreacted sugar (e.g., by chromatography). In other embodiments, isolating the one or more functionalized oligosaccharides further comprises separating at least a portion of the one or more functionalized oligosaccharides from at least a portion of any unreacted sugar and/or unreacted functionalization compounds (e.g., by chromatography)

The one or more oligosaccharides or functionalized oligosaccharides can be separated from insoluble material of the reaction mixture, such as a solid polymeric catalyst, using technology well known in the art such as, for example, centrifugation, filtration (e.g., vacuum filtration or pressure filtration), and gravity settling. The one or more oligosaccharides or functionalized oligosaccharides can be separated from the one or more sugars of the reaction mixture, or one or more functionalization compounds of the reaction mixture, using technology well known in the art including, but not limited to, chromatography, electrophoretic procedures, differential solubility, or extraction.

The oligosaccharides isolated from the vessel may be subjected to further processing steps (e.g., as drying) or subsequent chemical treatment.

In some embodiments, the one or more isolated oligosaccharides are substantially pure. With respect to the methods, "substantially pure" intends an isolated preparation of the one or more oligosaccharides that contains no more than 25% (w/w) of non-oligosaccharide material, as determined by analytical procedures known in the art, such as determination by high performance liquid chromatography (HPLC), nuclear magnetic resonance (NMR) spectroscopy, functionalization and analysis by gas chromatography, mass spectrometry, spectrophotometric procedures based on chromophore complexation and/or carbohydrate oxidation-reduction chemistry. In some embodiments, the substantially pure preparation contains no more than 20%, or no more than 15%, or no more than 10%, or no more than 7.5%, or no more than 5%, or no more than 3%, or no more than 2%, or no more than 1%, or no more than 0.5%, or no more than 0.1% of non-oligosaccharide material.

Recyclability of Catalysts

The catalysts containing acidic and ionic groups used in the methods of producing oligosaccharide compositions, including functionalized oligosaccharide compositions, as described herein may be recycled. Thus, in one aspect, provided herein are methods of producing oligosaccharide compositions using recyclable catalysts. These methods may include combining one or more sugars with a catalyst to produce a product mixture, wherein the product mixture comprises an oligosaccharide composition and residual catalyst; isolating at least a portion of the residual catalyst from the product mixture; and combining one or more additional sugars with the isolated residual catalyst to produce an additional product mixture.

It should be understood that during use and/or recycling, a portion of the catalyst may undergo chemical degradation (for example, oxidation, de-functionalization, de-polymerization, or fouling) and/or physical degradation (for example, cracking of the support for a solid-supported catalyst). Thus, in some embodiments, at least a portion of the residual catalyst is chemically and/or physically different than the initial catalyst combined with the sugars in the first step. In some embodiments, sugars or reaction biproducts may adsorb onto the catalyst, either reversibly or irreversibly.

In some embodiments of the recycling methods described above, the one or more sugars and catalyst are further combined with one or more functionalization compounds to produce a functionalized oligosaccharide composition. In other embodiments of the methods described above, the oligosaccharide composition is combined with one or more functionalization compounds and the isolated residual catalyst to produce a functionalized oligosaccharide composition.

Any method known in the art may be used to separate the catalyst for reuse, including, for example, centrifugation, filtration (e.g., pressure filtration, vacuum filtration), phase separation, and gravity settling.

The methods described herein may be performed as batch or continuous processes. Recycling in a batch process may involve, for example, recovering the catalyst from the reaction mixture and reusing the recovered catalyst in one or more subsequent reaction cycles. Recycling in a continuous process may involve, for example, introducing additional feed sugar into the reactor, without additional of fresh catalyst.

In some of embodiments wherein at least a portion of the catalyst is recycled, the catalyst is recycled at least 1, at least 2, at least 3, at least 4, at least 5, at least 6, at least 7, at least 8, at least 9 or at least 10 times. In some of these embodiments, the catalyst retains at least 20%, at least 25%, at least 30%, at least 35%, at least 40%, at least 50%, at least 60%, at least 70%, at least 80%, at least 85%, at least 90%, at least 95%, at least 96%, at least 97%, at least 98%, or at least 99% activity after being recycled 1, 2, 3, 4, 5, 6, 7, 8, 9 or 10 times, when compared to the catalytic activity under identical conditions prior to being recycled. In some variations, the catalytic activity of the isolated catalyst in the production of the additional oligosaccharide composition is at least 30%, at least 40%, at least 50%, at least 60%, at least 70%, at least 80%, at least 85%, at least 90%, at least 95%, at least 96%, at least 97%, at least 98%, or at least 99% of the catalytic activity of the catalyst in the production of the first oligosaccharide composition. In some variations, the catalytic activity of the residual catalyst in the production of the additional oligosaccharide composition is at least 30%, at least 40%, at least 50%, at least 60%, at least 70%, at least 80%, at least 85%, at least 90%, at least 95%, at least 96%, at least 97%, at least 98%, or at least 99% of the catalytic activity of the catalyst in the production of the first oligosaccharide composition.

As used herein, the "catalyst activity" refers to the effective first order kinetic rate constant for the molar conversion of reactants, $k=-\ln(1-X(t))/t$. The molar conversion of the reactant A at time t is defined as $X_A(t)=1-\text{mol}(A,t)/\text{mol}(A,0)$, where mol(A,t) refers to the number of moles of species A present in the reaction mixture at time t and mol(A,0) refers to the number of moles of species A present at the start of the reaction, t=0. In practice, the number of moles of the reactant A is often measured at several points in time, $t_1$, $t_2$, $t_3$, ..., $t_n$ during a single reaction cycle and used to calculate the conversions $X_A(t_1)$, $X_A(t_2)$, ... $X_A(t_n)$ at the corresponding times. The first order rate constant k is then calculated by fitting the data for $X_A(t)$.

As used herein, a reaction "cycle" refers to one period of use within a sequence of uses of the catalyst. For example, in a batch process, a reaction cycle corresponds to the discrete steps of charging a reactor system with reactants and catalyst, heating the reaction under suitable conditions to convert the reactants, maintaining the reaction conditions for a specified residence time, separating the reaction products from the catalyst, and recovering the catalyst for re-use. In a continuous process, a cycle refers a single reactor space time during the operation of the continuous process. For example, in a 1,000 liter reactor with a continuous volumetric flow of 200 liters per hour, the continuous reactor space time is two hours, and the first two hour period of continuous operation is the first reaction cycle, the next two hour period of continuous operation is the second reaction cycle, etc. Thus, the catalyst recycling methods described herein include a continuous process wherein the catalyst is used over multiple reaction cycles to produce a reaction mixture comprising an oligosaccharide composition.

As used herein, the "loss of activity" or "activity loss" of a catalyst is determined by the average fractional reduction in the catalyst activity between consecutive cycles. For example, if the catalyst activity in reaction cycle 1 is k(1) and the catalyst activity in reaction cycle 2 is k(2), then the loss in catalyst activity between cycle 1 and cycle 2 is calculated as [k(2)−k(1)]/k(1). Over N reaction cycles, the loss of activity is then determined as $$\frac{1}{(N-1)}\sum_{i=2}^{N}\frac{k(i)-k(i-1)}{k(i)},$$

measured in units of fractional loss per cycle.

In some variations, the rate constant for the conversion of additional feed sugar is less than 20% lower than the rate constant for the conversion of the reactant feed sugar in the first reaction. In certain variations, the rate constant for conversion of the additional feed sugar is less than 15%, less than 12%, less than 10%, less than 8%, less than 6%, less than 4%, less than 2%, or less than 1% lower than the rate constant for the conversion of the reactant feed sugar in the first reaction. In some variations, the loss of activity is less than 20% per cycle, less than 15% per cycle, less than 10% per cycle, less than 8% per cycle, less than 4% per cycle, less than 2% per cycle, less than 1% per cycle, less than 0.5% per cycle, or less than 0.2% per cycle.

In other variations, the rate constant for the conversion of additional functionalizing compounds is less than 20% lower than the rate constant for the conversion of the functionalizing compounds in the first reaction. In certain variations, the rate constant for conversion of the additional functionalizing compounds is less than 15%, less than 12%, less than 10%, less than 8%, less than 6%, less than 4%, less than 2%, or less than 1% lower than the rate constant for the conversion of the functionalizing compounds in the first reaction. In some variations, the loss of activity is less than 20% per cycle, less than 15% per cycle, less than 10% per cycle, less than 8% per cycle, less than 4% per cycle, less than 2% per cycle, less than 1% per cycle, less than 0.5% per cycle, or less than 0.2% per cycle.

As used herein "catalyst lifetime" refers to the average number of cycles that a catalyst particle can be re-used before it no longer effectively catalyzes the conversion of additional reactant feed sugar. The catalyst lifetime is calculated as the reciprocal of the loss of activity. For example, if the loss of activity is 1% per cycle, then the catalyst lifetime is 100 cycles. In some variations, the catalyst lifetime is at least 1 cycle, at least 2 cycles, at least 10 cycles, at least 50 cycles, at least 100 cycles, at least 200 cycles, at least 500 cycles.

In certain embodiments, a portion of the total mass of the catalyst in a reaction may be removed and replaced with fresh catalyst between reaction cycles. For example, in some variations, 0.1% of the mass of the catalyst may be replaced between reaction cycles, 1% of the mass of the catalyst may be replaced between reaction cycles, 2% of the mass of the catalyst may be replaced between reaction cycles, 5% of the mass of the catalyst may be replaced between reaction cycles, 10% of the mass of the catalyst may be replaced between reaction cycles, or 20% of the mass of the catalyst may be replaced between reaction cycles.

As used herein, the "catalyst make-up rate" refers to the fraction of the catalyst mass that is replaced with fresh catalyst between reaction cycles.

Bond Refactoring

The sugar used in the methods described herein typically have α-1,4 bonds, and when used as reactants in the methods described herein, at least a portion of the α-1,4 bonds are converted into β-1,4 bonds, α-1,3 bonds, β-1,3 bonds, α-1,6 bonds, and β-1,6 bonds.

Thus, in certain aspects, provided is a method of producing an oligosaccharide composition, by:
combining feed sugar with a catalyst to form a reaction mixture,
wherein the feed sugar comprises α-1,4 bonds, and
wherein the catalyst comprises acidic monomers and ionic monomers connected to form a polymeric backbone, or wherein the catalyst comprises a solid support, acidic moieties attached to the solid support, and ionic moieties attached to the solid support; and
converting at least a portion of the α-1,4 bonds in the feed sugar to one or more non-α-1,4 bonds selected from the group consisting of β-1,4 bonds, α-1,3 bonds, β-1,3 bonds, α-1,6 bonds, and β-1,6 bonds to produce an oligosaccharide composition from at least a portion of the reaction mixture.

It should generally be understood that α-1,4 bonds may also be referred to herein as α(1,4) bonds, and similarly, β-1,4 bonds, α-1,3 bonds, β-1,3 bonds, α-1,6 bonds, and β-1,6 bonds may be referred to as β(1,4), α(1,3), β(1,3), α(1,6), and β(1,6) bonds, respectively.

In another variation, described herein is a method of converting a polysaccharide with primarily one type of glycosodic bond to a polysaccharide with a mixture of different glycosidic bonds. In one embodiment, polysaccharides used in the methods described herein typically have α-1,4 bonds, and when used as reactants in the methods described herein, at least a portion of the α-1,4 bonds are converted into β-1,4 bonds, α-1,3 bonds, β-1,3 bonds, α-1,6 bonds, and β-1,6 bonds.

Thus, in certain aspects, provided is a method of converting an α-1,4 polysaccharide to a polysaccharide having a mixture of linkages, by:
contacting an α-1,4 polysaccharide with a catalyst,
wherein the catalyst comprises acidic monomers and ionic monomers connected to form a polymeric backbone, or wherein the catalyst comprises a solid support, acidic moieties attached to the solid support, and ionic moieties attached to the solid support; and
converting at least a portion of the α-1,4 bonds in the α-1,4 polysaccharide to one or more non-α-1,4 bonds selected from the group consisting of α-1,2 bonds, β-1,2 bonds, α-1,3 bonds, β-1,3 bonds, β-1,4 bonds, α-1,6 bonds, and β-1,6 bonds to produce a polysaccharide with a mixture of linkages from at least a portion of the α-1,4 polysaccharide. In some variations, the one or more non-α-1,4 bonds are selected from the group consisting of β-1,4 bonds, α-1,3 bonds, β-1,3 bonds, α-1,6 bonds, and β-1,6 bonds.

In some embodiments, a least 10%, at least 20%, at least 30%, at least 40%, at least 50%, at least 60%, at least 70%, at least 80%, at least 90%, at least 95%, or at least 99% of the α-1,4 polysaccharide comprises α-1,4 bonds. In some variations, the α-1,4 polysaccharide comprises starch. In certain variations, the α-1,4 polysaccharide is starch.

In some embodiments, the produced polysaccharide with a mixture of linkages comprises at least two or more, at least three or more, at least four or more, at least five or more, or at least six or more non-α-1,4 glycosidic bond types. In some variations, the non-α-1,4 glycosidic bond types are selected from the group consisting of α-1,2 bonds, β-1,2 bonds, α-1,3 bonds, β-1,3 bonds, β-1,4 bonds, α-1,6 bonds, and β-1,6 bonds.

In other embodiments, at least 10%, at least 20%, at least 30%, at least 40%, at least 50%, at least 60%, at least 70%, at least 80%, at least 90%, or at least 99% of the produced polysaccharide comprises a mixture of non-α-1,4 bonds.

It should generally be understood that α-1,4 bonds may also be referred to herein as α(1,4) bonds, and similarly, β-1,4 bonds, α-1,3 bonds, β-1,3 bonds, α-1,6 bonds, and β-1,6 bonds may be referred to as β(1,4), α(1,3), β(1,3), α(1,6), and β(1,6) bonds, respectively.

Oligosaccharide Compositions

Also provided herein are oligosaccharides (including functionalized oligosaccharides), as well as oligosaccharide compositions (including functionalized oligosaccharide compositions), obtained by any of the methods described herein.

The oligosaccharides produced from the methods described herein depend on both the selection of one or more sugars as well as the reaction conditions used. The oligosaccharide content of reaction products can be determined, e.g., by a combination of high performance liquid chromatography (HPLC) and spectrophotometric methods, as described in the Examples section below. For example, the average degree of polymerization (DP) for the oligosaccharides can be determined as the number average of species containing one, two, three, four, five, six, seven, eight, nine, ten to fifteen, and greater than fifteen, anhydrosugar monomer units.

In some embodiments, the oligosaccharide degree of polymerization (DP) distribution for the one or more oligosaccharides after combining the one or more sugars with the polymeric catalyst (e.g., at 2, 3, 4, 8, 12, 24, or 48 hours after combining the one or more sugars with the polymeric catalyst) is: DP2=0%-40%, such as less than 40%, less than 30%, less than 20%, less than 10%, less than 5%, or less than 2%; or 10%-30% or 15%-25%; DP3=0%-20%, such as less than 15%, less than 10%, less than 5%; or 5%-15%; and DP4+=greater than 15%, greater than 20%, greater than 30%, greater than 40%, greater than 50%; or 15%-75%, 20%-40% or 25%-35%.

In some embodiments, the oligosaccharide degree of polymerization (DP) distribution for the functionalized oligosaccharide composition after combining the one or more sugars, oligosaccharide composition, or combination thereof with the functionalizing compounds and the polymeric catalyst (e.g., at 2, 3, 4, 8, 12, 24, or 48 hours after combining with the polymeric catalyst) is: DP2=0%-40%, such as less than 40%, less than 30%, less than 20%, less than 10%, less than 5%, or less than 2%; or 10%-30% or 15%-25%; DP3=0%-20%, such as less than 15%, less than 10%, less than 5%; or 5%-15%; and DP4+=greater than 15%, greater than 20%, greater than 30%, greater than 40%, greater than 50%; or 15%-75%, 20%-40% or 25%-35%.

In some embodiments, the oligosaccharide degree of polymerization (DP) distribution for the one or more oligosaccharides after combining the one or more sugars with the catalyst (e.g., at 2, 3, 4, 8, 12, 24, or 48 hours after combining the one or more sugars with the catalyst) is any one of entries (1)-(192) of Table 1A.

TABLE 1A

| Entry | DP4 + (%) | DP3 (%) | DP2 (%) |
|---|---|---|---|
| 1 | 20-25 | 0-5 | 0-5 |
| 2 | 20-25 | 0-5 | 5-10 |
| 3 | 20-25 | 0-5 | 10-15 |
| 4 | 20-25 | 0-5 | 15-20 |
| 5 | 20-25 | 0-5 | 20-25 |
| 6 | 20-25 | 0-5 | 25-30 |
| 7 | 20-25 | 5-10 | 0-5 |
| 8 | 20-25 | 5-10 | 5-10 |
| 9 | 20-25 | 5-10 | 10-15 |
| 10 | 20-25 | 5-10 | 15-20 |
| 11 | 20-25 | 5-10 | 20-25 |
| 12 | 20-25 | 5-10 | 25-30 |
| 13 | 20-25 | 10-15 | 0-5 |
| 14 | 20-25 | 10-15 | 5-10 |
| 15 | 20-25 | 10-15 | 10-15 |
| 16 | 20-25 | 10-15 | 15-20 |
| 17 | 20-25 | 10-15 | 20-25 |
| 18 | 20-25 | 10-15 | 25-30 |
| 19 | 20-25 | 15-20 | 0-5 |
| 20 | 20-25 | 15-20 | 5-10 |
| 21 | 20-25 | 15-20 | 10-15 |
| 22 | 20-25 | 15-20 | 15-20 |
| 23 | 20-25 | 15-20 | 20-25 |
| 24 | 20-25 | 15-20 | 25-30 |
| 25 | 20-25 | 20-25 | 0-5 |
| 26 | 20-25 | 20-25 | 5-10 |
| 27 | 20-25 | 20-25 | 10-15 |
| 28 | 20-25 | 20-25 | 15-20 |
| 29 | 20-25 | 20-25 | 20-25 |
| 30 | 20-25 | 20-25 | 25-30 |
| 31 | 25-30 | 0-5 | 0-5 |
| 32 | 25-30 | 0-5 | 5-10 |
| 33 | 25-30 | 0-5 | 10-15 |
| 34 | 25-30 | 0-5 | 15-20 |
| 35 | 25-30 | 0-5 | 20-25 |
| 36 | 25-30 | 0-5 | 25-30 |
| 37 | 25-30 | 5-10 | 0-5 |
| 38 | 25-30 | 5-10 | 5-10 |
| 39 | 25-30 | 5-10 | 10-15 |
| 40 | 25-30 | 5-10 | 15-20 |
| 41 | 25-30 | 5-10 | 20-25 |
| 42 | 25-30 | 5-10 | 25-30 |
| 43 | 25-30 | 10-15 | 0-5 |
| 44 | 25-30 | 10-15 | 5-10 |
| 45 | 25-30 | 10-15 | 10-15 |
| 46 | 25-30 | 10-15 | 15-20 |
| 47 | 25-30 | 10-15 | 20-25 |
| 48 | 25-30 | 10-15 | 25-30 |
| 49 | 25-30 | 15-20 | 0-5 |
| 50 | 25-30 | 15-20 | 5-10 |
| 51 | 25-30 | 15-20 | 10-15 |
| 52 | 25-30 | 15-20 | 15-20 |
| 53 | 25-30 | 15-20 | 20-25 |
| 54 | 25-30 | 15-20 | 25-30 |
| 55 | 25-30 | 20-25 | 0-5 |
| 56 | 25-30 | 20-25 | 5-10 |
| 57 | 25-30 | 20-25 | 10-15 |
| 58 | 25-30 | 20-25 | 15-20 |
| 59 | 25-30 | 20-25 | 20-25 |
| 60 | 25-30 | 20-25 | 25-30 |
| 61 | 30-35 | 0-5 | 0-5 |
| 62 | 30-35 | 0-5 | 5-10 |
| 63 | 30-35 | 0-5 | 10-15 |
| 64 | 30-35 | 0-5 | 15-20 |
| 65 | 30-35 | 0-5 | 20-25 |
| 66 | 30-35 | 0-5 | 25-30 |
| 67 | 30-35 | 5-10 | 0-5 |
| 68 | 30-35 | 5-10 | 5-10 |
| 69 | 30-35 | 5-10 | 10-15 |
| 70 | 30-35 | 5-10 | 15-20 |
| 71 | 30-35 | 5-10 | 20-25 |
| 72 | 30-35 | 5-10 | 25-30 |
| 73 | 30-35 | 10-15 | 0-5 |
| 74 | 30-35 | 10-15 | 5-10 |
| 75 | 30-35 | 10-15 | 10-15 |
| 76 | 30-35 | 10-15 | 15-20 |
| 77 | 30-35 | 10-15 | 20-25 |
| 78 | 30-35 | 10-15 | 25-30 |
| 79 | 30-35 | 15-20 | 0-5 |
| 80 | 30-35 | 15-20 | 5-10 |
| 81 | 30-35 | 15-20 | 10-15 |
| 82 | 30-35 | 15-20 | 15-20 |
| 83 | 30-35 | 15-20 | 20-25 |
| 84 | 30-35 | 15-20 | 25-30 |
| 85 | 30-35 | 20-25 | 0-5 |
| 86 | 30-35 | 20-25 | 5-10 |
| 87 | 30-35 | 20-25 | 10-15 |
| 88 | 30-35 | 20-25 | 15-20 |
| 89 | 30-35 | 20-25 | 20-25 |
| 90 | 30-35 | 20-25 | 25-30 |
| 91 | 35-40 | 0-5 | 0-5 |
| 92 | 35-40 | 0-5 | 5-10 |
| 93 | 35-40 | 0-5 | 10-15 |
| 94 | 35-40 | 0-5 | 15-20 |
| 95 | 35-40 | 0-5 | 20-25 |
| 96 | 35-40 | 0-5 | 25-30 |
| 97 | 35-40 | 5-10 | 0-5 |
| 98 | 35-40 | 5-10 | 5-10 |
| 99 | 35-40 | 5-10 | 10-15 |
| 100 | 35-40 | 5-10 | 15-20 |
| 101 | 35-40 | 5-10 | 20-25 |
| 102 | 35-40 | 5-10 | 25-30 |
| 103 | 35-40 | 10-15 | 0-5 |
| 104 | 35-40 | 10-15 | 5-10 |
| 105 | 35-40 | 10-15 | 10-15 |
| 106 | 35-40 | 10-15 | 15-20 |
| 107 | 35-40 | 10-15 | 20-25 |
| 108 | 35-40 | 10-15 | 25-30 |
| 109 | 35-40 | 15-20 | 0-5 |
| 110 | 35-40 | 15-20 | 5-10 |
| 111 | 35-40 | 15-20 | 10-15 |
| 112 | 35-40 | 15-20 | 15-20 |
| 113 | 35-40 | 15-20 | 20-25 |
| 114 | 35-40 | 15-20 | 25-30 |
| 115 | 35-40 | 20-25 | 0-5 |
| 116 | 35-40 | 20-25 | 5-10 |
| 117 | 35-40 | 20-25 | 10-15 |
| 118 | 35-40 | 20-25 | 15-20 |
| 119 | 35-40 | 20-25 | 20-25 |
| 120 | 35-40 | 20-25 | 25-30 |
| 121 | 40-45 | 0-5 | 0-5 |
| 122 | 40-45 | 0-5 | 5-10 |
| 123 | 40-45 | 0-5 | 10-15 |
| 124 | 40-45 | 0-5 | 15-20 |
| 125 | 40-45 | 0-5 | 20-25 |
| 126 | 40-45 | 0-5 | 25-30 |
| 127 | 40-45 | 5-10 | 0-5 |
| 128 | 40-45 | 5-10 | 5-10 |
| 129 | 40-45 | 5-10 | 10-15 |
| 130 | 40-45 | 5-10 | 15-20 |
| 131 | 40-45 | 5-10 | 20-25 |

TABLE 1A-continued

| Entry | DP4 + (%) | DP3 (%) | DP2 (%) |
|---|---|---|---|
| 132 | 40-45 | 5-10 | 25-30 |
| 133 | 40-45 | 10-15 | 0-5 |
| 134 | 40-45 | 10-15 | 5-10 |
| 135 | 40-45 | 10-15 | 10-15 |
| 136 | 40-45 | 10-15 | 15-20 |
| 137 | 40-45 | 10-15 | 20-25 |
| 138 | 40-45 | 10-15 | 25-30 |
| 139 | 40-45 | 15-20 | 0-5 |
| 140 | 40-45 | 15-20 | 5-10 |
| 141 | 40-45 | 15-20 | 10-15 |
| 142 | 40-45 | 15-20 | 15-20 |
| 143 | 40-45 | 15-20 | 20-25 |
| 144 | 40-45 | 15-20 | 25-30 |
| 145 | 40-45 | 20-25 | 0-5 |
| 146 | 40-45 | 20-25 | 5-10 |
| 147 | 40-45 | 20-25 | 10-15 |
| 148 | 40-45 | 20-25 | 15-20 |
| 149 | 40-45 | 20-25 | 20-25 |
| 150 | 40-45 | 20-25 | 25-30 |
| 151 | >50 | 0-5 | 0-5 |
| 152 | >50 | 0-5 | 5-10 |
| 153 | >50 | 0-5 | 10-15 |
| 154 | >50 | 0-5 | 15-20 |
| 155 | >50 | 0-5 | 20-25 |
| 156 | >50 | 0-5 | 25-30 |
| 157 | >50 | 5-10 | 0-5 |
| 158 | >50 | 5-10 | 5-10 |
| 159 | >50 | 5-10 | 10-15 |
| 160 | >50 | 5-10 | 15-20 |
| 161 | >50 | 5-10 | 20-25 |
| 162 | >50 | 5-10 | 25-30 |
| 163 | >50 | 10-15 | 0-5 |
| 164 | >50 | 10-15 | 5-10 |
| 165 | >50 | 10-15 | 10-15 |
| 166 | >50 | 10-15 | 15-20 |
| 167 | >50 | 10-15 | 20-25 |
| 168 | >50 | 10-15 | 25-30 |
| 169 | >50 | 15-20 | 0-5 |
| 170 | >50 | 15-20 | 5-10 |
| 171 | >50 | 15-20 | 10-15 |
| 172 | >50 | 15-20 | 15-20 |
| 173 | >50 | 15-20 | 20-25 |
| 174 | >50 | 15-20 | 25-30 |
| 175 | >50 | 20-25 | 0-5 |
| 176 | >50 | 20-25 | 5-10 |
| 177 | >50 | 20-25 | 10-15 |
| 178 | >50 | 20-25 | 15-20 |
| 179 | >50 | 20-25 | 20-25 |
| 180 | >60 | 10-20 | 10-20 |
| 181 | >60 | 5-10 | 10-20 |
| 182 | >60 | 0-10 | 0-10 |
| 183 | >70 | 10-20 | 10-20 |
| 184 | >70 | 5-10 | 10-20 |
| 185 | >70 | 0-10 | 0-10 |
| 186 | >80 | 10-20 | 10-20 |
| 187 | >80 | 5-10 | 10-20 |
| 188 | >80 | 0-10 | 0-10 |
| 189 | >85 | 10-20 | 10-20 |
| 190 | >85 | 0-10 | 0-10 |
| 191 | >85 | 0-10 | 0-5 |
| 192 | >90 | 0-10 | 0-10 |

In some embodiments, at least 10%, at least 20%, at least 30%, at least 40%, at least 50%, at least 60%, at least 70%, at least 80%, at least 90%, at least 95%, at least 99%, or at least 100% of the oligosaccharide composition, including functionalized oligosaccharide compositions, produced according to the methods described herein has a number average molecular weight between 230 to 10,000 g/mol; between 420 to 9,000 g/mol; or between 500 to 8,000 g/mol. In one embodiment, at least 10% of the oligosaccharide composition has a number average molecular weight between 500 to 8,000 g/mol.

The yield of conversion for the one or more sugars to the one or more oligosaccharides, including functionalized oligosaccharides, in the methods described herein can be determined, e.g., as described in the Examples section below. In some embodiments, the yield of conversion to one or more oligosaccharides with DP>1 after combining the one or more sugars with the polymeric catalyst (e.g., at 2, 3, 4, 8, 12, 24, or 48 hours after combining the one or more sugars with the polymeric catalyst) is greater than about 50% (e.g., greater than about 55%, 60%, 65%, 70%, 75%, 80%, 85%, 90%, 95%, or 98%). In some embodiments, the yield of conversion to one or more oligosaccharides of >DP2 after combining the one or more sugars with the polymeric catalyst (e.g., at 2, 3, 4, 8, 12, 24, or 48 hours after combining the one or more sugars with the polymeric catalyst) is greater than 30% (e.g., greater than 35%, 40%, 45%, 50%, 55%. 60%, 65%, 70%, 75%, 80%, 85%, 90%, 95%, or 98%).

As shown in the Examples below, the methods described herein provide remarkably low levels of degradation products, resulting in relatively higher selectivity when compared to existing catalysts. The molar yield to sugar degradation products and selectivity may be determined, e.g., as describe in the Examples section below. In some embodiments, the amount of sugar degradation products after combining the one or more sugars and one or more functionalizing compounds, if applicable, with the polymeric catalyst (e.g., at 2, 3, 4, 8, 12, 24, or 48 hours after combining the one or more sugars with the polymeric catalyst) is less than about 24% (e.g., less than about 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.75%, 0.5%, 0.25%, or 0.1%), such as less than about 24% of any one or combination of 1,6-anhydroglucose (levoglucosan), 5-hydroxymethylfurfural, 2-furaldehyde, acetic acid, formic acid, levulinic acid and/or humins. In some embodiments, the molar selectivity to oligosaccharide (including functionalized oligosaccharide) product after combining the one or more sugars and one or more functional compounds, if applicable, with the polymeric catalyst (e.g., at 2, 3, 4, 8, 12, 24, or 48 hours after combining the one or more sugars with the polymeric catalyst) is greater than about 86% (e.g., greater than about 87%, 88%, 89%, 90%, 91%, 92%, 93%, 94%, 95%, 97%, 98%, 99%, 99.5%, or 99.9%). In one embodiment, the molar selectivity to oligosaccharide, including functionalized oligosaccharide, product after combining the one or more sugars and one or more functional compounds, if applicable, with the polymeric catalyst is greater than about 86%.

Digestibility

In some variations, "digestibility" refers to the ability of the human or animal stomach and/or small intestine to digest (e.g. hydrolyze) a compound. Compounds that are resistant to digestion include, for example, dietary fiber. The digestibility of the one or more oligosaccharides produced according to the methods described herein can be determined by standard methods known to one skilled in the art, e.g., by the in vitro method AOAC 2009.01 or the in vitro Englyst Assay. The AOAC 2009.01 is an enzyme assays that can determine the amount of a carbohydrate composition that is dietary fiber. See Official Methods of Analysis of AOAC International, AOAC International, Gaithersberg, USA. The Englyst Assay is an enzyme assay that can determine the amount of a carbohydrate composition that is rapidly digestible, slowly digestible, or resistant to digestion. See European Journal of Clinical Nutrition (1992) Volume 46, Suppl. 2, pages S33-S60.

In some embodiments, greater than 50% (e.g., greater than 55%, greater than 60%, greater than 70%, greater than 80%, greater than 90%, greater than 99%) of the one or more oligosaccharides produced by the methods described herein is dietary fiber. In some embodiments, less than 50%, less than 40%, less than 30%, less than 20%, less than 10%, less than 5%, or less than 1% of the oligosaccharide composition with a DP of 3 or greater is hydrolyzed to oligosaccharides with a DP of 2 and/or monosaccharides.

Glass Transition Temperature

In some variations, "glass transition" refers to the reversible transition of some compounds from a hard and relatively brittle state to a softer, flexible state. In some variations, "glass transition temperature" refers to the temperature determined by differential scanning calorimetry.

The glass transition temperature of a material can impart desirable characteristics to that material, and/or can impart desirable characteristics to a composition comprising that material. In some embodiments, the methods described herein are used to produce one or more oligosaccharides with a specific glass transition temperature, or within a glass transition temperature range. In some variations, the glass transition temperature of one or more oligosaccharides (including functionalized oligosaccharides) produced according to the methods described herein imparts desirable characteristics to the one or more oligosaccharides (e.g., texture, storage, or processing characteristics). In certain variations, the glass transition temperature of the one or more oligosaccharides imparts desirable characteristics to a composition including the one or more oligosaccharides (e.g., texture, storage, or processing characteristics).

In some embodiments, the glass transition temperature of the one or more oligosaccharides or functional oligosaccharides when prepared in a dry powder form with a moisture content below 6% is at least 0 degrees Celsius, at least 10 degrees Celsius, at least 20 degrees Celsius, at least 30 degrees Celsius, at least 40 degrees Celsius, at least 50 degrees Celsius, at least 60 degrees Celsius, at least 70 degrees Celsius, at least 80 degrees Celsius, at least 90 degrees Celsius, or at least 100 degrees Celsius. In certain embodiments, the glass transition temperature of the one or more oligosaccharides or functional oligosaccharides is between 40 degrees Celsius and 80 degrees Celsius.

Hygroscopicity

In some variations, "hygroscopicity" refers to the ability of a compound to attract and hold water molecules from the surrounding environment. The hygroscopicity of a material can impart desirable characteristics to that material, and/or can impart desirable characteristics to a composition comprising that material. In some embodiments, the methods described herein are used to produce one or more oligosaccharides with a specific hygroscopicity value or a range of hygroscopicity values. In some variations, the hygroscopicity of one or more oligosaccharides produced according to the methods described herein imparts desirable characteristics to the one or more oligosaccharides (e.g., texture, storage, or processing characteristics). In certain variations, the hygroscopicity of the one or more oligosaccharides (including functionalized oligosaccharides) imparts desirable characteristics to a composition including the one or more oligosaccharides (e.g., texture, storage, or processing characteristics).

The hygroscopicity of a composition, including the one or more oligosaccharides, can be determined by measuring the mass gain of the composition after equilibration in a fixed water activity atmosphere (e.g., a desiccator held at a fixed relative humidity).

In some embodiments, the hygroscopicity of the one or more oligosaccharides is at least 5% moisture content at a water activity of at least 0.6, at least 10% moisture content at a water activity of at least 0.6, at least 15% moisture content at a water activity of at least 0.6, at least 20% moisture content at a water activity of at least 0.6, or at least 30% moisture content at a water activity of at least 0.6. In certain embodiments, the hygroscopicity of the one or more oligosaccharides is between 5% moisture content and 15% moisture content at a water activity of at least 0.6.

Fiber Content

In some variations, "dietary fiber" refers to a carbohydrate (i.e., an oligosaccharide or a polysaccharide) with a degree of polymerization of at least 3 that is not effectively hydrolyzed to its constituent sugars in humans or animals by enzymes in the stomach or small intestine (e.g., α-amylase, amyloglucosidase, and protease). In some embodiments, the dietary fiber is insoluble in water. In other embodiments, the dietary fiber is soluble in water. In certain embodiments, the dietary fiber is soluble in water up to a maximum concentration of at least 10 Brix, of at least 20 Brix, of at least 30 Brix, of at least 40 Brix, of at least 50 Brix, of at least 60 Brix, of at least 70 Brix, of at least 80 Brix, or of at least 80 Brix. In one embodiment, the dietary fiber is soluble with a maximum concentration between 75 and 90 Brix.

The dietary fiber content of a composition, including, for example, the dietary fiber content of the one or more oligosaccharides described herein, can be determined by the in vitro method AOAC 2009.01 (Official Methods of Analysis of AOAC International, AOAC International, Gaithersberg, USA) to quantify the fraction of oligosaccharides in the composition that have a degree of polymerization (DP) of at least three and that are not hydrolyzed by a combination the enzymes: α-amylase, amyloglucosidase, and protease.

In some embodiments, the dietary fiber content of the one or more oligosaccharides is at least 50% on a dry mass basis, at least 60% on a dry mass basis, at least 70% on a dry mass basis, at least 80% on a dry mass basis, or at least 90% on a dry mass basis. In certain embodiments, the dietary fiber content of the one or more oligosaccharides is between 70% and 80% on a dry mass basis.

In some embodiments, the mean degree of polymerization (DP), glass transition temperature (Tg), hygroscopicity, and fiber content of the oligosaccharide composition produced by combining the one or more sugars with the catalyst (e.g., at 2, 3, 4, 8, 12, 24, or 48 hours after combining the one or more sugars with the catalyst) is any one of entries (1)-(180) of Table 1B.

TABLE 1B

| Number | Mean DP | Tg at + <10 wt % H2O (° C.) | Hygroscopicity (wt % H2O @ 0.6 Aw) | Fiber Content (wt %) |
| --- | --- | --- | --- | --- |
| 1 | 5-10 | >50 | >5% | >50% |
| 2 | 5-10 | >50 | >5% | >60% |
| 3 | 5-10 | >50 | >5% | >70% |
| 4 | 5-10 | >50 | >5% | >80% |
| 5 | 5-10 | >50 | >5% | >90% |
| 6 | 5-10 | >50 | >10% | >50% |
| 7 | 5-10 | >50 | >10% | >60% |
| 8 | 5-10 | >50 | >10% | >70% |
| 9 | 5-10 | >50 | >10% | >80% |
| 10 | 5-10 | >50 | >10% | >90% |
| 11 | 5-10 | >50 | >15% | >50% |
| 12 | 5-10 | >50 | >15% | >60% |
| 13 | 5-10 | >50 | >15% | >70% |
| 14 | 5-10 | >50 | >15% | >80% |
| 15 | 5-10 | >50 | >15% | >90% |
| 16 | 5-10 | >50 | >5% | >50% |
| 17 | 5-10 | >50 | >5% | >60% |

TABLE 1B-continued

| Number | Mean DP | Tg at + <10 wt % H2O (° C.) | Hygroscopicity (wt % H2O @ 0.6 Aw) | Fiber Content (wt %) |
|---|---|---|---|---|
| 18 | 5-10 | >50 | >5% | >70% |
| 19 | 5-10 | >50 | >5% | >80% |
| 20 | 5-10 | >50 | >5% | >90% |
| 21 | 5-10 | >50 | >10% | >50% |
| 22 | 5-10 | >50 | >10% | >60% |
| 23 | 5-10 | >50 | >10% | >70% |
| 24 | 5-10 | >50 | >10% | >80% |
| 25 | 5-10 | >50 | >10% | >90% |
| 26 | 5-10 | >50 | >15% | >50% |
| 27 | 5-10 | >50 | >15% | >60% |
| 28 | 5-10 | >50 | >15% | >70% |
| 29 | 5-10 | >50 | >15% | >80% |
| 30 | 5-10 | >50 | >15% | >90% |
| 31 | 5-10 | >75 | >5% | >50% |
| 32 | 5-10 | >75 | >5% | >60% |
| 33 | 5-10 | >75 | >5% | >70% |
| 34 | 5-10 | >75 | >5% | >80% |
| 35 | 5-10 | >75 | >5% | >90% |
| 36 | 5-10 | >75 | >10% | >50% |
| 37 | 5-10 | >75 | >10% | >60% |
| 38 | 5-10 | >75 | >10% | >70% |
| 39 | 5-10 | >75 | >10% | >80% |
| 40 | 5-10 | >75 | >10% | >90% |
| 41 | 5-10 | >75 | >15% | >50% |
| 42 | 5-10 | >75 | >15% | >60% |
| 43 | 5-10 | >75 | >15% | >70% |
| 44 | 5-10 | >75 | >15% | >80% |
| 45 | 5-10 | >75 | >15% | >90% |
| 46 | 5-10 | >75 | >5% | >50% |
| 47 | 5-10 | >75 | >5% | >60% |
| 48 | 5-10 | >75 | >5% | >70% |
| 49 | 5-10 | >75 | >5% | >80% |
| 50 | 5-10 | >75 | >5% | >90% |
| 51 | 5-10 | >75 | >10% | >50% |
| 52 | 5-10 | >75 | >10% | >60% |
| 53 | 5-10 | >75 | >10% | >70% |
| 54 | 5-10 | >75 | >10% | >80% |
| 55 | 5-10 | >75 | >10% | >90% |
| 56 | 5-10 | >75 | >15% | >50% |
| 57 | 5-10 | >75 | >15% | >60% |
| 58 | 5-10 | >75 | >15% | >70% |
| 59 | 5-10 | >75 | >15% | >80% |
| 60 | 5-10 | >75 | >15% | >90% |
| 61 | 5-10 | >100 | >5% | >50% |
| 62 | 5-10 | >100 | >5% | >60% |
| 63 | 5-10 | >100 | >5% | >70% |
| 64 | 5-10 | >100 | >5% | >80% |
| 65 | 5-10 | >100 | >5% | >90% |
| 66 | 5-10 | >100 | >10% | >50% |
| 67 | 5-10 | >100 | >10% | >60% |
| 68 | 5-10 | >100 | >10% | >70% |
| 69 | 5-10 | >100 | >10% | >80% |
| 70 | 5-10 | >100 | >10% | >90% |
| 71 | 5-10 | >100 | >15% | >50% |
| 72 | 5-10 | >100 | >15% | >60% |
| 73 | 5-10 | >100 | >15% | >70% |
| 74 | 5-10 | >100 | >15% | >80% |
| 75 | 5-10 | >100 | >15% | >90% |
| 76 | 5-10 | >100 | >5% | >50% |
| 77 | 5-10 | >100 | >5% | >60% |
| 78 | 5-10 | >100 | >5% | >70% |
| 79 | 5-10 | >100 | >5% | >80% |
| 80 | 5-10 | >100 | >5% | >90% |
| 81 | 5-10 | >100 | >10% | >50% |
| 82 | 5-10 | >100 | >10% | >60% |
| 83 | 5-10 | >100 | >10% | >70% |
| 84 | 5-10 | >100 | >10% | >80% |
| 85 | 5-10 | >100 | >10% | >90% |
| 86 | 5-10 | >100 | >15% | >50% |
| 87 | 5-10 | >100 | >15% | >60% |
| 88 | 5-10 | >100 | >15% | >70% |
| 89 | 5-10 | >100 | >15% | >80% |
| 90 | 5-10 | >100 | >15% | >90% |
| 91 | 10-15 | >50 | >5% | >50% |
| 92 | 10-15 | >50 | >5% | >60% |
| 93 | 10-15 | >50 | >5% | >70% |
| 94 | 10-15 | >50 | >5% | >80% |
| 95 | 10-15 | >50 | >5% | >90% |
| 96 | 10-15 | >50 | >10% | >50% |
| 97 | 10-15 | >50 | >10% | >60% |
| 98 | 10-15 | >50 | >10% | >70% |
| 99 | 10-15 | >50 | >10% | >80% |
| 100 | 10-15 | >50 | >10% | >90% |
| 101 | 10-15 | >50 | >15% | >50% |
| 102 | 10-15 | >50 | >15% | >60% |
| 103 | 10-15 | >50 | >15% | >70% |
| 104 | 10-15 | >50 | >15% | >80% |
| 105 | 10-15 | >50 | >15% | >90% |
| 106 | 10-15 | >50 | >5% | >50% |
| 107 | 10-15 | >50 | >5% | >60% |
| 108 | 10-15 | >50 | >5% | >70% |
| 109 | 10-15 | >50 | >5% | >80% |
| 110 | 10-15 | >50 | >5% | >90% |
| 111 | 10-15 | >50 | >10% | >50% |
| 112 | 10-15 | >50 | >10% | >60% |
| 113 | 10-15 | >50 | >10% | >70% |
| 114 | 10-15 | >50 | >10% | >80% |
| 115 | 10-15 | >50 | >10% | >90% |
| 116 | 10-15 | >50 | >15% | >50% |
| 117 | 10-15 | >50 | >15% | >60% |
| 118 | 10-15 | >50 | >15% | >70% |
| 119 | 10-15 | >50 | >15% | >80% |
| 120 | 10-15 | >50 | >15% | >90% |
| 121 | 10-15 | >75 | >5% | >50% |
| 122 | 10-15 | >75 | >5% | >60% |
| 123 | 10-15 | >75 | >5% | >70% |
| 124 | 10-15 | >75 | >5% | >80% |
| 125 | 10-15 | >75 | >5% | >90% |
| 126 | 10-15 | >75 | >10% | >50% |
| 127 | 10-15 | >75 | >10% | >60% |
| 128 | 10-15 | >75 | >10% | >70% |
| 129 | 10-15 | >75 | >10% | >80% |
| 130 | 10-15 | >75 | >10% | >90% |
| 131 | 10-15 | >75 | >15% | >50% |
| 132 | 10-15 | >75 | >15% | >60% |
| 133 | 10-15 | >75 | >15% | >70% |
| 134 | 10-15 | >75 | >15% | >80% |
| 135 | 10-15 | >75 | >15% | >90% |
| 136 | 10-15 | >75 | >5% | >50% |
| 137 | 10-15 | >75 | >5% | >60% |
| 138 | 10-15 | >75 | >5% | >70% |
| 139 | 10-15 | >75 | >5% | >80% |
| 140 | 10-15 | >75 | >5% | >90% |
| 141 | 10-15 | >75 | >10% | >50% |
| 142 | 10-15 | >75 | >10% | >60% |
| 143 | 10-15 | >75 | >10% | >70% |
| 144 | 10-15 | >75 | >10% | >80% |
| 145 | 10-15 | >75 | >10% | >90% |
| 146 | 10-15 | >75 | >15% | >50% |
| 147 | 10-15 | >75 | >15% | >60% |
| 148 | 10-15 | >75 | >15% | >70% |
| 149 | 10-15 | >75 | >15% | >80% |
| 150 | 10-15 | >75 | >15% | >90% |
| 151 | 10-15 | >100 | >5% | >50% |
| 152 | 10-15 | >100 | >5% | >60% |
| 153 | 10-15 | >100 | >5% | >70% |
| 154 | 10-15 | >100 | >5% | >80% |
| 155 | 10-15 | >100 | >5% | >90% |
| 156 | 10-15 | >100 | >10% | >50% |
| 157 | 10-15 | >100 | >10% | >60% |
| 158 | 10-15 | >100 | >10% | >70% |
| 159 | 10-15 | >100 | >10% | >80% |
| 160 | 10-15 | >100 | >10% | >90% |
| 161 | 10-15 | >100 | >15% | >50% |
| 162 | 10-15 | >100 | >15% | >60% |
| 163 | 10-15 | >100 | >15% | >70% |
| 164 | 10-15 | >100 | >15% | >80% |
| 165 | 10-15 | >100 | >15% | >90% |
| 166 | 10-15 | >100 | >5% | >50% |
| 167 | 10-15 | >100 | >5% | >60% |
| 168 | 10-15 | >100 | >5% | >70% |
| 169 | 10-15 | >100 | >5% | >80% |

TABLE 1B-continued

| Number | Mean DP | Tg at + <10 wt % H2O (° C.) | Hygroscopicity (wt % H2O @ 0.6 Aw) | Fiber Content (wt %) |
|---|---|---|---|---|
| 170 | 10-15 | >100 | >5% | >90% |
| 171 | 10-15 | >100 | >10% | >50% |
| 172 | 10-15 | >100 | >10% | >60% |
| 173 | 10-15 | >100 | >10% | >70% |
| 174 | 10-15 | >100 | >10% | >80% |
| 175 | 10-15 | >100 | >10% | >90% |
| 176 | 10-15 | >100 | >15% | >50% |
| 177 | 10-15 | >100 | >15% | >60% |
| 178 | 10-15 | >100 | >15% | >70% |
| 179 | 10-15 | >100 | >15% | >80% |
| 180 | 10-15 | >100 | >15% | >90% |

In one aspect, provided are compositions that include the one or more oligosaccharides described herein, and the polymeric catalysts described herein. In some embodiments, the composition further includes a solvent (e.g., water).

In yet another aspect, provided are compositions that include the polymeric catalysts described herein, the one or more oligosaccharides described herein, and residual one or more sugars described herein.

Enumerated Embodiments

The following enumerated embodiments are representative of some aspects of the invention.

1. A method for producing one or more oligosaccharides, comprising:
   combining one or more sugars with a catalyst to form a reaction mixture that produces one or more oligosaccharides,
   wherein the catalyst comprises acidic monomers and ionic monomers connected to form a polymeric backbone, or
   wherein the catalyst comprises a solid support, acidic moieties attached to the solid support, and ionic moieties attached to the solid support.
2. The method of embodiment 1, wherein the catalyst comprises acidic monomers and ionic monomers connected to form a polymeric backbone.
3. The method of embodiment 1 or 2, wherein each acidic monomer comprises at least one Bronsted-Lowry acid.
4. The method of embodiment 3, wherein the Bronsted-Lowry acid at each occurrence is independently selected from the group consisting of sulfonic acid, phosphonic acid, acetic acid, isophthalic acid, boronic acid, and perfluorinated acid.
5. The method of claim any one of embodiments 1-4, wherein one or more of the acidic monomers are directly connected to the polymeric backbone.
6. The method of embodiment 3 or 4, wherein one or more of the acidic monomers comprises a linker connecting the Bronsted-Lowry acid to the polymeric backbone.
7. The method of embodiment 6, wherein the linker at each occurrence is independently selected from the group consisting of unsubstituted or substituted alkylene, unsubstituted or substituted cycloalkylene, unsubstituted or substituted alkenylene, unsubstituted or substituted arylene, unsubstituted or substituted heteroarylene, unsubstituted or substituted alkylene ether, unsubstituted or substituted alkylene ester, and unsubstituted or substituted alkylene carbamate.
8. The method of embodiment 6, wherein the Bronsted-Lowry acid and the linker form a side chain, wherein each side chain is independently selected from the group consisting of:

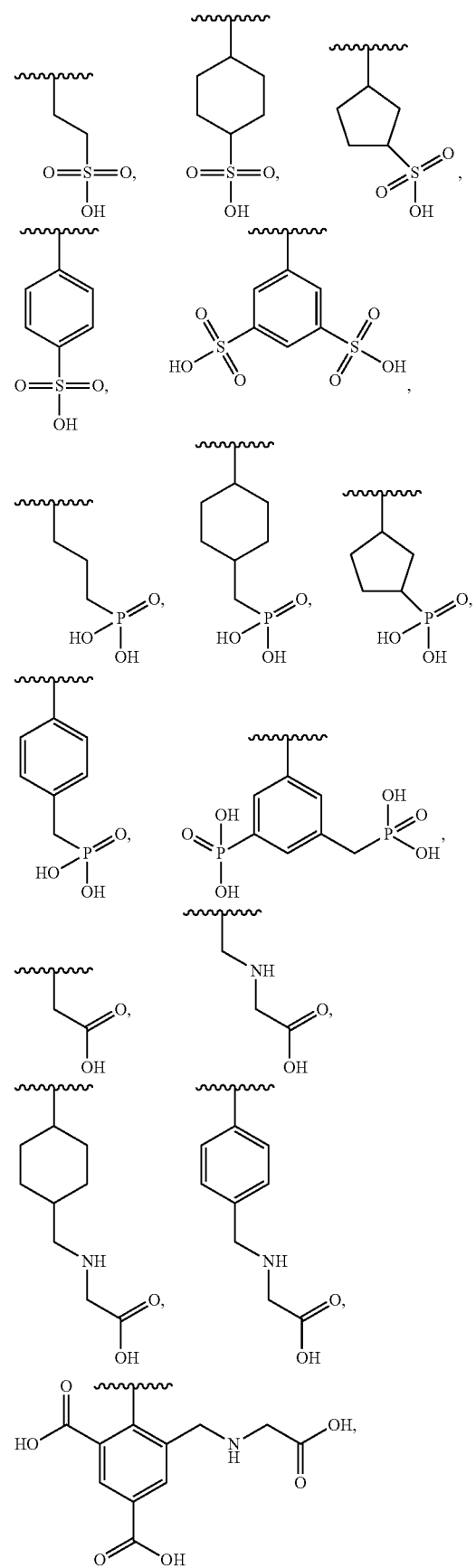

-continued

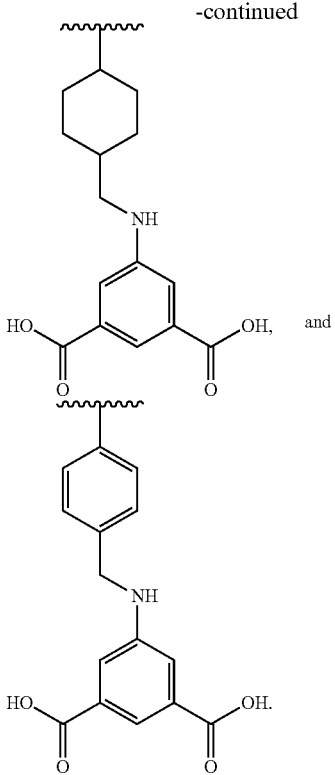

9. The method of any one of embodiments 1-8, wherein each ionic monomer independently comprises at least one nitrogen-containing cationic group or at least one phosphorous-containing cationic group.

10. The method of embodiment 9, wherein the nitrogen-containing cationic group at each occurrence is independently selected from the group consisting of pyrrolium, imidazolium, pyrazolium, oxazolium, thiazolium, pyridinium, pyrimidinium, pyrazinium, pyradizimium, thiazinium, morpholinium, piperidinium, piperizinium, and pyrollizinium.

11. The method of embodiment 9, wherein the phosphorous-containing cationic group at each occurrence is independently selected from the group consisting of triphenyl phosphonium, trimethyl phosphonium, triethyl phosphonium, tripropyl phosphonium, tributyl phosphonium, trichloro phosphonium, and trifluoro phosphonium.

12. The method of any one of embodiments 1-11, wherein one or more of the ionic monomers are directly connected to the polymeric backbone.

13. The method of any one of embodiments 9-11, wherein one or more of the ionic monomers comprises a linker connecting the nitrogen-containing cationic group or the phosphorous-containing cationic group to the polymeric backbone.

14. The method of embodiment 13, wherein the linker at each occurrence is independently selected from the group consisting of unsubstituted or substituted alkylene, unsubstituted or substituted cycloalkylene, unsubstituted or substituted alkenylene, unsubstituted or substituted arylene, unsubstituted or substituted heteroarylene, unsubstituted or substituted alkylene ether, unsubstituted or substituted alkylene ester, and unsubstituted or substituted alkylene carbamate.

15. The method of embodiment 13, wherein the nitrogen-containing cationic group and the linker form a side chain, wherein each side chain is independently selected from the group consisting of:

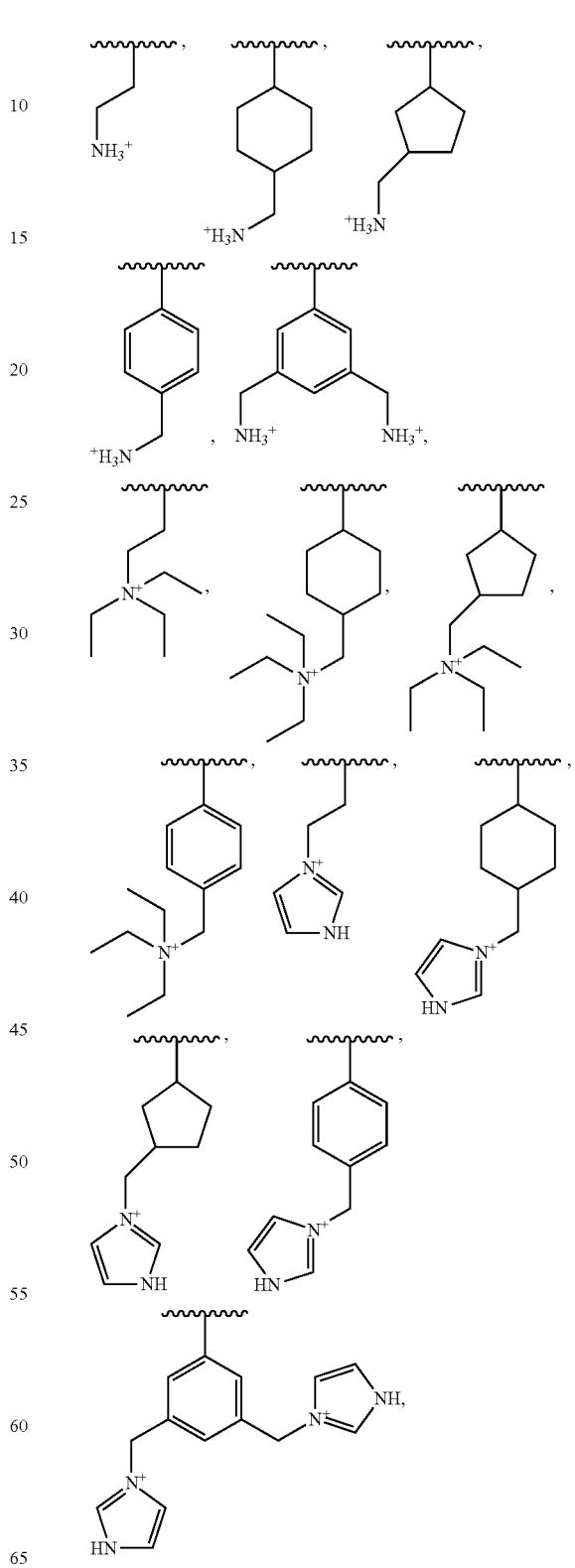

105
-continued
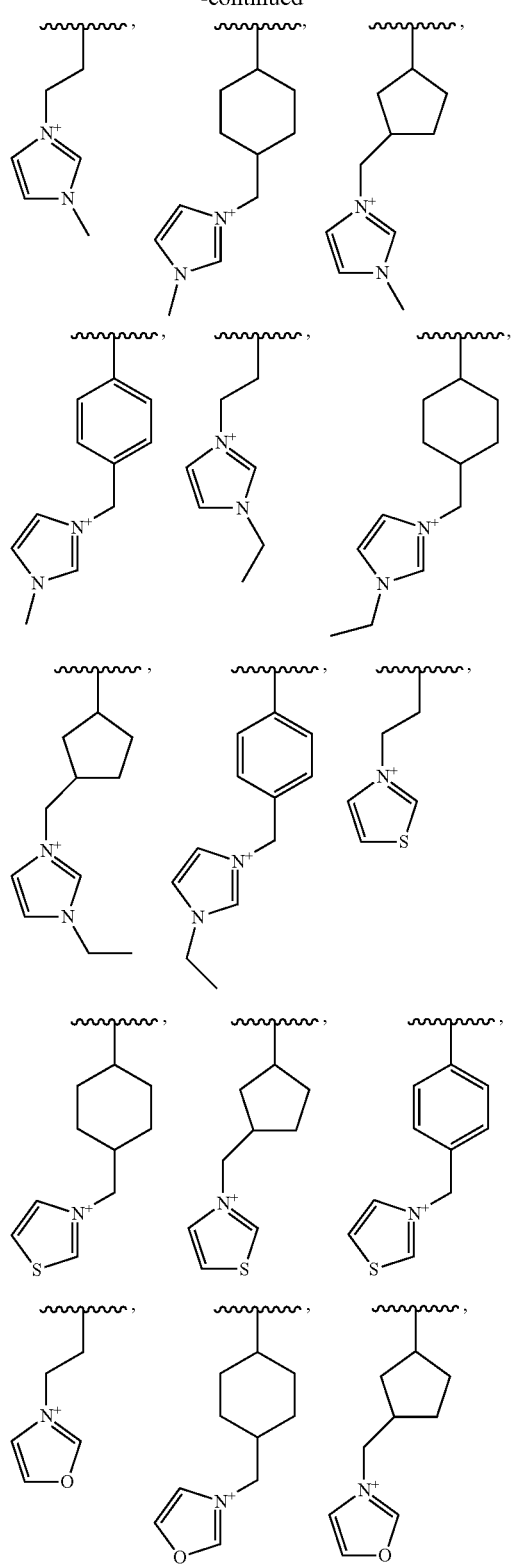
106
-continued
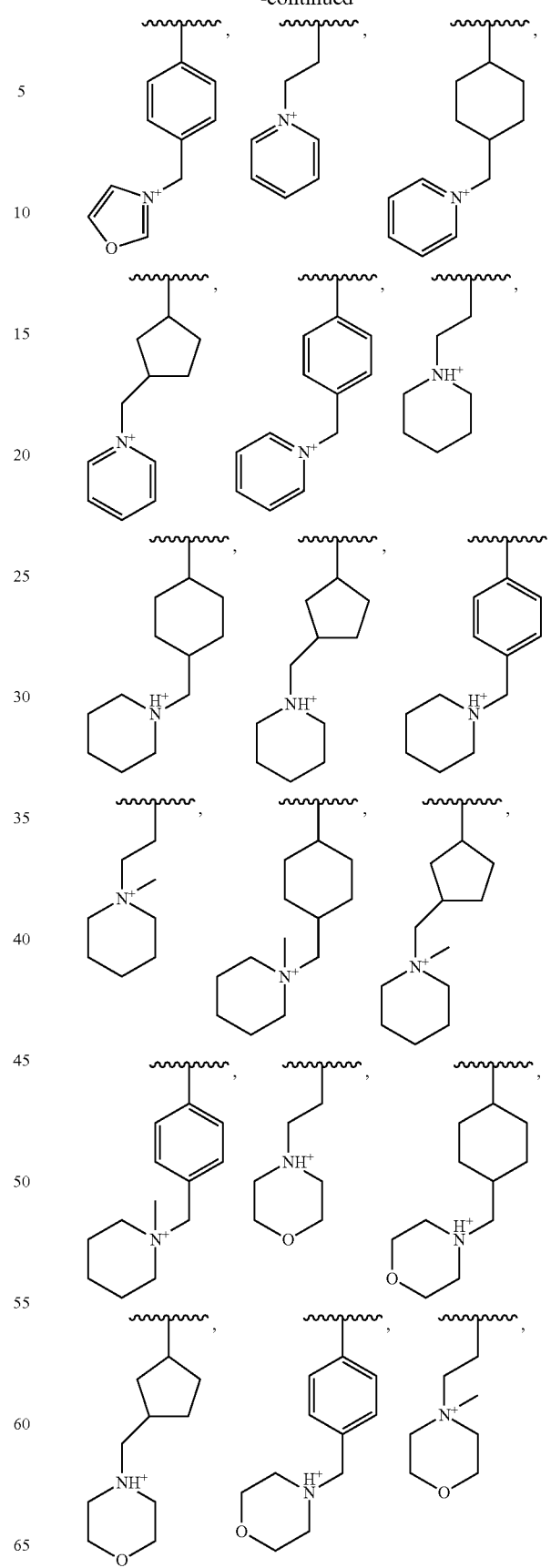

107

-continued

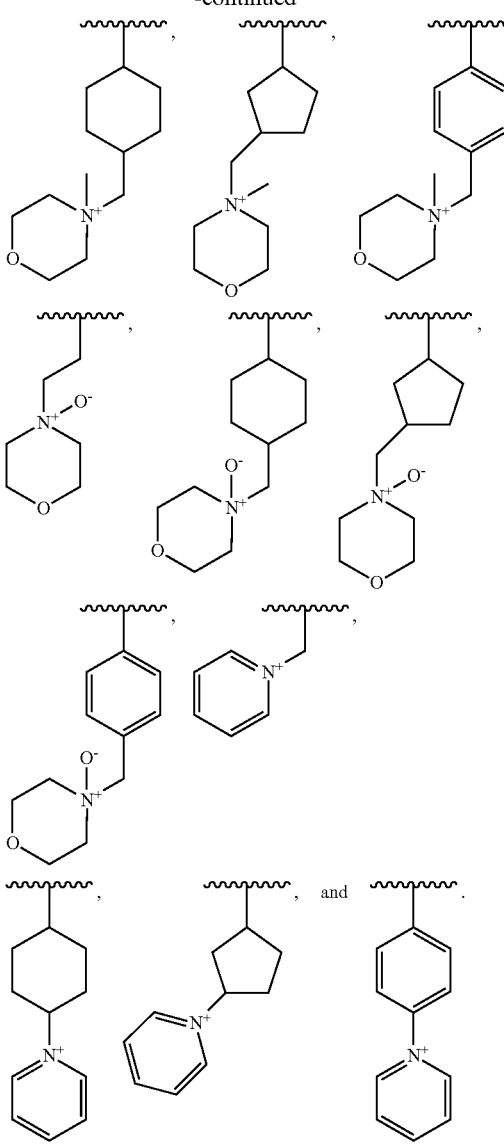

16. The method of embodiment 13, wherein the phosphorous-containing cationic group and the linker form a side chain, wherein each side chain is independently selected from the group consisting of:

108

-continued

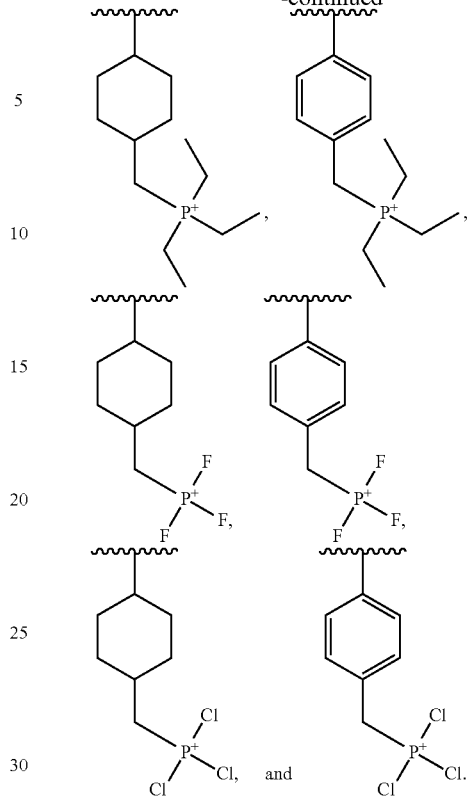

17. The method of any one of embodiments 1-16, wherein the polymeric backbone is selected from the group consisting of polyethylene, polypropylene, polyvinyl alcohol, polystyrene, polyurethane, polyvinyl chloride, polyphenol-aldehyde, polytetrafluoroethylene, polybutylene terephthalate, polycaprolactam, poly(acrylonitrile butadiene styrene), polyalkyleneammonium, polyalkylenediammonium, polyalkylenepyrrolium, polyalkyleneimidazolium, polyalkylenepyrazolium, polyalkyleneoxazolium, polyalkylenethiazolium, polyalkylenepyridinium, polyalkylenepyrimidinium, polyalkylenepyrazinium, polyalkylenepyradizimium, polyalkylenethiazinium, polyalkylenemorpholinium, polyalkylenepiperidinium, polyalkylenepiperizinium, polyalkylenepyrollizinium, polyalkylenetriphenylphosphonium, polyalkylenetrimethylphosphonium, polyalkylenetriethylphosphonium, polyalkylenetripropylphosphonium, polyalkylenetributylphosphonium, polyalkylenetrichlorophosphonium, polyalkylenetrifluorophosphonium, and polyalkylenediazolium.

18. The method of any one of embodiments 1-18, wherein the polymer is cross-linked.

19. The method of any one of embodiments 1-18, wherein the acidic monomers and the cationic monomers are randomly arranged in an alternating sequence or in blocks of monomers.

20. The method of embodiment 19, wherein each block has no more than twenty monomers.

21. The method of any one of embodiments 1-20, wherein the polymer further comprises hydrophobic monomers connected to the polymeric backbone, wherein each hydrophobic monomer comprises a hydrophobic group.

22. The method of embodiment 21, wherein the hydrophobic group at each occurrence is independently selected from the group consisting of an unsubstituted or substituted alkyl, an unsubstituted or substituted cycloalkyl, an unsubstituted or substituted aryl, or an unsubstituted or substituted heteroaryl.

23. The method of embodiment 21 or 22, wherein the hydrophobic group is directly connected to the polymeric backbone.

24. The method of any one of embodiments 1-23, wherein the polymer further comprises acidic-ionic monomers connected to the polymeric backbone, wherein each acidic-ionic monomer comprises a Bronsted-Lowry acid and a cationic group.

25. The method of embodiment 24, wherein the cationic group is a nitrogen-containing cationic group or a phosphorous-containing cationic group.

26. The method of embodiment 24 or 25, wherein one or more of the acidic-ionic monomers each further comprise a linker connecting the Bronsted-Lowry acid or the cationic group to the polymeric backbone.

27. The method of embodiment 26, wherein the linker at each occurrence is independently selected from the group consisting of unsubstituted or substituted alkylene, unsubstituted or substituted cycloalkylene, unsubstituted or substituted alkenylene, unsubstituted or substituted arylene, unsubstituted or substituted heteroarylene, unsubstituted or substituted alkylene ether, unsubstituted or substituted alkylene ester, and unsubstituted or substituted alkylene carbamate.

28. The method of embodiment 26, wherein the Bronsted-Lowry acid, the cationic group and the linker form a side chain, wherein each side chain is independently selected from the group consisting of:

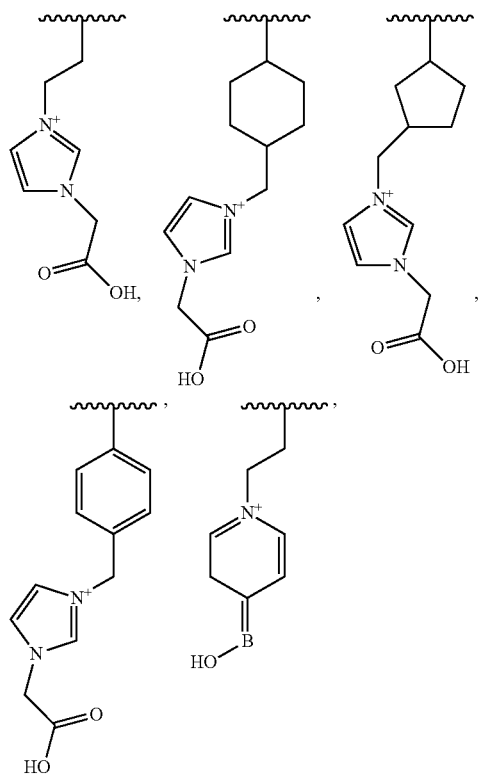

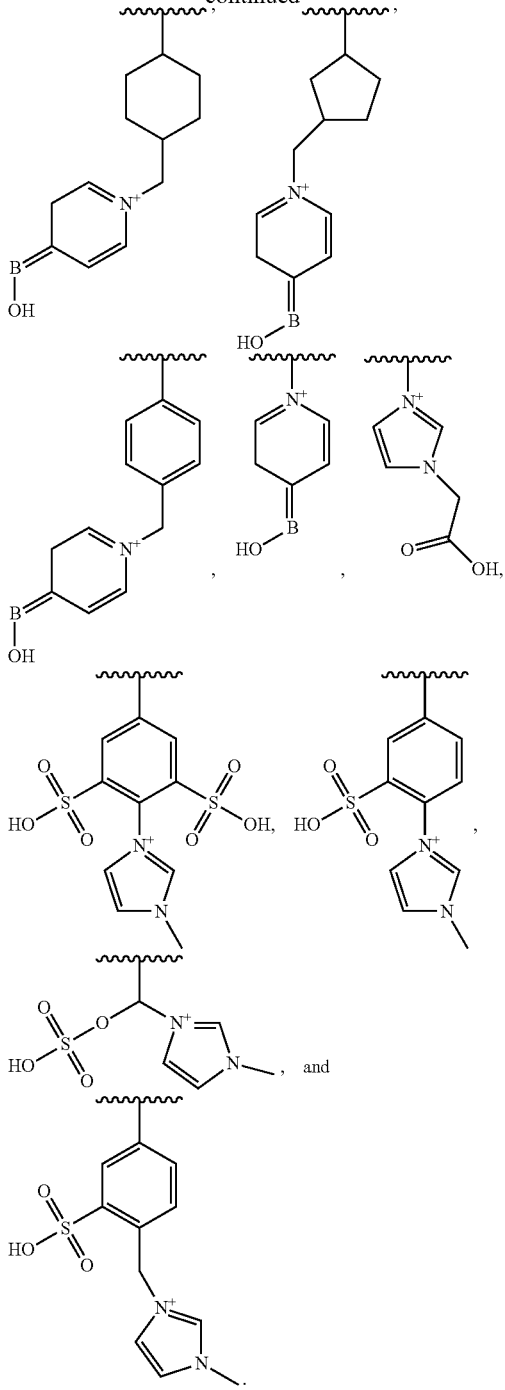

29. The method of any one of embodiments 1-28, wherein the polymer has a total amount of Bronsted-Lowry acid of between 0.01 and 20 mmol per gram of polymer (e.g., between 0.01 and 10 mmol per gram, between 0.1 and 5 mmol per gram, and between 0.1 and 3.0 mmol per gram).

30. The method of any one of embodiments 1-29, wherein at least a portion of the acidic monomers comprise sulfonic acid.

31. The method of embodiment 30, wherein the total amount of sulfonic acid in the polymer is between 0.05 to 10 mmol per gram of polymer.

32. The method of any one of embodiments 1-31, wherein at least a portion of the acidic monomers comprise phosphonic acid.

33. The method of embodiment 32, wherein the total amount of phosphonic acid in the polymer is between 0.01 and 12 mmol per gram of polymer.

34. The method of any one of embodiments 1-33, wherein at least a portion of the acidic monomers comprise acetic acid.

35. The method of embodiment 34, wherein the total amount of acetic acid in the polymer is between 0.01 and 12 mmol per gram of polymer.

36. The method of any one of embodiments 1-35, wherein at least a portion of the acidic monomers comprise isophthalic acid.

37. The method of embodiment 36, wherein the total amount of isophthalic acid in the polymer is between 0.01 and 5 mmol per gram of polymer.

38. The method of any one of embodiments 1-37, wherein at least a portion of the acidic monomers comprise boronic acid.

39. The method of embodiment 38, wherein the total amount of boronic acid in the polymer is between 0.01 and 20 mmol per gram of polymer.

40. The method of any one of embodiments 1-39, wherein at least a portion of the acidic monomers comprise perfluorinated acid.

41. The method of embodiment 40, wherein the total amount of perfluorinated acid in the polymer is between 0.01 and 5 mmol per gram of polymer.

42. The method of any one of embodiments 1-41, wherein each ionic monomer further comprises a counterion for each nitrogen-containing cationic group or phosphorous-containing cationic group.

43. The method of embodiment 42, wherein the counterion at each occurrence is independently selected from the group consisting of halide, nitrate, sulfate, formate, acetate, or organosulfonate.

44. The method of embodiment 42 or 43, wherein the polymer has a total amount of nitrogen-containing cationic groups and counterions or a total amount of phosphorous-containing cationic groups and counterions of between 0.01 and 10 mmol per gram of polymer.

45. The method of any one of embodiments 42-44, wherein at least a portion of the ionic monomers comprise imidazolium.

46. The method of embodiment 45, wherein the total amount of imidazolium and counterions in the polymer is between 0.01 and 8 mmol per gram of polymer.

47. The method of any one of embodiments 42-46, wherein at least a portion of the ionic monomers comprise pyridinium.

48. The method of embodiment 47, wherein the total amount of pyridinium and counterions in the polymer is between 0.01 and 8 mmol per gram of polymer.

49. The method of any one of embodiments 42-48, wherein at least a portion of the ionic monomers comprise triphenyl phosphonium.

50. The method of embodiment 49, wherein the total amount of triphenyl phosphonium and counterions in the polymer is between 0.01 and 5 mmol per gram of polymer.

51. The method of embodiment 1, wherein the polymer is selected from the group consisting of:

poly [styrene-co-4-vinylbenzenesulfonic acid-co-3-methyl-1-(4-vinylbenzyl)-3H-imidazol-1-ium chloride-co-divinylbenzene];

poly [styrene-co-4-vinylbenzenesulfonic acid-co-3-methyl-1-(4-vinylbenzyl)-3H-imidazol-1-ium sulfate-co-divinylbenzene];

poly [styrene-co-4-vinylbenzenesulfonic acid-co-3-methyl-1-(4-vinylbenzyl)-3H-imidazol-1-ium acetate-co-divinylbenzene];

poly [styrene-co-4-vinylbenzenesulfonic acid-co-3-methyl-1-(4-vinylbenzyl)-3H-imidazol-1-ium nitrate-co-divinylbenzene];

poly [styrene-co-4-vinylbenzenesulfonic acid-co-3-ethyl-1-(4-vinylbenzyl)-3H-imidazol-1-ium chloride-co-divinylbenzene];

poly [styrene-co-4-vinylbenzenesulfonic acid-co-3-ethyl-1-(4-vinylbenzyl)-3H-imidazol-1-ium sulfate-co-divinylbenzene];

poly [styrene-co-4-vinylbenzenesulfonic acid-co-3-ethyl-1-(4-vinylbenzyl)-3H-imidazol-1-ium acetate-co-divinylbenzene];

poly [styrene-co-4-vinylbenzenesulfonic acid-co-3-ethyl-1-(4-vinylbenzyl)-3H-imidazol-1-ium nitrate-co-divinylbenzene];

poly [styrene-co-4-vinylbenzenesulfonic acid-co-1-(4-vinylbenzyl)-3H-imidazol-1-ium chloride-co-divinylbenzene];

poly [styrene-co-4-vinylbenzenesulfonic acid-co-1-(4-vinylbenzyl)-3H-imidazol-1-ium iodide-co-divinylbenzene];

poly [styrene-co-4-vinylbenzenesulfonic acid-co-1-(4-vinylbenzyl)-3H-imidazol-1-ium bromide-co-divinylbenzene];

poly [styrene-co-4-vinylbenzenesulfonic acid-co-1-(4-vinylbenzyl)-3H-imidazol-1-ium sulfate-co-divinylbenzene];

poly [styrene-co-4-vinylbenzenesulfonic acid-co-1-(4-vinylbenzyl)-3H-imidazol-1-ium acetate-co-divinylbenzene];

poly [styrene-co-4-vinylbenzenesulfonic acid-co-3-methyl-1-(4-vinylbenzyl)-3H-benzoimidazol-1-ium chloride-co-divinylbenzene];

poly [styrene-co-4-vinylbenzenesulfonic acid-co-3-methyl-1-(4-vinylbenzyl)-3H-benzoimidazol-1-ium sulfate-co-divinylbenzene];

poly [styrene-co-4-vinylbenzenesulfonic acid-co-3-methyl-1-(4-vinylbenzyl)-3H-benzoimidazol-1-ium acetate-co-divinylbenzene];

poly [styrene-co-4-vinylbenzenesulfonic acid-co-3-methyl-1-(4-vinylbenzyl)-3H-benzoimidazol-1-ium formate-co-divinylbenzene];

poly [styrene-co-4-vinylbenzenesulfonic acid-co-1-(4-vinylbenzyl)-pyridinium-chloride-co-divinylbenzene];

poly [styrene-co-4-vinylbenzenesulfonic acid-co-1-(4-vinylbenzyl)-pyridinium-sulfate-co-divinylbenzene];

poly [styrene-co-4-vinylbenzenesulfonic acid-co-1-(4-vinylbenzyl)-pyridinium-acetate-co-divinylbenzene];

poly [styrene-co-4-vinylbenzenesulfonic acid-co-1-(4-vinylbenzyl)-pyridinium-nitrate-co-divinylbenzene];

poly[styrene-co-4-vinylbenzenesulfonic acid-co-1-(4-vinylbenzyl)-pyridinium-chloride-co-3-methyl-1-(4-vinylbenzyl)-3H-imidazol-1-ium sulfate-co-divinylbenzene];

poly[styrene-co-4-vinylbenzenesulfonic acid-co-1-(4-vinylbenzyl)-pyridinium-bromide-co-3-methyl-1-(4-vinylbenzyl)-3H-imidazol-1-ium sulfate-co-divinylbenzene];

poly[styrene-co-4-vinylbenzenesulfonic acid-co-1-(4-vinylbenzyl)-pyridinium-iodide-co-3-methyl-1-(4-vinylbenzyl)-3H-imidazol-1-ium sulfate-co-divinylbenzene];

poly[styrene-co-4-vinylbenzenesulfonic acid-co-1-(4-vinylbenzyl)-pyridinium-sulfate-co-3-methyl-1-(4-vinylbenzyl)-3H-imidazol-1-ium sulfate-co-divinylbenzene];
poly[styrene-co-4-vinylbenzenesulfonic acid-co-1-(4-vinylbenzyl)-pyridinium-acetate-co-3-methyl-1-(4-vinylbenzyl)-3H-imidazol-1-ium sulfate-co-divinylbenzene];
poly[styrene-co-4-vinylbenzenesulfonic acid-co-4-methyl-4-(4-vinylbenzyl)-morpholin-4-ium chloride-co-divinylbenzene];
poly[styrene-co-4-vinylbenzenesulfonic acid-co-4-methyl-4-(4-vinylbenzyl)-morpholin-4-ium sulfate-co-divinylbenzene];
poly[styrene-co-4-vinylbenzenesulfonic acid-co-4-methyl-4-(4-vinylbenzyl)-morpholin-4-ium acetate-co-divinylbenzene];
poly[styrene-co-4-vinylbenzenesulfonic acid-co-4-methyl-4-(4-vinylbenzyl)-morpholin-4-ium formate-co-divinylbenzene];
poly[styrene-co-4-vinylbenzenesulfonic acid-co-triphenyl-(4-vinylbenzyl)-phosphonium chloride-co-divinylbenzene];
poly[styrene-co-4-vinylbenzenesulfonic acid-co-triphenyl-(4-vinylbenzyl)-phosphonium sulfate-co-divinylbenzene];
poly[styrene-co-4-vinylbenzenesulfonic acid-co-triphenyl-(4-vinylbenzyl)-phosphonium acetate-co-divinylbenzene];
poly[styrene-co-4-vinylbenzenesulfonic acid-co-1-methyl-1-(4-vinylbenzyl)-piperidin-1-ium chloride-co-divinylbenzene];
poly[styrene-co-4-vinylbenzenesulfonic acid-co-1-methyl-1-(4-vinylbenzyl)-piperidin-1-ium sulfate-co-divinylbenzene];
poly[styrene-co-4-vinylbenzenesulfonic acid-co-1-methyl-1-(4-vinylbenzyl)-piperidin-1-ium acetate-co-divinylbenzene];
poly[styrene-co-4-vinylbenzenesulfonic acid-co-4-(4-vinylbenzyl)-morpholine-4-oxide-co-divinyl benzene];
poly[styrene-co-4-vinylbenzenesulfonic acid-co-triethyl-(4-vinylbenzyl)-ammonium chloride-co-divinylbenzene];
poly[styrene-co-4-vinylbenzenesulfonic acid-co-triethyl-(4-vinylbenzyl)-ammonium sulfate-co-divinylbenzene];
poly[styrene-co-4-vinylbenzenesulfonic acid-co-triethyl-(4-vinylbenzyl)-ammonium acetate-co-divinylbenzene];
poly[styrene-co-3-methyl-1-(4-vinylbenzyl)-3H-imidazol-1-ium chloride-co-4-boronyl-1-(4-vinylbenzyl)-pyridinium chloride-co-divinylbenzene];
poly[styrene-co-3-methyl-1-(4-vinylbenzyl)-3H-imidazol-1-ium chloride-co-1-(4-vinylphenyl)methylphosphonic acid-co-divinylbenzene];
poly[styrene-co-3-methyl-1-(4-vinylbenzyl)-3H-imidazol-1-ium sulfate-co-1-(4-vinylphenyl)methylphosphonic acid-co-divinylbenzene];
poly[styrene-co-3-methyl-1-(4-vinylbenzyl)-3H-imidazol-1-ium acetate-co-1-(4-vinylphenyl)methylphosphonic acid-co-divinylbenzene];
poly[styrene-co-3-methyl-1-(4-vinylbenzyl)-3H-imidazol-1-ium nitrate-co-1-(4-vinylphenyl)methylphosphonic acid-co-divinylbenzene];
poly[styrene-co-4-vinylbenzenesulfonic acid-co-vinylbenzylchloride-co-1-methyl-2-vinyl-pyridinium chloride-co-divinylbenzene];
poly[styrene-co-4-vinylbenzenesulfonic acid-co-vinylbenzylchloride-co-1-methyl-2-vinyl-pyridinium sulfate-co-divinylbenzene];
poly[styrene-co-4-vinylbenzenesulfonic acid-co-vinylbenzylchloride-co-1-methyl-2-vinyl-pyridinium acetate-co-divinylbenzene];
poly[styrene-co-4-vinylbenzenesulfonic acid-co-4-(4-vinylbenzyl)-morpholine-4-oxide-co-divinyl benzene];
poly [styrene-co-4-vinylphenylphosphonic acid-co-3-methyl-1-(4-vinylbenzyl)-3H-imidazol-1-ium chloride-co-divinylbenzene];
poly [styrene-co-4-vinylphenylphosphonic acid-co-3-methyl-1-(4-vinylbenzyl)-3H-imidazol-1-ium sulfate-co-divinylbenzene];
poly [styrene-co-4-vinylphenylphosphonic acid-co-3-methyl-1-(4-vinylbenzyl)-3H-imidazol-1-ium acetate-co-divinylbenzene];
poly[styrene-co-3-carboxymethyl-1-(4-vinylbenzyl)-3H-imidazol-1-ium chloride-co-divinylbenzene];
poly[styrene-co-3-carboxymethyl-1-(4-vinylbenzyl)-3H-imidazol-1-ium sulfate-co-divinylbenzene];
poly[styrene-co-3-carboxymethyl-1-(4-vinylbenzyl)-3H-imidazol-1-ium acetate-co-divinylbenzene];
poly[styrene-co-5-(4-vinylbenzylamino)-isophthalic acid-co-3-methyl-1-(4-vinylbenzyl)-3H-imidazol-1-ium chloride-co-divinylbenzene];
poly[styrene-co-5-(4-vinylbenzylamino)-isophthalic acid-co-3-methyl-1-(4-vinylbenzyl)-3H-imidazol-1-ium sulfate-co-divinylbenzene];
poly[styrene-co-5-(4-vinylbenzylamino)-isophthalic acid-co-3-methyl-1-(4-vinylbenzyl)-3H-imidazol-1-ium acetate-co-divinylbenzene];
poly[styrene-co-(4-vinylbenzylamino)-acetic acid-co-3-methyl-1-(4-vinylbenzyl)-3H-imidazol-1-ium chloride-co-divinylbenzene];
poly[styrene-co-(4-vinylbenzylamino)-acetic acid-co-3-methyl-1-(4-vinylbenzyl)-3H-imidazol-1-ium sulfate-co-divinylbenzene];
poly[styrene-co-(4-vinylbenzylamino)-acetic acid-co-3-methyl-1-(4-vinylbenzyl)-3H-imidazol-1-ium acetate-co-divinylbenzene];
poly(styrene-co-4-vinylbenzenesulfonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzenephosphonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzenesulfonic acid-co-vinylbenzylmethylimidazolium sulfate-co-vinylbenzylmethylmorpholinium sulfate-co-vinylbenzyltriphenyl phosphonium sulfate-co-divinylbenzene);
poly(styrene-co-4-vinylbenzenephosphonic acid-co-vinylbenzylmethylimidazolium sulfate-co-vinylbenzylmethylmorpholinium sulfate-co-vinylbenzyltriphenyl phosphonium sulfate-co-divinylbenzene);
poly(styrene-co-4-vinylbenzenesulfonic acid-co-vinylbenzylmethylimidazolium acetate-co-vinylbenzylmethylmorpholinium acetate-co-vinylbenzyltriphenyl phosphonium acetate-co-divinylbenzene);
poly(styrene-co-4-vinylbenzenephosphonic acid-co-vinylbenzylmethylimidazolium acetate-co-vinylbenzylmethylmorpholinium acetate-co-vinylbenzyltriphenyl phosphonium acetate-co-divinylbenzene);
poly(styrene-co-4-vinylbenzenesulfonic acid-co-vinylbenzylmethylmorpholinium chloride-co-vinylbenzyltriphenylphosphonium chloride-co-divinylbenzene);

poly(styrene-co-4-vinylbenzenephosphonic acid-co-vinylbenzylmethylmorpholinium chloride-co-vinylbenzyltriphenylphosphonium chloride-co-divinylbenzene);
poly(styrene-co-4-vinylbenzenesulfonic acid-co-vinylbenzylmethylmorpholinium sulfate-co-vinylbenzyltriphenylphosphonium sulfate-co-divinylbenzene);
poly(styrene-co-4-vinylbenzenephosphonic acid-co-vinylbenzylmethylmorpholinium sulfate-co-vinylbenzyltriphenylphosphonium sulfate-co-divinylbenzene);
poly(styrene-co-4-vinylbenzenesulfonic acid-co-vinylbenzylmethylmorpholinium acetate-co-vinylbenzyltriphenylphosphonium sulfate-co-divinylbenzene);
poly(styrene-co-4-vinylbenzenephosphonic acid-co-vinylbenzylmethylmorpholinium acetate-co-vinylbenzyltriphenylphosphonium sulfate-co-divinylbenzene) poly(styrene-co-4-vinylbenzenesulfonic acid-co-vinylmethylimidazolium chloride-co-divinylbenzene);
poly(styrene-co-4-vinylbenzenesulfonic acid-co-vinylmethylimidazolium sulfate-co-divinylbenzene);
poly(styrene-co-4-vinylbenzenesulfonic acid-co-vinylmethylimidazolium acetate-co-divinylbenzene);
poly(styrene-co-4-vinylbenzenesulfonic acid-co-vinylmethylimidazolium nitrate-co-divinylbenzene);
poly(styrene-co-4-vinylbenzenephosphonic acid-co-vinylmethylimidazolium chloride-co-divinylbenzene);
poly(styrene-co-4-vinylbenzenephosphonic acid-co-vinylmethylimidazolium sulfate-co-divinylbenzene);
poly(styrene-co-4-vinylbenzenephosphonic acid-co-vinylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium sulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium sulfate-co-divinylbenzene);
poly(styrene-co-4-vinylbenzenephosphonic acid-co-vinylbenzyltriphenylphosphonium acetate-co-divinylbenzene);
poly(styrene-co-4-vinylbenzenesulfonic acid-co-vinylbenzylmethylimidazolium chloride-co-divinylbenzene);
poly(styrene-co-4-vinylbenzenesulfonic acid-co-vinylbenzylmethylimidazolium sulfate-co-divinylbenzene);
poly(styrene-co-4-vinylbenzenesulfonic acid-co-vinylbenzylmethylimidazolium acetate-co-divinylbenzene);
poly(styrene-co-4-vinylbenzenephosphonic acid-co-vinylbenzylmethylimidazolium chloride-co-divinylbenzene);
poly(styrene-co-4-vinylbenzenephosphonic acid-co-vinylbenzylmethylimidazolium sulfate-co-divinylbenzene);
poly(styrene-co-4-vinylbenzenephosphonic acid-co-vinylbenzylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium sulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium sulfate-co-divinylbenzene);
poly(styrene-co-4-vinylbenzenephosphonic acid-co-vinylbenzyltriphenylphosphonium acetate-co-divinylbenzene);
poly(butyl-vinylimidazolium chloride-co-butylimidazolium sulfate-co-4-vinylbenzenesulfonic acid);
poly(butyl-vinylimidazolium sulfate-co-butylimidazolium sulfate-co-4-vinylbenzenesulfonic acid);
poly(benzyl alcohol-co-4-vinylbenzylalcohol sulfonic acid-co-vinylbenzyltriphenylphosphonium chloride-co-divinylbenzyl alcohol); and
poly(benzyl alcohol-co-4-vinylbenzylalcohol sulfonic acid-co-vinylbenzyltriphenylphosphonium sulfate-co-divinylbenzyl alcohol).

52. The method of any one of embodiments 1-51, wherein the polymer is substantially insoluble in water or an organic solvent.

53. The method of embodiment 1, wherein the catalyst comprises a solid support, acidic moieties attached to the solid support, and ionic moieties attached to the solid support.

54. The method of embodiment 53, wherein the solid support comprises a material, wherein the material is selected from the group consisting of carbon, silica, silica gel, alumina, magnesia, titania, zirconia, clays, magnesium silicate, silicon carbide, zeolites, ceramics, and any combinations thereof.

55. The method of embodiment 53 or 54, wherein each acidic moiety independently has at least one Bronsted-Lowry acid.

56. The method of any one of embodiments 53 to 55, wherein each ionic moiety independently has at least one nitrogen-containing cationic group or at least one phosphorous-containing cationic group, or a combination thereof.

57. The method of any one of embodiments 53 to 55, wherein the catalyst has a catalyst activity loss of less than 1% per cycle.

58. The method of any one of embodiments 1-57, wherein the one or more sugars is one or more monosaccharides and/or disaccharides.

59. The method of any one of embodiments 1-57, wherein the one or more sugars is one or more C5 or C6 monosaccharides (such as one or more C5 monosaccharides, or one or more C6 monosaccharides).

60. The method of any one of embodiments 1-57, wherein the one or more sugars are selected from glucose, galactose, mannose, lactose, fructose, xylose, arabinose (such as one or more sugars selected from glucose, galactose, mannose, lactose, or such as one or more sugars selected from fructose, xylose, arabinose) or their corresponding sugar alcohols.

61. The method of any one of embodiments 1-52, comprising combining two or more sugars with a polymeric catalyst to produce the one or more oligosaccharides.

62. The method of embodiment 61, wherein the two or more sugars are selected from glucose, galactose, mannose and lactose (e.g., glucose and galactose).

63. The method of any one of embodiments 1-52, wherein the weight ratio of the polymeric catalyst to the one or more sugars is about 0.1 g/g to about 50 g/g (e.g., about 0.1 g/g to about 5 g/g, about 0.5 g/g to about 1.0 g/g, about 0.1 g/g to about 0.6 g/g, about 0.2 g/g to about 0.5 g/g, or about 0.25 g/g to about 0.5 g/g).

64. The method of any one of embodiments 1-63, wherein the reaction mixture comprises an aqueous solvent.

65. The method of embodiment 68, wherein the aqueous solvent is less than about 50% of the reaction mixture (by mass), e.g., less than about 40%, less than about 30%, less than about 25%, less than about 20%, less than about 15%, less than about 10%, or less than about 5%, or about 5% to about 25%, or about 10% to about 20%; or from about 10% to about 50%, e.g., about 15% to about 40%, about 20% to about 35%, or about 25% to about 30%.

66. The method of embodiment 64 or 65, further comprising removing at least a portion of the aqueous solvent from the reaction mixture (e.g., removing at least about any of 10%, 20%, 30%, 40%, 50%, 60%, 70%, 80%, 90%, 95%, 97%, 99%, or 100%, such as by vacuum filtration).

67. The method of any one of embodiments 1-66, wherein the oligosaccharide degree of polymerization (DP) distribution for the one or more oligosaccharides at three (3) hours after combining the one or more sugars with the catalyst is:

DP2=0%-40%, such as less than 40%, less than 30%, less than 20%, less than 10%, less than 5%, or less than 2%; or 10%-30% or 15%-25%;

DP3=0%-20%, such as less than 15%, less than 10%, less than 5%; or 5%-15%; and

DP4+=greater than 15%, greater than 20%, greater than 30%, greater than 40%, greater than 50%; or 15%-75%, 20%-40% or 25%-35%.

68. The method of any one of embodiments 1-67, wherein the oligosaccharide degree of polymerization (DP) distribution for the one or more oligosaccharides at three (3) hours after combining the one or more sugars with the catalyst is any one of entries (1)-(179) of Table 1.

69. The method of any one of embodiments 1-68, wherein the yield of conversion to one or more oligosaccharides at three (3) hours after combining the one or more sugars with the catalyst is greater than about 50% (e.g., greater than about 55%, 60%, 65%, 70%, 75%, 80%, 85%, 90%, 95%, or 98%).

70. The method of any one of embodiments 1-69, wherein the yield of conversion to one or more oligosaccharides of >DP2 at three (3) hours after combining the one or more sugars with the catalyst is greater than 30% (e.g., greater than 35%, 40%, 45%, 50%, 55%. 60%, 65%, 70%, 75%, 80%, 85%, 90%, 95%, or 98%).

71. The method of any one of embodiments 1-70, wherein the amount of sugar degradation products at three (3) hours after combining the one or more sugars with the catalyst is less than about 10% (e.g., less than about 9%, 8%, 7%, 6%, 5%, 4%, 3%, 2%, 1%, 0.75%, 0.5%, 0.25%, or 0.1%), such as less than about 10% of any one or combination of 1,6-anhydroglucose (levoglucosan), 5-hydroxymethylfurfural, 2-furaldehyde, acetic acid, formic acid, levulinic acid and/or humins.

72. The method of any one of embodiments 1-71, further comprising isolating the one or more oligosaccharides.

73. The method of embodiment 72, wherein isolating the one or more oligosaccharides comprises separating at least a portion of the one or more oligosaccharides from at least a portion of the catalyst (e.g., by vacuum filtration).

74. The method of embodiment 73, wherein isolating the one or more oligosaccharides further comprises separating at least a portion of the one or more oligosaccharides from at least a portion of any unreacted sugar (e.g., by chromatography).

75. The method of embodiment 74, wherein the method is repeated in a sequential batch process, wherein the separated catalyst is recycled by further contacting one or more sugars.

76. The method of embodiment 75, wherein the catalyst is recycled at least 1, 2, 3, 4, 5, 6, 7, 8, 9 or 10 times.

77. The method of embodiment 76, wherein the catalyst retains at least 80% activity (e.g., at least 90%, 95%, 96%, 97%, 98%, or 99% activity) after being recycled 1, 2, 3, 4, 5, 6, 7, 8, 9 or 10 times, when compared to the catalytic activity under identical conditions prior to being recycled.

78. The method of any one of embodiments 72-74, wherein the method is conducted as a continuous process, wherein the steps of combining the one or more sugars with a catalyst and isolating the one or more oligosaccharides are performed concurrently.

79. A method for producing one or more oligosaccharides, comprising:
    a) combining one or more sugars with a catalyst to form a reaction mixture that produces one or more oligosaccharides,
        wherein the catalyst comprises a plurality of acidic monomers and a plurality of cationic monomers connected to form a polymeric backbone, or
        wherein the solid-supported catalyst comprises a solid support, a plurality of acidic moieties attached to the solid support, and a plurality of ionic moieties attached to the solid support;
    b) isolating the one or more oligosaccharides and the catalyst from the reaction mixture; and
    c) combining one or more additional sugars with the isolated catalyst to form an additional reaction mixture that produces one or more additional oligosaccharides.

80. The method of embodiment 79, wherein isolating the one or more oligosaccharides from the reaction mixture comprises separating at least a portion of the one or more oligosaccharides from i) at least a portion of the catalyst (e.g., by vacuum filtration), and ii) at least a portion at least a portion of any unreacted sugar (e.g., by chromatography).

81. The method of embodiment 79 or 80, wherein isolating the catalyst from the reaction mixture comprises (e.g., by vacuum filtration) separating at least a portion of the polymeric catalyst from at least a portion of the one or more oligosaccharides and at least a portion of any unreacted sugar.

82. The method of any one of embodiments 79-81, wherein following step c), steps b) and c) are repeated at least one (1) time (e.g., at least 2, 3, 4, 5, 6, 7, 8, 9, or 10 times).

83. The method of any one of embodiments 79-82, wherein the catalyst retains at least 80% activity (e.g., at least 90%, 95%, 96%, 97%, 98%, or 99% activity) after being isolated 1, 2, 3, 4, 5, 6, 7, 8, 9 or 10 times, when compared to the catalytic activity under identical conditions prior to being recycled.

84. The method of any one of embodiments 1-83, wherein the temperature of the combined one or more sugars and catalyst is maintained from about 60 to about 120 degrees Celsius (e.g., about 80 to about 115, about 90 to about 110, or about 95 to about 105).

85. The method of any one of embodiments 1-84, wherein the combined one or more sugars and catalyst are allowed to react for at least 1 hour (e.g., at least 2, 3, 4, 6, 8, 16, 24, 36, or 48 hours, such as 1-24 hours, 2-12 hours, 3-6 hours).

86. An oligosaccharide or oligosaccharide composition obtained by the method of any one of embodiments 1-85.

87. Use of a polymeric catalyst comprising a plurality of acidic monomers and a plurality of cationic monomers (e.g., any one of the polymeric catalysts described herein) for preparing one or more oligosaccharides from one or more sugars.

88. Use of a solid-supported catalyst comprising a plurality of acidic moieties and a plurality of cationic moieties (e.g., any one of the solid-supported catalysts described herein) for preparing one or more oligosaccharides from one or more sugars.

89. A method of producing an oligosaccharide composition, comprising:

combining feed sugar with a catalyst to form a reaction mixture,
wherein the feed sugar comprises α-1,4 bonds, and
wherein the catalyst comprises acidic monomers and ionic monomers connected to form a polymeric backbone, or wherein the catalyst comprises a solid support, acidic moieties attached to the solid support, and ionic moieties attached to the solid support; and
converting at least a portion of the α-1,4 bonds in the feed sugar to one or more non-α-1,4 bonds selected from the group consisting of β-1,4 bonds, α-1,3 bonds, β-1,3 bonds, α-1,6 bonds, and β-1,6 bonds to produce an oligosaccharide composition from at least a portion of the reaction mixture.

90. A method for producing an oligosaccharide composition, comprising:
a) combining one or more sugars with a catalyst to produce a first product mixture,
wherein the first product mixture comprises a first oligosaccharide composition and residual catalyst;
b) isolating at least a portion of the residual catalyst from the product mixture; and
c) combining one or more additional sugars with the isolated residual catalyst to produce an additional product mixture,
wherein the additional product mixture comprises an additional oligosaccharide composition; and
wherein the catalytic activity of the isolated residual catalyst in the production of the additional oligosaccharide composition is at least 30% of the catalytic activity of the catalyst in the production of the first oligosaccharide composition.

91. A method for producing an oligosaccharide composition, comprising:
a) combining one or more sugars with a catalyst to produce a first product mixture,
wherein the first product mixture comprises a first oligosaccharide composition and residual catalyst;
wherein the molar selectivity for the first oligosaccharide composition is at least 85%;
b) isolating at least a portion of the residual catalyst from the first product mixture;
c) combining one or more additional sugars with the isolated residual catalyst to produce an additional product mixture,
wherein the additional product mixture comprises an additional oligosaccharide composition; and
wherein the catalytic activity of the isolated catalyst in the production of the additional oligosaccharide composition is at least 30% of the catalytic activity of the catalyst in the production of the first oligosaccharide composition.

92. The method of embodiments 90 or 91, wherein:
the catalyst comprises acidic monomers and ionic monomers connected to form a polymeric backbone, or
the catalyst comprises a solid support, acidic moieties attached to the solid support, and ionic moieties attached to the solid support.

93. The method of any one of embodiments 90 to 92, wherein the at least a portion of the catalyst is isolated from the first product mixture by filtration or phase separation, or a combination thereof.

94. The method of any one of embodiments 90 to 93, wherein the selectivity for the additional oligosaccharide composition is at least 85%.

95. The method of any one of embodiments 90 to 94, wherein at least 10% of the first oligosaccharide composition has a degree of polymerization from 3 to 25.

96. The method of any one of embodiments 90 to 95, wherein at least 10% of the additional oligosaccharide composition has a degree of polymerization from 3 to 25.

97. The method of any one of embodiments 90 to 96, wherein at least 10% of the first oligosaccharide composition has a number average molecular weight between 230 to 10,000 g/mol.

98. The method of any one of embodiments 90 to 97, wherein at least 10% of the additional oligosaccharide composition has a number average molecular weight between 230 to 10,000 g/mol.

99. A method for producing an oligosaccharide composition, comprising:
combining one or more sugars with a catalyst to produce the oligosaccharide composition,
wherein the molar selectivity for the oligosaccharide composition is at least 85%; and
wherein:
the catalyst comprises acidic monomers and ionic monomers connected to form a polymeric backbone, or
the catalyst comprises a solid support, acidic moieties attached to the solid support, and ionic moieties attached to the solid support.

100. The method of embodiment 99, further comprising combining the oligosaccharide composition with one or more functionalizing compounds to produce a functionalized oligosaccharide composition,
wherein the one or more functionalizing compounds is independently selected from the group consisting of carboxylic acids, sugar alcohols, amino acids, amino sugars, alcohols, sulfates and phosphates.

101. A method of producing a functionalized oligosaccharide composition, comprising:
combining one or more sugars with a catalyst and one or more functionalizing compounds to produce the functionalized oligosaccharide composition;
wherein the one or more functionalizing compounds is independently selected from the group consisting of carboxylic acids, sugar alcohols, amino acids, amino sugars, alcohols, sulfates and phosphates.

102. The method of embodiment 101, wherein the molar selectivity for the functionalized oligosaccharide composition is at least 85%.

103. The method of any one of embodiments 90 to 102, wherein the one or more sugars are independently selected from the group consisting of glucose, galactose, xylose, arabinose, fructose, mannose, lactose, maltose, ribose, allose, fucose, glyceraldehyde and rhamnose.

104. The method of any one of embodiments 100 to 103, wherein the one or more functionalizing compounds are independently selected from the group consisting of glucosamine, galactosamine, lactic acid, acetic acid, citric acid, pyruvic acid, succinic acid, glutamic acid, aspartic acid, glucuronic acid, butyric acid, itaconic acid, malic acid, maleic acid, propionic acid, butanoic acid, pentanoic acid, hexanoic acid, adipic acid, isobutyric acid, formic acid, levulinic acid, valeric acid, isovaleric acid, sorbitol, xylitol, arabitol, glycerol, erythritol, mannitol, galacitol, fucitol, iditol, inositol, volemitol, lacitol, ethanol, propanol, butanol, pentanol, hexanol, propanediol, butanediol, pentanediol, sulfate and phosphate.

105. The method of any one of embodiments 99, 100, or 102 to 104, wherein at least 10% of the oligosaccharide composition has a degree of polymerization from 3 to 25.

106. The method of any one of embodiments 100 to 105, wherein at least 10% of the functionalized oligosaccharide composition has a degree of polymerization from 3 to 25.

107. The method of any one of embodiments 99, 100, or 102 to 105, wherein at least 10% of the oligosaccharide composition has a number average molecular weight between 230 to 10,000 g/mol.

108. The method of any one of embodiments 100 to 107, wherein at least 10% of the functionalized oligosaccharide composition has a number average molecular weight between 230 to 10,000 g/mol.

109. An oligosaccharide composition, comprising:
monosaccharide monomers connected by glycosidic bonds;
wherein:
the monosaccharide monomers are independently selected from the group consisting of C5 monosaccharides and C6 monosaccharides; and
each glycosidic bond is independently selected from the group consisting of α-1,4 bonds, α-1,2 bonds, β-1,2 bonds, α-1,3 bonds, β-1,3 bonds, β-1,4 bonds, α-1,6 bonds and α-1,6 bonds;
at least 10% of the oligosaccharide composition has a degree of polymerization of at least three; and
at least a portion of the oligosaccharide composition comprises at least two different glycosidic bonds.

110. The oligosaccharide composition of embodiment 109, wherein the monosaccharide monomers are independently selected from the group consisting of glucose, galactose, xylose, arabinose, fructose, mannose, ribose, allose, fucose, glyceraldehyde and rhamnose.

111. The oligosaccharide composition of embodiment 109 or 110, wherein the monosaccharide monomers connected by glycosidic bonds form oligomer backbones, and wherein the oligomer backbones are optionally substituted with one or more pendant functional groups independently selected from the group consisting of carboxylic acids, sugar alcohols, amino acids, amino sugars, alcohols, sulfate and phosphate.

112. The oligosaccharide composition of any one of embodiments 109 to 111, wherein the monosaccharide monomers connected by glycosidic bonds form oligomer backbones, and wherein at least a portion of the oligosaccharide composition further comprises one or more bridging functional groups, wherein:
each bridging functional group independently connects one of the oligomer backbones to an additional monosaccharide monomer, a disaccharide, or an additional oligomer backbone; and
the one or more bridging functional groups are independently selected from the group consisting of polyols, polycarboxylic acids and amino acids.

113. The oligosaccharide composition of embodiment 112, wherein each additional oligomer backbone is independently optionally substituted with one or more pendant functional groups independently selected from the group consisting of carboxylic acids, sugar alcohols, amino acids, amino sugars, alcohols, sulfate and phosphate.

114. The oligosaccharide composition of any one of embodiments 111 to 113, wherein the one or more pendant functional groups are independently selected from the group consisting of glucosamine, galactosamine, citric acid, succinic acid, glutamic acid, aspartic acid, glucuronic acid, butyric acid, itaconic acid, malic acid, maleic acid, propionic acid, butanoic acid, pentanoic acid, hexanoic acid, adipic acid, isobutyric acid, formic acid, levulinic acid, valeric acid, isovaleric acid, sorbitol, xylitol, arabitol, glycerol, erythritol, mannitol, galacitol, fucitol, iditol, inositol, volemitol, lacitol, ethanol, propanol, butanol, pentanol, hexanol, propanediol, butanediol, pentanediol, sulfate and phosphate.

115. The oligosaccharide composition of any one of embodiments 112 to 114, wherein the one or more bridging functional groups are independently selected from the group consisting of glucosamine, galactosamine, lactic acid, acetic acid, citric acid, pyruvic acid, succinic acid, glutamic acid, aspartic acid, glucuronic acid, itaconic acid, malic acid, maleic acid, adipic acid, sorbitol, xylitol, arabitol, glycerol, erythritol, mannitol, galacitol, fucitol, iditol, inositol, volemitol, lacitol, propanediol, butanediol, pentanediol, sulfate and phosphate.

116. The oligosaccharide composition of any of embodiments 109 to 115, wherein at least 10% of the oligosaccharide composition has a number average molecular weight between 230 to 10,000 g/mol.

117. A method of converting an α-1,4 polysaccharide to a polysaccharide having a mixture of linkages, comprising:
contacting an α-1,4 polysaccharide with a catalyst,
wherein the catalyst comprises acidic monomers and ionic monomers connected to form a polymeric backbone, or wherein the catalyst comprises a solid support, acidic moieties attached to the solid support, and ionic moieties attached to the solid support; and
converting at least a portion of the α-1,4 bonds in the α-1,4 polysaccharide to one or more non-α-1,4 bonds selected from the group consisting of α-1,2 bonds, β-1,2 bonds, α-1,3 bonds, β-1,3 bonds, β-1,4 bonds, α-1,6 bonds, and β-1,6 bonds to produce a polysaccharide with a mixture of linkages.

EXAMPLES

The following examples are provided by way of illustration and are not intended to be limiting of the invention.

Except where otherwise indicated, commercial reagents were obtained from Sigma-Aldrich, St. Louis, Mo., USA, and were purified prior to use following the guidelines of Perrin and Armarego. See Perrin, D. D. & Armarego, W. L. F., *Purification of Laboratory Chemicals,* 3rd ed.; Pergamon Press, Oxford, 1988. Nitrogen gas for use in chemical reactions was of ultra-pure grade, and was dried by passing it through a drying tube containing phosphorous pentoxide. Unless indicated otherwise, all non-aqueous reagents were transferred under an inert atmosphere via syringe or Schlenk flask. Organic solutions were concentrated under reduced pressure on a Buchi rotary evaporator. Where necessary, chromatographic purification of reactants or products was accomplished using forced-flow chromatography on 60 mesh silica gel according to the method described of Still et al., See Still et al., *J. Org. Chem.,* 43: 2923 (1978). Thin-layer chromatography (TLC) was performed using silica-coated glass plates. Visualization of the developed chromatogram was performed using either Cerium Molybdate (i.e., Hanessian) stain or $KMnO_4$ stain, with gentle heating, as required. Fourier-Transform Infrared (FTIR) spectroscopic analysis of solid samples was performed on a Perkin-Elmer 1600 instrument equipped with a horizontal attenuated total reflectance (ATR) attachment using a Zinc Selenide (ZnSe) crystal.

The moisture content of reagents was determined using a Mettler-Toledo MJ-33 moisture-analyzing balance with a sample size of 0.5-1.0 g. All moisture contents were determined as the average % wt loss on drying obtained from triplicate measurements.

The soluble sugar and oligosaccharide content of reaction products was determined by a combination of high performance liquid chromatography (HPLC) and spectrophotometric methods. HPLC determination of soluble sugars and oligosaccharides was performed on a Hewlett-Packard 1100 Series instrument equipped with a refractive index (RI) detector using a 30 cm×7.8 mm BioRad Aminex HPX-87P column with water as the mobile phase. The sugar column was protected by both a lead-exchanged sulfonated-polystyrene guard column and a tri-alkylammoniumhydroxide anionic-exchange guard column. All HPLC samples were microfiltered using a 0.2 μm syringe filter prior to injection. Sample concentrations were determined by reference to calibrations generated from a standard solution containing glucose, xylose, arabinose, galactose, and gluco-oligosaccharides in known concentrations.

The production of soluble sugar degradation products was determined by high performance liquid chromatography (HPLC) on a Hewlett-Packard 1100 Series instrument equipped with a refractive index (RI) detector using a 30 cm×7.8 mm BioRad Aminex HPX-87H column with 50 mM sulfuric acid as the mobile phase. The sugar column was protected by both a sulfonated-polystyrene guard column and all HPLC samples were microfiltered using a 0.2 μm syringe filter prior to injection. Sample concentrations were determined by reference to calibrations generated from a standard solution containing formic acid, acetic acid, levulinic acid, 5-hydroxymethylfurfural, and 2-furaldehyde.

The average degree of polymerization (DP) for oligosaccharides was determined as the number average of species containing one, two, three, four, five, six, seven, eight, nine, ten to fifteen, and greater than fifteen, anhydrosugar monomer units. The relative concentrations of oligosaccharides corresponding to these different DPs was determined by high performance liquid chromatography (HPLC) on a Hewlett-Packard 1100 Series instrument equipped with a refractive index (RI) detector using a 30 cm×7.8 mm BioRad Aminex HPX-87A column with water as the mobile phase. The analytical column was protected by a silver-coordinated, sulfonated-polystyrene guard column and all HPLC samples were microfiltered using a 0.2 μm syringe filter prior to injection.

The presence of glycosidic linkages was determined by proton nuclear magnetic resonance ($^1$H-NMR). For analysis, oligosaccharide samples were dried at 70° C. under vacuum, redissolved in deuterated water and allowed to equilibrate at room temperature for 2 hours, followed by a repeated cycle of drying under vacuum and redissolution in deuterated water. Proton NMR spectra were obtained at 400 MHz and peak assignments were made according to Roslund, M. U., et. al, *Carb. Res.*, 343, 101-112 (2008). Further resolution of peaks and identification of (1,4) linkages was accomplished through J-resolved (JRES) NMR.

The conversion X(t) of monomeric (DP 1) sugars at time t was determined according to $$X(t) = 1 - \frac{\text{mol}(DP1, t)}{\text{mol}(DP1, 0)},$$

where mol(DP1,t) denotes the total moles of monomeric sugars present in the reaction at time t and mol(DP1,0) denotes the total moles of monomeric sugars initially charged to the reaction. Similarly, the yield to oligosaccharides of a given DP was determined according to $$Y_n(t) = \frac{\text{mol}(DPn, t)}{\text{mol}(DP1, 0)},$$

where mol(DPn,t) denotes the total molar equivalents of species with a DP of n, measured in units of monomeric sugar equivalents. Total yield to oligosaccharides with DP>1 was determined according to $$Y_{n>1}(t) = \sum_{n>1} \frac{\text{mol}(DPn, t)}{\text{mol}(DP1, 0)}$$

and the total yield to oligosaccharides with DP>2 was determined according to $$Y_{n>2}(t) = \sum_{n>2} \frac{\text{mol}(DPn, t)}{\text{mol}(DP1, 0)}.$$

The molar yield to sugar degradation products was determined analogously to that for oligosaccharides, where molar quantities were measured as monomeric sugar equivalents. Finally, the molar selectivity to a given product species was determined as the ratio of the species yield to the sugar conversion, namely S(t)=Y(t)/X(t).

The production of undesirable non-carbohydrate by-products, such as polyfuranics, solid humins, and other condensation products, was determined by inference from the reaction molar balance. Specifically, the molar yield to undesirable by-products was determined as the arithmetic difference of the monomeric sugar conversion minus the sum of the yields to all quantifiable species. Equivalently, the total molar yield to carbohydrates was determined by hydrolyzing a given oligosaccharide mixture back to its constituent monomeric sugars under dilute acid conditions at elevated temperature (e.g., incubating at 121 degrees Celsius for 1 hour in 2%-4% sulfuric acid) and measuring the resulting moles of monomeric sugars, corrected by a standard monomeric control solution that was treated under identical hydrolysis conditions.

The viscosity of oligosaccharide mixtures was determined using a Brookfield viscosometer mounted above a temperature-controlled water bath used to set the temperature of the solution being measured from room temperature up to approximately 95 degrees Celsius. The acid content of catalyst samples and aqueous solutions was determined using a Hana Instruments 902-C autotitrator with sodium hydroxide as the titrant, calibrated against a standard solution of potassium hydrogen phthalate (KHP).

Concentration of liquid samples was performed using a Buchi r124 series rotary evaporator unit. For oligosaccharide solutions in water, a bath temperature of approximately 40-60 degrees Celsius was used. Vacuum pressure of 50-150 mTorr was provided by an oil-immersion pump, which was protected by an acetone-dry ice trap to prevent volatilized solvents from being drawn into the pump system.

Freeze drying of oligosaccharide samples for analytical analysis was performed by coating the walls of a 100 mL round bottom flask (RBF) with approximately 2 grams of the oligosaccharide solution with a starting concentration of 60-70 wt % dissolved solids. The loaded flask was placed in a −20 degree Celsius freezer for two hours, after which the flask was quickly removed to a room temperature environment and subjected to a vacuum. A resting pressure of 50-150 mTorr was provided by an oil-immersion pump, which was protected by an acetone-dry ice trap to prevent volatilized solvents from being drawn into the pump system. Typically three sequential freeze-pump cycles were performed.

Preparation of Polymeric Materials

Example 1: Preparation of Poly[Styrene-Co-Vinyl-benzylchloride-Co-Divinylbenzene]

To a 500 mL round bottom flask (RBF) containing a stirred solution of 1.08 g of poly(vinylalcohol) in 250.0 mL of deionized $H_2O$ at 0° C., was gradually added a solution containing 50.04 g (327.9 mmol) of vinylbenzyl chloride (mixture of 3- and 4-isomers), 10.13 g (97.3 mmol) of styrene, 1.08 g (8.306 mmol) of divinylbenzene (DVB, mixture of 3- and 4-isomers) and 1.507 g (9.2 mmol) of azobisisobutyronitrile (AIBN) in 150 mL of a 1:1 (by volume) mixture of benzene/tetrahydrofuran (THF) at 0° C. After 2 hours of stirring at 0° C. to homogenize the mixture, the reaction flask was transferred to an oil bath to increase the reaction temperature to 75° C., and the mixture was stirred vigorously for 28 hours. The resulting polymer beads were vacuum filtered using a fritted-glass funnel to collect the polymer product. The beads were washed repeatedly with 20% (by volume) methanol in water, THF, and MeOH, and dried overnight at 50° C. under reduced pressure to yield 59.84 g of polymer. The polymer beads were separated by size using sieves with mesh sizes 100, 200, and 400.

Example 2: Preparation of poly [styrene-co-3-methyl-1-(4-vinylbenzyl)-3H-imidazol-1-ium chloride-co-divinylbenzene]

Poly(styrene-co-vinylbenzylchloride-co-divinylbenzene) ($Cl^-$ density=~4.0 mmol/g, 50 g, 200 mmol) was charged into a 500 mL three neck flask (TNF) equipped with a mechanical stirrer, a dry nitrogen line, and purge valve. Dry dimethylformamide (185 ml) was added into the flask (via cannula under $N_2$) and stirred to form a viscous slurry of polymer resin. 1-Methylimidazole (36.5 g, 445 mmol) was then added and stirred at 95° C. for 8 h. After cooling, the reaction mixture was filtered using a fritted glass funnel under vacuum, washed sequentially with de-ionized water and ethanol, and finally air dried.

The chemical functionalization of the polymer material, expressed in millimoles of functional groups per gram of dry polymer resin (mmol/g) was determined by ion exchange titrimetry. For the determination of cation-exchangeable acidic protons, a known dry mass of polymer resin was added to a saturated aqueous solution of sodium chloride and titrated against a standard sodium hydroxide solution to the phenolphthalein end point. For the determination of anion-exchangeable ionic chloride content, a known dry mass of polymer resin was added to an aqueous solution of sodium nitrate and neutralized with sodium carbonate. The resulting mixture was titrated against a standardized solution of silver nitrate to the potassium chromate endpoint. For polymeric materials in which the exchangeable anion was not chloride, the polymer was first treated by stirring the material in aqueous hydrochloric acid, followed by washing repeatedly with water until the effluent was neutral (as determined by pH paper). The chemical functionalization of the polymer resin with methylimidazolium chloride groups was determined to be 2.60 mmol/g via gravimetry and 2.61 mmol/g via titrimetry.

Example 3: Preparation of poly [styrene-co-4-vinylbenzenesulfonic acid-co-3-methyl-1-(4-vinylbenzyl)-3H-imidazol-1-ium sulfate-co-divinylbenzene]

Poly[styrene-co-3-methyl-1-(4-vinylbenzyl)-3H-imidazol-1-iumchloride-co-divinylbenzene] (63 g) was charged into a 500 mL flask equipped with a magnetic stir bar and condenser. Cold concentrated sulfuric acid (>98% w/w, $H_2SO_4$, 300 mL) was gradually added into the flask under stirring which resulted in formation of dark-red colored slurry of resin. The slurry was stirred at 85° C. for 4 h. After cooling to room temperature, the reaction mixture was filtered using fritted glass funnel under vacuum and then washed repeatedly with de-ionized water until the effluent was neutral, as determined by pH paper. The sulfonated resin beads were finally washed with ethanol and air dried. The chemical functionalization of the polymer resin with sulfonic acid groups was determined to be 1.60 mmol/g, as determined by titrimetry following the procedure of Example 2.

Example 4: Preparation of poly [styrene-co-4-vinylbenzenesulfonic acid-co-3-methyl-1-(4-vinylbenzyl)-3H-imidazol-1-ium chloride-co-divinylbenzene]

Poly[styrene-co-4-vinylbenzenesulfonic acid-co-3-methyl-1-(4-vinylbenzyl)-3H-imidazol-1-ium sulfate-co-divinylbenzene] (sample of example 3), contained in fritted glass funnel, was washed repeatedly with 0.1 M HCl solution to ensure complete exchange of sulfate with $Cl^-$. The resin was then washed with de-ionized water until the effluent was neutral, as determined by pH paper. The resin was finally air-dried.

Example 5: Preparation of poly [styrene-co-4-vinylbenzenesulfonic acid-co-3-methyl-1-(4-vinylbenzyl)-3H-imidazol-1-ium acetate-co-divinylbenzene]

The suspension of poly[styrene-co-4-vinylbenzenesulfonic acid-co-3-methyl-1-(4-vinylbenzyl)-3H-imidazol-1-ium sulfate-co-divinylbenzene] (sample of example 3) in 10% aqueous acetic acid solution was stirred for 2 h at 60° C. to ensure complete exchange of sulfate with $AcO^-$. The resin was filtered using fritted glass funnel and then washed multiple times with de-ionized water until the effluent was neutral. The resin was finally air-dried.

Example 6: Preparation of poly [styrene-co-3-ethyl-1-(4-vinylbenzyl)-3H-imidazol-1-ium chloride-co-divinylbenzene]

Poly(styrene-co-vinylbenzylchloride-co-divinylbenzene) ($Cl^-$ density=~4.0 mmol/g, 10 g, 40 mmol) was charged into a 250 three neck flask (TNF) equipped with a mechanical stirrer, a dry nitrogen line, and purge valve. Dry dimethylformamide (80 ml) was added into the flask (via cannula under $N_2$) and stirred to give viscous resin slurry. 1-Ethylimidazole (4.3 g, 44.8 mmol) was then added to the resin slurry and stirred at 95° C. under 8 h. After cooling, the reaction mixture was filtered using fritted glass funnel under vacuum, washed sequentially with de-ionized water and ethanol, and finally air dried. The chemical functionalization of the polymer resin with ethylimidazolium chloride groups was determined to be 1.80 mmol/g, as determined by titrimetry following the procedure of Example 1.

Example 7: Preparation of poly [styrene-co-4-vinylbenzenesulfonic acid-co-3-ethyl-1-(4-vinylbenzyl)-3H-imidazol-1-ium sulfate-co-divinylbenzene]

Poly [styrene-co-3-ethyl-1-(4-vinylbenzyl)-3H-imidazol-1-ium chloride-co-divinylbenzene] (5 g) was charged into a 100 mL flask equipped with a magnetic stir bar and condenser. Cold concentrated sulfuric acid (>98% w/w, $H_2SO_4$, 45 mL) was gradually added into the flask under stirring which resulted in the formation of dark-red colored uniform slurry of resin. The slurry was stirred at 95-100° C. for 6 h. After cooling, the reaction mixture was filtered using fritted glass funnel under vacuum and then washed repeatedly with de-ionized water until the effluent was neutral, as determined by pH paper. The sulfonated beads were finally washed with ethanol and air dried. The chemical functionalization of the polymer with sulfonic acid groups was determined to be 1.97 mmol/g, as determined by titrimetry following the procedure of Example 2.

Example 8: Preparation of poly[styrene-co-4-vinylbenzenesulfonic acid-co-3-ethyl-1-(4-vinylbenzyl)-3H-imidazol-1-ium chloride-co-divinylbenzene]

Poly [styrene-co-4-vinylbenzenesulfonic acid-co-3-ethyl-1-(4-vinylbenzyl)-3H-imidazol-1-ium sulfate-co-divinylbenzene] resin beads (sample of example 7) contained in fritted glass funnel was washed multiple times with 0.1 M HCl solution to ensure complete exchange of sulfate with Cl$^-$. The resin was then washed with de-ionized water until the effluent was neutral, as determined by pH paper. The resin was finally washed with ethanol and air dried.

Example 9: Preparation of poly [styrene-co-1-(4-vinylbenzyl)-3H-imidazol-1-ium chloride-co-divinylbenzene]

Poly(styrene-co-vinylbenzylchloride-co-divinylbenzene) (Cl$^-$ density=~4.0 mmol/g, 10 g, 40 mmol) was charged into a 100 mL flask equipped with a magnetic stir bar and condenser. Chloroform (50 ml) was added into the flask and stirred to form slurry of resin. Imidazole (2.8 g, 41.13 mmol) was then added to the resin slurry and stirred at 40° C. for 18 h. After completion of reaction, the reaction mixture was filtered using fritted glass funnel under vacuum, washed sequentially with de-ionized water and ethanol, and finally air dried. The chemical functionalization of the polymer resin with imidazolium chloride groups was determined to be 2.7 mmol/g, as determined by titrimetry following the procedure of Example 2.

Example 10: Preparation of poly [styrene-co-4-vinylbenzenesulfonic acid-co-1-(4-vinylbenzyl)-3H-imidazol-1-ium sulfate-co-divinylbenzene]

Poly[styrene-co-1-(4-vinylbenzyl)-3H-imidazol-1-ium chloride-co-divinylbenzene] (5 g) was charged into a 100 mL flask equipped with a magnetic stir bar and condenser. Cold concentrated sulfuric acid (>98% w/w, $H_2SO_4$, 80 mL) was gradually added into the flask and stirred to form dark-red colored slurry of resin. The slurry was stirred at 95° C. for 8 h. After cooling, the reaction mixture was filtered using fritted glass funnel under vacuum and then washed repeatedly with de-ionized water until the effluent was neutral, as determined by pH paper. The sulfonated beads were finally washed with ethanol and air dried. The chemical functionalization of the polymer resin with sulfonic acid groups was determined to be 1.26 mmol/g, as determined by titrimetry following the procedure of Example 2.

Example 11: Preparation of poly [styrene-co-3-methyl-1-(4-vinylbenzyl)-3H-benzoimidazol-1-ium chloride-co-divinylbenzene]

Poly(styrene-co-vinylbenzylchloride-co-divinylbenzene) (Cl$^-$ density=~4.0 mmol/g, 4 g, 16 mmol) was charged into a 100 mL flask equipped with a magnetic stir bar and condenser. Dry dimethylformamide (50 ml) was added into the flask (via cannula under $N_2$) and stirred to form viscous slurry of polymer resin. 1-Methylbenzimidazole (3.2 g, 24.2 mmol) was then added to the resin slurry and the resulting reaction mixture was stirred at 95° C. for 18 h. After cooling, the reaction mixture was filtered using fritted glass funnel under vacuum, washed sequentially with de-ionized water and ethanol, and finally air dried. The chemical functionalization of the polymer with methylbenzimidazolium chloride groups was determined to be 1.63 mmol/g, as determined by titrimetry following the procedure of Example 2.

Example 12: Preparation of poly [styrene-co-4-vinylbenzenesulfonic acid-co-3-methyl-1-(4-vinylbenzyl)-3H-benzoimidazol-1-ium sulfate-co-divinylbenzene]

Poly[styrene-co-3-methyl-1-(4-vinylbenzyl)-3H-benzoimidazol-1-ium chloride-co-divinylbenzene] (5.5 g) was charged into a 100 mL flask equipped with a magnetic stir bar and condenser. Cold concentrated sulfuric acid (>98% w/w, $H_2SO_4$, 42 mL) and fuming sulfuric acid (20% free $SO_3$, 8 mL) was gradually added into the flask and stirred to form dark-red colored slurry of resin. The slurry was stirred at 85° C. for 4 h. After cooling, the reaction mixture was filtered using fritted glass funnel under vacuum and then washed repeatedly with de-ionized water until the effluent was neutral, as determined by pH paper. The sulfonated beads were finally washed with ethanol and air dried. The chemical functionalization of the polymer with sulfonic acid groups was determined to be 1.53 mmol/g, as determined by titrimetry following the procedure of Example 2.

Example 13: Preparation of poly [styrene-co-1-(4-vinylbenzyl)-pyridinium chloride-co-divinylbenzene]

Poly(styrene-co-vinylbenzylchloride-co-divinylbenzene) (Cl$^-$ density=~4.0 mmol/g, 5 g, 20 mmol) was charged into a 100 mL flask equipped with a magnetic stir bar and condenser. Dry dimethylformamide (45 ml) was added into the flask (via cannula under $N_2$) while stirring and consequently, the uniform viscous slurry of polymer resin was obtained. Pyridine (3 mL, 37.17 mmol) was then added to the resin slurry and stirred at 85-90° C. for 18 h. After cooling, the reaction mixture was filtered using fritted glass funnel under vacuum, washed sequentially with de-ionized water and ethanol, and finally air dried. The chemical functionalization of the polymer resin with pyridinium chloride groups was determined to be 3.79 mmol/g, as determined by titrimetry following the procedure of Example 2.

Example 14: Preparation of poly [styrene-co-4-vinylbenzenesulfonic acid-co-1-(4-vinylbenzyl)-pyridinium-sulfate-co-divinylbenzene]

Poly[styrene-co-1-(4-vinylbenzyl)-pyridinium chloride-co-divinylbenzene] (4 g) resin beads were charged into a 100 mL flask equipped with a magnetic stir bar and condenser. Cold concentrated sulfuric acid (>98% w/w, $H_2SO_4$, 45 mL) was gradually added into the flask under stirring which consequently resulted in the formation of dark-red colored uniform slurry of resin. The slurry was heated at 95-100° C. under continuous stirring for 5 h. After completion of reaction, the cooled reaction mixture was filtered using fritted glass funnel under vacuum and then washed repeatedly with de-ionized water until the effluent was neutral, as determined by pH paper. The resin beads were finally washed with ethanol and air dried. The chemical functionalization of the polymer with sulfonic acid groups was determined to be 0.64 mmol/g, as determined by titrimetry following the procedure of Example 2.

Example 15: Preparation of poly [styrene-co-1-(4-vinylbenzyl)-pyridinium chloride-co-3-methyl-1-(4-vinylbenzyl)-3H-imidazol-1-ium chloride-co-divinylbenzene]

Poly(styrene-co-vinylbenzylchloride-co-divinylbenzene) (Cl⁻ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring which resulted in the formation of viscous slurry of polymer resin. Pyridine (1.6 mL, 19.82 mmol) and 1-methylimidazole (1.7 mL, 21.62 mmol) were then added to the resin slurry and the resulting reaction mixture was stirred at 95° C. for 18 h. After completion of reaction, the reaction mixture was cooled, filtered using fritted glass funnel under vacuum, washed sequentially with de-ionized water and ethanol, and finally air dried. The chemical functionalization of the polymer with pyridinium chloride and 1-methylimidazolium chloride groups was determined to be 3.79 mmol/g, as determined by titrimetry following the procedure of Example 2.

Example 16: Preparation of poly[styrene-co-4-vinylbenzenesulfonic acid-co-1-(4-vinylbenzyl)-pyridiniumchloride-co-3-methyl-1-(4-vinylbenzyl)-3H-imidazol-1-ium sulfate-co-divinylbenzene]

Poly[styrene-co-1-(4-vinylbenzyl)-pyridinium chloride-co-3-methyl-1-(4-vinylbenzyl)-3H-imidazol-1-ium chloride-co-divinylbenzene] (5 g) was charged into a 100 mL flask equipped with a magnetic stir bar and condenser. Cold concentrated sulfuric acid (>98% w/w, $H_2SO_4$, 75 mL) and fuming sulfuric acid (20% free $SO_3$, 2 mL) were then gradually added into the flask under stirring which consequently resulted in the formation of dark-red colored uniform slurry of resin. The slurry was heated at 95-100° C. under continuous stirring for 12 h. After completion of reaction, the cooled reaction mixture was filtered using fritted glass funnel under vacuum and then washed repeatedly with de-ionized water until the effluent was neutral, as determined by pH paper. The sulfonated resin beads were finally washed with ethanol and air dried. The chemical functionalization of the polymer resin with sulfonic acid groups was determined to be 1.16 mmol/g, as determined by titrimetry following the procedure of Example 2.

Example 17: Preparation of poly[styrene-co-4-methyl-4-(4-vinylbenzyl)-morpholin-4-ium chloride-co-divinylbenzene]

Poly(styrene-co-vinylbenzylchloride-co-divinylbenzene) (Cl⁻ density=~4.0 mmol/g, 10 g, 40 mmol) was charged into a 100 mL flask equipped with a magnetic stir bar and condenser. Dry dimethylformamide (85 ml) was added into the flask (via cannula under $N_2$) while stirring which resulted in the formation of uniform viscous slurry of polymer resin. 1-Methylmorpholine (5.4 mL, 49.12 mmol) were then added to the resin slurry and the resulting reaction mixture was stirred at 95° C. for 18 h. After cooling, the reaction mixture was filtered using fritted glass funnel under vacuum, washed sequentially with de-ionized water and ethanol, and finally air dried. The chemical functionalization of the polymer with methylmorpholinium chloride groups was determined to be 3.33 mmol/g, as determined by titrimetry following the procedure of Example 2.

Example 18: Preparation of poly[styrene-co-4-vinylbenzenesulfonic acid-co-4-methyl-4-(4-vinylbenzyl)-morpholin-4-ium sulfate-co-divinylbenzene]

Poly [styrene-co-1-4-methyl-4-(4-vinylbenzyl)-morpholin-4-ium chloride-co-divinylbenzene] (8 g) was charged into a 100 mL flask equipped with a magnetic stir bar and condenser. Cold concentrated sulfuric acid (>98% w/w, $H_2SO_4$, 50 mL) was gradually added into the flask under stirring which consequently resulted in the formation of dark-red colored slurry. The slurry was stirred at 90° C. for 8 h. After cooling, the reaction mixture was filtered using fritted glass funnel under vacuum, washed repeatedly with de-ionized water until the effluent was neutral, as determined by pH paper. The sulfonated resin beads were finally washed with ethanol and air dried. The chemical functionalization of the polymer with sulfonic acid groups was determined to be 1.18 mmol/g, as determined by titrimetry following the procedure of Example 2.

Example 19: Preparation of [polystyrene-co-triphenyl-(4-vinylbenzyl)-phosphoniumchloride-co-divinylbenzene]

Poly(styrene-co-vinylbenzylchloride-co-divinylbenzene) (Cl⁻ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and the uniform viscous slurry of polymer resin was obtained. Triphenylphosphine (11.6 g, 44.23 mmol) was then added to the resin slurry and the resulting reaction mixture was stirred at 95° C. for 18 h. After cooling, the reaction mixture was filtered using fritted glass funnel under vacuum, washed sequentially with de-ionized water and ethanol, and finally air dried. The chemical functionalization of the polymer with triphenylphosphonium chloride groups was determined to be 2.07 mmol/g, as determined by titrimetry following the procedure of Example 2.

Example 20: Preparation of poly[styrene-co-4-vinylbenzenesulfonic acid-co-triphenyl-(4-vinylbenzyl)-phosphonium sulfate-co-divinylbenzene]

Poly (styrene-co-triphenyl-(4-vinylbenzyl)-phosphonium chloride-co-divinylbenzene) (7 g) was charged into a 100 mL flask equipped with a magnetic stir bar and condenser. Cold concentrated sulfuric acid (>98% w/w, $H_2SO_4$, 40 mL) and fuming sulfuric acid (20% free $SO_3$, 15 mL) were gradually added into the flask under stirring which consequently resulted in the formation of dark-red colored slurry. The slurry was stirred at 95° C. for 8 h. After cooling, the reaction mixture was filtered using fritted glass funnel under vacuum, washed repeatedly with de-ionized water until the effluent was neutral, as determined by pH paper. The sulfonated resin beads were finally washed with ethanol and air dried. The chemical functionalization of the polymer with sulfonic acid groups was determined to be 2.12 mmol/g, as determined by titrimetry following the procedure of Example 2.

Example 21: Preparation of poly[styrene-co-1-(4-vinylbenzyl)-piperidine-co-divinyl benzene]

Poly(styrene-co-vinylbenzyl chloride-co-divinylbenzene) ($Cl^-$ density=~4.0 mmol/g, 10 g, 40 mmol) was charged into a 100 mL flask equipped with a magnetic stir bar and condenser. Dry dimethylformamide (50 ml) was added into the flask (via cannula under $N_2$) while stirring which resulted in the formation of uniform viscous slurry of polymer resin. Piperidine (4 g, 46.98 mmol) was then added to the resin slurry and the resulting reaction mixture was stirred at 95° C. for 16 h. After cooling, the reaction mixture was filtered using fritted glass funnel under vacuum, washed sequentially with de-ionized water and ethanol, and finally air dried.

Example 22: Preparation of poly[styrene-co-4-vinylbenzenesulfonic acid-co-1-(4-vinylbenzyl)-piperidine-co-divinyl benzene]

Poly[styrene-co-1-(4-vinylbenzyl)-piperidine-co-divinyl benzene] (7 g) was charged into a 100 mL flask equipped with a magnetic stir bar and condenser. Cold concentrated sulfuric acid (>98% w/w, $H_2SO_4$, 45 mL) and fuming sulfuric acid (20% free S03, 12 mL) were gradually added into the flask under stirring which consequently resulted in the formation of dark-red colored slurry. The slurry was stirred at 95° C. for 8 h. After completion of reaction, the cooled reaction mixture was filtered using fritted glass funnel under vacuum and then washed repeatedly with de-ionized water until the effluent was neutral, as determined by pH paper. The resin beads were finally washed with ethanol and air dried. The chemical functionalization of the polymer with sulfonic acid groups was determined to be 0.72 mmol/g, as determined by titrimetry following the procedure of Example 2.

Example 23: Preparation of poly[styrene-co-4-vinylbenzenesulfonic acid-co-1-methyl-1-(4-vinylbenzyl)-piperidin-1-ium chloride-co-divinyl benzene]

Poly (styrene-co-4-(1-piperidino)methylstyrene-co-divinylbenzene) (4 g) was charged into a 100 mL flask equipped with a magnetic stir bar and condenser. Dry dimethylformamide (40 ml) was added into the flask (via cannula under $N_2$) under stirring to obtain uniform viscous slurry. Iodomethane (1.2 ml) and potassium iodide (10 mg) were then added into the flask. The reaction mixture was stirred at 95° C. for 24 h. After cooling, the reaction mixture was filtered using fitted glass funnel under vacuum and then washed multiple times with dilute HCl solution to ensure complete exchange of $I^-$ with $Cl^-$. The resin was finally washed with de-ionized water until the effluent was neutral, as determined by pH paper. The resin was finally air-dried.

Example 24: Preparation of poly[styrene-co-4-(4-vinylbenzyl)-morpholine-co-divinyl benzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (50 ml) was added into the flask (via cannula under $N_2$) while stirring and consequently, the uniform viscous slurry of polymer resin was obtained. Morpholine (4 g, 45.92 mmol) was then added to the resin slurry and the resulting reaction mixture was heated at 95° C. under continuous stirring for 16 h. After completion of reaction, the reaction mixture was cooled, filtered using fritted glass funnel under vacuum, washed sequentially with de-ionized water and ethanol, and finally air dried.

Example 25: Preparation of poly[styrene-co-4-vinylbenzenesulfonic acid-co-4-(4-vinylbenzyl)-morpholine-co-divinyl benzene]

Poly[styrene-co-4-(4-vinylbenzyl)-morpholine-co-divinyl benzene] (10 g) was charged into a 200 mL flask equipped with a magnetic stir bar and condenser. Cold concentrated sulfuric acid (>98% w/w, $H_2SO_4$, 90 mL) and fuming sulfuric acid (20% free S03, 10 mL) were gradually added into the flask while stirring which consequently resulted in the formation of dark-red colored slurry. The slurry was stirred at 95° C. for 8 h. After cooling, the reaction mixture was filtered using fritted glass funnel under vacuum and then washed repeatedly with de-ionized water until the effluent was neutral, as determined by pH paper. The sulfonated resin beads were finally washed with ethanol and air dried. The chemical functionalization of the polymer with sulfonic acid groups was determined to be 0.34 mmol/g, as determined by titrimetry following the procedure of Example 2.

Example 26: Preparation of poly[styrene-co-4-vinylbenzenesulfonic acid-co-4-(4-vinylbenzyl)-morpholine-4-oxide-co-divinyl benzene]

Poly[styrene-co-4-vinylbenzenesulfonic acid-co-4-(4-vinylbenzyl)-morpholine-co-divinyl benzene] (6 g) was charged into a 100 mL flask equipped with a magnetic stir bar and condenser. Methanol (60 mL) was then charged into the flask, followed by addition of hydrogen peroxide (30% solution in water, 8.5 mL). The reaction mixture was refluxed under continuous stirring for 8 h. After cooling, the reaction mixture was filtered, washed sequentially with de-ionized water and ethanol, and finally air dried.

Example 27: Preparation of poly[styrene-co-4-vinylbenzyl-triethylammonium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and consequently the uniform viscous slurry of polymer resin was obtained. Triethylamine (5 mL, 49.41 mmol) was then added to the resin slurry and the resulting reaction mixture was stirred at 95° C. for 18 h. After cooling, the reaction mixture was filtered using fritted glass funnel under vacuum, washed sequentially with de-ionized water and ethanol, and finally air dried. The chemical functionalization of the polymer resin with triethylammonium chloride groups was determined to be 2.61 mmol/g, as determined by titrimetry following the procedure of Example 2.

Example 28: Preparation of poly[styrene-co-4-vinylbenzenesulfonic acid-co-triethyl-(4-vinylbenzyl)-ammonium chloride-co-divinylbenzene]

Poly[styrene-co-triethyl-(4-vinylbenzyl)-ammonium chloride-co-divinylbenzene] (6 g) was charged into a 100 mL flask equipped with a magnetic stir bar and condenser. Cold concentrated sulfuric acid (>98% w/w, $H_2SO_4$, 60 mL) was gradually added into the flask under stirring which consequently resulted in the formation of dark-red colored uniform slurry of resin. The slurry was stirred at 95-100° C. for 8 h. After cooling, the reaction mixture was filtered using fritted glass funnel under vacuum and then washed repeatedly with de-ionized water until the effluent was neutral, as determined by pH paper. The sulfonated resin beads were finally washed with ethanol and air dried. The chemical functionalization of the polymer with sulfonic acid groups was determined to be 0.31 mmol/g, as determined by titrimetry following the procedure of Example 2.

Example 29: Preparation of poly[styrene-co-4-vinylbenzenesulfonic acid-co-vinylbenzylchloride-co-divinylbenzene]

Poly(styrene-co-vinylbenzyl chloride-co-divinylbenzene) (6 g) was charged into a 100 mL flask equipped with a magnetic stir bar and condenser. Fuming sulfuric acid (20% free $SO_3$, 25 mL) was gradually added into the flask under stirring which consequently resulted in the formation of dark-red colored slurry. The slurry was stirred at 90° C. for 5 h. After cooling, the reaction mixture was filtered using fritted glass funnel under vacuum, washed sequentially with de-ionized water and ethanol, and finally air dried. The chemical functionalization of the polymer with sulfonic acid groups was determined to be 0.34 mmol/g, as determined by titrimetry following the procedure of Example 2.

Example 30: Preparation of poly[styrene-co-4-vinylbenzenesulfonic acid-co-3-methyl-1-(4-vinylbenzyl)-3H-imidazol-1-ium chloride-co-divinylbenzene]

Poly [styrene-co-4-vinylbenzenesulfonic acid-co-vinylbenzylchloride-co-divinylbenzene] (5 g) was charged into a 100 mL flask equipped with a magnetic stir bar and condenser. Dry dimethylformamide (20 ml) was added into the flask (via cannula under $N_2$) while stirring and the uniform viscous slurry of polymer resin was obtained. 1-Methylimidazole (3 mL, 49.41 mmol) was then added to the resin slurry and the resulting reaction mixture was stirred at 95° C. for 18 h. After cooling, reaction mixture was filtered using fritted glass funnel under vacuum and then washed repeatedly with de-ionized water. The resin beads were finally washed with ethanol and air dried. The chemical functionalization of the polymer with sulfonic acid group and methylimidazolium chloride groups was determined to be 0.23 mmol/g and 2.63 mmol/g, respectively, as determined by titrimetry following the procedure of Example 2.

Example 31: Preparation of poly[styrene-co-3-methyl-1-(4-vinylbenzyl)-3H-imidazol-1-ium chloride-co-4-boronyl-1-(4-vinylbenzyl)-pyridinium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and consequently the uniform viscous slurry of polymer resin was obtained. 4-Pyridyl-boronic acid (1.8 g, 14.6 mmol) was then added to the resin slurry and the resulting reaction mixture was stirred at 95° C. for 2 days. 1-Methylimidazole (3 mL, 49.41 mmol) was then added to the reaction mixture and stirred further at 95° C. for 1 day. After cooling to room temperature, the reaction mixture was filtered using fritted glass funnel under vacuum, washed sequentially with de-ionized water and ethanol, and finally air dried. The chemical functionalization of the polymer with boronic acid group was determined to be 0.28 mmol/g respectively, as determined by titrimetry following the procedure of Example 2.

Example 32: Preparation of poly[styrene-co-3-methyl-1-(4-vinylbenzyl)-3H-imidazol-1-ium chloride-co-1-(4-vinylphenyl)methylphosphonic acid-co-divinylbenzene]

Poly[styrene-co-3-methyl-1-(4-vinylbenzyl)-3H-imidazol-1-ium chloride-co-divinylbenzene]($Cl^-$ density=~2.73 mmol/g, 5 g) was charged into a 100 mL flask equipped with a magnetic stir bar and condenser. Triethylphosphite (70 ml) was added into the flask and the resulting suspension was stirred at 120° C. for 2 days. The reaction mixture was filtered using fritted glass funnel and the resin beads were washed repeatedly with de-ionized water and ethanol. These resin beads were then suspended in concentrated HCl (80 ml) and refluxed at 115° C. under continuous stirring for 24 h. After cooling to room temperature, the reaction mixture was filtered using fritted glass funnel under vacuum and then washed repeatedly with de-ionized water. The resin beads were finally washed with ethanol and air dried. The chemical functionalization of the polymer with phosphonic acid group and methylimidazolium chloride groups was determined to be 0.11 mmol/g and 2.81 mmol/g, respectively, as determined by titrimetry following the procedure of Example 2.

Example 33: Preparation of poly[styrene-co-4-vinylbenzenesulfonic acid-co-vinylbenzylchloride-co-vinyl-2-pyridine-co-divinylbenzene]

Poly (styrene-co-vinylbenzylchloride-co-vinyl-2-pyridine-co-divinylbenzene) (5 g) was charged into a 100 mL flask equipped with a magnetic stir bar and condenser. Cold concentrated sulfuric acid (>98% w/w, $H_2SO_4$, 80 mL) was gradually added into the flask under stirring which consequently resulted in the formation of dark-red colored slurry. The slurry was stirred at 95° C. for 8 h. After cooling to room temperature, the reaction mixture was filtered using fritted glass funnel under vacuum, washed repeatedly with de-ionized water until the effluent was neutral, as determined by pH paper. The sulfonated beads were finally washed with ethanol and air dried. The chemical functionalization of the polymer with sulfonic acid groups was determined to be 3.49 mmol/g, as determined by titrimetry following the procedure of Example 2.

Example 34: Preparation of poly[styrene-co-4-vinylbenzenesulfonic acid-co-vinylbenzylchloride-co-1-methyl-2-vinyl-pyridinium chloride-co-divinylbenzene]

Poly [styrene-co-4-vinylbenzenesulfonic acid-co-vinylbenzylchloride-co-vinyl-2-pyridine-co-divinylbenzene] (4 g) was charged into a 100 mL flask equipped with a magnetic stir bar and condenser. Dry dimethylformamide (80 ml) was added into the flask (via cannula under $N_2$) under stirring to obtain uniform viscous slurry. Iodomethane (1.9 ml) was then gradually added into the flask followed by addition of potassium iodide (10 mg). The reaction mixture was stirred at 95° C. for 24 h. After cooling to room temperature, the cooled reaction mixture was filtered using fritted glass funnel under vacuum and then washed multiple times with dilute HCl solution to ensure complete exchange of $I^-$ with $Cl^-$. The resin beads were finally washed with de-ionized water until the effluent was neutral, as determined by pH paper and then air-dried.

Example 35: Preparation of poly[styrene-co-4-vinylbenzenesulfonic acid-co-4-(4-vinylbenzyl)-morpholine-4-oxide-co-divinyl benzene]

Poly[styrene-co-4-(4-vinylbenzyl)-morpholine-4-oxide-co-divinyl benzene] (3 g) was charged into a 100 mL flask equipped with a magnetic stir bar and condenser. Cold concentrated sulfuric acid (>98% w/w, $H_2SO_4$, 45 mL) was gradually added into the flask under stirring which consequently resulted in the formation of dark-red colored slurry. The slurry was stirred at 95° C. for 8 h. After cooling to room temperature, the reaction mixture was filtered using fritted glass funnel under vacuum, washed repeatedly with de-ionized water until the effluent was neutral, as determined by pH paper. The sulfonated beads were finally washed with ethanol and air dried.

Example 36: Preparation of poly [styrene-co-4-vinylphenylphosphonic acid-co-3-methyl-1-(4-vinylbenzyl)-3H-imidazol-1-ium chloride-co-divinylbenzene]

Poly[styrene-co-3-methyl-1-(4-vinylbenzyl)-3H-imidazol-1-iumchloride-co-divinylbenzene] ($Cl^-$ density=~2.73 mmol/g, 5 g) was charged into a 100 mL flask equipped with a magnetic stir bar and condenser. Diethylphosphite (30 ml) and t-butylperoxide (3.2 ml) were added into the flask and the resulting suspension was stirred at 120° C. for 2 days. The reaction mixture was filtered using fritted glass funnel and the resin beads were washed repeatedly with de-ionized water and ethanol. These resin beads were then suspended in concentrated HCl (80 ml) and refluxed at 115° C. under continuous stirring for 2 days. After cooling to room temperature, the reaction mixture was filtered using fritted glass funnel under vacuum and then washed repeatedly with de-ionized water. The resin beads were finally washed with ethanol and air dried. The chemical functionalization of the polymer with aromatic phosphonic acid group was determined to be 0.15 mmol/g, as determined by titrimetry following the procedure of Example 2.

Example 37: Preparation of poly[styrene-co-3-carboxymethyl-1-(4-vinylbenzyl)-3H-imidazol-1-ium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dimethylformamide (50 ml) was added into the flask and stirred to form a slurry of resin. Imidazole (2.8 g, 41.13 mmol) was then added to the resin slurry and stirred at 80° C. for 8 h. The reaction mixture was then cooled to 40° C. and t-butoxide (1.8 g) was added into the reaction mixture and stirred for 1 h. Bromoethylacetate (4 ml) was then added to and the reaction mixture was stirred at 80° C. for 6 h. After cooling to room temperature, the reaction mixture was filtered using fritted glass funnel under vacuum and then washed repeatedly with de-ionized water. The washed resin beads were suspended in the ethanolic sodium hydroxide solution and refluxed overnight. The resin beads were filtered and successively washed with deionized water multiple times and ethanol, and finally air dried. The chemical functionalization of the polymer with carboxylic acid group was determined to be 0.09 mmol/g, as determined by titrimetry following the procedure of Example 2.

Example 38: Preparation of poly[styrene-co-5-(4-vinylbenzylamino)-isophthalic acid-co-3-methyl-1-(4-vinylbenzyl)-3H-imidazol-1-ium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and consequently the uniform viscous slurry of polymer resin was obtained. Dimethyl aminoisophthalate (3.0 g, 14.3 mmol) was then added to the resin slurry and the resulting reaction mixture was stirred at 95° C. for 16 h. 1-Methylimidazole (2.3 mL, 28.4 mmol) was then added to the reaction mixture and stirred further at 95° C. for 1 day. After cooling to room temperature, the reaction mixture was filtered using fritted glass funnel under vacuum, washed sequentially with de-ionized water and ethanol. The washed resin beads were suspended in the ethanolic sodium hydroxide solution and refluxed overnight. The resin beads were filtered and successively washed with deionized water multiple times and ethanol, and finally air dried. The chemical functionalization of the polymer with carboxylic acid group was determined to be 0.16 mmol/g, as determined by titrimetry following the procedure of Example 2.

Example 39: Preparation of poly[styrene-co-(4-vinylbenzylamino)-acetic acid-co-3-methyl-1-(4-vinylbenzyl)-3H-imidazol-1-ium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and consequently the uniform viscous slurry of polymer resin was obtained. Glycine (1.2 g, 15.9 mmol) was then added to the resin slurry and the resulting reaction mixture was stirred at 95° C. for 2 days. 1-Methylimidazole (2.3 mL, 28.4 mmol) was then added to the reaction mixture and stirred further at 95° C. for 12 hours. After cooling to room temperature, the reaction mixture was filtered using fritted glass funnel under vacuum, washed sequentially with de-ionized water and ethanol, and finally air dried. The chemical functionalization of the polymer with carboxylic acid group was determined to be 0.05 mmol/g, as determined by titrimetry following the procedure of Example 2.

Example 40: Preparation of poly[styrene-co-(1-vinyl-1H-imidazole)-co-divinylbenzene]

To a 500 mL round bottom flask (RBF) containing a stirred solution of 1.00 g of poly(vinylalcohol) in 250.0 mL of deionized $H_2O$ at 0° C. is gradually added a solution containing 35 g (371 mmol) of 1-vinylimidazole, 10 g (96 mmol) of styrene, 1 g (7.7 mmol) of divinylbenzene (DVB) and 1.5 g (9.1 mmol) of azobisisobutyronitrile (AIBN) in 150 mL of a 1:1 (by volume) mixture of benzene/tetrahydrofuran (THF) at 0° C. After 2 hours of stirring at 0° C. to homogenize the mixture, the reaction flask is transferred to an oil bath to increase the reaction temperature to 75° C., and the mixture is stirred vigorously for 24 hours. The resulting polymer is vacuum filtered using a fritted-glass funnel, washed repeatedly with 20% (by volume) methanol in water, THF, and MeOH, and then dried overnight at 50° C. under reduced pressure.

Example 41: Preparation of poly(styrene-co-vinylbenzylmethylimidazolium chloride-co-vinylbenzylmethylmorpholinium chloride-co-vinylbenzyltriphenylphosphonium chloride-co-divinylbenzene)

1-methylimidazole (4.61 g, 56.2 mmol), 4-methylmorpholine (5.65 g, 56.2 mmol), and triphenylphosphine (14.65, 55.9 mmol) were charged into a 500 mL flask equipped with a magnetic stir bar and a condenser. Acetone (100 ml) was added into the flask and mixture was stirred at 50° C. for 10 min. Poly(styrene-co-vinylbenzylchloride-co-divinylbenzene) (1% DVB, Cl⁻ density=4.18 mmol/g dry resin, 40.22 g, 168 mmol) was charged into the flask while stirring until a uniform polymer suspension was obtained. The resulting reaction mixture was refluxed for 24 h. After cooling, the reaction mixture was filtered using a fritted glass funnel under vacuum, washed sequentially with acetone and ethyl acetate, and dried overnight at 70° C. The chemical functionalization of the polymer resin with chloride groups was determined to be 2.61 mmol/g dry resin via titrimetry.

Example 42: Preparation of sulfonated poly(styrene-co-vinylbenzylmethylimidazolium sulfate-co-vinylbenzylmethylmorpholinium sulfate-co-vinylbenzyltriphenyl phosphonium sulfate-co-divinylbenzene)

Poly(styrene-co-vinylbenzylmethylimidazolium chloride-co-vinylbenzylmethylmorpholinium chloride-co-vinylbenzyltriphenylphosphonium chloride-co-divinylbenzene) (35.02 g) was charged into a 500 mL flask equipped with a magnetic stir bar and condenser. Fuming sulfuric acid (20% free $SO_3$, 175 mL) was gradually added into the flask and stirred to form dark-red resin suspension. The mixture was stirred overnight at 90° C. After cooling to room temperature, the reaction mixture was filtered using fritted glass funnel under vacuum and then washed repeatedly with de-ionized water until the effluent was neutral, as determined by pH paper. The sulfonated polymer resin was air dried to a final moisture content of 56% g $H_2O$/g wet polymer. The chemical functionalization of the polymer resin with sulfonic acid groups was determined to be 3.65 mmol/g dry resin.

Example 43: Preparation of poly(styrene-co-vinylbenzylmethylimidazolium chloride-co-vinylbenzylmethylmorpholinium chloride-co-vinylbenzyltriphenylphosphonium chloride-co-divinylbenzene)

1-methylimidazole (7.02 g, 85.5 mmol), 4-methylmorpholine (4.37 g, 43.2 mmol) and triphenylphosphine (11.09, 42.3 mmol) were charged into a 500 mL flask equipped with a magnetic stir bar and condenser. Acetone (100 ml) was added into the flask and mixture was stirred at 50° C. for 10 min. Poly(styrene-co-vinylbenzylchloride-co-divinylbenzene) (1% DVB, Cl⁻ density=4.18 mmol/g dry resin, 40.38 g, 169 mmol) was charged into flask while stirring until a uniform suspension was obtained. The resulting reaction mixture was refluxed for 18 h. After cooling, the reaction mixture was filtered using fritted glass funnel under vacuum, washed sequentially with acetone and ethyl acetate, and dried at 70° C. overnight. The chemical functionalization of the polymer resin with chloride groups was determined to be 2.36 mmol/g dry resin dry resin via titrimetry.

Example 44: Preparation of sulfonated poly(styrene-co-vinylbenzylmethylimidazolium sulfate-co-vinylbenzylmethylmorpholinium sulfate-co-vinylbenzyltriphenyl phosphonium sulfate-co-divinylbenzene)

Poly(styrene-co-vinylbenzylmethylimidazolium chloride-co-vinylbenzylmethylmorpholinium chloride-co-vinylbenzyltriphenylphosphonium chloride-co-divinylbenzene) (35.12 g) was charged into a 500 mL flask equipped with a magnetic stir bar and condenser. Fuming sulfuric acid (20% free $SO_3$, 175 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were finally air dried. The chemical functionalization of the polymer resin with sulfonic acid groups was determined to be 4.38 mmol/g dry resin.

Example 45: Preparation of poly(styrene-co-vinylbenzylmethylmorpholinium chloride-co-vinylbenzyltriphenylphosphonium chloride-co-divinylbenzene)

4-methylmorpholine (8.65 g, 85.5 mmol) and triphenylphosphine (22.41, 85.3 mmol) were charged into a 500 mL flask equipped with a magnetic stir bar and condenser. Acetone (100 ml) was added into the flask and mixture was stirred at 50° C. for 10 min. Poly(styrene-co-vinylbenzylchloride-co-divinylbenzene) (1% DVB, Cl⁻ density=4.18 mmol/g dry resin, 40.12 g, 167 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with chloride groups was determined to be 2.22 mmol/g dry resin via titrimetry.

Example 46: Preparation of sulfonated poly(styrene-co-vinylbenzylmethylmorpholinium sulfate-co-vinylbenzyltriphenylphosphonium sulfate-co-divinylbenzene)

Poly(styrene-co-vinylbenzylmethylimidazolium chloride-co-vinylbenzylmethylmorpholinium chloride-co-vinylbenzyltriphenylphosphonium chloride-co-divinylbenzene) (35.08 g) was charged into a 500 mL flask equipped with a magnetic stir bar and condenser. Fuming sulfuric acid (20% free 503, 175 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 52% g $H_2O$/g wet resin. The chemical functionalization of the polymer resin with sulfonic acid groups was determined to be 4.24 mmol/g dry resin.

Example 47: Preparation of Phenol-Formaldehyde Resin

Phenol (12.87 g, 136.8 mmol) was dispensed into a 100 mL round bottom flask (RBF) equipped with a stir bar and condenser. De-ionized water (10 g) was charged into the flask. 37% Formalin solution (9.24 g, 110 mmol) and oxalic acid (75 mg) were added. The resulting reaction mixture was refluxed for 30 min. Additional oxalic acid (75 mg) was then added and refluxing was continued for another 1 hour. Chunk of solid resin was formed, which was ground to a coarse powder using a mortar and pestle. The resin was repeatedly washed with water and methanol and then dried at 70° C. overnight.

Example 48: Preparation of Chloromethylated Phenol-Formaldehyde Resin

Phenol-formaldehyde resin (5.23 g, 44 mmol) was dispensed into a 100 mL three neck round bottom flask (RBF) equipped with a stir bar, condenser and nitrogen line. Anhydrous dichloroethane (DCE, 20 ml) was then charged into the flask. To ice-cooled suspension of resin in DCE, zinc chloride (6.83 g, 50 mmol) was added. Chloromethyl methyl ether (4.0 ml, 51 mmol) was then added dropwise into the reaction. The mixture was warmed to room temperature and stirred at 50° C. for 6 h. The product resin was recovered by vacuum filtration and washed sequentially with water, acetone and dichloromethane. The washed resin was dried at 40° C. overnight.

Example 49: Preparation of Triphenylphosphine Functionalized Phenol-Formaldehyde Resin Triphenylphosphine (10.12, 38.61 mmol) were charged into a 100 mL flask equipped with a magnetic stir bar and condenser. Acetone (30 ml) was added into the flask and mixture was stirred at 50° C. for 10 min. Chloromethylated phenol-formaldehyde resin (4.61 g, 38.03 mmol) was charged into flask while stirring. The resulting reaction mixture was refluxed for 24 h. After cooling, the reaction mixture was filtered using fritted glass funnel under vacuum, washed sequentially with acetone and ethyl acetate, and dried at 70° C. overnight.

Example 50: Preparation of Sulfonated Triphenylphosphine-Functionalized Phenol-Formaldehyde Resin Triphenylphosphine-functionalized phenol-formaldehyde resin (5.12 g, 13.4 mmol) was charged into a 100 mL flask equipped with a magnetic stir bar and condenser. Fuming sulfuric acid (20% free $SO_3$, 25 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated resin was dried under air to a final moisture content of 49% g $H_2O$/g wet resin. The chemical functionalization of the polymer resin with sulfonic acid groups was determined to be 3.85 mmol/g dry resin.

Example 51: Preparation of Poly(Styrene-Co-Vinylimidazole-Co-Divinylbenzene)

De-ionized water (75 mL) was charged into flask into a 500 mL three neck round bottom flask equipped with a mechanical stirrer, condenser and $N_2$ line. Sodium chloride (1.18 g) and carboxymethylcellulose (0.61 g) were charged into the flask and stirred for 5 min. The solution of vinylimidazole (3.9 mL, 42.62 mmol), styrene (4.9 mL, 42.33 mmol) and divinylbenzene (0.9 mL, 4.0 mmol) in iso-octanol (25 mL) was charged into flask. The resulting emulsion was stirred at 500 rpm at room temperature for 1 h. Benzoyl peroxide (75%, 1.205 g) was added, and temperature was raised to 80° C. The reaction mixture was heated for 8 h at 80° C. with stirring rate of 500 rpm. The polymer product was recovered by vacuum filtration and washed with water and acetone multiple times. The isolated polymer was purified by soxhlet extraction with water and acetone. The resin was dried at 40° C. overnight.

Example 52: Preparation of Poly(Styrene-Co-Vinylmethylimidazolium Iodide-Co-Divinylbenzene)

Poly(styrene-co-vinylimidazole-co-divinylbenzene) (3.49 g, 39 mmol) was dispensed into a 100 mL three neck round bottom flask (RBF) equipped with a stir bar, condenser and nitrogen line. Anhydrous tetrahydrofuran (20 ml) was then charged into the flask. To ice-cooled suspension of resin in tetrahydrofuran, potassium t-butoxide (5.62 g, 50 mmol) was added and stirred for 30 min. Iodomethane (3.2 ml, 51 mmol) was then added dropwise into the reaction. The mixture was warmed to room temperature and stirred at 50° C. for 6 h. The product resin was recovered by vacuum filtration and washed sequentially with water, acetone and dichloromethane. The washed resin was dried at 40° C. overnight.

Example 53: Preparation of Sulfonated Poly(Styrene-Co-Vinylmethylimidazolium Sulfate-Co-Divinylbenzene)

Poly(styrene-co-vinylmethylimidazolium iodide-co-divinylbenzene) (3.89 g, 27.8 mmol) was charged into a 100 mL flask equipped with a magnetic stir bar and condenser. Fuming sulfuric acid (20% free SO3, 20 mL) was gradually added into the flask and stirred to form dark-red colored slurry. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated polymer was dried under air to a final moisture content of 51% g $H_2O$/g wet resin.

Example 54: Preparation of Poly(Styrene-Co-Vinylbenzyltriphenylphosphonium Chloride-Co-Divinylbenzene)

To a 250 mL flask equipped with a magnetic stir bar and condenser was charged triphenylphosphine (38.44 g, 145.1 mmol). Acetone (50 mL) was added into the flask and mixture was stirred at 50° C. for 10 min. Poly(styrene-co-vinylbenzylchloride-co-divinylbenzene) (8% DVB, Cl⁻ density=4.0 mmol/g dry resin, 30.12 g, 115.6 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with triphenylphosphonium chloride groups was determined to be 1.94 mmol/g dry resin via titrimetry.

Example 55: Preparation of Sulfonated Poly(Styrene-Co-Vinylbenzyltriphenyl Phosphonium Sulfate-Co-Divinylbenzene)

Poly(styrene-co-vinylbenzyltriphenylphosphonium chloride-co-divinylbenzene) (40.12 g) was charged into a 500 mL flask equipped with a magnetic stir bar and condenser. Fuming sulfuric acid (20% free SO3, 160 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 54% g $H_2O$/g wet resin. The chemical functionalization of the polymer resin with sulfonic acid groups was determined to be 4.39 mmol/g dry resin.

Example 56: Preparation of Poly(Styrene-Co-Vinylbenzyltriphenylphosphonium Chloride-Co-Divinylbenzene To a 250 mL flask equipped with a magnetic stir bar and condenser was charged triphenylphosphine (50.22 g, 189.6 mmol). Acetone (50 mL) was added into the flask and mixture was stirred at 50° C. for 10 min. Poly(styrene-co-vinylbenzylchloride-co-divinylbenzene) (4% DVB, Cl⁻ density=5.2 mmol/g dry resin, 30.06 g, 152.08 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with triphenylphosphonium chloride groups was determined to be 2.00 mmol/g dry resin via titrimetry.

Example 57: Preparation of Sulfonated Poly(Styrene-Co-Vinylbenzyltriphenyl Phosphonium Sulfate-Co-Divinylbenzene)

Poly(styrene-co-vinylbenzyltriphenylphosphonium chloride-co-divinylbenzene) (40.04 g,) was charged into a 500 mL flask equipped with a magnetic stir bar and condenser. Fuming sulfuric acid (20% free S03, 160 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 47% g $H_2O$/g wet resin. The chemical functionalization of the polymer resin with sulfonic acid groups was determined to be 4.36 mmol/g dry resin.

Example 58: Preparation of Poly(Styrene-Co-Vinylbenzylmethylimidazolium Chloride-Co-Divinylbenzene)

To a 250 mL flask equipped with a magnetic stir bar and condenser was charged 1-methylimidazole (18 mL, 223.5 mmol). Acetone (75 mL) was added into the flask and mixture was stirred at 50° C. for 10 min. Poly(styrene-co-vinylbenzylchloride-co-divinylbenzene) (8% DVB, Cl⁻ density=4.0 mmol/g dry resin, 40.06, 153.7 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with methylimidazolium chloride groups was determined to be 3.54 mmol/g dry resin via titrimetry.

Example 59: Preparation of Sulfonated Poly(Styrene-Co-Vinylbenzylmethylimidazolium Sulfate-Co-Divinylbenzene)

Poly(styrene-co-vinylbenzylmethylimidazolium chloride-co-divinylbenzene) (30.08 g) was charged into a 500 mL flask equipped with a magnetic stir bar and condenser. Fuming sulfuric acid (20% free $SO_3$, 120 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 50% g $H_2O$/g wet resin. The chemical functionalization of the polymer resin with sulfonic acid groups was determined to be 2.87 mmol/g dry resin.

Example 60: Preparation of Poly(Styrene-Co-Vinylbenzylmethylimidazolium Chloride-Co-Divinylbenzene)

To a 250 mL flask equipped with a magnetic stir bar and condenser was charged 1-methylimidazole (20 mL, 248.4 mmol). Acetone (75 mL) was added into the flask and mixture was stirred at 50° C. for 10 min. Poly(styrene-co-vinylbenzylchloride-co-divinylbenzene) (4% DVB, Cl⁻ density=5.2 mmol/g dry resin, 40.08, 203.8 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with methylimidazolium chloride groups was determined to be 3.39 mmol/g dry resin via titrimetry.

Example 61: Preparation of Sulfonated Poly(Styrene-Co-Vinylbenzylmethylimidazolium Sulfate-Co-Divinylbenzene)

Poly(styrene-co-vinylbenzylmethylimidazolium chloride-co-divinylbenzene) (30.14 g) was charged into a 500 mL flask equipped with a magnetic stir bar and condenser. Fuming sulfuric acid (20% free $SO_3$, 120 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 55% g $H_2O$/g wet resin. The chemical functionalization of the polymer resin with sulfonic acid groups was determined to be 2.78 mmol/g dry resin.

Example 62: Preparation of Poly(Styrene-Co-Vinylbenzyltriphenylphosphonium Chloride-Co-Divinylbenzene)

To a 250 mL flask equipped with a magnetic stir bar and condenser was charged triphenylphosphine (44.32 g, 163.9 mmol). Acetone (50 mL) was added into the flask and mixture was stirred at 50° C. for 10 min. Poly(styrene-co-vinylbenzylchloride-co-divinylbenzene) (13% DVB macroporous resin, Cl$^-$ density=4.14 mmol/g dry resin, 30.12 g, 115.6 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight.

Example 63: Preparation of Sulfonated Poly(Styrene-Co-Vinylbenzyltriphenyl Phosphonium Sulfate-Co-Divinylbenzene)

Poly(styrene-co-vinylbenzyltriphenylphosphonium chloride-co-divinylbenzene) (30.22 g) was charged into a 500 mL flask equipped with a magnetic stir bar and condenser. Fuming sulfuric acid (20% free S03, 90 mL) was gradually added into the flask and stirred to form dark-red colored slurry of resin. The slurry was stirred at 90° C. for 1 hour. After cooling, the reaction mixture was filtered using fritted glass funnel under vacuum and then washed repeatedly with de-ionized water until the effluent was neutral, as determined by pH paper. The sulfonated beads were dried under air to a final moisture content of 46% g H$_2$O/g wet resin. The chemical functionalization of the polymer resin with sulfonic acid groups was determined to be 2.82 mmol/g dry resin.

Example 64: Preparation of Poly(Styrene-Co-Vinylbenzyltriphenylphosphonium Chloride-Co-Divinylbenzene)

To a 250 mL flask equipped with a magnetic stir bar and condenser was charged triphenylphosphine (55.02 g, 207.7 mmol). Acetone (50 mL) was added into the flask and mixture was stirred at 50° C. for 10 min. Poly(styrene-co-vinylbenzylchloride-co-divinylbenzene) (6.5% DVB macroporous resin, Cl$^-$ density=5.30 mmol/g dry resin, 30.12 g, 157.4 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight.

Example 65: Preparation of Sulfonated Poly(Styrene-Co-Vinylbenzyltriphenyl Phosphonium Sulfate-Co-Divinylbenzene)

Poly(styrene-co-vinylbenzyltriphenylphosphonium chloride-co-divinylbenzene) (30.12 g) was charged into a 500 mL flask equipped with a magnetic stir bar and condenser. Fuming sulfuric acid (20% free S03, 90 mL) was gradually added into the flask and stirred to form dark-red colored slurry of resin. The slurry was stirred at 90° C. for 1 hour. After cooling, the reaction mixture was filtered using fritted glass funnel under vacuum and then washed repeatedly with de-ionized water until the effluent was neutral, as determined by pH paper. The sulfonated beads were dried under air to a final moisture content of 49% g H$_2$O/g wet resin. The chemical functionalization of the polymer resin with sulfonic acid groups was determined to be 2.82 mmol/g dry resin.

Example 66: Preparation of Poly(Styrene-Co-Vinylbenzyltriphenylphosphonium Chloride-Co-Divinylbenzene)

To a 250 mL flask equipped with a magnetic stir bar and condenser was charged triphenylphosphine (38.42 g, 145.0 mmol). Acetone (50 mL) was added into the flask and mixture was stirred at 50° C. for 10 min. Poly(styrene-co-vinylbenzylchloride-co-divinylbenzene) (4% DVB, Cl$^-$ density=4.10 mmol/g dry resin, 30.12 g, 115.4 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight.

Example 67: Preparation of Sulfonated Poly(Styrene-Co-Vinylbenzyltriphenylphosphonium Sulfate-Co-Divinylbenzene)

Poly(styrene-co-vinylbenzyltriphenylphosphonium chloride-co-divinylbenzene) (30.18 g) was charged into a 500 mL flask equipped with a magnetic stir bar and condenser. Fuming sulfuric acid (20% free S03, 120 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 59% g H$_2$O/g wet resin. The chemical functionalization of the polymer resin with sulfonic acid groups was determined to be 3.03 mmol/g dry resin.

Example 68: Preparation of Poly(Styrene-Co-Vinylbenzyltriphenylphosphonium Chloride-Co-Divinylbenzene)

To a 500 mL flask equipped with a magnetic stir bar and condenser was charged triphenylphosphine (44.22 g, 166.9 mmol). Acetone (70 mL) was added into the flask and mixture was stirred at 50° C. for 10 min. Poly(styrene-co-vinylbenzylchloride-co-divinylbenzene) (4% DVB, Cl$^-$ density=3.9 mmol/g dry resin, 35.08 g, 130.4 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight.

Example 69: Preparation of Sulfonated Poly(Styrene-Co-Vinylbenzyltriphenyl Phosphonium Sulfate-Co-Divinylbenzene)

Poly(styrene-co-vinylbenzyltriphenylphosphonium chloride-co-divinylbenzene) (30.42 g) was charged into a 500 mL flask equipped with a magnetic stir bar and condenser. Fuming sulfuric acid (20% free S03, 120 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 57% g $H_2O$/g wet resin. The chemical functionalization of the polymer resin with sulfonic acid groups was determined to be 3.04 mmol/g dry resin.

Example 70: Preparation of Poly(Butyl-Vinylimidazolium Chloride-Co-Butylimidazolium Chloride-Co-Styrene)

To a 500 mL flask equipped with a mechanical stirrer and reflux condenser is added 250 mL of acetone, 10 g of imidazole, 14 g of vinylimidazole, 15 g of styrene, 30 g of dichlorobutane and 1 g of azobisisobutyronitrile (AIBN). The solution is stirred under reflux conditions for 12 hours to produce a solid mass of polymer. The solid polymer is removed from the flask, washed repeatedly with acetone, and ground to a coarse powder using a mortar and pestle to yield the product.

Example 71: Preparation of Sulfonated Poly(Butyl-Vinylimidazolium Sulfate-Co-Butylimidazolium Sulfate-Co-Styrene)

Poly(butyl-vinylimidazolium chloride-co-butylimidazolium chloride-co-styrene) 30.42 g) is charged into a 500 mL flask equipped with a mechanical stirrer. Fuming sulfuric acid (20% free S03, 120 mL) is gradually added into the flask until the polymer is fully suspended. The resulting slurry is stirred at 90° C. for 5 hours. After cooling, the reaction mixture is filtered using fritted glass funnel under vacuum and then washed repeatedly with de-ionized water until the effluent is neutral, as determined by pH paper.

Example 72: Additional Preparation of poly [styrene-co-4-vinylbenzenesulfonic acid-co-1-(4-vinylbenzyl)-3H-imidazol-1-ium sulfate-co-divinylbenzene]

To a 30 L jacketed glass reactor, housed within a walk-in fume hood and equipped with a 2 inch bottom drain port and a multi-element mixer attached to an overhead air-driven stirrer, was charged 14 L of N,N-dimethylformamide (DMF, ACS Reagent Grade, Sigma-Aldrich, St. Louis, Mo., USA) and 2.1 kg of 1H-imidazole (ACS Reagent Grade, Sigma-Aldrich, St. Louis, Mo., USA) was charged at room temperature. The DMF was stirred with continuous mixing at a stirrer speed of approximately 300 RPM to dissolve the imidazole. 7.0 kg of cross-linked poly-(styrene-co-divinylbenzene-co-vinylbenzyl chloride) was then added to the reactor to form a stirred suspension. The reaction mixture was heated to 90 degrees Celsius by pumping heated bath fluid through the reactor jacket, and the resulting heated suspension was maintained for 24 hours, after which it was gradually cooled.

The DMF and residual unreacted 1H-imidazole was drained from the resin through the bottom port of the reactor, after which the retained resin was washed repeatedly with acetone to remove any residual heavy solvent or unreacted reagents that had become entrained in the resin bed. The reaction yielded cross-linked poly-(styrene-co-divinylbenzene-co-1H-imidazolium chloride) as off-white spherical resin beads. The resin beads were removed from the reactor through the bottom port and heated at 70 degrees Celsius in air to dry.

After being thoroughly cleaned, the 30 L reactor system was charged with 2.5 L of 95% sulfuric acid (ACS Reagent Grade) and then approximately 13 L of oleum (20% free $SO_3$ content by weight, Puritan Products, Inc., Philadelphia, Pa., USA). To the stirred acid solution was gradually added 5.1 kg of the cross-linked poly-(styrene-co-divinylbenzene-co-1H-imidazolium chloride). After the addition, the reactor was flushed with dry nitrogen gas, the stirred suspension was heated to 90 degrees Celsius by pumping heated bath fluid through the reactor jacket, and the suspension was maintained at 90 degrees Celsius for approximately four hours. After completion of the reaction, the mixture was allowed to cool to approximately 60 degrees Celsius and the residual sulfuric acid mixture was drained from the reactor through the bottom port. After thorough draining, the resin was washed gradually with 80 wt % sulfuric acid solution and then 60 wt % sulfuric acid solution. Finally the resin was washed repeatedly with distilled water until the pH of the wash water was above 5.0, as determined by pH paper. The resin was removed from the reactor through the bottom port to yield the solid catalyst. The acid functional density of catalyst was determined to be at least 2.0 mmol H+/g dry resin by ion-exchange acid-base titration.

Example 73: Preparation of Gluco-Oligosaccharides (GLOS) from Monomeric Glucose Monomeric glucose was converted to gluco-oligosaccharides (GLOS) in a reaction vessel consisting of a 1000 mL three neck flask (TNF) equipped with a 3" paddle-shaped stirring element driven by an overhead mechanical mixer attached through a vacuum-capable bearing in the center port of the flask. To one of the side ports of the TNF was attached a vacuum distillation apparatus comprising a riser, a jacketed condenser, a descending elbow with a vacuum fitting, and a 500 mL round bottom flask (RBF) collection vessel. The walls of the 1000 mL TNF were maintained at 105±2 degrees Celsius using a temperature-controlled oil bath and the condenser jacket was maintained at approximately 2 degrees Celsius using a circulator-chiller with bath fluid made from 50% ethylene glycol in distilled water. Vacuum was provided a rotary vane pump equipped with an adjustable manifold and a vacuum gauge.

To the TNF was added approximately 102 grams of D-(+)-glucose (ACS, Reagent Grade) with a moisture content of 1.8% and 81.2 grams of the catalyst from Example 72 with a moisture content of 38.45%. The temperature of the mixture was maintained between about 95 to about 98 degrees Celsius with slow mixing to form a suspension of catalyst in a molten sugar syrup. The viscosity of the syrup suspension was determined using a standard #6 spindle to be approximately 4,300 cP at 20 RPM, 3,300 cP at 60 RPM and 2,400 cP at 100 RPM. The TNF was then sealed and vacuum was applied to establish a pressure of −5 psig, which was then gradually reduced over the course of three hours to −14 psig.

The progress of the reaction was monitored by removing a small (approximately 250 mg) sample of the reaction mixture at 30 minute intervals, dissolving the sample in 15 mL of distilled water, and analyzing the resulting mixture by HPLC to determine the conversion of monomeric sugars to oligosaccharides. Yield data as a function of the reaction time are provided in Table 2, indicating conversion of the monomeric glucose to oligosaccharides with DP as high as 10. The total glucose conversion exceeded 71% in three hours, with about 99% selectivity to carbohydrate products (i.e., about 1% molar conversion to sugar degradation products).

TABLE 2

Yield to sugars and oligosaccharides of varying DP as a function of time

| Sample Time | 0 min | 30 min | 60 min | 90 min | 120 min | 150 min | 180 min |
|---|---|---|---|---|---|---|---|
| Y(DP7+) | 0.0% | 0.0% | 0.0% | 0.0% | 0.0% | 20.6% | 26.1% |
| Y(DP4-DP6) | 0.0% | 6.7% | 13.7% | 17.4% | 23.8% | 18.4% | 16.8% |
| Y(DP3) | 0.0% | 7.6% | 11.0% | 12.6% | 13.7% | 10.6% | 9.7% |
| Y(DP2) | 0.0% | 15.6% | 21.7% | 24.4% | 26.4% | 19.1% | 17.6% |
| Y(DP1) | 100.0% | 69.3% | 52.7% | 44.9% | 35.1% | 30.2% | 28.7% |

Example 74: Recovery of the Catalyst from the Reaction in Example 73

At the completion of the reaction in Example 73, approximately 100 mL of distilled water was added to the mixture to dilute the products. The solid catalyst was recovered from the resulting solution by vacuum filtration using a 500 mL fritted-glass funnel with a coarse frit. The catalyst was then washed twice with 100 mL of distilled water to recover additional sugars from the solid catalyst. Filtration and washing yielded approximately 280 mL of a very pale-yellow non-viscous solution and 50 dry g of catalyst, reflecting essentially quantitative mass recovery of the catalyst, to within experimental error.

Example 75: Concentration and Purification of the Oligosaccharide Mixture from Example The combined filtrate obtained in Example 74 was concentrated to approximately 70 wt % by vacuum rotary evaporation to yield a thick, pale-yellow syrup with a sweet, caramel aroma with no detectable suspended solids. The oligosaccharide content of the syrup was then separated from residual monomers and other soluble species by standard column chromatography. 20 mL of the syrup was loaded onto a 1000×25 mm silica column and eluted with distilled water as the mobile phase under approximately 5 psig pressure. 100 mL fractions were collected and analyzed by HPLC to confirm that the residual monomeric sugar content in the oligosaccharide product was reduced to below 5% on a mass basis with respect to total carbohydrates. Alternatively, monomer separation was performed using a column packed with calcium-exchanged Dowex 50WX2 resin or a silica/activated-charcoal mixture.

Example 76: Decolorization of the Oligosaccharide Product from Example 75

The oligosaccharide product obtained in Example 75 was re-concentrated to approximately 50 wt % by vacuum rotary evaporation to yield a pale-yellow syrup with no detectable suspended solids. 50 mL of the syrup were stirred with 5 grams of washed activated charcoal at 50 degrees Celsius for approximately 30 minutes, after which, the carbon was removed by simple filtration to yield a visually clear solution.

Example 77: Recovery of a Solid Oligosaccharide Product 2 mL of the clear solution from Example 76 were freeze dried to yield a solid-white oligosaccharide powder. Re-dissolving the power in distilled water and analyzing the resulting solution by HPLC confirmed that the distribution of oligosaccharides by DP was substantially unchanged by the steps in Examples 75-76 from that in Example 74.

Example 78: Repeated Reuse of the Catalyst

The procedure of Examples 72-73 was performed repeatedly using the same physical sample of catalyst to demonstrate consistent yield and product distribution upon reuse of the catalyst. In the first cycle of the series of recycle reactions, the procedure in Example 73 was performed using a fresh sample of the catalyst from Example 72, while in all subsequent reactions, the catalyst used was that recovered from the previous reaction cycle according to the procedure in Example 74. In each reaction cycle, fresh charge of reagent sugar was used. The yield to oligosaccharides of various DP was determined as reported in Table 3. From these data, the average loss of catalyst activity upon re-use was determined as the average fractional decrease in monomeric sugar conversion from cycle to cycle and found to be less than 0.3% mol/mol/cycle. In none of the reaction cycles was the yield to degradation products observed to exceed 1% mol/mol.

TABLE 3

Yield to oligosaccharides of varying degree of polymerization (DP) upon re-use of the catalyst per the procedure in Example 77

| Reaction | Initial Sugar (g) | Initial Catalyst (g) | Initial Water (g) | Y(DP1) (mol/mol) | Y(DP2) (mol/mol) | Y(DP3) (mol/mol) | Y(DP4+) (mol/mol) |
|---|---|---|---|---|---|---|---|
| Cycle 1 | 100 | 50 | 31 | 42% | 23% | 14% | 22% |
| Cycle 2 | 100 | 50 | 31 | 42% | 24% | 14% | 20% |
| Cycle 3 | 100 | 50 | 31 | 40% | 24% | 14% | 21% |
| Cycle 4 | 100 | 50 | 31 | 41% | 24% | 15% | 20% |
| Cycle 5 | 100 | 50 | 31 | 39% | 23% | 15% | 22% |
| Cycle 6 | 100 | 50 | 31 | 42% | 23% | 15% | 19% |
| Cycle 7 | 100 | 50 | 31 | 43% | 22% | 14% | 21% |
| Cycle 8 | 100 | 50 | 31 | 43% | 22% | 15% | 20% |

TABLE 3-continued

Yield to oligosaccharides of varying degree of polymerization (DP)
upon re-use of the catalyst per the procedure in Example 77

| Reaction | Initial Sugar (g) | Initial Catalyst (g) | Initial Water (g) | Y(DP1) (mol/mol) | Y(DP2) (mol/mol) | Y(DP3) (mol/mol) | Y(DP4+) (mol/mol) |
|---|---|---|---|---|---|---|---|

Example 79: Effect of Varying Catalyst Loading and Reaction Time

The procedure of Example 73 was repeated as stated with the exception that the mass of catalyst and the reaction time was varied as described in Table 4. In none of the reactions was the yield to sugar degradation products observed to exceed 1% mol/mol.

TABLE 4

Yield to sugars and oligosaccharides of different
DP as a function of the reaction time and catalyst

| Reaction Time (min) | Initial Sugar (g) | Initial Catalyst (g) | Initial Water (g) | Y(DP1) (mol/mol) | Y(DP2) (mol/mol) | Y(DP3) (mol/mol) | Y(DP4+) (mol/mol) |
|---|---|---|---|---|---|---|---|
| 60 | 100 | 25 | 15 | 78% | 12% | 6% | 4% |
| 60 | 100 | 50 | 31 | 53% | 22% | 11% | 14% |
| 60 | 100 | 75 | 46 | 52% | 22% | 11% | 15% |
| 120 | 100 | 25 | 15 | 68% | 16% | 9% | 8% |
| 120 | 100 | 50 | 31 | 35% | 26% | 14% | 24% |
| 120 | 100 | 75 | 46 | 41% | 22% | 12% | 25% |
| 180 | 100 | 25 | 15 | 60% | 18% | 10% | 11% |
| 180 | 100 | 50 | 31 | 29% | 18% | 10% | 43% |
| 180 | 100 | 75 | 46 | 42% | 22% | 12% | 23% |

Example 80: Conversion of Monomeric Glucose and Galactose into Galacto-Oligosaccharides The procedure of Example 73 was repeated using 75 g of glucose, 75 g of galactose, 74 dry g of the catalyst from Example 72, an initial water content of 50 g, and a reaction temperature of 95 degrees Celsius. After three hours of reaction, the conversion of sugars was determined to be: 75.1% mol/mol, the yield to DP2 oligosaccharides was determined to be 18.7% mol/mol, the yield to DP3 oligosaccharides was determined to be 8.8% mol/mol, the yield to DP4-DP10 oligosaccharides was determined to be 29.0% mol/mol, the yield to DP11+ oligosaccharides was determined to be 18.5% mol/mol and the yield to sugar degradation products was determined to be <0.1% mol/mol.

Example 81: Conversion of Monomeric Fructose to Fructo-Oligosaccharides

The procedure of Example 73 was repeated using 100 g of fructose as the reagent sugar, 25 dry g of the catalyst from Example 72, an initial water content of 15 g, and a reaction temperature of 80 degrees Celsius. After three hours of reaction, the conversion of DP1 sugars was determined to be 73% mol/mol, the yield to DP2 oligosaccharides and di-anhydro-disaccharides was determined to be 37% mol/mol, the yield to DP3-DP5 oligosaccharides was determined to be 7% mol/mol, and the yield to DP6+ oligosaccharides was determined to be 22% mol/mol.

Example 82: Conversion of Monomeric Mannose to Manno-Oligosaccharides

The procedure of Example 73 was repeated using 20 g of mannose as the reagent sugar, 10 dry g of the catalyst from Example 72, an initial water content of 9 g, and a reaction temperature of 90 degrees Celsius. After three hours of reaction, the conversion of sugars was determined to be: 80% mol/mol, the yield to DP2 oligosaccharides was determined to be 8%, the yield to DP3 oligosaccharides was determined to be 25%, the yield to DP4-DP9 oligosaccharides was determined to be 30% mol/mol, the yield to DP10+ oligosaccharides was determined to be 15% and the yield to sugar degradation products was determined to be 2%.

Example 83: Conversion of Monomeric Arabinose and Galactose into Arabino-Galacto-Oligosaccharides The procedure of Example 73 was repeated using a 250 mL RBF, 5.1 g of galactose and 5.2 g of arabinose as the starting sugars, 4.8 dry g of the catalyst from Example 72, an initial water content of 2.8 g and a reaction temperature of 92 degrees Celsius. After three hours of reaction, the conversion of sugars was determined to be: 66.2% mol/mol, the yield to DP2 oligosaccharides was determined to be 21.5% mol/mol, the yield to DP3 oligosaccharides was determined to be 11.0% mol/mol, the yield to DP4-DP6 oligosaccharides was determined to be 5.6% mol/mol, the yield to DP7-DP10 oligosaccharides was determined to be 5.6% mol/mol, the yield to DP11+ oligosaccharides was determined to be 22.5% and the yield to sugar degradation products was determined to be <0.1% mol/mol.

Example 84: Production of Gluco-Oligosaccharides in a Sealed Sequential Batch Pilot Process Multi-kilogram-scale oligomerization of food-grade dextrose was performed in a 22 L jacketed 316L stainless steel reactor (M/DVT-22 mixer/reactor unit, Littleford-Day, Inc., Florence, Ky., USA) that was temperature controlled by pumping heated/chilled oil through the reactor jacket. The reactor cylinder was mounted in horizontal configuration, such that the mixing shaft was oriented parallel to the ground. The mixing element consisted of four ploughs, with an effective diameter of approximately 95% that of the reactor clear diameter. The reactor system was equipped with a bottom-mounted 2 inch diameter outlet port, fitted with an 80 mesh stainless steel screen to prevent solid particles from passing through it, and was accessed through a manual ball valve assembly. The reactor was also equipped with a top-mounted 3 inch diameter inlet port, also accessed through a manual ball valve assembly. Additional fittings provided the ability to inject compressed gases, steam, and to vent the reactor to relieve pressure. The temperature of the reactor's contents was measured with a thermocouple installed along the internal wall of the reactor cylinder.

Oligomerization reactions were performed according to a standard operating procedure, summarized as follows. The reactor was charged with 1.7 dry kg of the catalyst from Example 72 and 1.1 kg of water (entrained with the catalyst) and heated to bring the materials to 100 degrees Celsius. Then, 3.4 kilograms of food grade dextrose (include 0.3 kg of entrained water) were added gradually to the reactor with mixing at 51 RPM. The reactor was then sealed and its contents maintained at 100 degrees Celsius for a period of six hours with mixing maintained at 51 rotations per minute. Approximately once per hour, the vent valve was opened to relieve pressure. After the six hours residence time, 3.4 kilograms of deionized water was added to the reactor and the contents were mixed and cooled to 60 degrees Celsius over a period of 15 minutes. The mixing was stopped, and the bottom outlet port was opened to collect the liquid product, leaving the solid catalyst in the reactor vessel. A total of 4.9 kg of product liquor was collected. Subsequently, 7.0 kilograms of deionized water was added to extract additional soluble products entrained in the residual solids and a total of 7.8 kilograms of liquor was collected from the bottom outlet. Finally, compressed air was injected into a small inlet at the top of the reactor, with the bottom outlet open (through the screen) to dry the remaining solids and extract more product. Another 1.1 kilograms of liquor was collected during the air blow procedure. The three samples of liquor were combined and analyzed by HPLC to determine the yield to gluco-oligosaccharides, the product distribution over DP, the extent of formation of sugar degradation products, and the reaction mass balance closure. The washed solid catalyst was not removed from the reactor system.

Sequential batch reactions were performed by heating the reactor contents, containing mainly retained catalyst, back to 100 degrees Celsius, charging the reactor with an additional 3.4 kg of sugar and repeating the reaction and washing process as described above in this example. Following each reaction, the combined product liquor was analyzed by HPLC to determine the yield to gluco-oligosaccharides, the product distribution over DP, the extent of formation of sugar degradation products, and the reaction mass balance closure. In this manner, a total of nine sequential batch dextrose oligomerization experiments were performed. The yield to gluco-oligosaccharides for each of the sequential batch reactions was determined as reported in Table 5.

TABLE 5

Yield to oligosaccharides and sugar degradation products in 9 sequential batch reactions using recycled catalyst

| Reactor Batch | Y(DP1) (mol/mol) | Y(DP2) (mol/mol) | Y(DP3) (mol/mol) | Y(DP4+) (mol/mol) | Y(deg) (mol/mol) |
|---|---|---|---|---|---|
| Batch 1 | 42% | 21% | 10% | 27% | <0.1% |
| Batch 2 | 42% | 22% | 10% | 26% | <0.1% |
| Batch 3 | 43% | 22% | 11% | 24% | <0.1% |
| Batch 4 | 44% | 22% | 11% | 23% | <0.1% |
| Batch 5 | 44% | 23% | 11% | 22% | <0.1% |
| Batch 6 | 44% | 23% | 11% | 21% | <0.1% |
| Batch 7 | 44% | 24% | 12% | 20% | <0.1% |
| Batch 8 | 46% | 24% | 12% | 18% | <0.1% |
| Batch 9 | 46% | 25% | 12% | 16% | <0.1% |

Example 85: Production of Galacto-Oligosaccharides in a Sealed Sequential Batch Pilot Process Starting from a Mixture of Galactose and Glucose The batch oligomerization of Example 84 was repeated using 1.1 kg of galactose and 0.3 kg of glucose as the starting sugar, 0.7 dry kg of the catalyst from Example 72, and 0.4 kg initial water. The reaction was performed at 105 degrees Celsius for 4 hours, resulting in the production of galacto-oligosaccharides (GOS). The conversion of sugars was determined to be 80.3% mol/mol, the yield to DP2 oligosaccharides was determined to be 14.4% mol/mol, the yield to DP3 oligosaccharides was determined to be 7.7% mol/mol, the yield to DP4-DP9 oligosaccharides was determined to be 15.3% mol/mol, the yield to DP10+ oligosaccharides was determined to be 42.8% mol/mol and the yield to sugar degradation products was determined to be <0.1% mol/mol.

Example 86: Production of Galacto-Oligosaccharides in a Sealed Sequential Batch Pilot Process Starting from a Mixture of Galactose and Glucose The batch oligomerization of Example 84 was repeated using 1.1 kg of galactose and 0.3 kg of glucose as the starting sugar, 0.7 dry kg of the catalyst from Example 72, and 0.5 kg initial water. The reaction was performed at 105 degrees Celsius for 4 hours, resulting in production of galacto-oligosaccharides (GOS). The conversion of sugars was determined to be 78.8% mol/mol, the yield to DP2 oligosaccharides was determined to be 11.6% mol/mol, the yield to DP3 oligosaccharides was determined to be 12.0% mol/mol, the yield to DP4-DP9 oligosaccharides was determined to be 29.6% mol/mol, the yield to DP10+ oligosaccharides was determined to be 25.6% mol/mol and the yield to sugar degradation products was determined to be <0.1% mol/mol.

Example 87: Production of Galacto-Oligosaccharides in a Sealed Sequential Batch Pilot Process Starting from Food Grade Lactose The batch oligomerization of Example 84 was repeated using 1.3 kg of lactose as the starting sugar, 0.6 dry kg catalyst, and 0.4 kg initial water, resulting in production of galacto-oligosaccharides (GOS). The conversion of sugars was determined to be: 81.4% mol/mol, the yield to DP2 oligosaccharides was determined to be 13.8% mol/mol, the yield to DP3 oligosaccharides was determined to be 7.8% mol/mol, the yield to DP4-DP9 oligosaccharides was determined to be 23.7% mol/mol, the yield to DP10+ oligosaccharides was determined to be 36.2% mol/mol and the yield to sugar degradation products was determined to be <0.1% mol/mol.

Example 88: Production of Gluco-Oligosaccharides in an Open Sequential Batch Pilot Process The batch oligomerization of Example 84 was repeated without sealing the reactor closed, enabling the gradual evaporation of water from the reaction mixture and resulting in the production of gluco-oligosaccharides (GLOS). The conversion of sugars was determined to be: 80.6% mol/mol, the yield to DP2 oligosaccharides was determined to be 14.9% mol/mol, the yield to DP3 oligosaccharides was determined to be 6.6% mol/mol, the yield to DP4-DP9 oligosaccharides was determined to be 31.1% mol/mol, the yield to DP10+ oligosaccharides was determined to be 28.1% mol/mol and the yield to sugar degradation products was determined to be <0.1% mol/mol.

Example 89: Production of Gluco-Oligosaccharides in a Continuous Pilot Process Multi-kilogram scale oligomerization of dextrose was performed in a continuous stirred-tank reactor system using the 22 L jacketed reactor described in Example 84. Sugar syrup was fed continuously to the reactor from a stainless steel jacketed feed tank that was temperature-controlled by circulation of hot water through the tank jacket. A clamp-mount agitator (Lightnin, Rochester, N.Y., USA) fitted with a shaft containing four vertically-spaced impellers was used to maintain uniform concentration and temperature in the feed tank. Reactant sugar was drawn by peristaltic pump from the bottom outlet of the feed tank through a heated, braided metal hose, and injected to the 22 L reactor system through a'/4-inch input port. Product oligosaccharides were drawn continuously from the screened bottom outlet port by a peristaltic pump and directed into a 45 gal stainless steel receiving tank through a heated braided metal tube.

The reactor was heated to 90 degrees Celsius and charged with 2.3 kilograms of the catalyst from Example 72 (including 1.5 kilograms of entrained water), 4.6 kilograms of dextrose and 2.3 kilograms of deionized water. During the material addition, the reactor mixer plows were driven at 102 RPM and the temperature was maintained at 65 degrees Celsius or higher. After all raw materials were added, the reactor was sealed, and its contents were maintained at 90 degrees Celsius for three hours. A solution of 55 wt % dextrose in deionized water was prepared in the feed tank and heated to 60 degrees Celsius. At the end of the three-hour mixing period, the feed and offtake pumps were started, such that the 55 wt % dextrose solution was fed into the reactor at 18 mL/min through and product was drawn from the reactor at 18 mL/min. The flow rates were maintained for 12 days of continuous operation. Product samples were drawn periodically and analyzed by HPLC. No systematic loss of sugar conversion was observed over the 12 day period and no detectable formation of sugar degradation products was observed in the reactor output.

Example 90: In Vitro Digestibility Testing of the Oligosaccharide Product from Example 87

Fiber composition analysis and in vitro determination of the digestibility of the oligosaccharide product from Example 87 was performed according to standard methods known to one skilled in the art (method AOAC 2009.01, Official Methods of Analysis of AOAC International, AOAC International, Gaithersberg, USA). The resulting sample composition was determined to be: 0.0% ash, 0.0% protein, 0.1% high molecular weight dietary fiber, 67.9% indigestible soluble dietary fiber, 0.0% digestible DP3+ soluble oligosaccharides, and 32.1% initial DP1 and DP2 carbohydrates.

Example 91. In Vitro Digestibility Testing of the Oligosaccharide Product from Example 88

Fiber composition analysis and in vitro determination of the digestibility of the oligosaccharide product from Example 88 was performed according to standard methods known to one skilled in the art (method AOAC 2009.01, Official Methods of Analysis of AOAC International, AOAC International, Gaithersberg, USA). The resulting sample composition was determined to be: 0.0% ash, 0.0% protein, 0% high molecular weight dietary fiber, 63.8% indigestible soluble dietary fiber, 1.9% digestible DP3+ soluble oligosaccharides, and 34.3% initial DP1 and DP2 carbohydrates.

Example 92: Comparative Example for Conversion of Glucose to Gluco-Oligosaccharides Using Dowex 50WX8 Strong Acid Ion Exchange Resin The procedure of Example 73 was repeated using 100 g of glucose, 50 dry g of the strong acid ion exchange resin Dowex® 50WX8 (sulfonated polystyrene-co-divinylbenzene, with 8 wt % DVB cross-linking, Sigma-Aldrich, St. Louis, Mo., USA), an initial water content of about 31 g, and a reaction temperature of 95 degrees Celsius. After three hours of reaction, the conversion of sugars was determined to be 68.5% mol/mol, the yield to DP2 oligosaccharides was determined to be 15.3% mol/mol, the yield to DP3 oligosaccharides was determined to be 7.7% mol/mol, the yield to DP4-DP19 oligosaccharides was determined to be 18.5% mol/mol, the yield to DP10+ oligosaccharides was determined to be 3.2% mol/mol and the yield to sugar degradation products was determined to be 23.8% mol/mol, with 6.1% mol/mol appearing as either formic acid, acetic acid, levulinic acid, 5-hydroxymethylfurfural, or furfural, and 17.7% mol/mol appearing as insoluble products and tars. The resulting catalyst selectivity was determined to be 65% mol/mol.

Example 93: Comparative Example for Conversion of Glucose to Gluco-Oligosaccharides Using Amberlite IRH-110 Strong Acid Ion Exchange Resin The procedure of Example 73 was repeated using 100 g of glucose, 50 dry g of the strong acid ion exchange resin Amberlite IRH-110 (sulfonated polystyrene-co-divinylbenzene, Sigma-Aldrich, St. Louis, Mo., USA), an initial water content of about 31 g, and a reaction temperature of 95 degrees Celsius. After three hours of reaction, the conversion of sugars was determined to be 81.4% mol/mol, the yield to DP2 oligosaccharides was determined to be 15.8% mol/mol, the yield to DP3 oligosaccharides was determined to be 8.1% mol/mol, the yield to DP4-DP19 oligosaccharides was determined to be 30.8% mol/mol, the yield to DP10+ oligosaccharides was determined to be 10.4% mol/mol and the yield to sugar degradation products was determined to be 16.5% mol/mol, with 4.2% mol/mol appearing as either formic acid, acetic acid, levulinic acid, 5-hydroxymethylfurfural, or furfural, and 12.2% mol/mol appearing as insoluble products and tars. The resulting catalyst selectivity was determined to be 80% mol/mol.

Example 94: Comparative Example for Conversion of Glucose to Gluco-Oligosaccharides Using Dowex Marathon H Strong Acid Ion Exchange Resin The procedure of Example 73 was repeated using 100 g of glucose, 50 dry g of the strong acid ion exchange resin Dowex Marathon C (sulfonated polystyrene-co-divinylbenzene, Sigma-Aldrich, St. Louis, Mo., USA), an initial water content of about 31 g, and a reaction temperature of 95 degrees Celsius. After three hours of reaction, the conversion of sugars was determined to be 72.4% mol/mol, the yield to DP2 oligosaccharides was determined to be 17.6% mol/mol, the yield to DP3 oligosaccharides was determined to be 10.3% mol/mol, the yield to DP4-DP19 oligosaccharides was determined to be 23.5% mol/mol, the yield to DP10+ oligosaccharides was determined to be 11.0% mol/mol and the yield to sugar degradation products was determined to be 10.1% mol/mol, with 0.9% mol/mol appearing as either formic acid, acetic acid, levulinic acid, 5-hydroxymethylfurfural, or furfural, and 9.2% mol/mol appearing as insoluble products and tars. The resulting catalyst selectivity was determined to be 86% mol/mol.

Example 95: Comparative Example for Conversion of Glucose to Gluco-Oligosaccharides Using Dupont Nafion NR-50 Strong Super-Acid Resin The procedure of Example 73 was repeated using 50 g of glucose, 25 dry g of the strong superacid resin Dupont Nafion NR-50 (sulfonated tetrafluoroethylene, Sigma-Aldrich, St. Louis, Mo., USA), an initial water content of about 15 g, and a reaction temperature of 95 degrees Celsius. After three hours of reaction, the conversion of sugars was determined to be 29.1% mol/mol, the yield to DP2 oligosaccharides was determined to be 5.1% mol/mol, the yield to DP3 oligosaccharides was determined to be 2.2% mol/mol, the yield to DP4-DP19 oligosaccharides was determined to be 2.0% mol/mol, the yield to DP10+ oligosaccharides was determined to be 1.4% mol/mol and the yield to sugar degradation products was determined to be 18.5% mol/mol, with 2.6% mol/mol appearing as either formic acid, acetic acid, levulinic acid, 5-hydroxymethylfurfural, or furfural, and 15.9% mol/mol appearing as insoluble products and tars. The resulting catalyst selectivity was determined to be 36% mol/mol.

Example 96: Comparative Example for Reuse of the Amberlite IRH-110 Catalyst

The procedure of Example 78 was repeated using 100 g of glucose, 50 dry g of the strong acid ion exchange resin Amberlite IRH-110 (sulfonated polystyrene-co-divinylbenzene, Sigma-Aldrich, St. Louis, Mo., USA), an initial water content of about 31 g, and a reaction temperature of 95 degrees Celsius. Three reaction cycles were performed, with the total conversion of sugars determined to be 86.3% mol/mol in the first reaction cycle, 65.0% mol/mol in the second reaction cycle, and 34% mol/mol in the third reaction cycle, reflecting an average catalyst inactivation rate of 34% mol/mol/cycle.

Example 97: Production of Oligosaccharides Using Polymeric Catalysts

The procedures of Examples 73-78 are repeated using, in place of glucose as the reactant sugar, approximately 100 g total of any combination of sugars selected from the group consisting of glucose, maltose, cellobiose, galactose, xylose, arabinose, fructose, mannose, raffinose, stachyose, glycerol, glucitol, sorbitol, arabitol, and xylitol as the reactant, and in place of the catalyst from Example 72, any of the catalysts selected from Examples 3, 4, 5, 7, 8, 10, 12, 14, 16, 18, 20, 22, 23, 25, 26, 28, 29, 30, 31, 32, 33, 34, 35, 36, 38, 39, 42, 50, 55, 57, 59, 61, 63, 65, 67, 69, and 71.

Example 98: Production of Oligosaccharides Using Polymeric Catalysts

The procedures of Examples 73-78 are repeated using, in place of glucose as the reactant sugar, corn syrup as the reactant sugar, and in place of the catalyst from Example 72, any of the catalysts selected from Examples 3, 4, 5, 7, 8, 10, 12, 14, 16, 18, 20, 22, 23, 25, 26, 28, 29, 30, 31, 32, 33, 34, 35, 36, 38, 39, 42, 50, 55, 57, 59, 61, 63, 65, 67, 69, and 71.

Example 99: Production of Oligosaccharides Using Polymeric Catalysts

The procedures of Examples 73-78 are repeated using, in place of glucose as the reactant sugar, corn starch as the reactant carbohydrate, and in place of the catalyst from Example 72, any of the catalysts selected from Examples 3, 4, 5, 7, 8, 10, 12, 14, 16, 18, 20, 22, 23, 25, 26, 28, 29, 30, 31, 32, 33, 34, 35, 36, 38, 39, 42, 50, 55, 57, 59, 61, 63, 65, 67, 69, and 71.

Example 100: Preparation of Poly-(Styrene Sulfonic Acid-Co-Vinylbenzylimidazolium Sulfate-Co-Divinylbenzene)

To a 30 L jacketed glass reactor, housed within a walk-in fume hood and equipped with a 2 inch bottom drain port and a multi-element mixer attached to an overhead air-driven stirrer, was charged 14 L of N,N-dimethylformamide (DMF, ACS Reagent Grade, Sigma-Aldrich, St. Louis, Mo., USA) and 2.1 kg of 1H-imidazole (ACS Reagent Grade, Sigma-Aldrich, St. Louis, Mo., USA) at room temperature. The DMF was stirred to dissolve the imidazole. To the reactor was then added 7.0 kg of cross-linked poly-(styrene-co-divinylbenzene-co-vinylbenzyl chloride) to form a stirred suspension. The reaction mixture was heated to 90 degrees Celsius by pumping heated bath fluid through the reactor jacket, and the reaction mixture was allowed to react for 24 hours, after which it was gradually cooled.

Then, the DMF and residual unreacted 1H-imidazole was drained from the resin, after which the retained resin was washed repeatedly with acetone to remove residual heavy solvent or unreacted reagents. The reaction yielded cross-linked poly-(styrene-co-divinylbenzene-co-1H-imidazolium chloride) as off-white spherical resin beads. The resin beads were removed from the reactor and heated at 70 degrees Celsius in air to dry.

The cleaned 30 L reactor system was charged with 2.5 L of 95% sulfuric acid (ACS Reagent Grade) and then approximately 13 L of oleum (20% free $SO_3$ content by weight, Puritan Products, Inc., Philadelphia, Pa., USA). To the stirred acid solution was gradually added 5.1 kg of the cross-linked poly-(styrene-co-divinylbenzene-co-1H-imidazolium chloride). After the addition, the reactor was flushed with dry nitrogen gas, the stirred suspension was heated to 90 degrees Celsius by pumping heated bath fluid through the reactor jacket, and the suspension was maintained at 90 degrees Celsius for approximately four hours. After completion of the reaction, the mixture was allowed to cool to approximately 60 degrees Celsius and the residual sulfuric acid mixture was drained from the reactor. The resin was washed with 80 wt % sulfuric acid solution, followed by 60 wt % sulfuric acid solution. Then the resin was washed repeatedly with distilled water until the pH of the wash water was above 5.0, as determined by pH paper, to yield the solid catalyst. The acid functional density of catalyst was determined to be at least 2.0 mmol H+/g dry resin by ion-exchange acid-base titration

Example 101: Refactoring of 18DE Corn Syrup to an Indigestible Gluco-Oligosaccharide A digestible starting oligosaccharide was reacted with the catalyst prepared as in Example 100 at 100 g scale to convert it to an indigestible carbohydrate in a single step procedure. Corn syrup (malto-dextrin), with an initial average degree of polymerization (DP) of 9 and an initial dextrose equivalent (DE) of 18, was analyzed for its digestibility by α-amylase/aminoglucosidase. It was found that 94.2% of the DP3+ component and 67.5% of the DP2 component of the corn syrup were digested to glucose, indicating that the chemical structure of the starting oligosaccharides consisted predominantly of α(1,4) glycosidic linkages.

100 g of the 18 DE corn syrup was combined with 25.8 g of de-ionized water and 20.2 dry g of the catalyst from Example 100 in a 400 mL glass cylindrical reactor. The resulting mixture was mixed continuously and gradually heated to 105° C. by heating the walls of the reaction vessel using a temperature-controlled oil bath. Mixing was provided by an overhead mechanical stirrer equipped with a stainless steel three-blade impeller, where the ratio of the diameter of the mixing element to the diameter of the reaction vessel was approximately 0.8. The stirred suspension was maintained at temperature for approximately four hours. At 0, 1, 2, 3, and 4 hours, a 250 mg aliquot of the reaction mixture was diluted into 10 mL of deionized water and analyzed by HPLC to determine the concentrations of sugars and the concentration distribution of oligosaccharides with respect to their degree of polymerization (DP).

Figure 13:
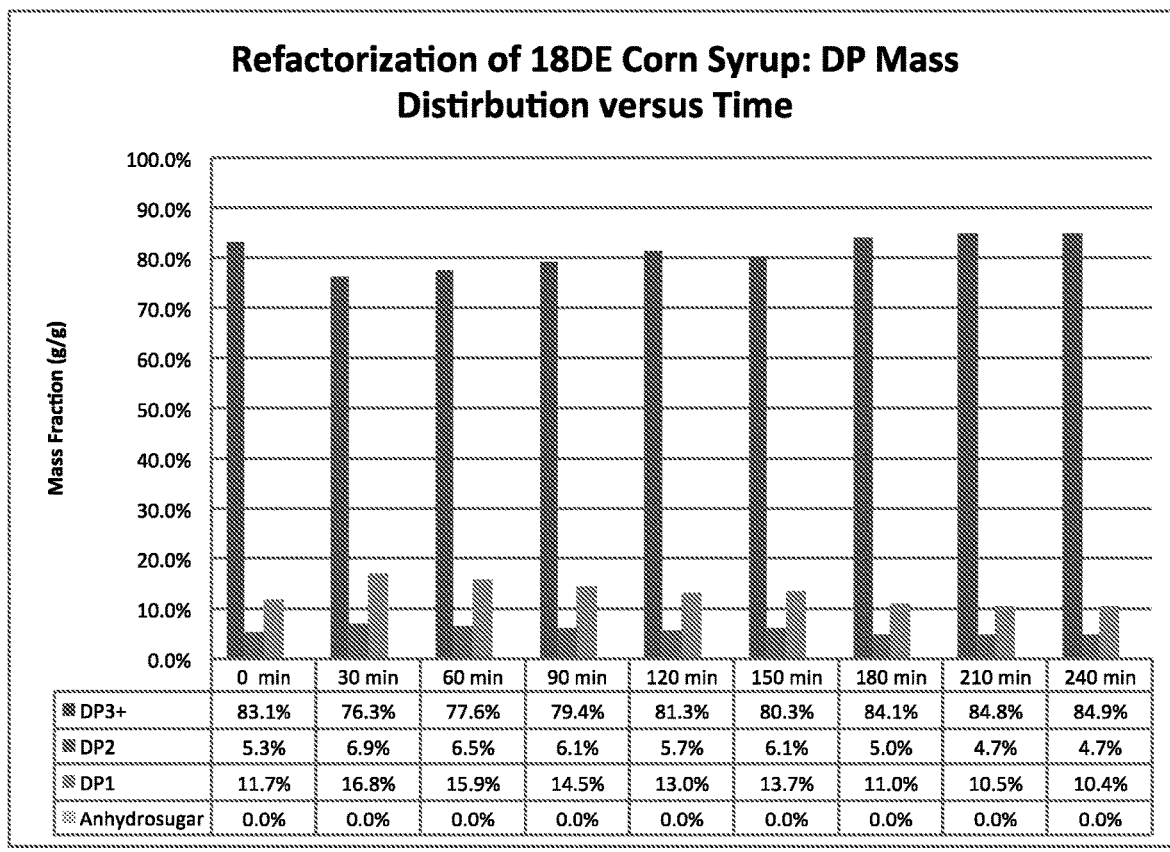
FIG. 13 is a graph depicting the changes in distribution of degree of polymerization over time of corn syrup during refactoring with a catalyst with both acidic and ionic moieties.

The distribution over DP over the course of the reaction is shown in FIG. 13. At no point during the reaction did the mass fraction of DP3+ species decrease below 76% g/g, indicating that minimal hydrolysis of the starting corn syrup took place. The mass fraction of glucose (DP1) was maintained between about 10% and 17% throughout the reaction.

Following the reaction, approximately 100 g of de-ionized water was added to dilute the mixture to about 50 Brix. The resulting gluco-oligosaccharide syrup was separated from the catalyst by vacuum filtration using a fritted glass funnel (pore size 50-100 micron). Additional water was used to wash the catalyst to remove additional soluble species, resulting in a final syrup concentration of approximately 25 Brix. The syrup was concentrated to 75 Brix by vacuum rotary evaporation.

The resulting gluco-oligosaccharide composition was analyzed for digestibility. It was found that only 10.8% of the DP3+ component and 8.8% of the DP2 component were digestible, indicating that the α(1,4) glycosidic linkages in the starting oligosaccharide had been effectively refactored into other, non-digestible, linkage types. Analysis of the DP2 component by HPLC indicated the presence of at least β(1,4), α(1,3), β(1,3), α(1,6), and β(1,6) linkages in the product species.

Example 102: Rapid Conversion of Glucose to Gluco-Oligosaccharides

To a 1000 mL three neck flask (TNF) equipped with a 3" paddle stirring element driven by an overhead mechanical mixer attached through a vacuum-capable bearing was attached a vacuum distillation apparatus comprising a riser, a jacketed condenser, a descending elbow with a vacuum fitting, and a 500 mL round bottom flask (RBF) to collect condensate. The walls of the 1000 mL TNF were heated with an electric mantle powered by a variac, the condenser was cooled to 2° C. using a circulating chiller with 50% ethylene glycol in water. Vacuum was provided a rotary vane pump equipped with an adjustable manifold and a vacuum gauge.

To the TNF was added approximately 200 grams of food grade dextrose (Cantab®, Stauber, USA) and 28 dry gram of the catalyst from Example 72. Sufficient water was added to bring the sugar concentration to between 0.50-0.70 grams of sugar per grams solution. The dextrose was dissolved with constant stirring and heating at a pressure of −5.6 psig and the mixture was heated with a variac setting of 50%. The temperatures of the reaction mixture and the headspace atmosphere were monitored with J-type thermocouples. After 22 minutes, the reaction mixture reached a final temperature ($T_{final}$) of 131° C. and was stopped by removing heat.

The reaction yield was determined by removing a small (approximately 1 g) sample of the reaction mixture, dissolving in hot distilled water, and analyzing the resulting solution by HPLC to determine the conversion of monomeric sugars to oligosaccharides. The total conversion of monomeric glucose to DP3+ oligosaccharides was determined to be 68% mol/mol. The presence of α(1,2), β(1,2), α(1,3), α(1,4), β(1,4), α(1,6), and β(1,6) linkages was confirmed by NMR analysis.

Example 103: Fast Oligomerization of Glucose at Various Temperatures, Pressures, and Catalyst Loadings The procedure of Example 102 was repeated with different heating rates, catalyst loadings, and reaction pressures, resulting in the following yields:

| Example Reaction Number | Glucose mass (dry grams) | Catalyst mass (dry grams) | Reaction Time (min) | Reaction Pressure (psig) | $T_{final}$ (degrees C.) | Y(DP3+) (mol/mol) |
| --- | --- | --- | --- | --- | --- | --- |
| Ex. 103-1 | 200 | 0 | 46 | −9.3 | 185 | 0% |
| Ex. 103-2 | 200 | 3.5 | 39 | −9.3 | 185 | 46% |
| Ex. 103-3 | 200 | 3.5 | 51 | −9.3 | 185 | 39% |
| Ex. 103-4 | 200 | 7.0 | 27 | −9.3 | 185 | 53% |

-continued

| Example Reaction Number | Glucose mass (dry grams) | Catalyst mass (dry grams) | Reaction Time (min) | Reaction Pressure (psig) | $T_{final}$ (degrees C.) | Y(DP3+) (mol/mol) |
|---|---|---|---|---|---|---|
| Ex. 103-5  | 200 | 7.0 | 51  | −9.3 | 185 | 50% |
| Ex. 103-6  | 200 | 7.0 | 57  | −9.3 | 185 | 75% |
| Ex. 103-7  | 200 | 7.0 | 165 | 0.0  | 140 | 52% |
| Ex. 103-8  | 200 | 7.0 | 220 | 0.0  | 155 | 68% |
| Ex. 103-9  | 200 | 14  | 45  | −9.3 | 150 | 33% |
| Ex. 103-10 | 200 | 14  | 50  | −9.3 | 160 | 35% |
| Ex. 103-11 | 200 | 14  | 55  | −9.3 | 195 | 79% |
| Ex. 103-12 | 200 | 14  | 65  | −9.3 | 185 | 73% |
| Ex. 103-13 | 200 | 14  | 70  | −9.3 | 175 | 59% |
| Ex. 103-14 | 200 | 28  | 22  | −5.6 | 131 | 68% |
| Ex. 103-15 | 200 | 28  | 30  | −9.3 | 161 | 66% |
| Ex. 103-16 | 200 | 28  | 60  | 0    | 150 | 85% |

Example 104: Synthesis of Acetyl-Functionalized Gluco-Oligosaccharides 2.0 grams of glucose, 2.0 dry grams of the catalyst from Example 72, 2.0 grams of acetic acid, and 10 mL of water were added to an aluminum weighing dish and mixed by spatula to homogenize the mixture. The mixture was then placed in a vacuum oven and incubated at 78° C. for four hours at a pressure of 0.1 bar. The solid reaction product was recovered from the solid catalyst by adding 25 mL of hot water to the dish to dissolve the soluble species. The solution was filtered through a 0.2 micron syringe filter to remove the catalyst. The functionalized oligomeric product was precipitated from solution by adding 85 mL of cold acetone and recovered by gravity filtration. The product was dried under vacuum for two hours at 40° C. to yield 1.4 dry grams of product. The average degree of polymerization of the functionalized oligosaccharide was determined to be approximately 6 by HPLC.

Incorporation of acetyl pendant groups was confirmed by re-hydrolysis of the functionalized oligosaccharide product. Approximately 500 mg of the functionalized oligosaccharide was dissolved in 5 mL of 1% sulfuric acid. The solution was transferred to a serum vial, sealed, and autoclaved at 121° C. for 60 minutes. Glucose and acetic acid were observed in the resulting digest, confirming the incorporation of those species into the functionalized oligosaccharide.

Example 105: Synthesis of Various Functionalized Oligosaccharides

The procedure of Example 104 was repeated, with the exception that the 2.0 grams of glucose (sugar reactant) and 2.0 grams of acetic acid (other reactant) were replaced as follows:

| Example Reaction Number | Sugar Reactants | Other Reactants | Incorporated Sugars Confirmed by Rehydrolysis | Incorporated Pendant Groups Confirmed by Rehydrolysis |
|---|---|---|---|---|
| Ex. 104-1 | glucose | acetic acid | glucose | acetic acid |
| Ex. 104-2 | glucose | maleic acid | glucose | maleic acid |
| Ex. 104-3 | glucose | glucuronic acid | glucose | glucuronic acid |
| Ex. 104-4 | glucose | aspartic acid | glucose | aspartic acid |
| Ex. 104-5 | glucose | 1-propanol | glucose | 1-propanol |
| Ex. 104-6 | glucose | succinic acid | glucose | succinic acid |
| Ex. 104-7 | glucose | lactic acid | glucose | lactic acid |
| Ex. 104-8 | glucose | levulinic acid, 1-propanol | glucose | levulinic acid, 1-propanol |
| Ex. 104-9 | glucose | glucosamine | glucose | glucosamine |
| Ex. 104-10 | glucose, galactose | glucosamine | glucose, galactose | glucosamine |
| Ex. 104-11 | glucose, galactose | lactic acid | glucose, galactose | lactic acid |
| Ex. 104-12 | glucose, galactose, xylose | 1-propanol | glucose, galactose, xylose | 1-propanol |
| Ex. 104-13 | glucose, xylose | butyric acid | glucose, xylose | butyric acid |
| Ex. 104-14 | xylose | xylitol | xylose | xylitol |
| Ex. 104-15 | xylose, arabinose | acetic acid, 1-propanol | xylose, arabinose | acetic acid |

In cases where more than one sugar reactant was used, the sugar reactants were dispensed in equal proportion by mass to a total mass of 2.0 grams. In cases where more than one other reactant was used, the other reactants were dispensed in equal proportion by mass to a total mass of 2.0 grams.

Example 106: Synthesis of a Sulfated Oligosaccharide

In a 100 mL round bottom flask (RBF) containing a magnetic stir bar, 2.0 dry grams of the oligosaccharide from Example 102 were dissolved in 20 mL of N,N-dimethylformamide (DMF) at room temperature. Approximately 0.45 grams (approximately 0.25 molar equivalents) of dimethylformamide sulfur trioxide complex (DMF-SO$_3$) was then added to RBF and the resulting solution was stirred for two hours at 25° C. After two hours, the reaction was terminated by quickly transferring the contents to 250 mL of ice cold acetone, resulting in an off-white precipitate. The precipitate was recovered by filtration, washed five times with 150 mL of ice cold acetone and dried over night at 40° C. under vacuum. Sulfation of the oligosaccharide was confirmed by acid-base titration against 0.1 N sodium hydroxide.

Example 107: Synthesis of a Sialated Oligo-Saccharide 2.0 grams of glucose, 0.25 grams of N-acetylneuraminic acid, 2.0 dry grams of the catalyst from Example 72 and 10 mL of water are added to an aluminum weighing dish and mixed by spatula to homogenize the mixture. The mixture is then placed in a vacuum oven and incubated at 78° C. for four hours at a pressure of 0.1 bar. The solid reaction product is recovered from the solid catalyst by adding 25 mL of hot water to dissolve the soluble species. The solution is filtered through a 0.2 micron syringe filter to remove the catalyst. The product is precipitated from solution by adding 85 mL of cold acetone, recovered by gravity filtration, and dried under vacuum for two hours at 40° C. to yield the sialated oligosaccharide.

Example 108: Washing of Used Catalyst

Recovered catalyst from each the reactions in Example 103 was combined and rinsed with 500 mL of room temperature distilled water in a fritted glass funnel. The catalyst was next rinsed with 500 mL of 1 wt % sodium hydroxide solution, followed by 500 mL of distilled water. The catalyst was then rinsed with 500 mL of 1 wt % sulfuric acid followed by 1,000 mL of distilled water. Excess water was removed from the catalyst by vacuum filtration. The moisture content of the rinsed content was determined to be at least 30% by mass.

Example 109: Preparation of Gluco-Oligosaccharides Using a Recyclable Catalyst 150 g of glucose and 30 g of the catalyst from Example 3 were combined with 50 g of distilled water in an atmospheric-pressure cylindrical glass reactor equipped with an overhead mechanical stirrer. With continuous mixing, the reactor contents were maintained at 110° C. for 300 minutes, after which the product mixture was rapidly diluted with warm water to a final concentration of 50% by mass. The product solution was separated from the residual catalyst by vacuum filtration to yield 30 g of recovered catalyst. The product was purified by running the solution through a 100 mL column of Dowex Monosphere 88 at a flow rate of 2 bed volumes per hour, a 100 mL column of Dowex Monosphere 77 at a flow rate of 2 bed volumes per hour, and a column of Dow Optipore-SD2 at a flow rate of 1 bed volume per hour. The pH of the resulting solution was determined by pH meter to be between 6.0 and 7.0. The color of the resulting solution was determined to be below 120 ICUMSA. The total yield of glucose to gluco-oligosaccharides with DP3+ was determined by HPLC to be 70% mol/mol. The conversion of glucose monosaccharides was determined by HPLC to be 83.7% mol/mol and the first order rate constant was determined to be 0.36 per hour. No levulinic acid, formic acid, or hydroxymethylfurfural was observed in the final product by HPLC.

A second reaction cycle was performed by combining 150 g of additional glucose with the 30 g of recovered catalyst and 50 g of distilled water in the same atmospheric-pressure cylindrical glass rector. With continuous mixing, the reactor contents were maintained at 110° C. for 280 minutes, after which the product mixture was rapidly diluted with warm water to a final concentration of 50% by mass. The product solution from this second reaction cycle was separated from the residual catalyst by vacuum filtration to yield 30 g of recovered catalyst. The product was purified by running the solution through a 100 mL column of Dowex Monosphere 88 at a flow rate of 2 bed volumes per hour, a 100 mL column of Dowex Monosphere 77 at a flow rate of 2 bed volumes per hour, and a 100 mL column of Dow Optipore-SD2 at a flow rate of one bed volume per hour. The pH of the resulting solution was determined by pH meter to be between 6.0 and 7.0. The color of the resulting solution was determined to be below 120 ICUMSA. The total yield of glucose to gluco-oligosaccharides with DP3+ was determined by HPLC to be 65% mol/mol. The conversion of glucose monosaccharides was determined by HPLC to be 80.7% mol/mol and the first order rate constant was determined to be 0.35 per hour. No levulinic acid, formic acid, or hydroxymethylfurfural was observed in the final product by HPLC. The loss of activity between the first and second reaction cycles was determined to be approximately 2%.

Example 110: Preparation of Gluco-Oligosaccharides Using a Recyclable Catalyst

The procedure of Example 109 was repeated using, in place of the catalyst from Example 3, the catalyst from Example 18. The loss of activity between the first and second reaction cycles was determined to be less than 1%.

Example 111: Comparative Example Demonstrating a Non-Recyclable Catalyst

The procedure of Example 109 was repeated using, in place of the catalyst from Example 3, strong acid ion exchange resin Dowex® 50WX8 (Sigma-Aldrich, St. Louis, Mo., USA) containing sulfonic acid groups but no cationic groups. The loss of activity between the first and second reaction cycles was determined to be more than 80%.

What is claimed is:

1. An oligosaccharide composition prepared according to a method comprising condensation polymerization of one or more sugars to produce the oligosaccharide composition;
    the oligosaccharide composition comprising:
        monosaccharide monomers connected by glycosidic bonds;
        wherein:
            each of the monosaccharide monomers is selected from the group consisting of C5 monosaccharides and C6 monosaccharides; at least 15% of the oligosaccharide composition has a degree of polymerization (DP) of at least four; 5 to 25% of the oligosaccharide composition has a degree of polymerization (DP) of three; and 5 to 30% of the oligosaccharide composition has a degree of polymerization (DP) of two;
            the mean DP of the oligosaccharide composition is 10-15; and
        at least a portion of the glycosidic bonds in the oligosaccharide composition comprises β-1,2 bonds and α-1,3 bonds.

2. The oligosaccharide composition of claim 1, wherein the monosaccharide monomers are glucose, galactose, xylose, arabinose, fructose, mannose, ribose, allose, fucose, or rhamnose.

3. The oligosaccharide composition of claim 1, wherein the monosaccharide monomers are connected by glycosidic bonds to form oligomer backbones, and wherein the oligomer backbones are optionally substituted with one or more pendant functional groups, wherein the pendant functional groups are carboxylic acids, sugar alcohols, amino acids, amino sugars, alcohols, sulfate, or phosphate.

4. The oligosaccharide composition of claim 1, wherein the monosaccharide monomers are connected by glycosidic bonds to form oligomer backbones, and wherein at least a portion of the oligosaccharide composition further comprises one or more bridging functional groups, wherein:

each bridging functional group connects one of the oligomer backbones to an additional monosaccharide monomer, a disaccharide, or an additional oligomer backbone; and the one or more bridging functional groups are polyols, polycarboxylic acids, or amino acids.

5. The oligosaccharide composition of claim 4, wherein each additional oligomer backbone is optionally substituted with one or more pendant functional groups, wherein the pendant functional groups are carboxylic acids, sugar alcohols, amino acids, amino sugars, alcohols, sulfate, or phosphate.

6. The oligosaccharide composition of claim 3, wherein the one or more pendant functional groups are glucosamine, galactosamine, citric acid, succinic acid, glutamic acid, aspartic acid, glucuronic acid, butyric acid, itaconic acid, malic acid, maleic acid, propionic acid, butanoic acid, pentanoic acid, hexanoic acid, adipic acid, isobutyric acid, formic acid, levulinic acid, valeric acid, isovaleric acid, sorbitol, xylitol, arabitol, glycerol, erythritol, mannitol, galacitol, fucitol, iditol, inositol, volemitol, lacitol, ethanol, propanol, butanol, pentanol, hexanol, propanediol, butanediol, pentanediol, sulfate, or phosphate.

7. The oligosaccharide composition of claim 4, wherein the one or more bridging functional groups are glucosamine, galactosamine, lactic acid, acetic acid, citric acid, pyruvic acid, succinic acid, glutamic acid, aspartic acid, glucuronic acid, itaconic acid, malic acid, maleic acid, adipic acid, sorbitol, xylitol, arabitol, glycerol, erythritol, mannitol, galacitol, fucitol, iditol, inositol, volemitol, lacitol, propanediol, butanediol, pentanediol, sulfate, or phosphate.

8. The oligosaccharide composition of claim 1, wherein greater than 50% of the oligosaccharide composition has a DP of at least four.

9. The oligosaccharide composition of claim 1, wherein at least 90% of the oligosaccharide composition comprises a mixture of non-alpha-1,4-bonds.

10. The oligosaccharide composition of claim 1, wherein at least 99% of the oligosaccharide composition comprises a mixture of non-alpha-1,4-bonds.

11. The oligosaccharide composition of claim 1, wherein the hygroscopicity of the oligosaccharide composition is between 5% moisture content and 15% moisture content at a water activity of at least 0.6.

12. The oligosaccharide composition of claim 1, wherein the oligosaccharide composition is soluble in water up to a maximum concentration of at least 50 Brix.

13. The oligosaccharide composition of claim 1, wherein the oligosaccharide composition is soluble in water up to a maximum concentration of at least 70 Brix.

14. The oligosaccharide composition of claim 1, wherein the oligosaccharide composition is a syrup.

15. The oligosaccharide composition of claim 1, wherein the oligosaccharide composition is a powder.

16. The oligosaccharide composition of claim 1, wherein the monosaccharide monomers are C6 monosaccharides.

17. The oligosaccharide composition of claim 1, wherein the glycosidic bonds in said oligosaccharide composition are $\alpha$-1,4 bonds, $\alpha$-1,2 bonds, $\beta$-1,2 bonds, $\alpha$-1,3 bonds, $\beta$-1,3 bonds, $\beta$-1,4 bonds, $\alpha$-1,6 bonds, or $\beta$-1,6 bonds.

18. The oligosaccharide composition of claim 1, wherein the monosaccharide monomers are C5 monosaccharides.

19. The oligosaccharide composition of claim 1, wherein the monosaccharide monomers are arabinose and galactose.

20. The oligosaccharide composition of claim 1, wherein the monosaccharide monomers are glucose.

21. The oligosaccharide composition of claim 1, wherein the monosaccharide monomers are galactose and glucose.

22. The oligosaccharide composition of claim 1, wherein the monosaccharide monomers are galactose.

23. The oligosaccharide composition of claim 1, wherein the oligosaccharide composition comprises non-carbohydrate by-products.

24. The oligosaccharide composition of claim 23, wherein the non-carbohydrate by-products comprise polyfuranics or solid humins.

* * * * *